US011130995B2

(12) United States Patent
Quake et al.

(10) Patent No.: US 11,130,995 B2

(45) Date of Patent: Sep. 28, 2021

(54) SIMULTANEOUS DETERMINATION OF ANEUPLOIDY AND FETAL FRACTION

(71) Applicant: Verinata Health, Inc., Redwood City, CA (US)

(72) Inventors: Stephen Quake, Stanford, CA (US); Richard P Rava, Redwood City, CA (US); Manjula Chinnappa, Foster City, CA (US); David A Comstock, Sunnyvale, CA (US); Gabrielle Heilek, Mountain View, CA (US)

(73) Assignee: Verinata Health, Inc., San Carlos, CA (US)

( * ) Notice: Subject to any disclaimer, the term of this patent is extended or adjusted under 35 U.S.C. 154(b) by 0 days.

(21) Appl. No.: 15/664,008

(22) Filed: Jul. 31, 2017

(65) Prior Publication Data

US 2017/0327883 A1 Nov. 16, 2017

Related U.S. Application Data

(63) Continuation of application No. 13/365,240, filed on Feb. 2, 2012, now abandoned, which is a continuation of application No. 12/958,356, filed on Dec. 1, 2010, now abandoned.

(60) Provisional application No. 61/455,849, filed on Oct. 26, 2010, provisional application No. 61/407,017, filed on Oct. 26, 2010, provisional application No. 61/360,837, filed on Jul. 1, 2010, provisional application No. 61/296,358, filed on Jan. 19, 2010.

(51) Int. Cl.

| | |
|---|---|
| ***C12Q 1/6869*** | (2018.01) |
| ***C12Q 1/6806*** | (2018.01) |
| ***C12Q 1/6809*** | (2018.01) |
| ***C12Q 1/6883*** | (2018.01) |
| ***G16B 30/10*** | (2019.01) |
| ***G16H 10/40*** | (2018.01) |
| ***G16B 20/10*** | (2019.01) |

(52) U.S. Cl.

CPC ......... *C12Q 1/6869* (2013.01); *C12Q 1/6806* (2013.01); *C12Q 1/6809* (2013.01); *G16B 20/10* (2019.02); *G16B 30/10* (2019.02); *G16H 10/40* (2018.01); *C12Q 1/6883* (2013.01); *C12Q 2600/106* (2013.01); *C12Q 2600/112* (2013.01)

(58) Field of Classification Search

None

See application file for complete search history.

(56) References Cited

U.S. PATENT DOCUMENTS

| | | | |
|---|---|---|---|
| 5,994,057 A | 11/1999 | Mansfield | |
| 6,258,540 B1 | 7/2001 | Lo et al. | |
| 6,440,706 B1 | 8/2002 | Vogelstein et al. | |
| 6,555,315 B1 | 4/2003 | Short | |
| 7,252,946 B2 | 8/2007 | Szasz | |
| 7,332,277 B2 | 2/2008 | Dhallan | |
| 7,645,576 B2 | 1/2010 | Lo et al. | |
| 7,888,017 B2 | 2/2011 | Quake et al. | |
| 8,008,018 B2 | 8/2011 | Quake et al. | |
| 8,137,912 B2 | 3/2012 | Kapur et al. | |
| 8,168,389 B2 * | 5/2012 | Shoemaker .......... | C12Q 1/6809 435/6.12 |
| 8,195,415 B2 | 6/2012 | Fan et al. | |
| 8,318,430 B2 | 11/2012 | Chuu et al. | |
| 8,532,936 B2 | 9/2013 | Rava | |
| 2002/0142324 A1 | 10/2002 | Wang et al. | |
| 2003/0044388 A1 | 3/2003 | Lo et al. | |
| 2003/0064368 A1 | 4/2003 | Sakai et al. | |
| 2003/0194704 A1 | 10/2003 | Penn et al. | |
| 2004/0209299 A1 | 10/2004 | Pinter et al. | |
| 2005/0221341 A1 | 10/2005 | Shimkets et al. | |
| 2006/0046258 A1 | 3/2006 | Lapidus et al. | |
| 2006/0121452 A1 | 6/2006 | Dhallan | |
| 2006/0134599 A1 | 6/2006 | Toner et al. | |
| 2006/0257895 A1 | 11/2006 | Pinkel et al. | |
| 2006/0286558 A1 | 12/2006 | Novoradovskaya et al. | |
| 2007/0134658 A1 | 6/2007 | Bohmer et al. | |
| 2007/0207466 A1 | 9/2007 | Cantor et al. | |
| 2008/0020390 A1 | 1/2008 | Mitchell et al. | |
| 2008/0050739 A1 | 2/2008 | Stoughton et al. | |
| 2008/0064098 A1 | 3/2008 | Allickson | |
| 2008/0070792 A1 | 3/2008 | Stoughton et al. | |
| 2008/0138809 A1 | 6/2008 | Kapur et al. | |
| 2008/0193927 A1 | 8/2008 | Mann et al. | |
| 2008/0220422 A1 | 9/2008 | Shoemaker et al. | |

(Continued)

FOREIGN PATENT DOCUMENTS

| | | |
|---|---|---|
| EP | 2334812 | 6/2011 |
| GB | 2479471 | 10/2011 |

(Continued)

OTHER PUBLICATIONS

European Office Action issued in EP 12 716 939.9, dated Mar. 10, 2015.

(Continued)

*Primary Examiner* — Katherine D Salmon

(74) *Attorney, Agent, or Firm* — Mueting Raasch Group

(57) ABSTRACT

The invention provides compositions and methods for simultaneously determining the presence or absence of fetal aneuploidy and the relative amount of fetal nucleic acids in a sample obtained from a pregnant female. The method encompasses the use of sequencing technologies and exploits the occurrence of polymorphisms to provide a streamlined noninvasive process applicable to the practice of prenatal diagnostics.

17 Claims, 18 Drawing Sheets

Specification includes a Sequence Listing.

(56) References Cited

U.S. PATENT DOCUMENTS

| | | | |
|---|---|---|---|
| 2008/0299562 | A1 | 12/2008 | Oeth et al. |
| 2009/0029377 | A1 | 1/2009 | Lo et al. |
| 2009/0087847 | A1 | 4/2009 | Lo et al. |
| 2009/0098547 | A1 | 4/2009 | Ghosh |
| 2009/0117542 | A1 | 5/2009 | Maybruck et al. |
| 2009/0215042 | A1 | 8/2009 | Sella-Tavor et al. |
| 2009/0270601 | A1 | 10/2009 | Benner et al. |
| 2009/0291443 | A1 | 11/2009 | Stoughton et al. |
| 2009/0299645 | A1 | 12/2009 | Colby et al. |
| 2009/0307181 | A1 | 12/2009 | Colby et al. |
| 2009/0317817 | A1 | 12/2009 | Oeth et al. |
| 2009/0317818 | A1 | 12/2009 | Ehrich et al. |
| 2010/0068711 | A1 | 3/2010 | Umansky et al. |
| 2010/0093835 | A1 | 4/2010 | McSwiggen et al. |
| 2010/0112575 | A1 | 5/2010 | Fan et al. |
| 2010/0112590 | A1 | 5/2010 | Lo et al. |
| 2010/0138165 | A1 | 6/2010 | Fan et al. |
| 2010/0167954 | A1 | 7/2010 | Earnshaw et al. |
| 2010/0184043 | A1 | 7/2010 | Mitchell et al. |
| 2010/0184075 | A1 | 7/2010 | Cantor et al. |
| 2010/0196426 | A1 | 8/2010 | Skog et al. |
| 2010/0216151 | A1 | 8/2010 | Lapidus et al. |
| 2010/0216153 | A1 | 8/2010 | Lapidus et al. |
| 2011/0105353 | A1 | 5/2011 | Lo et al. |
| 2011/0118145 | A1 | 5/2011 | Akmaev et al. |
| 2011/0177517 | A1 | 7/2011 | Rava et al. |
| 2011/0201507 | A1 | 8/2011 | Rava et al. |
| 2011/0224087 | A1 | 9/2011 | Quake et al. |
| 2011/0230358 | A1 | 9/2011 | Rava |
| 2011/0245085 | A1 | 10/2011 | Rava et al. |
| 2011/0312503 | A1 | 12/2011 | Chuu et al. |
| 2012/0010085 | A1 | 1/2012 | Rava et al. |
| 2012/0034603 | A1 | 2/2012 | Oliphant et al. |
| 2012/0034685 | A1 | 2/2012 | Sparks et al. |
| 2012/0040859 | A1 | 2/2012 | Sparks et al. |
| 2012/0094849 | A1 | 4/2012 | Rava et al. |
| 2012/0100548 | A1 | 4/2012 | Rava et al. |
| 2012/0149582 | A1 | 6/2012 | Rava et al. |
| 2012/0149583 | A1 | 6/2012 | Rava et al. |
| 2012/0184449 | A1 | 7/2012 | Hixson et al. |
| 2012/0208710 | A1 | 8/2012 | Fan et al. |
| 2012/0214678 | A1 | 8/2012 | Rava et al. |
| 2012/0214680 | A1 | 8/2012 | Oeth et al. |
| 2012/0237928 | A1 | 9/2012 | Rava et al. |
| 2012/0238738 | A1 | 9/2012 | Hendrickson |
| 2013/0029852 | A1 | 1/2013 | Rava et al. |
| 2013/0034546 | A1 | 2/2013 | Rava et al. |
| 2013/0096011 | A1 | 4/2013 | Rava et al. |
| 2014/0038830 | A1 | 2/2014 | Srinivasan et al. |
| 2014/0199691 | A1 | 7/2014 | Chuu et al. |

FOREIGN PATENT DOCUMENTS

| | | |
|---|---|---|
| GB | 2479476 | 10/2011 |
| GB | 2479080 | 1/2012 |
| GB | 2484764 | 4/2012 |
| WO | 1996/19586 | 6/1996 |
| WO | 1998/14275 | 4/1998 |
| WO | 1998/44151 | 10/1998 |
| WO | 00/18957 | 4/2000 |
| WO | 2000/18957 | 4/2000 |
| WO | 2003/004677 | 1/2003 |
| WO | 03/074740 | 9/2003 |
| WO | 2003/074740 | 9/2003 |
| WO | 2006/010610 | 2/2006 |
| WO | 2006/028152 | 3/2006 |
| WO | 2006/028153 | 3/2006 |
| WO | 2007/092473 | 8/2007 |
| WO | 2007/100911 | 9/2007 |
| WO | 2007/147079 | 12/2007 |
| WO | 2009/013492 | 1/2009 |
| WO | 2009/013496 | 1/2009 |
| WO | 2010/033578 | 3/2010 |
| WO | 2011/051283 | 5/2011 |
| WO | 2012/019187 | 2/2012 |
| WO | 2012/019193 | 2/2012 |
| WO | 2012/019198 | 2/2012 |
| WO | 2012/019200 | 2/2012 |
| WO | 2012/071621 | 6/2012 |
| WO | 2012/078792 | 6/2012 |
| WO | 2012/088348 | 6/2012 |
| WO | 2012/103031 | 8/2012 |
| WO | 2012/108920 | 8/2012 |
| WO | 2012/142334 | 10/2012 |
| WO | 2013/015793 | 1/2013 |

OTHER PUBLICATIONS

Extended European Search Report for European Patent Application No. 14192160.1, dated Feb. 13, 2015, 10 pages.
"European Search Report in EP Patent Application No. 10825822.9", dated Feb. 22, 2012, 4 pages.
"European Search Report in EP Patent Application No. 10830938.6", dated Feb. 22, 2012, 4 pages.
"European Search Report in EP Patent Application No. 10830939.4", dated Feb. 22, 2012, 4 pages.
"Examination Report in EP Patent Application No. 10830939.4", dated Oct. 17, 2012.
"Examination Report in EP Patent Application No. 10830939.4", dated Mar. 16, 2012.
"Examination Report in GB Patent Application No. 1106394.8", dated Jun. 24, 2011.
"Examination Report in GB Patent Application No. 1107268.3", dated Nov. 15, 2011.
"Examination Report in GB Patent Application No. 1107268.3", dated Jul. 15, 2011.
"Examination Report in GB Patent Application No. 1108794.7", dated Jul. 15, 2011.
"Examination Report in GB Patent Application No. 1108795.4", dated Dec. 16, 2011.
"Examination Report in GB Patent Application No. 1108795.4", dated Mar. 9, 2012.
"Examination Report in GB Patent Application No. 1108795.4", dated Jul. 15, 2011.
"International Search Report in PCT Application No. PCT/US2010/058606", dated Feb. 28, 2011.
"International Search Report in PCT Application No. PCT/US2010/058609", dated Apr. 4, 2011.
"International Search Report in PCT Application No. PCT/US2010/058612", dated May 19, 2011.
"International Search Report in PCT Application No. PCT/US2010/058614", dated Mar. 1, 2011.
"International Search Report in PCT Application No. PCT/US2011/021729", dated Apr. 11, 2011.
"International Search Report in PCT Application No. PCT/US2011/045412", dated Feb. 24, 2012.
"Notice of Allowance in U.S. Appl. No. 12/696,509", dated Mar. 1, 2012.
"Notice of Allowance in U.S. Appl. No. 13/452,083", dated Jul. 12, 2012.
"Office Action in U.S. Appl. No. 13/365,134", dated Aug. 15, 2012.
"Office Action in U.S. Appl. No. 13/365,240", dated Jun. 3, 2012.
"Office Action in U.S. Appl. No. 13/368,035", dated Mar. 13, 2012.
Ashoor, et al., "Fetal Fraction in maternal plasma cell-free DNA at 11-13 weeks' gestation: effect of maternal and fetal factors", AFetal Diagn Ther, published online, A copy of a reference cited in the instructions, May 4, 2012, 7 pages.
Bentley, et al., "Accurate whole human genome sequencing using reversible terminator chemistry", Nature, vol. 456, Nov. 6, 2008, 53-59.
Beroukhim, et al., "The landscape of somatic copy-number alteration across human cancers", Nature, vol. 463, Feb. 2010, 899-905.
Borsting, , "Multiplex PCR, amplicon size and hybridization efficiency on the NanoChip electronic microarray", Int J. Legal Med. vol. 118, 2004, 75-82.
Botezatu, et al., "Genetic Analysis of DNA excreted in urine: a new approach for detecting specific genomic DNA sequences from cells dying in an organism", Clin Chem. 46(8 Pt1), Aug. 2000, 1078-84.

(56) References Cited

OTHER PUBLICATIONS

Buck, et al., "Design Strategies and Performance of Custom DNA Sequencing Primers", Biotechniques vol. 27, 1999, 528-536.
Butler, et al., "Short tandem repeat typing technologies used in human identity testing", Biotechniques 43(4), Oct. 2007, ii-v.
Butler, et al., "The Development of reduced size STR amplicons as tools for analysis of degraded DNA", J. Forensic Sci 48(5), 2003, 1054-64.
Chan, et al., "Size Distributions of maternal and fetal DNA in Maternal Plasma", Clin. Chem 50(1), Jan. 2004, 88-92.
Chen, et al., "Microsatellite alterations in plasma DNA of small cell lung cancer patients", Nat Med. 2(9), 1996, 1033-5.
Chiang, et al., "High-resolution mapping of copy-number alterations with massively parallel sequencing", Nature Methods, vol. 6, No. 1 (2009), published online: doi:10.1038/nmeth.1276, Jan. 2009, 99-103.
Chiu, et al., "Maternal Plasma DNA Analysis with Massively Parallel Sequencing by Ligation for Noninvasive Prenatal Diagnosis of Trisomy 21", Clinical Chemistry 56:3, 2010, 459-463.
Chiu, et al., "Non-invasive prenatal assessment of trisomy 21 by multiplexed maternal plasma DNA sequencing: large scale validity study", BMJ 342, Jan. 11, 2011, c7401.
Chiu, et al., "Non-invasive prenatal diagnosis by single molecule counting technologies", Trends Genet. 25 (7), Jul. 1, 2009, pp. 324-331.
Chiu, et al., "Noninvasive prenatal diagnosis of fetal chromosomal aneuploidy by massively parallel genomic sequencing of DNA in maternal plasma", PNAS, vol. 105, No. 51, Dec. 23, 2008, pp. 20458-20463.
Chu, et al., "Statistical model for whole genome sequencing and its application to minimally invasive of fetal genetic disease", Bioinformatics 25(10), May 15, 2009, 1244-1250.
Chuu et al., , "U.S. Appl. No. 13/012,222", filed Jan. 24, 2010.
Clarke, et al., "Effects of chemotherapy and hormonal therapy for early breast cancer on recurrence and 15-year survival: an overview of randomised trials", Lancet vol. 365, 2005, 1687-1717.
Clarke, et al., "Effects of radiotherapy and of differences in the extent of surgery for early breast cancer on local recurrence and 15-year survival: an overview of the randomised trials", Lancet vol. 366, 2005, 2087-2106.
Coble, et al., "Characterization of New MiniSTR Loci to Aid Analysis of Degraded DNA", J Forensic Sci, 50(1), Jan. 2005, 43-53.
Deng, et al., "Enumeration and microfluidic chip separation of circulating fetal cells early in pregnancy from maternal blood", American Journal of Obstetrics & Gynecology, vol. 199, Issue 6, Dec. 2008, S134.
Dhallan, et al., "A non-invasive test for prenatal diagnosis based on fetal DNA present in maternal blood: a preliminary study", Lancet 369(9560), Feb. 10, 2007, 474-481.
Ding, et al., "MS analysis of single-nucleotide differences in circulating nucleic acids: Application to noninvasive prenatal diagnosis", Proceedings of National Academy of Sciences 101(29), 2004, pp. 10762-10767.
Dixon, et al., "Analysis of artificially degraded DNA using STRs and SNPs—results of a collaborative European (EDNAP) exercise", Forensic Sci Int 164(1), Dec. 1, 2006, 33-44.
Ehrich, , "Noninvasive detection of fetal trisomy 21 by sequencing of DNA in maternal blood: a study in a clinical setting", Am J Obstet Gynecol, 204(3), Mar. 2011, 205.el-11.
Fan, et al., "Analysis of the size distributions of fetal and maternal cell-free DNA by paired-end sequencing", Clin. Chem 56(8), Aug. 1, 2010, 1279-1286.
Fan, et al., "Detection of aneuploidy with digital polymerase chain reaction", Anal Chem. 79(19), Oct. 1, 2007, 7576-7579.
Fan, et al., "In principle method for noninvasive determination of the fetal genome", Nature Precedings: Nature Precedings 10.1038/npre, Dec. 8, 2010, 5373.1.
Fan, et al., "Microfluidic digital PCR enables rapid prenatal diagnosis of fetal aneuploidy", Am J Obstet Gynecol 200(5), May 2009, 543.el-7.
Fan, et al., "Noninvasive diagnosis of fetal aneuploidy by shotgun sequencing DNA from maternal blood", Proceedings of the National Academy of Sciences, vol. 105, No. 42, also available at: http://www.pnas.org/cgi/doi/10.1073/pnas.0808319105, Oct. 21, 2008, 16266-71.
Fan, et al., "Sensitivity of noninvasive prenatal detection of fetal aneuploidy from maternal plasma using shotgun sequencing is limited only by counting statistics", PLoS One 5(5), May 3, 2010, e10439.
Fan, et al., "Supporting Information", 10.1073/pnas.0808319105, PNAS 105(42):16222, Oct. 2008, 7 pages.
Fan, et al., "U.S. Appl. No. 13/452,083", filed Apr. 20, 2012.
Fan, et al., "Whole-genome molecular haplotyping of single cells", Nature Biotechnology, Advanced Online Publication, Dec. 19, 2010, 9 pages.
Frohling, et al., "Chromosomal Abnormalities in Cancer", New England Journal of Medicine, vol. 359, 2008, 722-734.
Ghanta, et al., "Non-Invasive Prenatal Detection of Trisomy 21 Using Tandem Single Nucleotide Polymorphisms", PLos ONE, vol. 5, Issue 10, e13184, Oct. 2010, 10 pages.
Goossens, et al., "Simultaneous Mutation and Copy Number Variation (CNV) Detection by Multiplex PCR-Based GS-FLX Sequencing", Human Mutation, vol. 30, Issue 3, Dec. 2008, 472-476.
Grubweiser, et al., "A new "miniSTR-multiplex" displaying reduced amplicon lengths for the analysis of degrade DNA", Int J. Legal Med 120(2), 2006, 115-20.
Hanson, et al., "Whole genome amplification strategy for forensic genetic analysis using single or few cell equivalents of genomic DNA", Anal Biochem. 346(2), Nov. 15, 2005, 246-57.
Harris, et al., "Single-Molecule DNA Sequencing of a Viral Genome", Science 320, Apr. 4, 2008, 106-109 and Suppl. Materials 1-25.
Harrison, et al., "Polymer-stimulated ligation: enhanced ligation of oligo-and polynucleotides by T4 RNA ligase in polymer solutions", Nucleic Acids Research vol. 12 No. 21 1984, 1984, 8235-51.
Hayashi, et al., "Regulation of inter-and intramolecular ligation with T4 DNA ligase in the presence of polyethylene glycol", Nucleic Acids Res. 14(19), Oct. 10, 1986, 7617-31.
Hill, et al., "Characterization of 26 new miniSTR Loci", Poster #44—17th International Symposium on Human Identification, Nashville, TN, Oct. 10-12, 2006.
Hoffman, et al., "The genome-enabled electronic medical record", Journal of Biomedical Informatics 10 (2007) published online, Mar. 15, 2006, 44-46.
Huang, , "Isolation of cell-free DNA from maternal plasma using manual and automated systems", Methods Mol Biol. 444, 2008, 203-8.
Hung, , "Detection of circulating fetal nucleic acids: a review of methods and applications", J Clin Pathol 62(4), 2009, 308-13.
Illumina, , "Preparing Samples for ChIP sequencing of DNA", E-pub at grcf.jhmi.edu/hts/protocols/11257047_ChIP_Sample_Prep.pdf., 2007.
International, , "The International HapMap Consortium Project", Nature 426:789-96, 2003.
Jama, et al., "Quantification of cell-free fetal DNA Levels on maternal plasma by STR analysis", 2010 ACMG Annual Clinical Genetics Meeting, 2010, 2 pages.
Jensen, et al., "Detection of Microdeletion 22q11.2 in a Fetus by Next-Generation Sequencing of Maternal Plasma", Clinical Chemistry 58:7; doi:10.1373/clinchem.2011.180794, May 4, 2012, 1148-1151.
Jorgez, et al., "Improving Enrichment of circulating fetal DNA for genetic testing: size fractionation followed by whole gene amplification", Fetal Diagnosis and Therapy, Karger Basel, CH, vol. 25, No. 3, 2009, pp. 314-319.
Ju, et al., "Four-Color DNA Sequencing by Synthesis Using Cleavable Florescent Nucleotide Reversible Terminators", PNAS vol. 103, No. 52, 2006, 19635-19640.
Kidd, et al., "Developing a SNP panel for forensic identification of individuals", Forensic Science International 164 ( 2006), 2006, 20-32.

(56) References Cited

OTHER PUBLICATIONS

Kim, et al., "rSW-seq: algorithm for detection of copy number alterations in deep sequencing data", BMC Bioinformatics, vol. 11, Aug. 18, 2010, 432.
Klintschar, et al., "Genetic variation at the STR loci D12S391 and CSF1PO in four populations from Austria, Italy, Egypt and Yemen", Forensic Science International, vol. 97, Oct. 1, 1998, 37-45.
Koide, et al., "Fragmentation of cell-free fetal DNA in plasma and urine of pregnant women", Prenat Diagn. Jul. 2005;25(7), www.interscience.wiley.com, Mar. 14, 2005, 604-7.
Kozarewa, et al., "Amplification-free Illumina sequencing-library preparation facilitates improved mapping and assembly of GC-biased genomes", Nat. Methods, 6(4), Apr. 2009, 291-295.
Lazinski, et al., "Modified Protocol for Illumina Paired-End Library Construction", http://genomics.med.tufts.edu/documents/htseq_protocol_for_illumina_paired.pdf, Feb. 27, 2009, 10.
Leon, et al., "Free DNA in the Serum of Cancer Patients and the Effect of Therapy", Cancer Research 37, Mar. 1977, 646-650.
Levy, et al., "The Diploid Genome Sequence of an Individual Human", PLoS Biology, vol. 5, Issue 10, Oct. 2007, 2113-2144.
Li, et al., "Size Separation of Circulatory DNA in Maternal Plasma Permits Ready Detection of Fetal DNA Polymorphisms", Clin. Chem., vol. 50, No. 6, 2004, 1002-1011.
Liao, et al., "Targeted Massively parallel sequencing of maternal plasma DNA permits efficient and unbiased detection of fetal alleles", Clinical Chemistry 57:1, 2011, 92-101.
Liu, et al., "Feasibility study of using fetal DNA in maternal plasma for non-invasive prenatal diagnosis", Acta Obstet Gynecol Scand. 86(5), 2007, 535-41.
Lo, et al., "Digital PCR for the molecular detection of fetal chromosomal aneuploidy", Proc Natl Acad Sci USA. 104(32), Aug. 7, 2007, 13116-13121.
Lo, et al., "Increased fetal DNA concentrations in the plasma of pregnant women carrying fetuses with trisomy 21", Clinical Chemistry 45:10, 1999, 1747-51.
Lo, et al., "Maternal Plasma DNA Sequencing Reveals the Genome-Wide Genetic and Mutational Profile of the Fetus", Sci Transl Med. 2(61):, Dec. 8, 2010, 61ra91.
Lo, et al., "Noninvasive prenatal detection of fetal chromosomal aneuploidies by maternal plasma nucleic acid analysis: a review of the current state of the art", BJOG, vol. 116, 2009, 152-157.
Lo, et al., "Noninvasive prenatal diagnosis of fetal chromosomal aneuploidies by maternal plasma nucleic acid analysis", Clin Chem. 54(3), Jan. 2008, 461-466.
Lo, et al., "Prenatal diagnosis of fetal RhD Status by molecular analysis of maternal plasma", The New England Journal of Medicine, vol. 339, Dec. 10, 1998, 1734-1738.
Lo, et al., "Presence of fetal DNA in maternal plasma and serum", Lancet. 350(9076), Aug. 16, 1997, 485-487.
Lo, et al., "Quantitative analysis of fetal DNA in maternal plasma and serum: implications for noninvasive prenatal diagnosis", Am J Hum Genet 62(4), Apr. 1998, 768-775.
Lo, et al., "Rapid Clearance of fetal DNA from Maternal Plasma", Am J Hum Genet. 64(1), 1999, 218-24.
Lun, et al., "Microfluidics digital PCR Reveals a Higher than expected fraction of fetal DNA in maternal plasma", Clinical Chemistry, vol. 54, No. 10, Oct. 1, 2008, 1664-1672.
Lun, et al., "Noninvasive prenatal diagnosis of monogenic diseases by digital size selection and relative mutation dosage on DNA in maternal plasma", Proceedings of National Academy of Sciences 105(50), 2008, pp. 19920-19925.
Mckernan, et al., "Sequence and structural variation in a human genome uncovered by short-read, massively parallel ligation sequencing using two-base encoding", Genome Res. 19(9), Sep. 2009, 1527-41.
Metzker, M.L. , "Applications of Next-Generation Sequencing: Sequencing technologies—the next generation", Nature Reviews Genetics, Nature Publishing Group, GB, vol. 11(1), Jan. 1, 2010, pp. 31-46.
Meyerson, et al., "Advances in understanding cancer genomes through second-generation sequencing", Nature Reviews Genetics, vol. 11, 2010, 685-696.
Mullighan, et al., "Genome-wide profiling of genetic alterations in acute lymphoblastic leukemia: recent insights and future directions.", Leukemia vol. 23, Feb. 26, 2009, 1209-1218.
Nakamoto, , "Detection of Microsatellite alterations in Plasma DNA of Malignant Mucosal Melanoma Using Whole Genome Amplification", Bull Tokyo Dent Coll. May 2008; 49(2), May 2008, 77-87.
Nicklas, , "A real-time multiplex SNP melting assay to discriminate individuals", J. Forensic Sci. 53(6):, Nov. 2008, 1316-24.
Norton, et al., "Non-invasive chromosomal evaluation (NICE) study: results of multicenter, prospective, cohort study for detection of fetal trisomy 21 and trisomy 18", American Journal of Obstetrics and Gynecology, doi: 10.1016/j.ajog.2012.05.021., May 21, 2012, 30 pages.
Oliphant et al., U.S. Appl. No. 61/371,605, filed on Aug. 6, 2010.
Pakstis, et al., "Candidate SNPs for a universal individual identification panel", Hum Genet. 121(3-4), May 2007, 305-17.
Pakstis, et al., "SNPs for a universal individual identification panel", Hum Genet. 127(3), Mar. 2010, 315-24.
Pandey, et al., "Chapter 3 Applied Biosystems Solid Systems: Ligation-Based Sequencing", Next Generation Genome Sequencing: Towards Personalized Medicine 2008. Edited by Michael Janitz., 2008.
Pathak, et al., "Circulating Cell-Free DNA in Plasma/Serum of Lung Cancer Patients as a Potential Screening and Prognostic Tool", Clin Chem. 52(10):, Oct. 2006, 1833-42.
Pertl, et al., "Detection of male and female fetal DNA in maternal plasma by multiplex fluorescent polymerase chain reaction amplification of short tandem repeats", Hum Genet. 106(1), Jan. 2000, 45-9.
Peters, D. et al., "Noninvasive Prenatal Diagnosis of a Fetal Microdeletion Syndrome", New England Journal of Medicine 365;19, Correspondence, Nov. 10, 2011, 1847-1848.
Pheiffer, et al., "Polymer-stimulated ligation: enhanced blunt- or cohesive-end ligation of DNA or deoxyribooligonucleotides by T4 DNA ligase in polymer solutions", Nucleic Acids Res. 11(22), Nov. 25, 1983, 7853-71.
Pui, et al., "Acute lymphoblastic leukaemia", Lancet vol. 371, 2008, 1030-1043.
Pushkarev, et al., "Single-molecule sequencing of an individual human genome", Nat Biotechnol. 27(9):, Sep. 2009, 847-50.
Quail, et al., "A large genome center's improvements to the Illumina sequencing system", Nature Methods, 5, 2008, 1005-1010.
Quake et al., "U.S. Appl. No. 13/400,028", filed Feb. 17, 2012.
Rava, et al., "U.S. Appl. No. 12/958,352", filed Dec. 1, 2010.
Rava, et al., "U.S. Appl. No. 12/958,353", filed Dec. 1, 2010.
Rava et al., "U.S. Appl. No. 12/958,347", filed Dec. 1, 2010.
Rava, "U.S. Appl. No. 13/087,842", filed Apr. 15, 2011.
Rava, et al., "U.S. Appl. No. 13/009,718", filed Jan. 19, 2010.
Rava et al., "U.S. Appl. No. 13/191,136", filed Jul. 26, 2011.
Rava et al., "U.S. Appl. No. 13/333,832", filed Dec. 21, 2011.
Rava et al., "U.S. Appl. No. 13/364,809", filed Feb. 2, 2012.
Rava et al., "U.S. Appl. No. 13/365,134", filed Feb. 2, 2012.
Rava et al., "U.S. Appl. No. 13/400,028", filed Feb. 17, 2012.
Rava et al., "U.S. Appl. No. 13/461,582", filed May 1, 2012.
Schwarzenbach, et al., "Cell-free Tumor DNA in Blood Plasma As a Marker for Circulating Tumor Cells in Prostate Cancer", Clin Cancer Res. 15(3):, Feb. 1, 2009, 1032-8.
Schwarzenbach, et al., "Comparative evaluation of cell-free tumor DNA in blood and disseminated tumor cells in bone marrow of patients with primary breast cancer", Breast Cancer Res. 11(5), 2009, R71.
Sehnert, et al., "Optimal Detection of Fetal Chromosomal Abnormalities by Massively Parallel DNA Sequencing of Cell-Free Fetal DNA from Maternal Blood", Clinical Chemistry, Jul. 2011, vol. 57 No. 7, E-pub on Apr. 25, 2011 as doi:10.1373/clinchem.2011.165910., Apr. 25, 2011, 1042-1049.
Shendure, et al., "Next-generation DNA sequencing", Nature Biotechnology 26(10), 2008, 1135-1145.
Sparks, et al., "Non-invasive prenatal detection and selective analysis of cell-free DNA obtained from maternal blood: evaluation for

(56) References Cited

OTHER PUBLICATIONS trisomy 21 and trisomy 18", American Journal of Obstetrics and Gynecology, doi: 10.1016/j.ajog.2012.01.030, Jan. 30, 2012, 33 pages.
SS139539, , NCBI dbSNP rs131828, Jun. 8, 2000.
SS3206919, , NCBI dbSNP rs560681, Sep. 5, 2001.
SS3470339, , NCBI dbSNP rs807841, Sep. 24, 2001.
Stoughton et al., U.S. Appl. No. 13/433,232, filed Mar. 28, 2012.
Su, et al., "Human Urine Contains Small, 150 to 250 Nucleotide-Sized, Soluble DNA Derived from the Circulation and May be useful in the Detection of Colorectal Cancer", J Mol Diagn. 6(2), May 2004, 101-7.
Teixeira, et al., "Multiple numerical chromosome aberrations in cancer: what are their causes and what are their consequences?", Seminars in Cancer Biology, vol. 15, Issue 1, Feb. 2005, 3-12.
Thorstenson, et al., "An Automated Hydrodynamic Process for Controlled, Unbiased DNA Shearing", Genome Research 8, 1998, 848-855.
Tong, et al., "Noninvasive Prenatal Detection of Fetal Trisomy 18 by Epigenetic Allelic Ratio Analysis in Maternal Plasma: Theoretical and Empirical Considerations", Clinical Chemistry 52:12, 2006, 2194-2202.
Tong, et al., "Noninvasive prenatal detection of trisomy 21 by an epigenetic-genetic chromosome-dosage approach", Clin Chem. 56(1), Jan. 2010, 90-8.
Vallone, et al., "Demonstration of rapid multiplex PCR amplification involving 16 genetic loci", Forensic Sci Int Genet. 3(1), Dec. 2008, 42-5.
Voelkerding, et al., "Digital Fetal Aneuploidy Diagnosis by Next-Generation Sequencing", Clin Chem. 56(3), Mar. 2010, 336-8.
Voelkerding, et al., "Next-Generation Sequencing: From Basic Research to Diagnostics", Clinical Chemistry 55:4, 2009, 641-658.
Vogelstein, et al., "Digital PCR", PNAS USA, vol. 96, Aug. 3, 1999, 9236-9241.
Wheeler, et al., "The complete genome of an individual by massively parallel DNA sequencing", Nature. 452(7189), Apr. 17, 2008, 872-6.
Wright, et al., "The use of cell-free fetal nucleic acids in maternal blood for non-invasive prenatal diagnosis", Hum Reprod Update. 15(1), Jan. 1, 2009, 139-151.
Yamazawa, et al., "Monozygotic female twins for Silver-Russell syndrome and hypomethylation of H19-DMR", J. Human Genetics, vol. 53, 2008, 950-955.
Zimmerman, et al., "Macromolecular crowding allows blunt-end ligation by DNA ligases from rat liver or *Escherichia coli*", Proc Natl Acas Sci USA. 80(19), Oct. 1983, 5852-6.

* cited by examiner

SEQUENCE LISTING

```
<160> NUMBER OF SEQ ID NOS: 427

<210> SEQ ID NO 1
<211> LENGTH: 111
<212> TYPE: DNA
<213> ORGANISM: Homo sapiens

<400> SEQUENCE: 1

cacatgcaca gccagcaacc ctgtcagcag gagttcccac cagtttcttt ctgagaacat      60

ctgttcaggt ttctctccat ctctatttac tcaggtcaca ggaccttggg g              111


<210> SEQ ID NO 2
<211> LENGTH: 111
<212> TYPE: DNA
<213> ORGANISM: Homo sapiens

<400> SEQUENCE: 2

cacatgcaca gccagcaacc ctgtcagcag gagttcccac cagtttcttt ctgagaacat      60

ctgttcaggt ttctctccat ctctgtttac tcaggtcaca ggaccttggg g              111


<210> SEQ ID NO 3
<211> LENGTH: 126
<212> TYPE: DNA
<213> ORGANISM: Homo sapiens

<400> SEQUENCE: 3
```

-continued tgaggaagtg aggctcagag ggtaagaaac tttgtcacag agctggtggt gagggtggag 60
attttacact ccctgcctcc cacaccagtt tctccagagt ggaaagactt tcatctcgca 120
ctggca 126

<210> SEQ ID NO 4
<211> LENGTH: 126
<212> TYPE: DNA
<213> ORGANISM: Homo sapiens

<400> SEQUENCE: 4
tgaggaagtg aggctcagag ggtaagaaac tttgtcacag agctggtggt gagggtggag 60
attttacact ccctgcctcc cacaccagtt tctccggagt ggaaagactt tcatctcgca 120
ctggca 126

<210> SEQ ID NO 5
<211> LENGTH: 121
<212> TYPE: DNA
<213> ORGANISM: Homo sapiens

<400> SEQUENCE: 5
gtgccttcag aacctttgag atctgattct atttttaaag cttcttagaa gagagattgc 60
aaagtgggtt gtttctctag ccagacaggg caggcaaata ggggtggctg gtgggatggg 120
a 121

<210> SEQ ID NO 6
<211> LENGTH: 121
<212> TYPE: DNA
<213> ORGANISM: Homo sapiens

<400> SEQUENCE: 6
gtgccttcag aacctttgag atctgattct atttttaaag cttcttagaa gagagattgc 60
aaagtgggtt gtttctctag ccagacaggg caggtaaata ggggtggctg gtgggatggg 120
a 121

<210> SEQ ID NO 7
<211> LENGTH: 111
<212> TYPE: DNA
<213> ORGANISM: Homo sapiens

<400> SEQUENCE: 7
aggtgtgtct ctcttttgtg aggggagggg tcccttctgg cctagtagag ggcctggcct 60
gcagtgagca ttcaaatcct caaggaacag ggtggggagg tgggacaaag g 111

<210> SEQ ID NO 8
<211> LENGTH: 111
<212> TYPE: DNA
<213> ORGANISM: Homo sapiens

<400> SEQUENCE: 8
aggtgtgtct ctcttttgtg aggggagggg tcccttctgg cctagtagag ggcctggcct 60
gcagtgagca ttcaaatcct cgaggaacag ggtggggagg tgggacaaag g 111

<210> SEQ ID NO 9
<211> LENGTH: 139
<212> TYPE: DNA
<213> ORGANISM: Homo sapiens

<400> SEQUENCE: 9

```
cctcgcctac tgtgctgttt ctaaccatca tgcttttccc tgaatctctt gagtcttttt     60

ctgctgtgga ctgaaacttg atcctgagat tcacctctag tccctctgag cagcctcctg    120

gaatactcag ctgggatgg                                                  139


<210> SEQ ID NO 10
<211> LENGTH: 139
<212> TYPE: DNA
<213> ORGANISM: Homo sapiens

<400> SEQUENCE: 10

cctcgcctac tgtgctgttt ctaaccatca tgcttttccc tgaatctctt gagtcttttt     60

ctgctgtgga ctgaaacttg atcctgagat tcacctctag tccctctggg cagcctcctg    120

gaatactcag ctgggatgg                                                  139


<210> SEQ ID NO 11
<211> LENGTH: 117
<212> TYPE: DNA
<213> ORGANISM: Homo sapiens

<400> SEQUENCE: 11

aattgcaatg gtgagaggtt gatggtaaaa tcaaacggaa cttgttattt tgtcattctg     60

atggactgga actgaggatt ttcaatttcc tctccaaccc aagacacttc tcactgg       117


<210> SEQ ID NO 12
<211> LENGTH: 117
<212> TYPE: DNA
<213> ORGANISM: Homo sapiens

<400> SEQUENCE: 12

aattgcaatg gtgagaggtt gatggtaaaa tcaaacggaa cttgttattt tgtcattctg     60

atggactgga actgaggatt ttcaatttcc tttccaaccc aagacacttc tcactgg       117


<210> SEQ ID NO 13
<211> LENGTH: 114
<212> TYPE: DNA
<213> ORGANISM: Homo sapiens

<400> SEQUENCE: 13

gaaatgcctt ctcaggtaat ggaaggttat ccaaatattt ttcgtaagta tttcaaatag     60

caatggctcg tctatggtta gtctcacagc cacattctca gaactgctca aacc          114


<210> SEQ ID NO 14
<211> LENGTH: 114
<212> TYPE: DNA
<213> ORGANISM: Homo sapiens

<400> SEQUENCE: 14

gaaatgcctt ctcaggtaat ggaaggttat ccaaatattt ttcgtaagta tttcaaatag     60

caatggctcg tctatggtta gtctcgcagc cacattctca gaactgctca aacc          114


<210> SEQ ID NO 15
<211> LENGTH: 128
<212> TYPE: DNA
<213> ORGANISM: Homo sapiens

<400> SEQUENCE: 15

acccaaaaca ctggaggggc ctcttctcat tttcggtaga ctgcaagtgt tagccgtcgg     60
```

gaccagcttc tgtctggaag ttcgtcaaat tgcagttaag tccaagtatg ccacatagca 120
gataaggg 128

<210> SEQ ID NO 16
<211> LENGTH: 128
<212> TYPE: DNA
<213> ORGANISM: Homo sapiens

<400> SEQUENCE: 16
acccaaaaca ctggaggggc ctcttctcat tttcggtaga ctgcaagtgt tagccgtcgg 60
gaccagcttc tgtctggaag ttcgtcaaat tgcagttagg tccaagtatg ccacatagca 120
gataaggg 128

<210> SEQ ID NO 17
<211> LENGTH: 110
<212> TYPE: DNA
<213> ORGANISM: Homo sapiens

<400> SEQUENCE: 17
gcaccagaat ttaaacaacg ctgacaataa atatgcagtc gatgatgact tcccagagct 60
ccagaagcaa ctccagcaca cagagaggcg ctgatgtgcc tgtcaggtgc 110

<210> SEQ ID NO 18
<211> LENGTH: 110
<212> TYPE: DNA
<213> ORGANISM: Homo sapiens

<400> SEQUENCE: 18
gcaccagaat ttaaacaacg ctgacaataa atatgcagtc gatgatgact tcccagagct 60
ccagaagcaa ctccagcaca cggagaggcg ctgatgtgcc tgtcaggtgc 110

<210> SEQ ID NO 19
<211> LENGTH: 116
<212> TYPE: DNA
<213> ORGANISM: Homo sapiens

<400> SEQUENCE: 19
tgactgtata ccccaggtgc acccttgggt catctctatc atagaactta tctcacagag 60
tataagagct gatttctgtg tctgcctctc acactagact tccacatcct tagtgc 116

<210> SEQ ID NO 20
<211> LENGTH: 116
<212> TYPE: DNA
<213> ORGANISM: Homo sapiens

<400> SEQUENCE: 20
tgactgtata ccccaggtgc acccttgggt catctctatc atagaactta tctcacagag 60
tataagagct gatttctgtg tctgcctgtc acactagact tccacatcct tagtgc 116

<210> SEQ ID NO 21
<211> LENGTH: 110
<212> TYPE: DNA
<213> ORGANISM: Homo sapiens

<400> SEQUENCE: 21
tgtacgtggt caccagggga cgcctggcgc tgcgagggag gccccgagcc tcgtgccccc 60
gtgaagcttc agctcccctc cccggctgtc cttgaggctc ttctcacact 110

-continued

<210> SEQ ID NO 22
<211> LENGTH: 110
<212> TYPE: DNA
<213> ORGANISM: Homo sapiens

<400> SEQUENCE: 22
tgtacgtggt caccagggga cgcctggcgc tgcgagggag gccccgagcc tcgtgccccc 60
gtgaagcttc agctcccctc cctggctgtc cttgaggctc ttctcacact 110

<210> SEQ ID NO 23
<211> LENGTH: 114
<212> TYPE: DNA
<213> ORGANISM: Homo sapiens

<400> SEQUENCE: 23
cagtggaccc tgctgcacct ttcctcccct cccatcaacc tcttttgtgc ctccccctcc 60
gtgtaccacc ttctctgtca ccaaccctgg cctcacaact ctctcctttg ccac 114

<210> SEQ ID NO 24
<211> LENGTH: 114
<212> TYPE: DNA
<213> ORGANISM: Homo sapiens

<400> SEQUENCE: 24
cagtggaccc tgctgcacct ttcctcccct cccatcaacc tcttttgtgc ctccccctcc 60
gtgtaccacc ttctctgtca ccacccctgg cctcacaact ctctcctttg ccac 114

<210> SEQ ID NO 25
<211> LENGTH: 110
<212> TYPE: DNA
<213> ORGANISM: Homo sapiens

<400> SEQUENCE: 25
cagtggcata gtagtccagg ggctcctcct cagcacctcc agcaccttcc aggaggcagc 60
agcgcaggca gagaacccgc tggaagaatc ggcggaagtt gtcggagagg 110

<210> SEQ ID NO 26
<211> LENGTH: 110
<212> TYPE: DNA
<213> ORGANISM: Homo sapiens

<400> SEQUENCE: 26
cagtggcata gtagtccagg ggctcctcct cagcacctcc agcaccttcc aggaggcagc 60
agcgcaggca gagaacccgc tggaaggatc ggcggaagtt gtcggagagg 110

<210> SEQ ID NO 27
<211> LENGTH: 129
<212> TYPE: DNA
<213> ORGANISM: Homo sapiens

<400> SEQUENCE: 27
aggtctgggg gccgctgaat gccaagctgg gaatcttaaa tgttaaggaa caaggtcata 60
caatgaatgg tgtgatgtaa aagcttggga ggtgatttct gagggtaggt gctgggttta 120
atgggagga 129

<210> SEQ ID NO 28
<211> LENGTH: 129
<212> TYPE: DNA
<213> ORGANISM: Homo sapiens

<400> SEQUENCE: 28
aggtctgggg gccgctgaat gccaagctgg gaatcttaaa tgttaaggaa caaggtcata 60
caatgaatgg tgtgatgtaa aagcttggga ggtgattttt gagggtaggt gctgggttta 120
atgggagga 129

<210> SEQ ID NO 29
<211> LENGTH: 107
<212> TYPE: DNA
<213> ORGANISM: Homo sapiens

<400> SEQUENCE: 29
acggttctgt cctgtagggg agaaaagtcc tcgttgttcc tctgggatgc aacatgagag 60
agcagcacac tgaggcttta tggattgccc tgccacaagt gaacagg 107

<210> SEQ ID NO 30
<211> LENGTH: 107
<212> TYPE: DNA
<213> ORGANISM: Homo sapiens

<400> SEQUENCE: 30
acggttctgt cctgtagggg agaaaagtcc tcgttgttcc tctgggatgc aacatgagag 60
agcagcacac tgaggcttta tgggttgccc tgccacaagt gaacagg 107

<210> SEQ ID NO 31
<211> LENGTH: 127
<212> TYPE: DNA
<213> ORGANISM: Homo sapiens

<400> SEQUENCE: 31
gcgcagtcag atgggcgtgc tggcgtctgt cttctctctc tcctgctctc tggcttcatt 60
tttctctcct tctgtctcac cttctttcgt gtgcctgtgc acacacacgt ttgggacaag 120
ggctgga 127

<210> SEQ ID NO 32
<211> LENGTH: 127
<212> TYPE: DNA
<213> ORGANISM: Homo sapiens

<400> SEQUENCE: 32
gcgcagtcag atgggcgtgc tggcgtctgt cttctctctc tcctgctctc tggcttcatt 60
tttctctcct tctgtctcac cttctttcgt gtgcctgtgc atacacacgt ttgggacaag 120
ggctgga 127

<210> SEQ ID NO 33
<211> LENGTH: 130
<212> TYPE: DNA
<213> ORGANISM: Homo sapiens

<400> SEQUENCE: 33
gccggacctg cgaaatccca aaatgccaaa cattcccgcc tcacatgatc ccagagagag 60
gggacccagt gttcccagct tgcagctgag gagcccgagg ttgccgtcag atcagagccc 120
cagttgcccg 130

<210> SEQ ID NO 34
<211> LENGTH: 130
<212> TYPE: DNA
<213> ORGANISM: Homo sapiens

<400> SEQUENCE: 34
gccggacctg cgaaatccca aaatgccaaa cattcccgcc tcacatgatc ccagagagag 60
gggacccagt gttcccagct tgcagctgag gagcccgagt ttgccgtcag atcagagccc 120
cagttgcccg 130

<210> SEQ ID NO 35
<211> LENGTH: 121
<212> TYPE: DNA
<213> ORGANISM: Homo sapiens

<400> SEQUENCE: 35
agcagcctcc ctcgactagc tcacactacg ataaggaaaa ttcatgagct ggtgtccaag 60
gagggctggg tgactcgtgg ctcagtcagc atcaagattc ctttcgtctt tcccctctgc 120
c 121

<210> SEQ ID NO 36
<211> LENGTH: 121
<212> TYPE: DNA
<213> ORGANISM: Homo sapiens

<400> SEQUENCE: 36
agcagcctcc ctcgactagc tcacactacg ataaggaaaa ttcatgagct ggtgtccaag 60
gagggctggg tgactcgtgg ctcagtcagc gtcaagattc ctttcgtctt tcccctctgc 120
c 121

<210> SEQ ID NO 37
<211> LENGTH: 138
<212> TYPE: DNA
<213> ORGANISM: Homo sapiens

<400> SEQUENCE: 37
tggcattgcc tgtaatatac atagccatgg ttttttatag gcaatttaag atgaatagct 60
tctaaactat agataagttt cattacccca ggaagctgaa ctatagctac tttacccaaa 120
atcattagaa tggtgctt 138

<210> SEQ ID NO 38
<211> LENGTH: 138
<212> TYPE: DNA
<213> ORGANISM: Homo sapiens

<400> SEQUENCE: 38
tggcattgcc tgtaatatac atagccatgg ttttttatag gcaatttaag atgaatagct 60
tctaaactat agataagttt cattacccca ggaagctgaa ctatagctac tttccccaaa 120
atcattagaa tggtgctt 138

<210> SEQ ID NO 39
<211> LENGTH: 136
<212> TYPE: DNA
<213> ORGANISM: Homo sapiens

<400> SEQUENCE: 39
atgaagcctt ccaccaactg cctgtatgac tcatctgggg acttctgctc tatactcaaa 60
gtggcttagt cactgccaat gtatttccat atgagggacg atgattacta aggaaatata 120
gaaacaacaa ctgatc 136

<210> SEQ ID NO 40
<211> LENGTH: 136
<212> TYPE: DNA
<213> ORGANISM: Homo sapiens

<400> SEQUENCE: 40
atgaagcctt ccaccaactg cctgtatgac tcatctgggg acttctgctc tatactcaaa 60
gtggcttagt cactgccaat gtatttccat atgagggacg gtgattacta aggaaatata 120
gaaacaacaa ctgatc 136

<210> SEQ ID NO 41
<211> LENGTH: 118
<212> TYPE: DNA
<213> ORGANISM: Homo sapiens

<400> SEQUENCE: 41
acaacagaat caggtgattg gagaaaagat cacaggccta ggcacccaag gcttgaagga 60
tgaaagaatg aaagatggac ggaacaaaat taggacctta attctttgtt cagttcag 118

<210> SEQ ID NO 42
<211> LENGTH: 118
<212> TYPE: DNA
<213> ORGANISM: Homo sapiens

<400> SEQUENCE: 42
acaacagaat caggtgattg gagaaaagat cacaggccta ggcacccaag gcttgaagga 60
tgaaagaatg aaagatggac ggaagaaaat taggacctta attctttgtt cagttcag 118

<210> SEQ ID NO 43
<211> LENGTH: 150
<212> TYPE: DNA
<213> ORGANISM: Homo sapiens

<400> SEQUENCE: 43
ttggggtaaa ttttcattgt catatgtgga atttaaatat accatcatct acaaagaatt 60
ccacagagtt aaatatctta agttaaacac ttaaaataag tgtttgcgtg atattttgat 120
gacagataaa cagagtctaa ttcccacccc 150

<210> SEQ ID NO 44
<211> LENGTH: 150
<212> TYPE: DNA
<213> ORGANISM: Homo sapiens

<400> SEQUENCE: 44
ttggggtaaa ttttcattgt catatgtgga atttaaatat accatcatct acaaagaatt 60
ccacagagtt aaatatctta agttaaacac ttaaaataag tgtttgcgtg atattttgat 120
gatagataaa cagagtctaa ttcccacccc 150

<210> SEQ ID NO 45
<211> LENGTH: 145
<212> TYPE: DNA
<213> ORGANISM: Homo sapiens

<400> SEQUENCE: 45
tgcaattcaa atcaggaagt atgaccaaaa gacagagatc ttttttggat gatccctagc 60
ctagcaatgc ctggcagcca tgcaggtgca atgtcaacct taaataatgt attgcaaact 120
cagagctgac aaacctcgat gttgc 145

<210> SEQ ID NO 46
<211> LENGTH: 145
<212> TYPE: DNA
<213> ORGANISM: Homo sapiens

<400> SEQUENCE: 46
tgcaattcaa atcaggaagt atgaccaaaa gacagagatc ttttttggat gatccctagc 60
ctagcaatgc ctggcagcca tgcaggtgca atgtcaacct taaataatgt attgcaaatt 120
cagagctgac aaacctcgat gttgc 145

<210> SEQ ID NO 47
<211> LENGTH: 124
<212> TYPE: DNA
<213> ORGANISM: Homo sapiens

<400> SEQUENCE: 47
ctgtgctctg cgaatagctg cagaagtaac ttggggaccc aaaataaagc agaatgctaa 60
tgtcaagtcc tgagaaccaa gccctgggac tctggtgcca tttcggattc tccatgagca 120
tggt 124

<210> SEQ ID NO 48
<211> LENGTH: 124
<212> TYPE: DNA
<213> ORGANISM: Homo sapiens

<400> SEQUENCE: 48
ctgtgctctg cgaatagctg cagaagtaac ttggggaccc aaaataaagc agaatgctaa 60
tgtcaagtcc tgagaaccaa gccctgggac tctggtgcca ttttggattc tccatgagca 120
tggt 124

<210> SEQ ID NO 49
<211> LENGTH: 118
<212> TYPE: DNA
<213> ORGANISM: Homo sapiens

<400> SEQUENCE: 49
tttttccagc caactcaagg ccaaaaaaaa tttcttaata tagttattat gcgaggggag 60
gggaagcaaa ggagcacagg tagtccacag aataagacac aagaaacctc aagctgtg 118

<210> SEQ ID NO 50
<211> LENGTH: 118
<212> TYPE: DNA
<213> ORGANISM: Homo sapiens

<400> SEQUENCE: 50
tttttccagc caactcaagg ccaaaaaaaa tttcttaata tagttattat gcgaggggag 60
gggaagcaaa ggagcacagg tagtccacag aataggacac aagaaacctc aagctgtg 118

<210> SEQ ID NO 51
<211> LENGTH: 110
<212> TYPE: DNA
<213> ORGANISM: Homo sapiens

<400> SEQUENCE: 51
tcttctcgtc ccctaagcaa acaacatccg cttgcttctg tctgtgtaac cacagtgaat 60
gggtgtgcac gcttgatggg cctctgagcc cctgttgcac aaaccagaaa 110

<210> SEQ ID NO 52
<211> LENGTH: 110
<212> TYPE: DNA
<213> ORGANISM: Homo sapiens

<400> SEQUENCE: 52
tcttctcgtc ccctaagcaa acaacatccg cttgcttctg tctgtgtaac cacagtgaat 60
gggtgtgcac gcttggtggg cctctgagcc cctgttgcac aaaccagaaa 110

<210> SEQ ID NO 53
<211> LENGTH: 110
<212> TYPE: DNA
<213> ORGANISM: Homo sapiens

<400> SEQUENCE: 53
cacatggggg cattaagaat cgcccaggga ggaggaggga gaacgcgtgc ttttcacatt 60
tgcatttgaa ttttcgagtt cccaggatgt gtttttgtgc tcatcgatgt 110

<210> SEQ ID NO 54
<211> LENGTH: 110
<212> TYPE: DNA
<213> ORGANISM: Homo sapiens

<400> SEQUENCE: 54
cacatggggg cattaagaat cgcccaggga ggaggaggga gaacgcgtgc ttttcacatt 60
tgcatttgaa tttttgagtt cccaggatgt gtttttgtgc tcatcgatgt 110

<210> SEQ ID NO 55
<211> LENGTH: 128
<212> TYPE: DNA
<213> ORGANISM: Homo sapiens

<400> SEQUENCE: 55
gggctctgag gtgtgtgaaa taaaaacaaa tgtccatgtc tgtcctttta tggcattttg 60
ggactttaca tttcaaacat ttcagacatg tatcacaaca cgaaggaata acagttccag 120
ggatatct 128

<210> SEQ ID NO 56
<211> LENGTH: 128
<212> TYPE: DNA
<213> ORGANISM: Homo sapiens

<400> SEQUENCE: 56
gggctctgag gtgtgtgaaa taaaaacaaa tgtccatgtc tgtcctttta tggcattttg 60
ggactttaca tttcaaacat ttcagacatg tatcacaaca cgagggaata acagttccag 120
ggatatct 128

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 57
cacatgcaca gccagcaacc c 21

<210> SEQ ID NO 58

<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 58
ccccaaggtc ctgtgacctg agt 23

<210> SEQ ID NO 59
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 59
tgaggaagtg aggctcagag ggt 23

<210> SEQ ID NO 60
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 60
tgccagtgcg agatgaaagt cttt 24

<210> SEQ ID NO 61
<211> LENGTH: 27
<212> TYPE: DNA
<213> ORGANISM: Artificial Sequence
<220> FEATURE:
<223> OTHER INFORMATION: Description of Artificial Sequence: Synthetic
primer

<400> SEQUENCE: 61
gtgccttcag aacctttgag atctgat 27

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 62
tcccatccca ccagccaccc 20

<210> SEQ ID NO 63
<211> LENGTH: 25
<212> TYPE: DNA
<213> ORGANISM: Artificial Sequence
<220> FEATURE:
<223> OTHER INFORMATION: Description of Artificial Sequence: Synthetic
primer

<400> SEQUENCE: 63
aggtgtgtct ctcttttgtg agggg 25

<210> SEQ ID NO 64
<211> LENGTH: 21

<212> TYPE: DNA
<213> ORGANISM: Artificial Sequence
<220> FEATURE:
<223> OTHER INFORMATION: Description of Artificial Sequence: Synthetic
primer

<400> SEQUENCE: 64
cctttgtccc acctccccac c 21

<210> SEQ ID NO 65
<211> LENGTH: 26
<212> TYPE: DNA
<213> ORGANISM: Artificial Sequence
<220> FEATURE:
<223> OTHER INFORMATION: Description of Artificial Sequence: Synthetic
primer

<400> SEQUENCE: 65
cctcgcctac tgtgctgttt ctaacc 26

<210> SEQ ID NO 66
<211> LENGTH: 25
<212> TYPE: DNA
<213> ORGANISM: Artificial Sequence
<220> FEATURE:
<223> OTHER INFORMATION: Description of Artificial Sequence: Synthetic
primer

<400> SEQUENCE: 66
ccatcccagc tgagtattcc aggag 25

<210> SEQ ID NO 67
<211> LENGTH: 26
<212> TYPE: DNA
<213> ORGANISM: Artificial Sequence
<220> FEATURE:
<223> OTHER INFORMATION: Description of Artificial Sequence: Synthetic
primer

<400> SEQUENCE: 67
aattgcaatg gtgagaggtt gatggt 26

<210> SEQ ID NO 68
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 68
ccagtgagaa gtgtcttggg ttgg 24

<210> SEQ ID NO 69
<211> LENGTH: 27
<212> TYPE: DNA
<213> ORGANISM: Artificial Sequence
<220> FEATURE:
<223> OTHER INFORMATION: Description of Artificial Sequence: Synthetic
primer

<400> SEQUENCE: 69
gaaatgcctt ctcaggtaat ggaaggt 27

<210> SEQ ID NO 70
<211> LENGTH: 27
<212> TYPE: DNA

<213> ORGANISM: Artificial Sequence
<220> FEATURE:
<223> OTHER INFORMATION: Description of Artificial Sequence: Synthetic
primer

<400> SEQUENCE: 70
ggtttgagca gttctgagaa tgtggct 27

<210> SEQ ID NO 71
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 71
acccaaaaca ctggaggggc ct 22

<210> SEQ ID NO 72
<211> LENGTH: 27
<212> TYPE: DNA
<213> ORGANISM: Artificial Sequence
<220> FEATURE:
<223> OTHER INFORMATION: Description of Artificial Sequence: Synthetic
primer

<400> SEQUENCE: 72
cccttatctg ctatgtggca tacttgg 27

<210> SEQ ID NO 73
<211> LENGTH: 27
<212> TYPE: DNA
<213> ORGANISM: Artificial Sequence
<220> FEATURE:
<223> OTHER INFORMATION: Description of Artificial Sequence: Synthetic
primer

<400> SEQUENCE: 73
gcaccagaat ttaaacaacg ctgacaa 27

<210> SEQ ID NO 74
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 74
gcacctgaca ggcacatcag cg 22

<210> SEQ ID NO 75
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 75
tgactgtata ccccaggtgc accc 24

<210> SEQ ID NO 76
<211> LENGTH: 27
<212> TYPE: DNA
<213> ORGANISM: Artificial Sequence
<220> FEATURE:
<223> OTHER INFORMATION: Description of Artificial Sequence: Synthetic
primer

<400> SEQUENCE: 76
gcactaagga tgtggaagtc tagtgtg 27

<210> SEQ ID NO 77
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 77
tgtacgtggt caccagggga cg 22

<210> SEQ ID NO 78
<211> LENGTH: 26
<212> TYPE: DNA
<213> ORGANISM: Artificial Sequence
<220> FEATURE:
<223> OTHER INFORMATION: Description of Artificial Sequence: Synthetic
primer

<400> SEQUENCE: 78
agtgtgagaa gagcctcaag gacagc 26

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 79
cagtggaccc tgctgcacct t 21

<210> SEQ ID NO 80
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 80
gtggcaaagg agagagttgt gagg 24

<210> SEQ ID NO 81
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 81
cagtggcata gtagtccagg ggct 24

<210> SEQ ID NO 82
<211> LENGTH: 21
<212> TYPE: DNA
<213> ORGANISM: Artificial Sequence
<220> FEATURE:

-continued

<223> OTHER INFORMATION: Description of Artificial Sequence: Synthetic
primer

<400> SEQUENCE: 82
cctctccgac aacttccgcc g 21

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 83
aggtctgggg gccgctgaat 20

<210> SEQ ID NO 84
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 84
tcctcccatt aaacccagca cct 23

<210> SEQ ID NO 85
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 85
acggttctgt cctgtagggg aga 23

<210> SEQ ID NO 86
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 86
cctgttcact tgtggcaggg ca 22

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 87
gcgcagtcag atgggcgtgc 20

<210> SEQ ID NO 88
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 88
tccagccctt gtcccaaacg tgt 23

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 89
gccggacctg cgaaatccca a 21

<210> SEQ ID NO 90
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 90
cgggcaactg gggctctgat c 21

<210> SEQ ID NO 91
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 91
agcagcctcc ctcgactagc t 21

<210> SEQ ID NO 92
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 92
ggcagagggg aaagacgaaa gga 23

<210> SEQ ID NO 93
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 93
tggcattgcc tgtaatatac atag 24

<210> SEQ ID NO 94
<211> LENGTH: 23
<212> TYPE: DNA
<213> ORGANISM: Artificial Sequence
<220> FEATURE:
<223> OTHER INFORMATION: Description of Artificial Sequence: Synthetic
primer -continued

<400> SEQUENCE: 94
aagcaccatt ctaatgattt tgg 23

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 95
atgaagcctt ccaccaactg 20

<210> SEQ ID NO 96
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 96
gatcagttgt tgtttctata tttcctt 27

<210> SEQ ID NO 97
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 97
acaacagaat caggtgattg ga 22

<210> SEQ ID NO 98
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 98
ctgaactgaa caaagaatta aggtc 25

<210> SEQ ID NO 99
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 99
ttggggtaaa ttttcattgt ca 22

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 100
ggggtgggaa ttagactctg 20

<210> SEQ ID NO 101
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 101
tgcaattcaa atcaggaagt atg 23

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 102
gcaacatcga ggtttgtcag 20

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 103
ctgtgctctg cgaatagctg 20

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 104
accatgctca tggagaatcc 20

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 105
tttttccagc caactcaagg 20

<210> SEQ ID NO 106
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 106
cacagcttga ggtttcttgt g 21

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 107
tcttctcgtc ccctaagcaa 20

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 108
tttctggttt gtgcaacagg 20

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 109
cacatggggg cattaagaat 20

<210> SEQ ID NO 110
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 110
acatcgatga gcacaaaaac ac 22

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 111
gggctctgag gtgtgtgaaa 20

<210> SEQ ID NO 112
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 112
agatatccct ggaactgtta ttcc 24

<210> SEQ ID NO 113
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 113
acagtaactg ccttcataga tag 23

<210> SEQ ID NO 114
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 114
gtgtcagacc ctgttctaag ta 22

<210> SEQ ID NO 115
<211> LENGTH: 26
<212> TYPE: DNA
<213> ORGANISM: Artificial Sequence
<220> FEATURE:
<223> OTHER INFORMATION: Description of Artificial Sequence: Synthetic
primer

<400> SEQUENCE: 115
aaataaaatt aggcatattt acaagc 26

<210> SEQ ID NO 116
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 116
gctgagtgat ttgtctgtaa ttg 23

<210> SEQ ID NO 117
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 117
cctgttcctc ccttatttcc c 21

<210> SEQ ID NO 118
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 118
gggaacacag actccatggt g 21

<210> SEQ ID NO 119
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 119
cttagggaac cctcactgaa tg 22

<210> SEQ ID NO 120
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 120
gtccttgtca gcgtttattt gc 22

<210> SEQ ID NO 121
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 121
aataatcagt atgtgacttg gattga 26

<210> SEQ ID NO 122
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 122
ataggatgga tggatagatg ga 22

<210> SEQ ID NO 123
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 123
cagagcaaga ccctgtctca t 21

<210> SEQ ID NO 124
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 124
tcaacagagg cttgcatgta t 21

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 125
gggtgatttt cctctttggt 20

<210> SEQ ID NO 126
<211> LENGTH: 33
<212> TYPE: DNA
<213> ORGANISM: Artificial Sequence
<220> FEATURE:
<223> OTHER INFORMATION: Description of Artificial Sequence: Synthetic
primer

<400> SEQUENCE: 126
aacatttgta tctttatctg tatccttatt tat 33

<210> SEQ ID NO 127
<211> LENGTH: 27
<212> TYPE: DNA
<213> ORGANISM: Artificial Sequence
<220> FEATURE:
<223> OTHER INFORMATION: Description of Artificial Sequence: Synthetic
primer

<400> SEQUENCE: 127
gaacacttgt catagtttag aacgaac 27

<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 128
tcattgacag aattgcacca 20

<210> SEQ ID NO 129
<211> LENGTH: 27
<212> TYPE: DNA
<213> ORGANISM: Artificial Sequence
<220> FEATURE:
<223> OTHER INFORMATION: Description of Artificial Sequence: Synthetic
primer

<400> SEQUENCE: 129
tttgtatttc atgtgtacat tcgtatc 27

<210> SEQ ID NO 130
<211> LENGTH: 28
<212> TYPE: DNA
<213> ORGANISM: Artificial Sequence
<220> FEATURE:
<223> OTHER INFORMATION: Description of Artificial Sequence: Synthetic
primer

<400> SEQUENCE: 130
acctatcctg tagattattt tcactgtg 28

<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 131
tctgacccat ctaacgccta 20

<210> SEQ ID NO 132
<211> LENGTH: 27
<212> TYPE: DNA
<213> ORGANISM: Artificial Sequence
<220> FEATURE:
<223> OTHER INFORMATION: Description of Artificial Sequence: Synthetic
primer

<400> SEQUENCE: 132
cagacagaaa gatagataga tgattga 27

<210> SEQ ID NO 133
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 133
atacagacag acagacaggt g 21

<210> SEQ ID NO 134
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 134
gcatgtatct atcatccatc tct 23

<210> SEQ ID NO 135
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 135
tgagtgacaa attgagacct t 21

<210> SEQ ID NO 136
<211> LENGTH: 26
<212> TYPE: DNA
<213> ORGANISM: Artificial Sequence
<220> FEATURE:
<223> OTHER INFORMATION: Description of Artificial Sequence: Synthetic
primer

<400> SEQUENCE: 136
gtcttacaat aacagttgct actatt 26

<210> SEQ ID NO 137

-continued

<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 137
attccccaag tgaattgc 18

<210> SEQ ID NO 138
<211> LENGTH: 26
<212> TYPE: DNA
<213> ORGANISM: Artificial Sequence
<220> FEATURE:
<223> OTHER INFORMATION: Description of Artificial Sequence: Synthetic
primer

<400> SEQUENCE: 138
ggtagataga ctggatagat agacga 26

<210> SEQ ID NO 139
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 139
tggaaacaga aatggcttgg 20

<210> SEQ ID NO 140
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 140
gattgcagga gggaaggaag 20

<210> SEQ ID NO 141
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 141
gagcaagaca ccatctcaag aa 22

<210> SEQ ID NO 142
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 142
gaaattttac atttatgttt atgattctct 30

<210> SEQ ID NO 143
<211> LENGTH: 18

<212> TYPE: DNA
<213> ORGANISM: Artificial Sequence
<220> FEATURE:
<223> OTHER INFORMATION: Description of Artificial Sequence: Synthetic primer

<400> SEQUENCE: 143
ggcgactgag caagactc 18

<210> SEQ ID NO 144
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 144
ggttattaat tgagaaaact ccttaca 27

<210> SEQ ID NO 145
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 145
attttccccg atgatagtag tct 23

<210> SEQ ID NO 146
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 146
gcgaatgtat gattggcaat attttt 26

<210> SEQ ID NO 147
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 147
acatgtatcc cagaacttaa agtaaac 27

<210> SEQ ID NO 148
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 148
gcagaaggga aaattgaagc tg 22

<210> SEQ ID NO 149
<211> LENGTH: 22
<212> TYPE: DNA

<213> ORGANISM: Artificial Sequence
<220> FEATURE:
<223> OTHER INFORMATION: Description of Artificial Sequence: Synthetic
primer

<400> SEQUENCE: 149
cagagacacc gaaccaataa ga 22

<210> SEQ ID NO 150
<211> LENGTH: 27
<212> TYPE: DNA
<213> ORGANISM: Artificial Sequence
<220> FEATURE:
<223> OTHER INFORMATION: Description of Artificial Sequence: Synthetic
primer

<400> SEQUENCE: 150
gccacatgaa tcaattccta taataaa 27

<210> SEQ ID NO 151
<211> LENGTH: 25
<212> TYPE: DNA
<213> ORGANISM: Artificial Sequence
<220> FEATURE:
<223> OTHER INFORMATION: Description of Artificial Sequence: Synthetic
primer

<400> SEQUENCE: 151
gcacatgtac cctaaaactt aaaat 25

<210> SEQ ID NO 152
<211> LENGTH: 26
<212> TYPE: DNA
<213> ORGANISM: Artificial Sequence
<220> FEATURE:
<223> OTHER INFORMATION: Description of Artificial Sequence: Synthetic
primer

<400> SEQUENCE: 152
gtcaaccaaa actcaacaag tagtaa 26

<210> SEQ ID NO 153
<211> LENGTH: 25
<212> TYPE: DNA
<213> ORGANISM: Artificial Sequence
<220> FEATURE:
<223> OTHER INFORMATION: Description of Artificial Sequence: Synthetic
primer

<400> SEQUENCE: 153
aagatgaaat tgccatgtaa aaata 25

<210> SEQ ID NO 154
<211> LENGTH: 27
<212> TYPE: DNA
<213> ORGANISM: Artificial Sequence
<220> FEATURE:
<223> OTHER INFORMATION: Description of Artificial Sequence: Synthetic
primer

<400> SEQUENCE: 154
gtgtgtataa caaaattcct atgatgg 27

<210> SEQ ID NO 155
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 155
gcacccaaaa ctgaatgtca ta 22

<210> SEQ ID NO 156
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 156
ggtgagagtg agaccctgtc 20

<210> SEQ ID NO 157
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 157
tgtaataact ctacgactgt ctgtctg 27

<210> SEQ ID NO 158
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 158
gaataggagg tggatggatg g 21

<210> SEQ ID NO 159
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 159
gagcgagacc ctgtctcaag 20

<210> SEQ ID NO 160
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 160
ggaaaagaca taggatagca attt 24

<210> SEQ ID NO 161
<211> LENGTH: 21
<212> TYPE: DNA
<213> ORGANISM: Artificial Sequence
<220> FEATURE:

<223> OTHER INFORMATION: Description of Artificial Sequence: Synthetic
primer

<400> SEQUENCE: 161
tctggattga tctgtctgtc c 21

<210> SEQ ID NO 162
<211> LENGTH: 26
<212> TYPE: DNA
<213> ORGANISM: Artificial Sequence
<220> FEATURE:
<223> OTHER INFORMATION: Description of Artificial Sequence: Synthetic
primer

<400> SEQUENCE: 162
gaattaaata ccatctgagc actgaa 26

<210> SEQ ID NO 163
<211> LENGTH: 27
<212> TYPE: DNA
<213> ORGANISM: Artificial Sequence
<220> FEATURE:
<223> OTHER INFORMATION: Description of Artificial Sequence: Synthetic
primer

<400> SEQUENCE: 163
tgttataatg cattgagttt tattctg 27

<210> SEQ ID NO 164
<211> LENGTH: 28
<212> TYPE: DNA
<213> ORGANISM: Artificial Sequence
<220> FEATURE:
<223> OTHER INFORMATION: Description of Artificial Sequence: Synthetic
primer

<400> SEQUENCE: 164
gcctgtctca aaaataaaga gatagaca 28

<210> SEQ ID NO 165
<211> LENGTH: 25
<212> TYPE: DNA
<213> ORGANISM: Artificial Sequence
<220> FEATURE:
<223> OTHER INFORMATION: Description of Artificial Sequence: Synthetic
primer

<400> SEQUENCE: 165
ttaatgaatt gaacaaatga gtgag 25

<210> SEQ ID NO 166
<211> LENGTH: 25
<212> TYPE: DNA
<213> ORGANISM: Artificial Sequence
<220> FEATURE:
<223> OTHER INFORMATION: Description of Artificial Sequence: Synthetic
primer

<400> SEQUENCE: 166
gcaactctgg ttgtattgtc ttcat 25

<210> SEQ ID NO 167
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 167
caaagcgaga ctctgtctca a 21

<210> SEQ ID NO 168
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 168
gaaaatgcta tcctctttgg tataaat 27

<210> SEQ ID NO 169
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 169
gggtatttca agataactgt agatagg 27

<210> SEQ ID NO 170
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 170
gcttctgaaa gcttctagtt tacc 24

<210> SEQ ID NO 171
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 171
tccacatcct caccaacac 19

<210> SEQ ID NO 172
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 172
gcctaggaag gctactgtca a 21

<210> SEQ ID NO 173
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 173
ccacccgtcc atttaggc 18

<210> SEQ ID NO 174
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 174
gtgaaaaagt agatataatg gttggtg 27

<210> SEQ ID NO 175
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 175
ggttttccaa gagatagacc aatta 25

<210> SEQ ID NO 176
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 176
gtcctctcat aaatccctac tcatatc 27

<210> SEQ ID NO 177
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 177
ctgttggtac ataataggta ggtaggt 27

<210> SEQ ID NO 178
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 178
gtcgtgggcc ccataaatc 19

<210> SEQ ID NO 179
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 179
aaggtacata acagttcaat agaaagc 27

<210> SEQ ID NO 180
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 180
gtgaaatgac tgaaaaatag taacca 26

<210> SEQ ID NO 181
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 181
ctaggagatc atgtgggtat gatt 24

<210> SEQ ID NO 182
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 182
gcagtgaata aatgaacgaa tgga 24

<210> SEQ ID NO 183
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 183
cccaaaatta cttgagccaa t 21

<210> SEQ ID NO 184
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 184
gagacaaaat gaagaaacag acag 24

<210> SEQ ID NO 185
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 185
tctttgctct catgaataga tcagt 25

<210> SEQ ID NO 186
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 186
gtttgtgata atgaacccac tcag 24

<210> SEQ ID NO 187
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 187
tgaacacaga tgttaagtgt gtatatg 27

<210> SEQ ID NO 188
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 188
gtctgaggtg gacagttatg aaa 23

<210> SEQ ID NO 189
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 189
ctgtggctca tctatgaaaa ctt 23

<210> SEQ ID NO 190
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 190
gaagtggctg tggtgttatg at 22

<210> SEQ ID NO 191
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 191
ttctgttggt atagagcagt gttt 24

<210> SEQ ID NO 192
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 192
gtgacaggaa ggacggaatg 20

<210> SEQ ID NO 193
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 193
catgaggttt gcaaatacta tcttaac 27

<210> SEQ ID NO 194
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 194
gttttaattt tctccaaatc tcca 24

<210> SEQ ID NO 195
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 195
tcttagccta gatagatact tgcttcc 27

<210> SEQ ID NO 196
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 196
gtcaaccttt gaggctatag gaa 23

<210> SEQ ID NO 197
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 197
tcctggaaac aaaagtatt 19

<210> SEQ ID NO 198
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 198
aaccttacaa caaagctaga a 21

<210> SEQ ID NO 199
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 199
actaagcctt ggggatccag 20

<210> SEQ ID NO 200
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 200
tgctgtggaa atactaaaag g 21

<210> SEQ ID NO 201
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 201
ctccagaggt aatcctgtga 20

<210> SEQ ID NO 202
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 202
tggtgtgaga tggtatctag g 21

<210> SEQ ID NO 203
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 203
gtataatcca tgaatcttgt tt 22

<210> SEQ ID NO 204
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 204
ttcaaattgt atataagaga gt 22

<210> SEQ ID NO 205
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 205
gcaggaaagt tatttttaat 20

<210> SEQ ID NO 206
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 206
tgcttgagaa agctaacact t 21

<210> SEQ ID NO 207
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 207
cagtgtttgg aaattgtctg 20

<210> SEQ ID NO 208
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 208
ggcactggga gattattgta 20

<210> SEQ ID NO 209
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 209
tcctgttgtt aagtacacat 20

```
<210> SEQ ID NO 210
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 210

gggccgtaat tacttttg                                                18


<210> SEQ ID NO 211
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 211

actcagtagg cactttgtgt c                                            21


<210> SEQ ID NO 212
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 212

tcttccacca caccaatc                                                18


<210> SEQ ID NO 213
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 213

tggcttttca aaggtaaaa                                               19


<210> SEQ ID NO 214
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 214

gcaacgttaa catctgaatt t                                            21


<210> SEQ ID NO 215

<400> SEQUENCE: 215

000


<210> SEQ ID NO 216
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 216
attttatatg tcatgatcta ag 22

<210> SEQ ID NO 217
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 217
agagattaca ggtgtgagc 19

<210> SEQ ID NO 218
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 218
atgatcctca actgcctct 19

<210> SEQ ID NO 219
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 219
tgaaactcaa aagagaaaag 20

<210> SEQ ID NO 220
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 220
acagatttct acttaaaatt 20

<210> SEQ ID NO 221
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 221
tgaaactcaa aagagaaaag 20

<210> SEQ ID NO 222
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 222
acagatttct acttaaaatt 20

<210> SEQ ID NO 223
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 223
gcaaaggggt actctatgta 20

<210> SEQ ID NO 224
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 224
tatcgggtca tcttgttaaa 20

<210> SEQ ID NO 225
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 225
tctaacaaag ctctgtccaa aa 22

<210> SEQ ID NO 226
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 226
ccacactgaa taactggaac a 21

<210> SEQ ID NO 227
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 227
gcaagcaagc tctctacctt c 21

<210> SEQ ID NO 228
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 228
tgttcttcca aaattcacat gc 22

<210> SEQ ID NO 229
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 229
atttcactat tccttcattt t 21

<210> SEQ ID NO 230
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 230
taattgttgc acactaaatt ac 22

<210> SEQ ID NO 231
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 231
aaaaagccac agaaatcagt c 21

<210> SEQ ID NO 232
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 232
ttcttatatc tcactgggca tt 22

<210> SEQ ID NO 233
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 233
ggatggtaga agagaagaaa gg 22

<210> SEQ ID NO 234
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 234

```
ggatggtaga agagaagaaa gg                                              22


<210> SEQ ID NO 235
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 235

tgcaaagatg cagaaccaac                                                 20


<210> SEQ ID NO 236
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 236

ttttgttcct tgtcctggct ga                                              22


<210> SEQ ID NO 237
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 237

tgcaaagatg cagaaccaac                                                 20


<210> SEQ ID NO 238
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 238

gcctccagct ctatccaagt t                                               21


<210> SEQ ID NO 239
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 239

ccttaatatc ttcccatgtc ca                                              22


<210> SEQ ID NO 240
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 240

attgttagtg cctcttctgc tt                                              22
```

<210> SEQ ID NO 241
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 241
gagaagtgag gtcagcagct 20

<210> SEQ ID NO 242
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 242
tttctaaatt tccattgaac ag 22

<210> SEQ ID NO 243
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 243
gaaattggca atctgattct 20

<210> SEQ ID NO 244
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 244
caacttgtcc tttattgatg t 21

<210> SEQ ID NO 245
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 245
ctatgttgat aaaacattga aa 22

<210> SEQ ID NO 246
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 246
gcctgtctgg aatatagttt 20

<210> SEQ ID NO 247
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 247
cagggcatat aatctaagct gt 22

<210> SEQ ID NO 248
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 248
caatgactct gagttgagca c 21

<210> SEQ ID NO 249
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 249
actctctccc tcccctct 18

<210> SEQ ID NO 250
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 250
tatggcccca aaactattct 20

<210> SEQ ID NO 251
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 251
acaagtactg ggcagattga 20

<210> SEQ ID NO 252
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 252
gccaggttta gctttcaagt 20

<210> SEQ ID NO 253
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 253
ttttatatca ggagaaacac tg 22

<210> SEQ ID NO 254
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 254
ccagaatttt ggaggtttaa t 21

<210> SEQ ID NO 255
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 255
tgtcattcct cctttatctc ca 22

<210> SEQ ID NO 256
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 256
ttcttttgcc tctcccaaag 20

<210> SEQ ID NO 257
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 257
accctggcac agtgttgact 20

<210> SEQ ID NO 258
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 258
tgggcctgag ttgagaagat 20

<210> SEQ ID NO 259

<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 259
aatttgtaag tatgtgcaac g 21

<210> SEQ ID NO 260
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 260
tttttcccat ttccaactct 20

<210> SEQ ID NO 261
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 261
aaaagatgag acaggcaggt 20

<210> SEQ ID NO 262
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 262
acccctgtga atctcaaaat 20

<210> SEQ ID NO 263
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 263
gcacttgctt ctattgtttg t 21

<210> SEQ ID NO 264
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 264
cccttcctct cttccattct 20

<210> SEQ ID NO 265
<211> LENGTH: 13

<212> TYPE: DNA
<213> ORGANISM: Artificial Sequence
<220> FEATURE:
<223> OTHER INFORMATION: Description of Artificial Sequence: Synthetic primer

<400> SEQUENCE: 265
agcactgcag gta 13

<210> SEQ ID NO 266
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 266
acagatacca aagaactgca a 21

<210> SEQ ID NO 267
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 267
tggacacctt tcaacttaga 20

<210> SEQ ID NO 268
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 268
gaacagtaat gttgaacttt tt 22

<210> SEQ ID NO 269
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 269
tcttgcaaaa agcttagcac a 21

<210> SEQ ID NO 270
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 270
aaaaagatct caaagggtcc a 21

<210> SEQ ID NO 271
<211> LENGTH: 20
<212> TYPE: DNA

<213> ORGANISM: Artificial Sequence
<220> FEATURE:
<223> OTHER INFORMATION: Description of Artificial Sequence: Synthetic
primer

<400> SEQUENCE: 271
gcttttgctg aacatcaagt 20

<210> SEQ ID NO 272
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 272
ccttccagca gcatagtct 19

<210> SEQ ID NO 273
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 273
aaatccagga tgtgcagt 18

<210> SEQ ID NO 274
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 274
atgatgaggt cagtggtgt 19

<210> SEQ ID NO 275
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 275
catcacagat catagtaaat gg 22

<210> SEQ ID NO 276
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 276
aattattatt ttgcaggcaa t 21

<210> SEQ ID NO 277
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 277
catgaggcaa acacctttcc 20

<210> SEQ ID NO 278
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 278
gctggactca ggataaagaa ca 22

<210> SEQ ID NO 279
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 279
tggaagcctg agctgactaa 20

<210> SEQ ID NO 280
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 280
ccttcttttc ccccagaatc 20

<210> SEQ ID NO 281
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 281
taggagaaca gaagatcaga g 21

<210> SEQ ID NO 282
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 282
aaagactatt gctaaatgct tg 22

<210> SEQ ID NO 283
<211> LENGTH: 20
<212> TYPE: DNA
<213> ORGANISM: Artificial Sequence
<220> FEATURE:

<223> OTHER INFORMATION: Description of Artificial Sequence: Synthetic
primer

<400> SEQUENCE: 283
taagcgtagg gctgtgtgtg 20

<210> SEQ ID NO 284
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 284
ggacggatag actccagaag g 21

<210> SEQ ID NO 285
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 285
gaatgacctt ggcactttta tca 23

<210> SEQ ID NO 286
<211> LENGTH: 27
<212> TYPE: DNA
<213> ORGANISM: Artificial Sequence
<220> FEATURE:
<223> OTHER INFORMATION: Description of Artificial Sequence: Synthetic
primer

<400> SEQUENCE: 286
aaggatagag atatacagat gaatgga 27

<210> SEQ ID NO 287
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 287
catgcaccgc gcaaatac 18

<210> SEQ ID NO 288
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 288
atgcctcacc cacaaacac 19

<210> SEQ ID NO 289
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 289
tccaagccct tctcactcac 20

<210> SEQ ID NO 290
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 290
ctgggacggt gacattttct 20

<210> SEQ ID NO 291
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 291
cccaggaaga gtggaaagat t 21

<210> SEQ ID NO 292
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 292
ttagcttgca tgtacctgtg t 21

<210> SEQ ID NO 293
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 293
agctagatgg ggtgaatttt 20

<210> SEQ ID NO 294
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 294
tgggctgagg ggagattc 18

<210> SEQ ID NO 295
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 295
atcaagctaa ttaatgttat ct 22

<210> SEQ ID NO 296
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 296
aatgaataag gtcctcagag 20

<210> SEQ ID NO 297
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 297
tttaatctga tcattgccct a 21

<210> SEQ ID NO 298
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 298
agctgtgggt gaccttga 18

<210> SEQ ID NO 299
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 299
tgtcccacca ttgtgtatta 20

<210> SEQ ID NO 300
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 300
tcagacttga agtccaggat 20

<210> SEQ ID NO 301
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 301
gcttcagggg tgttagtttt 20

<210> SEQ ID NO 302
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 302
ctttgtgaaa agtcgtccag 20

<210> SEQ ID NO 303
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 303
ccatcatgga aagcatgg 18

<210> SEQ ID NO 304
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 304
tcatctccat gactgcacta 20

<210> SEQ ID NO 305
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 305
gagatgacgg agtagctcat 20

<210> SEQ ID NO 306
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 306
cccagctgca ctgtctac 18

<210> SEQ ID NO 307
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 307
tcttgttcca atcacaggac 20

<210> SEQ ID NO 308
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 308
atgctgttag ctgaagctct 20

<210> SEQ ID NO 309
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 309
tgaaagctcc taaagcagag 20

<210> SEQ ID NO 310
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 310
ttgaagagat gtgctatcat 20

<210> SEQ ID NO 311
<211> LENGTH: 54
<212> TYPE: DNA
<213> ORGANISM: Artificial Sequence
<220> FEATURE:
<223> OTHER INFORMATION: Description of Artificial Sequence: Synthetic primer

<400> SEQUENCE: 311
gccgcctgca gcccgcgccc cccgtgcccc cgccccgccg ccggcccggg cgcc 54

<210> SEQ ID NO 312
<211> LENGTH: 601
<212> TYPE: DNA
<213> ORGANISM: Homo sapiens

<400> SEQUENCE: 312
catagtgaca ggtatatgcc caactaactg tggaaaacag ttctttcttt caaccttact 60
catcaccctc acggtctgtt tatgaggctc tcctccacca gccagaaagg atgacgtgcc 120
atacctgcaa aacttataca gcatcaacag aatgaatctt tccaacaagc cgaaacattg 180
agtattgtgg cacagaatat gccccaccca ttactcaatc tagatatcct tttattccac 240
cgtctcatga ttttcttttt cctggaaaac aaaagtattt ctttcatagc ccagctagca 300
ygataaatca gcgagtcaga attctagctt tgttgtaagg ttttgcgaat atctgatcct 360
cttattttgt acttttctat ttcctaggca aatctgagta tttcacccag ttttccttaa 420
ctaggcattg aaaactcagt ttttttctta caaaccttca tgtcttcctg ctcatttgca 480
cagtcttatc ttgcacctcc tataaaatgg agaaacttga cattaaaacg taatttttat 540
tacattttga gggattccca gagaattttt ccccaatctc cttaggtagg gacttcttta 600
c 601

<210> SEQ ID NO 313
<211> LENGTH: 601
<212> TYPE: DNA
<213> ORGANISM: Homo sapiens

<400> SEQUENCE: 313
gtgggaacta tagtaaagaa gtccctacct aaggagattg gggaaaaatt ctctgggaat 60
ccctcaaaat gtaataaaaa ttacgtttta atgtcaagtt tctccatttt ataggaggtg 120
caagataaga ctgtgcaaat gagcaggaag acatgaaggt ttgtaagaaa aaaactgagt 180
tttcaatgcc tagttaagga aaactgggtg aaatactcag atttgcctag gaaatagaaa 240
agtacaaaat aagaggatca gatattcgca aaaccttaca acaaagctag aattctgact 300
ygctgattta tcgtgctagc tggctatga aagaaatact tttgttttcc aggaaaaaga 360
aaatcatgag acggtggaat aaaaggatat ctagattgag taatgggtgg ggcatattct 420
gtgccacaat actcaatgtt tcggcttgtt ggaaagattc attctgttga tgctgtataa 480
gttttgcagg tatggcacgt catcctttct ggctggtgga ggagagcctc ataaacagac 540
cgtgagggtg atgagtaagg ttgaaagaaa gaactgtttt ccacagttag ttgggcatat 600
a 601

<210> SEQ ID NO 314
<211> LENGTH: 650
<212> TYPE: DNA
<213> ORGANISM: Homo sapiens

<400> SEQUENCE: 314
tttattggtc ctgactggta caaatactga taaaaaggat tttaagatca tattcatact 60
tttggggaat gagagccaca attaattaac aatgtctgcc atgagattgg atgcaagagt 120
atggcactca tactattcct acttctgtct aattacacta tttgtttctg tgtgcaaaaa 180
tctttggtag gtggtggatg tgcccaagac acagggaaga aaaagaagta aacagggaag 240
tacaacacag actctgaaat ggggcatcat ggaagacgga gctttgtcgt cttggtcttt 300
gctgtatatt cacttcctac aacagtgcta aataccttgt ggatgcttaa atatattaaa 360
tgaatgcata aatgaaaaga gtaaataaag agtgtatatg aaagtatgta gataaaattc 420
ttcactaagc cttggggatc cagctgcttm aggactaaga ccgtatctag ctccttttag 480
tatttccaca gcatgccatg gagatacatg tttctgatta tatatgatac atggaaatta 540
tatgttgttg aatgagtgat tgagtaaatg tgtactaggg cagctaatca taaatatttc 600
tactattgct aaaatgactg gatttatcca ttccttctga gagtttatac 650

<210> SEQ ID NO 315
<211> LENGTH: 626
<212> TYPE: DNA
<213> ORGANISM: Homo sapiens

<400> SEQUENCE: 315
ctgcttaagg actaagaccr tatctagctc cttttagtat ttccacagca tgccatggag 60
atacatgttt ctgattatat atgatacatg gaaattatat gttgttgaat gagtgattga 120
gtaaatgtgt actagggcag ctaatcataa atatttctac tattgctaaa atgactggat 180

```
ttatccattc cttctgagag tttatactga ttgcttatat tgtatcaaat accgtaactg    240

agggcaatgt ttactcaaac taatagcacc attcaaattt atgcaaacaa taacactata    300

tctttaaaat gttttcacta aaagctgcat aaagagtgta ttcaacaaca atagaataat    360

tttacaatct tttttcttgc ttaatggcca tttgtgcctt ctgacatgct gctagccatt    420

caaaggtcac actaccttga agttgaagat caagacaaat gattagactc ataaaagaca    480

aatcacgtct ttctggacag gtgattatta ataattaatt agcatttaaa catgtattat    540

ttaagttctt tttaagttat aaagtctttg atttgctaaa cagtttaaat aatgaataaa    600

acataaaata ataatagtta ccattt                                         626
```

<210> SEQ ID NO 316
<211> LENGTH: 1113
<212> TYPE: DNA
<213> ORGANISM: Homo sapiens

<400> SEQUENCE: 316

```
caagagctgc atctcactcc aatttttctt ctccctataa ccttatctag attcccagtt     60

gagggaaccg atgacctaat tcctctcagt ttaaatgcaa cacaggagca aattccaaat    120

atctatgctg gtcttgctgg gattgcagaa ccccagggtg gttatcctcc tccagaggta    180

atcctgtgat cagcactaac rccacatacc agccctttca tcagcttgtt ggagaagcat    240

ctttacttcc caccaagcag tgacctagat accatctcac accagttaga atcaggatca    300

ttaaaaagtc aagaaaaaac agatgctgaa gaggatgtgg agaaatagga atgcttttac    360

actgttagtg ggaatgtaaa ttagttcaac cattgtcaaa gacagtgtgg cgatccctca    420

cagatctaga accagaaata ccatttgacc cagcaatccc attactgggt ctatacccaa    480

aggattataa attactctac tataaagaca catgcacaca tatgtttatt gcagcaccat    540

tcacaatagc aaagaattgc aaccaaccct aatgcccatc aatgacagac tggataaaga    600

aaatctggca catatacacc atggaatact acgcagccat aaaaaaggat gagtttatgt    660

cctttacagg gacatggatg aagctggaaa ccatcattct cagcaaacta acacaggaac    720

agaaaaccaa acacatgttc tcactcacaa gtgggagttg aacaatgaga acacatggac    780

acagggaggg gaacatcaca caccactgct tgtcaggggg tgggggggcta ggggaaggat    840

agcattagga gaaataccta atgtagatga agggttgatg ggtgcagcaa accaccatgg    900

catgtgtata cctgtgtaac aaacctccat gttctgcacg tgtatcccag aacttaaagt    960

acaatacaaa aaaaaaaaaa agtgtaatcc agtttacatt ttcaaggtca aagtgggtac   1020

aatgctatct atcttgggct aagaagagaa aaggaaaaat tcttgcttta aatcttagaa   1080

gtctggtttt tttccctgtt ttgtacccca tcc                                1113
```

<210> SEQ ID NO 317
<211> LENGTH: 1113
<212> TYPE: DNA
<213> ORGANISM: Homo sapiens

<400> SEQUENCE: 317

```
ttcccagttg agggaaccga tgacctaatt cctctcagtt taaatgcaac acaggagcaa     60

attccaaata tctatgctgg tcttgctggg attgcagaac cccagggtgg ttatcctcct    120

ccagaggtaa tcctgtgatc agcactaacg ccacatacca gccctttcat cagcttgttg    180

gagaagcatc tttacttccc rccaagcagt gacctagata ccatctcaca ccagttagaa    240
```

```
tcaggatcat taaaaagtca agaaaaaaca gatgctgaag aggatgtgga gaaataggaa    300
tgcttttaca ctgttagtgg gaatgtaaat tagttcaacc attgtcaaag acagtgtggc    360
gatccctcac agatctagaa ccagaaatac catttgaccc agcaatccca ttactgggtc    420
tatacccaaa ggattataaa ttactctact ataaagacac atgcacacat atgtttattg    480
cagcaccatt cacaatagca aagaattgca accaacccta atgcccatca atgacagact    540
ggataaagaa aatctggcac atatacacca tggaatacta cgcagccata aaaaaggatg    600
agtttatgtc ctttacaggg acatggatga agctggaaac catcattctc agcaaactaa    660
cacaggaaca gaaaaccaaa cacatgttct cactcacaag tgggagttga acaatgagaa    720
cacatggaca cagggagggg aacatcacac accactgctt gtcagggggt ggggggctag    780
gggaaggata gcattaggag aaatacctaa tgtagatgaa gggttgatgg gtgcagcaaa    840
ccaccatggc atgtgtatac ctgtgtaaca aacctccatg ttctgcacgt gtatcccaga    900
acttaaagta caatacaaaa aaaaaaaaaa gtgtaatcca gtttacattt tcaaggtcaa    960
agtgggtaca atgctatcta tcttgggcta agaagagaaa aggaaaaatt cttgctttaa   1020
atcttagaag tctggttttt ttccctgttt tgtaccccat cctcttggtc tctctagata   1080
tatttaagac tcacatagga cttgtctttt cta                                1113
```

<210> SEQ ID NO 318
<211> LENGTH: 1001
<212> TYPE: DNA
<213> ORGANISM: Homo sapiens

<400> SEQUENCE: 318

```
tcatcaacta aatagttgat gaggggaaat tgttctgtat atgttcatac ttcagctaat     60
caattaaaaa tgatgaaata ataagattac cattttgcaa acccctaatg caatgttgga    120
tccaggcaat gatcatcaat ggccactaaa atcacacaaa aggagataac cagaatatgt    180
gctttgtgat ggaagcatta aatacaacta atgagatatt gtttataaga aagaaaggaa    240
gcaagaaagc aatcacacca agctctgtat ctagctacca catttaagga aaaaaagaga    300
cagaagagca tgttaaatgt taccaagaag atacagtcag tcggaaaaaa tacagacaag    360
aaaatacaga gcaaaacaac ccagcttctt cagcaaatca atataaaaaa attttaagaa    420
agagttaaag tataaactga gagacttcag aaacatatta tccaagtata atccatgaat    480
cttgtttaaa tatagatcaa rtaaaccact ataccaaaaa catcaaaaga caactgggta    540
aattttttaa atgactagct atttgatgtt aaggaagtaa tgttactctc ttatatacaa    600
tttgaaataa tctagcgagg agcagcaaat gtgcggctat gaggaagaaa cacaattggc    660
cattcttgaa tcattagctg gatggtggct atatgggggt agattttact actctctaat    720
tttacatata tttaaaatgt tccataataa attgttgagt tatcaaaaga aatatttcta    780
tataatagct aaaattattt ataaaagtta gtggtctcat aactttattt atttatttac    840
ttattttgag accgagtctc cctctgttat gcaggctgga gtgcagtggc tccatctcgg    900
ctcactgcaa acttcacctc ctggattgaa gcgattctcc tgcctcagcc cccccgagta    960
gctgggatta caggcttgca cccccacgcc cagctaattt t                       1001
```

<210> SEQ ID NO 319
<211> LENGTH: 601
<212> TYPE: DNA
<213> ORGANISM: Homo sapiens

<400> SEQUENCE: 319

```
agctaccaca tttaaggaaa aaaagagaca gaagagcatg ttaaatgtta ccaagaagat     60
acagtcagtc ggaaaaaata cagacaagaa aatacagagc aaaacaaccc agcttcttca    120
gcaaatcaat ataaaaaaat tttaagaaag agttaaagta taaactgaga gacttcagaa    180
acatattatc caagtataat ccatgaatct tgtttaaata tagatcaaat aaaccactat    240
accaaaaaca tcaaaagaca actgggtaaa ttttttaaat gactagctat ttgatgttaa    300
rgaagtaatg ttactctctt atatacaatt tgaaataatc tagcgaggag cagcaaatgt    360
gcggctatga ggaagaaaca caattggcca ttcttgaatc attagctgga tggtggctat    420
atgggggtag attttactac tctctaattt tacatatatt taaaatgttc cataataaat    480
tgttgagtta tcaaaagaaa tatttctata taatagctaa aattatttat aaaagttagt    540
ggtctcataa ctttatttat ttatttactt attttgagac cgagtctccc tctgttatgc    600
a                                                                    601
```

<210> SEQ ID NO 320
<211> LENGTH: 601
<212> TYPE: DNA
<213> ORGANISM: Homo sapiens

<400> SEQUENCE: 320

```
ccaactgatc taattagata aacttagtca atatatttga atcccacatt ccagcagcta     60
ttttctccat ttgcttttat tgctgtttgt ggtgagtttg atatataatt tttaaggtgtt    120
aacatcccta acttatgtat gggtacagct cataaatacg aacctgtgtc atgcaactca    180
tatatgactg tgttcaaaat aatgtgtatt agactgtaaa acgattttaa tattttaaat    240
aactttcctg catttgtcgg tttcagcagg aaagttattt ttaataactt ccctgtattt    300
sttggtttca gtattaatta atctcattaa tgctaaactt tgtgatccta ggttaaaaaa    360
catattcaag atagcttcag aatgtttggt atacaaatag gtctggctaa atataagtgt    420
tagctttctc aagcatctaa atgctggcgg gcttttaaaa aaccagggct ttaaggagaa    480
aacacctgct ctgtggtttt gtagcagata tgaagtattc aaatttctta ataaatagaa    540
aaagaaatat ataacagaaa caggttgcac ttgtctttct cattaagcag gtggttagta    600
c                                                                    601
```

<210> SEQ ID NO 321
<211> LENGTH: 501
<212> TYPE: DNA
<213> ORGANISM: Homo sapiens

<400> SEQUENCE: 321

```
agctcataaa tacgaacctg tgtcatgcaa ctcatatatg actgtgttca aaataatgtg     60
tattagactg taaaacgatt ttaatatttt aaataacttt cctgcatttg tcggtttcag    120
caggaaagtt atttttaata acttccctgt atttgttggt ttcagtatta attaatctca    180
ttaatgctaa actttgtgat cctaggttaa aaaacatatt caagatagct tcagaatgtt    240
tggtatacaa rtaggtctgg ctaaatataa gtgttagctt tctcaagcat ctaaatgctg    300
gcgggctttt aaaaaaccag ggctttaagg agaaaacacc tgctctgtgg ttttgtagca    360
gatatgaagt attcaaattt cttaataaat agaaaaagaa atatataaca gaaacaggtt    420
gcacttgtct ttctcattaa gcaggtggtt agtaccatta tttgcattct catagcctta    480
atatacattt tccttctcta g                                              501
```

<210> SEQ ID NO 322
<211> LENGTH: 601
<212> TYPE: DNA
<213> ORGANISM: Homo sapiens

<400> SEQUENCE: 322
ttttgagttt ctactttagt gtcttagtgc tttctcgata tgggagaatt catgtcctcc 60
attcagaagt atgcactaag taagaggtat catgtctggt tcttgattag gtactaatct 120
tgaaatatta tcctacaata ggttagagca cgtatatctc ctgataatat attgaatatg 180
atagatttaa ataattggtt aactaaatac taaagcaaat tgctgcacgt atcatttatt 240
attcattgtg tagaaagtgc ctgactcagt gtttggaaat tgtctgactt ttcctcatat 300
rtagtgtggt ttcatgttat tgtatataag acctgacatg aactctgttt acaataatct 360
cccagtgcca taaagaccat aataaataat ataaccaatt ggtttcttta tgctgtcatt 420
tattagggca tatggcatta gtggaggatt accttgtatt acccatagtg cttagagtat 480
gaatcacaca tgcaccttga aggaaaagag gtgcaatgta ataagaaacc agatattgaa 540
aatgcaagtt ttgttatgtt attctgggta tgttaacctt tattcctgcc ctccatatgc 600
a 601

<210> SEQ ID NO 323
<211> LENGTH: 501
<212> TYPE: DNA
<213> ORGANISM: Homo sapiens

<400> SEQUENCE: 323
aagaggtatc atgtctggtt cttgattagg tactaatctt gaaatactat cctacagtag 60
gttagagcac gtatatctcc tgataatata ttgaatatga tagatttaaa taattggtta 120
actaaatact aaagcaaatt gctgcacgta tcatttatta ttcattgtgt agaaagtgcc 180
tgactcagtg tttggaaatt gtctgacttt tcctcatata tagtgtggtt tcatgttatt 240
gtatataaga mctgacatga accctgttta caataatctc ccagtgccat aaagaccata 300
ataaataata taaccaattg gtttctttat gctgtcattt attagggcat atggcattag 360
tggaggatta ccttgtatta cccatagtgc ttagagtatg aatcacacat gcaccttgaa 420
ggaaaagagg tgcaatgtaa taagaaacca gatattgaaa atgcaagttt tgttatgtta 480
ttctgggtat gttaaccttt a 501

<210> SEQ ID NO 324
<211> LENGTH: 854
<212> TYPE: DNA
<213> ORGANISM: Homo sapiens

<400> SEQUENCE: 324
tttcagcact gagagccaga gtggaattgt ctccttcatt gccactgcct tcacgttttg 60
tgtgtcgtat ctgttttgtg atcactgaga cccaagaacc cccgacttgc cgacatacta 120
tgtggccccg agagaggact tgagctctct gggtttcatc attaccatca attaaataaa 180
caggacagta gcttcttcct tggattgtta atttaaggct ctggataata catgtaaccg 240
ccttatgata gagcagaatt gtaagtaggc tcatggtaga atcgttcaat gacatttccc 300
tttcctttgg gagaaacaga aattcacagg tctaattctt ttcctattaa tagttcctgr 360
ccattattcc agaactgtcc taaaggaatt ctttctcctt aaggacacca cctcccagga 420
gggtatttaa agatttgcac aggccgggca cggtggctca tgcttgtaat cccagcagtt 480

```
tgggaggcca aggcgggtgg atcacttgtg ctcaggggtt caagaccggc ctggccaaca    540

tggtgaaacc ctatctctac taaaaacaca aaagttagct gggcctggct atgcatgcct    600

gtaattccag ctactcggga ggctgaggct ggagaatagc ttgaaccagg gaggtggaga    660

taacagtgag ctgagatgcc actatgacac tccagcctgg gtgacagagc aagactctct    720

ctcaaaaaaa aaaaaagatt tttatagtcc agtattcaac gttcatagta cacctttctt    780

atcctagtaa atcttctttt atcaaggtat atgatcccat atagtagtta actcttactc    840

ttactttatg acaa                                                      854
```

<210> SEQ ID NO 325
<211> LENGTH: 501
<212> TYPE: DNA
<213> ORGANISM: Homo sapiens

<400> SEQUENCE: 325

```
aaatacttac tattaaatat gagaaactgt ggtgtttatc ggtaagatcc acgaaggaag     60

aagttttaaa gaaaaatact ttaaccgtgg aaaaaaaaaa ctttaatgtc tattatcgaa    120

taggggccgt aattactttt gcaaaataaa aaaacaaaca agactagcta tagtgtaaat    180

gtaatctgta tgctttttaa tgaaacaatt aagtaggttg cccatttaca attagcctga    240

ttttctcctg ygtggtatta tgtgtactta acaacaggac ccagtggaaa ttcactcatt    300

taacaaagtc tgcctacatg gtttcaaata tgggcctaac ttgaaaattc agtcataatt    360

aaatctaagg actaaaacaa atctgtataa aaagattctg ctaaataagg gaaaattcaa    420

gtctagggct acattctgaa agatattgaa gtagaacctc tgcagcaaga ctaggcttgg    480

aaagtgcggg gaggagggaa a                                              501
```

<210> SEQ ID NO 326
<211> LENGTH: 601
<212> TYPE: DNA
<213> ORGANISM: Homo sapiens

<400> SEQUENCE: 326

```
ccacatcaga aacatgagga aattctacat ggtaaaaaca gcaacaacca aaaaatactt     60

aaagtcaaca aaccaggaaa agacatctct gaatatagga atgccaaacc tttaacacaa    120

taaaacacag attatatttc agaaggctat attatatgtg tataccaaca tcaatatgtc    180

cagagtagct gcacagagtt ccatatttta gtctttataa gttcccctcc tcaccctact    240

cagtaggcac tttgtgtcta gaaacttctg tgtcaacagt tttccctctc tctggaattc    300

mtcaggacag aagtgattgg tgtggtggaa gagggttgtg ctaagagtga agttatatga    360

aagtaggatg gaggttagca agtagttaaa gtccagaaag gcaataaggt gttaaggaag    420

aacttttcca ttttacaggt ctgagcaagc aggaaatcaa ctctacaaac tttgaaactt    480

ggtaaatatg aaaacattct caataccatt tgtcatttaa taaatacaaa ttatactatt    540

ttactgcttg catctagaag tttgtcaaag atctcgtctt aattattcat tgtgtcggcg    600

a                                                                    601
```

<210> SEQ ID NO 327
<211> LENGTH: 601
<212> TYPE: DNA
<213> ORGANISM: Homo sapiens

<400> SEQUENCE: 327

```
gacgagatct ttgacaaact tctagatgca agcagtaaaa tagtataatt tgtatttatt      60
aaatgacaaa tggtattgag aatgttttca tatttaccaa gtttcaaagt ttgtagagtt     120
gatttcctgc ttgctcagac ctgtaaaatg gaaaagttct tccttaacac cttattgcct     180
ttctggactt taactacttg ctaacctcca tcctactttc atataacttc actcttagca     240
caaccctctt ccaccacacc aatcacttct gtcctgatga attccagaga gagggaaaac     300
ygttgacaca gaagtttcta gacacaaagt gcctactgag tagggtgagg aggggaactt     360
ataaagacta aaatatggaa ctctgtgcag ctactctgga catattgatg ttggtataca     420
catataatat agccttctga aatataatct gtgttttatt gtgttaaagg tttggcattc     480
ctatattcag agatgtcttt tcctggtttg ttgactttaa gtattttttg gttgttgctg     540
tttttaccat gtagaatttc ctcatgtttc tgatgtggaa agtataagaa tatcagccag     600
a                                                                     601
```

```
<210> SEQ ID NO 328
<211> LENGTH: 811
<212> TYPE: DNA
<213> ORGANISM: Homo sapiens

<400> SEQUENCE: 328

taaataatct ctaattagta taatgggtgt tcttagtgca gtgggtactt ttaaagtgct      60
ttgtggcttt tgatgaaaat tgtcttagta tttaaaactt tttcttaccc aatttttttgt     120
tcccatcgaa ttagcaatgc tgtaaagaaa ggcatcttat tccatttttt gttgctataa     180
aggaatactt gaggctgggt aatttataaa gatgaaaagt ttatttggct cgcaattctg     240
gatggctgga aggttaagta ctgggccaca gcatctggtg gggcctcga gctgcttcta     300
gtcataatgg aaggtgaagg gtgtaaagat catgtgacaa gggaggaaag aagagaagga     360
aggaggtgct ggttctttct atcaaccaat tcgcaagaga actaatagag aaagaactca     420
cttagccctg tgggaacaca ttaatctatt cataagggat ctggctgtat gatacaaaca     480
cctcccatta ggccccacct ccaaattgta tcccattggg gatcaaattt caaaaagaga     540
tttggaagga acaaacaaac catatctaag ccatagtaaa aggaatggct tttcaaaggt     600
aaaatttact ragtgtatta atattttacc aatttccagc caggagagta tgaatgttgc     660
attattacat tgctttgaaa caaagcatta gtcttaattc agaagtttaa attcagatgt     720
taacgttgca tatttaataa tgcacaacca gtactaaaat cctcattgaa atgacaaata     780
attttatttc gaatccctta tagaggttca c                                   811
```

```
<210> SEQ ID NO 329
<211> LENGTH: 811
<212> TYPE: DNA
<213> ORGANISM: Homo sapiens

<400> SEQUENCE: 329

tgtcttagta tttaaaactt tttcttaccc aatttttttgt tcccatcgaa ttagcaatgc      60
tgtaaagaaa ggcatcttat tccatttttt gttgctataa aggaatactt gaggctgggt     120
aatttataaa gatgaaaagt ttatttggct cgcaattctg gatggctgga aggttaagta     180
ctgggccaca gcatctggtg gggcctcga gctgcttcta gtcataatgg aaggtgaagg     240
gtgtaaagat catgtgacaa gggaggaaag aagagaagga aggaggtgct ggttctttct     300
atcaaccaat tcgcaagaga actaatagag aaagaactca cttagccctg tgggaacaca     360
ttaatctatt cataagggat ctggctgtat gatacaaaca cctcccatta ggccccacct     420
```

ccaaattgta tcccattggg gatcaaattt caaaaagaga tttggaagga acaaacaaac 480
catatctaag ccatagtaaa aggaatggct tttcaaaggt aaaatttact aagtgtatta 540
atattttacc aatttccagc caggagagta tgaatgttgc attattacat tgctttgaaa 600
caaagcatta ktcttaattc agaagtttaa attcagatgt taacgttgca tatttaataa 660
tgcacaacca gtactaaaat cctcattgaa atgacaaata attttatttc gaatccctta 720
tagaggttca caatgtttta acaatgtagt tttgactaaa tagaagtagt caaaacctgt 780
cagattggaa atagtattta taaaacataa a 811

<210> SEQ ID NO 330
<211> LENGTH: 601
<212> TYPE: DNA
<213> ORGANISM: Homo sapiens

<400> SEQUENCE: 330
gctcatcaat tttgacttaa gaaaattcta gcaacattta tagattttgc caaaattcag 60
cttcttccca aatcaatcta taagaaggct cttccttaaa cataattttt atatctatga 120
actgcactag catttactat atatttttat cactctcacc attactggat aataaataaa 180
agctcattaa aagagttaac aaaacatatt tattttaggc atcctgaaaa aaagattcaa 240
ttttattatc atttctacaa taagtattga agaaaggaga atttaaatta cttcatatac 300
stgataaagg aaaacatatg caaggcaaat aaacatctta gatcatgaca tataaaataa 360
tagattatta ctaaagatta aaatactttc ttaagaatta aagcaattct aaaagcaata 420
gtaaataaca ttctttctag tgatcagaca ctggatacta tgtttgagat agacagtgaa 480
ttgggaatgt tgttttacag aagctcctac cttgcaagga caggcaagtt taaatgtcag 540
ctagaaaact atcttgagtt ttcagtaatg taagattttc ctattcaatt tcacacttta 600
a 601

<210> SEQ ID NO 331
<211> LENGTH: 601
<212> TYPE: DNA
<213> ORGANISM: Homo sapiens

<400> SEQUENCE: 331
agaaaattct agcaacattt atagattttg ccaaaattca gcttcttccc aaatcaatct 60
ataagaaggc tcttccttaa acataatttt tatatctatg aactgcacta gcatttacta 120
tatattttta tcactctcac cattactgga taataaataa aagctcatta aaagagttaa 180
caaaacatat ttattttagg catcctgaaa aaaagattca attttattat catttctaca 240
ataagtattg aagaaaggag aatttaaatt acttcatata cctgataaag gaaaacatat 300
rcaaggcaaa taaacatctt agatcatgac atataaaata atagattatt actaaagatt 360
aaaatacttt cttaagaatt aaagcaattc taaaagcaat agtaaataac attctttcta 420
gtgatcagac actggatact atgtttgaga tagacagtga attgggaatg ttgttttaca 480
gaagctccta ccttgcaagg acaggcaagt ttaaatgtca gctagaaaac tatcttgagt 540
tttcagtaat gtaagatttt cctattcaat ttcacacttt aaattttata tatatataaa 600
a 601

<210> SEQ ID NO 332
<211> LENGTH: 1110
<212> TYPE: DNA

<213> ORGANISM: Homo sapiens

<400> SEQUENCE: 332
tgtagaagtt cttatcactt cctggccttt tggctaagat caagtgtgaa atgtagaagt 60
tcctctaagc tttacttccc tcaaaaacta gttttatctt gtcagcagga ttcacttaaa 120
aagacaaatt cagattatga attttttct tttttacagg gtctgctctg ttgcccaggc 180
tggagtgcag aggcacaatc tcggctcact gcagcctccg cctcctgggt tcaagcaatt 240
ctcttgcctc agcctcccga gtaactggga ttacaggcat gtgccaccac ccagctaatt 300
tttgtatttt tagtagagat ggggtttcac cacattggtc aggctggtct cgaactgctg 360
gcctcaagtg atccacttgc ctcggcctcc caaagtgcag agattacagg tgtgagccac 420
cgtgcccagc ctcataaccg tttcaactac tttttcactt gacaagcaga tgtgaagtta 480
acaaagtcac ccatatttga aataaagata gtatattcct ggggyaggca gaggcagttg 540
aggatcatga aataactatg ttggcatagt tatttaggtg ttgatactgt tattatgcca 600
ttgaaagtta aacagagaac cctctgggta catgttttat accaatgcac actatcttat 660
tagtccctct cataatgtgc agtcatcatt actgttacgg gttgaggtgt ccccatcctc 720
tatgggacac ctctatgttg aagtctcaga ttccctagaa tctcagaatg tgaccttgtt 780
tggaaacaga tttgctacag acgcaattag ttgagatgcg cttatatggg taggtcctaa 840
ttcagtgact ggtgtcctta aaaaaatgga aatgtacaca cggtggtaga catgcataga 900
gggaagagag atggagaaaa tggtcaccta caagccaaag acaggggtct ggagcagatc 960
cttccctcac agccctcaga aggaaccaat cttgccaata ccttgatttt ggacttccac 1020
ctccagaact ataacacatt tctgttcttc aagcaatttg tagccatttg ttacagctaa 1080
tacaatcaca catagaaatg acttgtaaat 1110

<210> SEQ ID NO 333
<211> LENGTH: 691
<212> TYPE: DNA
<213> ORGANISM: Homo sapiens

<400> SEQUENCE: 333
taaaacatgt acccagaggg ttctctgttt aactttcaat ggcataataa cagtatcaac 60
acctaaataa ctatgccaac atagttattt catgatcctc aactgcctct gcctacccca 120
ggaatatact atctttattt caaatatggg tgactttgtt aacttcacat ctgcttgtca 180
agtgaaaaag tagttgaaac rgttatgagg ctgggcacgg tggctcacac ctgtaatctc 240
tgcactttgg gaggccgagg caagtggatc acttgaggcc agcagttcga gaccagcctg 300
accaatgtgg tgaaacccca tctctactaa aaatacaaaa attagctggg tggtggcaca 360
tgcctgtaat cccagttact cgggaggctg aggcaagaga attgcttgaa cccaggaggc 420
ggaggctgca gtgagccgag attgtgcctc tgcactccag cctgggcaac agagcagacc 480
ctgtaaaaaa gaaaaaaatt cataatctga atttgtcttt ttaagtgaat cctgctgaca 540
agataaaact agtttttgag ggaagtaaag cttagaggaa cttctacatt tcacacttga 600
tcttagccaa aaggccagga agtgataaga acttctacat tttaagttat tcacaagata 660
actattaatg aacctgaaat agtttgtaaa g 691

<210> SEQ ID NO 334
<211> LENGTH: 640
<212> TYPE: DNA
<213> ORGANISM: Homo sapiens

<400> SEQUENCE: 334
aaaccttttt cctgttttac tattactaaa ggtggcacaa cagcaacctc aacaactttg 60
caccatgcca acactgatgt ttacacccag cacagcattt ttggtctcta tttttattct 120
cctctgaatg taatgaggat tcctagatgg ctagccaatt cgaatattta aggcaactga 180
aagttagaat gtttctgaaa catagtgttg ttgccagaga gtacgaaagt tttcaagaat 240
atcgggcaat tctgaaagta caaagaagcc agattaaatg aaataacact ggcgaagttt 300
tagcaaggtg actctcatat aatgatcatt atcattacca cagttaaaag aaaagagttg 360
tttatgaaag gccatgtgtc tgcaatgaaa ctcaaaagag aaaagttaac aggtgcaara 420
ggtagtttta ttataaaagg agggtaggca acaagaatat gtttaatttt tcttcctttt 480
catgagtaag gacaagagtt tcatatatgt gaatattttt atttaatttt aagtagaaat 540
ctgtttttaa aatatgggta tatgcttatt tgtgtaagtg taagaaacag aagtaagtac 600
agcaaaccag aaataggcca aacactcctg agcataattt 640

<210> SEQ ID NO 335
<211> LENGTH: 919
<212> TYPE: DNA
<213> ORGANISM: Homo sapiens

<400> SEQUENCE: 335
tacacccagc acagcatttt tggtctctat ttttattctc ctctgaatgt aatgaggatt 60
cctagatggc tagccaattc gaatatttaa ggcaactgaa agttagaatg tttctgaaac 120
atagtgttgt tgccagagag tacgaaagtt ttcaagaata tcgggcaatt ctgaaagtac 180
aaagaagcca gattaaatga aataacactg gcgaagtttt agcaaggtga ctctcatata 240
atgatcatta tcattaccac agttaaaaga aaagagttgt ttatgaaagg ccatgtgtct 300
gcaatgaaac tcaaaagaga aaagttaaca ggtgcaaaag gtagttttat tataaaagga 360
gggtaggcaa caagaatatg tttaattttt cttccttttc atgagtaagg acaagagtkt 420
catatatgtg aatattttta tttaatttta agtagaaatc tgtttttaaa atatgggtat 480
atgcttattt gtgtaagtgt aagaaacaga agtaagtaca gcaaaccaga aataggccaa 540
acactcctga gcataatttt acttggtaga ttattcctga aacttaagga atcatctttg 600
aactcttttc ctcacttgac ttccaggatt caccatgcac ttgtgatttt cctttcattt 660
cactctccgt tcctcctcag tctttttttc tcccccaggt cttttttgtt catcttaaac 720
tctaaatttt agaatatccc aggggtctgc cttcggcctt ctcttttata tctacactgg 780
cctcatacat aatcttaacc aagtcattat tttaaatacc tacaatatac tgaaaacttc 840
taaatttgta ttttaattct tgacttcttc catacagtct agatttgtat gtccataggc 900
tgacatcatt ggctgatac 919

<210> SEQ ID NO 336
<211> LENGTH: 1001
<212> TYPE: DNA
<213> ORGANISM: Homo sapiens

<400> SEQUENCE: 336
ttactaaata ttctccaaca aatatatact tagtatatac tattagtgat gcatgctttc 60
aaatatttgg actatatcaa tgaatgaaac aaaaaaattat ttgcccttaa ggagcttaga 120
ttctaacaga tggattcaga tgatttttat gccttatttc gtaggtttaa aagagcaatg 180

-continued

```
gggaaaaggg aagaagagag ggattgaaaa tattgagaag gttgggagac ttagcaattt    240

taagtaaggt agtgagggta ggttttattg gcaaagtgat ttttcagcag agactgggaa    300

agatgaacgt ggtatcctgg aggaaagcct cccaggcaga gttaagctgc taacaaaagt    360

gcccttaggc tggagtgggc ttgtttgatt aaggaacaaa gaggtcagca tggttgcact    420

agagagaaaa aatcagatgg cgtaaggaga tgaaatcaga aagatacgag gctaggcaaa    480

ggggtactct atgtaatgaa yatgacctgg cagtactgac atctcctgag ggactgttag    540

aagtgcagac tcttgtatct tttctcaagt ctatgaaatc tagacttcat tttaacaaga    600

tgacccgata tttacataca cattaaagtt ccagaagcac tgatataaca cattgtaaga    660

tcgcacagga cttcaattct ttttctggtt tttagaggca gtcctttggg gtgttttgtg    720

tagagtataa tgacctgaaa tatctaggat cactctagct actatcttga ggaaagagtg    780

caataaggcg gaacagttca gaggcaatgg tggtcttcta aatgaaagac acacagcact    840

caaaccaggc agttgaggag ggatgggaag aagttgtcaa attctagaca tattttaaag    900

gtagtgtcca gagaatttcc ttagatgcgt aggaacatgg aggataggac atagggtgga    960

aataaacgaa ataaagaaac tgaagctgat tctgacattt t                       1001
```

<210> SEQ ID NO 337
<211> LENGTH: 1576
<212> TYPE: DNA
<213> ORGANISM: Homo sapiens

<400> SEQUENCE: 337

```
atacctttta agtgacatcc tagtgaatct ccatttgtca cgagacctca agctttccag     60

ttctggcaca aagtgattac tcataccatc acttcaaaat gatgattatc ttcatttatt    120

ttagttatat tgaacaaaat atacatttaa aaaatctaat tactaaatat tctccaacaa    180

atatatactt agtatatact attagtgatg catgctttca aatatttgga ctatatcaat    240

gaatgaaaca aaaaattatt tgcccttaag gagcttagat tctaacagat ggattcagat    300

gatttttatg ccttatttcg taggtttaaa agagcaatgg ggaaaaggga agaagagagg    360

gattgaaaat attgagaagg ttgggagact tagcaatttt aagtaaggta gtgagggtag    420

gttttattgg caaagtgatt tttcagcaga gactgggaaa gatgaacgtg gtatcctgga    480

ggaaagcctc ccaggcagag ttaagctgct aacaaaagtg cccttaggct ggagtgggct    540

tgtttgatta aggaacaaag aggtcagcat ggttgcacta gagagaaaaa atcagatggc    600

gtaaggagat gaaatcagaa agatacgagg ctaggcaaag gggtactcta tgtaatgaac    660

atgacctggc agtactgaca tctcctgagg gactgttaga agtgcagact cttgtatctt    720

ttctcaartc tatgaaatct agacttcatt ttaacaagat gacccgatat ttacatacac    780

attaaagttc cagaagcact gatataacac attgtaagat cgcacaggac ttcaattctt    840

tttctggttt ttagaggcag tcctttgggg tgttttgtgt agagtataat gacctgaaat    900

atctaggatc actctagcta ctatcttgag gaaagagtgc aataaggcgg aacagttcag    960

aggcaatggt ggtcttctaa atgaaagaca cacagcactc aaaccaggca gttgaggagg   1020

gatgggaaga agttgtcaaa ttctagacat attttaaagg tagtgtccag agaatttcct   1080

tagatgcgta ggaacatgga ggataggaca tagggtggaa ataaacgaaa taaagaaact   1140

gaagctgatt ctgacatttt agacctaaaa tctcaactaa aagttgccaa gatgggaaaa   1200

actaggtgca tcttgtttgg tgagtggaaa tcagccttgt gaattaagac ttaaactgat   1260

gtctttaatc ccgtagaaat accatgaagg cagtagaaga tggctaaaga gaggtctaga   1320
```

ctgtaggtac aaatttaaaa gtcacttgca tttggatgct taaagtcagg atattgtgaa 1380
gtcaacagag gaataaataa atgcagagag gggaaagaaa aggcccatag actgagccat 1440
tgtctggttt atttacatat tagtatatat tttcttaaag atgtttgcta tataataatg 1500
agttacctaa agtgtgactt ttctaaattt atggggaatt ttctacattg tgttatggca 1560
ctactaaaaa taataa 1576

<210> SEQ ID NO 338
<211> LENGTH: 1275
<212> TYPE: DNA
<213> ORGANISM: Homo sapiens

<400> SEQUENCE: 338
gtaaaactaa ttataattaa aatcaaaata tttactgaac ctacttactc ctataatttg 60
cgttgctggt taaaacccag ctataaaaat tttgatcaaa aatttttatt ttgtaaatga 120
tctgacacag cataaatgtt aatcacattt ctttatttta tttgcagatt aatttgagta 180
atttgaaaaa ttattaatgt tacttaatta ctctcaacac cttacagtgt ctcctgtaag 240
cactattggt gatactgaat ttaagttaca tttaacaact atcagaaaat agtttttaaa 300
gtaaaaatta tgatttggag tttaccaact aaatcttgtt agctttcact gcctctattg 360
agaagagcag cagttcttat cttcctcctt tttcttcttt aattaacaag agattatttg 420
tatcatagcc ataaaatcag ttcaggtatt acatgaacga cacccctgac tgcaatggtg 480
tagtttattg tattagtcca ttttcatgct gctgataaag acatacataa gactgggtaa 540
tttataaaga aatagaagtt taacggactc acagttccat gtggctgggg aagcctcaca 600
atcatgatcg aaggcaaaag gcacatctta catggcaaca ggcaagagag aatgagagcc 660
aagtgaaagg agaaacccct tataaaacct tcagacctca tgagacttat tcactaccac 720
aagaacagta tgtgagaaac agtcccatga tccagttatc tcccactggg tccctcccac 780
cacacaaggg aattatggga actgcaattc aagatgaaat gtgggtggaa gcacaacgga 840
actatatcat gatcaaagca ttattgtttt ctctgataag ctgatctaga aagtgctgct 900
tgtgatcagc tttggtgacc atgatcagtg aaatggttaa ggaaatctac agattttgta 960
ggtttgtgcc ttgacagacg accggtatct gtttctcttt tcatgatgaa gtatctaaca 1020
aagctctgtc caaaatttg aatttctcgt taaawgcatc atgattatag aacagaggtt 1080
acaatcaatt attcagtcac acaatcactc tcatcagtca ttaaggtgca tacctggtgt 1140
tccagttatt cagtgtggta taacaaacta cctggaactt aatggcttga aatagtcacc 1200
attacattat gattgtccat tctctgcatc aataattagg atttggcaaa gagggaatgg 1260
tttgtttaca gacag 1275

<210> SEQ ID NO 339
<211> LENGTH: 1275
<212> TYPE: DNA
<213> ORGANISM: Homo sapiens

<400> SEQUENCE: 339
gtaaaactaa ttataattaa aatcaaaata tttactgaac ctacttactc ctataatttg 60
cgttgctggt taaaacccag ctataaaaat tttgatcaaa aatttttatt ttgtaaatga 120
tctgacacag cataaatgtt aatcacattt ctttatttta tttgcagatt aatttgagta 180
atttgaaaaa ttattaatgt tacttaatta ctctcaacac cttacagtgt ctcctgtaag 240

-continued

```
cactattggt gatactgaat ttaagttaca tttaacaact atcagaaaat agtttttaaa    300

gtaaaaatta tgatttggag tttaccaact aaatcttgtt agctttcact gcctctattg    360

agaagagcag cagttcttat cttcctcctt tttcttcttt aattaacaag agattatttg    420

tatcatagcc ataaaatcag ttcaggtatt acatgaacga cacccctgac tgcaatggtg    480

tagtttattg tattagtcca ttttcatgct gctgataaag acatacataa gactgggtaa    540

tttataaaga aatagaagtt taacggactc acagttccat gtggctgggg aagcctcaca    600

atcatgatcg aaggcaaaag gcacatctta catggcaaca ggcaagagag aatgagagcc    660

aagtgaaagg agaaacccct tataaaacct tcagacctca tgagacttat tcactaccac    720

aagaacagta tgtgagaaac agtcccatga tccagttatc tcccactggg tccctcccac    780

cacacaaggg aattatggga actgcaattc aagatgaaat gtgggtggaa gcacaacgga    840

actatatcat gatcaaagca ttattgtttt ctctgataag ctgatctaga aagtgctgct    900

tgtgatcagc tttggtgacc atgatcagtg aaatggttaa ggaaatctac agattttgta    960

ggtttgtgcc ttgacagacg accggtatct gtttctcttt tcatgatgaa gtatctaaca   1020

aagctctgtc caaaatttg aatttctcgt taaatgcatc atgattatag aacagaggtt   1080

acaatcaatt attcagtcac acaatcactc tcatcagtca ttaaggtgcr tacctggtgt   1140

tccagttatt cagtgtggta taacaaacta cctggaactt aatggcttga aatagtcacc   1200

attacattat gattgtccat tctctgcatc aataattagg atttggcaaa gagggaatgg   1260

tttgtttaca gacag                                                      1275
```

<210> SEQ ID NO 340
<211> LENGTH: 1001
<212> TYPE: DNA
<213> ORGANISM: Homo sapiens

<400> SEQUENCE: 340

```
gaaacaaaaa attgcttttt atatattgat atttttgcac ggatttctta ggattttcta     60

tgtacatgac catgtcatct gcaaatgaaa tagttttatt tctttatcaa tccggatgaa    120

tttattaaaa ttatcttgcc taatttccca aatagggcct ccatgttgaa cataagtggt    180

ggcaagggtg atctgttgct aatctcagtg gatgatattc agtgttttac aatgatcttc    240

gacagctctg gctgttaaat tatcatagtc tgtatggcct aaacaaacaa aatacttatg    300

attatggggg aggctgggat atccaagatc aagttgctgg caggtctagc aacctgccac    360

tgggaagccc tgcttcccag ttttcagatg gccaccttct tatagtatct tcaccaaaga    420

tagggcagag agagcaagca agctctctac cttctcatat aagggcacta atcccaccat    480

gaaggcgcca ctgtcatgac stgattatgt cacaaagacc ccggggcaaa tattaccact    540

gtgaggagta cagttttagc atgtgaattt tggaagaaca caaacattta gtacagagtg    600

actattaagt atgttattaa ctatggagtt tttgtaggca ttttttaaca cattgagaaa    660

gtttcctcta ttcctacttt tgttgagaag tttttatgat gacaaggcat tacattttat    720

ccaatgactt ttctgtgtgt attgagatga ctgatttgtt ctgccaattt aaatccattg    780

ttgattctct ctaggatttt ttttatttca gttattaaat ttttcaacag gagaattact    840

gtcttgttct tttttttgta atttctgtcc ccttactggt attccatatt taataaggca    900

tcataatagt actcttcttt agtttcttaa agatggtttt ctttagtttt taacatattt    960

atgtctattt agaagtcttt gttaagtctg acatctgagc t                       1001
```

-continued

<210> SEQ ID NO 341
<211> LENGTH: 1001
<212> TYPE: DNA
<213> ORGANISM: Homo sapiens

<400> SEQUENCE: 341
ggatttctta ggattttcta tgtacatgac catgtcatct gcaaatgaaa tagttttatt 60
tctttatcaa tccggatgaa tttattaaaa ttatcttgcc taatttccca aatagggcct 120
ccatgttgaa cataagtggt ggcaagggtg atctgttgct aatctcagtg gatgatattc 180
agtgttttac aatgatcttc gacagctctg gctgttaaat tatcatagtc tgtatggcct 240
aaacaaacaa aatacttatg attatggggg aggctgggat atccaagatc aagttgctgg 300
caggtctagc aacctgccac tgggaagccc tgcttcccag ttttcagatg gccaccttct 360
tatagtatct tcaccaaaga tagggcagag agagcaagca agctctctac cttctcatat 420
aagggcacta atcccaccat gaaggcgcca ctgtcatgac ctgattatgt cacaaagacc 480
ccggggcaaa tattaccact stgaggagta cagttttagc atgtgaattt tggaagaaca 540
caaacattta gtacagagtg actattaagt atgttattaa ctatggagtt tttgtaggca 600
ttttttaaca cattgagaaa gtttcctcta ttcctacttt tgttgagaag tttttatgat 660
gacaaggcat tacattttat ccaatgactt ttctgtgtgt attgagatga ctgatttgtt 720
ctgccaattt aaatccattg ttgattctct ctaggatttt ttttatttca gttattaaat 780
ttttcaacag gagaattact gtcttgttct tttttttgta atttctgtcc ccttactggt 840
attccatatt taataaggca tcataatagt actcttcttt agtttcttaa agatggtttt 900
ctttagtttt taacatattt atgtctattt agaagtcttt gttaagtctg acatctgagc 960
tctctcaaag tttctgctga ttttttttt cctatgtttg g 1001

<210> SEQ ID NO 342
<211> LENGTH: 701
<212> TYPE: DNA
<213> ORGANISM: Homo sapiens

<400> SEQUENCE: 342
ggaaaccctg gcctcttgat cacactttcc tggagtttag tcccctctgc aatatgtacc 60
tgggagtcat aagaaatgcc agttacaaaa acttcctgta cagatatcct agcactcaac 120
tggaaaccgg ggagagtcac aattctgtct ttccagccat atgtaactga aatggagatc 180
ttttcaccct gagccagggg tgatgggaaa gggagctggt catggctcaa tgtttagcct 240
tttcttggtc ttcaagattt catagacatt cttaaataca tgtttctttc aatgaagttt 300
gcccttagga caattcacag ctacattagg tactttttaa ataatacttt tgaccatccg 360
tggttatttc attgaagaaa atctatagag cacctcagcc atcattccag aagtgactat 420
cctcctcagt aatggttctt attctaattt taaatatcat tgatgtagaa cattctattt 480
cactattcct tcattttatt rttatgggaa attatataca gttctccaga tttttaaagc 540
cttgctaaca tgttttaagt cacacaaata ttcttctgtg ggaaaatgac agtaatttag 600
tgtgcaacaa ttatatagaa ctatttttca aacttataaa cgaagtgaaa ttctaaataa 660
aatcatttat caaacacaaa aatttgagcc agaataagga a 701

<210> SEQ ID NO 343
<211> LENGTH: 701
<212> TYPE: DNA
<213> ORGANISM: Homo sapiens -continued

<400> SEQUENCE: 343
aatgccagtt acaaaaactt cctgtacaga tatcctagca ctcaactgga aaccggggag 60
agtcacaatt ctgtctttcc agccatatgt aactgaaatg gagatctttt caccctgagc 120
caggggtgat gggaaaggga gctggtcatg gctcaatgtt tagccttttc ttggtcttca 180
agatttcata gacattctta aatacatgtt tctttcaatg aagtttgccc ttaggacaat 240
tcacagctac attaggtact ttttaaataa tacttttgac catccgtggt tatttcattg 300
aagaaaatct atagagcacc tcagccatca ttccagaagt gactatcctc ctcagtaatg 360
gttcttattc taattttaaa tatcattgat gtagaacatt ctatttcact attccttcat 420
tttattatta tgggaaatta tatacagttc tccagatttt taaagccttg ctaacatgtt 480
ttaagtcaca caaatattct yctgtgggaa aatgacagta atttagtgtg caacaattat 540
atagaactat ttttcaaact tataaacgaa gtgaaattct aaataaaatc atttatcaaa 600
cacaaaaatt tgagccagaa taaggaatgt aaattacaat ttaaacacag attataaact 660
atcttacttt taaaatgtta aaattcctaa cttgtttgaa a 701

<210> SEQ ID NO 344
<211> LENGTH: 768
<212> TYPE: DNA
<213> ORGANISM: Homo sapiens

<400> SEQUENCE: 344
ctaaaatcta ccattatatg atatccttcc caatacataa attaaaaaaa aaaacactgt 60
agaggaaaaa gcaatatttt gaaatgatat gcttttcttt gtttgtcttc aaacaattac 120
atcttcatca taatggttgt attagtctgt ttttacactg ctataaagaa ttgcctgaga 180
ctgagtaaca tataaagaaa aaagttttaa ttgaccacag tttcacaggc ttaataggaa 240
gcatgactgg gaaacttaga atcatggcag aagaggaagg ggaagcaagg atcttcttca 300
catggtagca ggagagagag cacaaagggg gacacgctac acactttcaa acaacgagat 360
ctcctgagaa ctctatcggg agaacagcaa gagggaagtt cacccctatg attcaatcag 420
ctcccaccgg gcttctcccc tgacacatga ggaattacaa ttggatgaga gatttgggtg 480
gggacacaca gacaaaccat atcaactgtc atggacttaa acaattgtct ttgaattgtc 540
ttttttcata cttttatttg catctttyca ctaaaaagat gacacaaagt aatcctagtt 600
tacatttttt accatgtaat tccatattac tttttcctga aagttactta tttttaaatc 660
tcaaagctct tcatacttat ggtttgatct gcacttacaa ctggatctca gaaagattga 720
attctcccat cataccaagt tcatgtctct cactcttaat atttgttc 768

<210> SEQ ID NO 345
<211> LENGTH: 701
<212> TYPE: DNA
<213> ORGANISM: Homo sapiens

<400> SEQUENCE: 345
aaatgatatg cttttctttg tttgtcttca aacaattaca tcttcatcat aatggttgta 60
ttagtctgtt tttacactgc tataaagaat tgcctgagac tgagtaacat ataaagaaaa 120
aagttttaat tgaccacagt ttcacaggct taataggaag catgactggg aaacttagaa 180
tcatggcaga agaggaaggg gaagcaagga tcttcttcac atggtagcag gagagagagc 240
acaaaggggg acacgctaca cactttcaaa caacgagatc tcctgagaac tctatcggga 300
gaacagcaag agggaagttc acccctatga ttcaatcagc tcccaccggg cttctcccct 360

```
gacacatgag gaattacaat tggatgagag atttgggtgg ggacacacag acaaaccata    420
tcaactgtca tggacttaaa caattgtctt tgaattgtct tttttcatac ttttatttgc    480
atcttttcac taaaaagatg rcacaaagta atcctagttt acattttttta ccatgtaatt    540
ccatattact ttttcctgaa agttacttat ttttaaatct caaagctctt catacttatg    600
gtttgatctg cacttacaac tggatctcag aaagattgaa ttctcccatc ataccaagtt    660
catgtctctc actcttaata tttgttccca agacaacaat t                        701
```

```
<210> SEQ ID NO 346
<211> LENGTH: 6758
<212> TYPE: DNA
<213> ORGANISM: Homo sapiens

<400> SEQUENCE: 346
```

```
agagtgggcc attgttctga ctagtctggg gctccccaaa gaactggtat ctgtctcacc     60
tgactcagaa caatgataag gctgtagatc tttttggaag tctatgaaaa caggcacaat    120
gaaggcagca tgttagagat ataattccac aggaagatgc caggtaaaac aaaagagaaa    180
aagcaggaac aagctgatta ggaaatttgt gatgactaaa agtatataca caagcccaaa    240
taagatactc caaagatgtt tgataggttc tagatctcta gatatactgc tcaatgaaag    300
tgtccccctg aacaaagcca gtctgcaaag actgggtgag atgatttttt ttaaatgtca    360
agtctcagca acaacaaaaa tgacaagaca tgcacagaag caagaaaata taacacaatc    420
aaagaaaaaa aagccacaga aatcagtcct agagaaaacy gatctatgag ctgcctgaca    480
ataattataa aataactatc ataaaaatgc ccagtgagat ataagaaaac acagacaact    540
aaatgaatca ggaaaatgat gcatgaacaa aatgggcata tcaacagaga tggaaatgac    600
aaagataaac aaacagaaat tttggagctt aaaaatacag taagtaaagt gaataattca    660
ctaaaaatat tcaatagcag actagatcag gcagaagaaa atatcaatga acttgaagac    720
agatcatcaa gtcagaggaa caacagcaac aaaaaagaat gaaaaaagtg aagacagcct    780
aagggactta ggagtcagta ccaaggaaat caatatatac gttatagatg tatcagaaga    840
aaaagggaga aaaatgaaaa gaaagcatat ttgaaaaaat aatagctgaa gaattctcaa    900
tttcaaagag agaaattgat atacaaattc aagaagttca aaagactcta gccataataa    960
atctaaagag actcacacta agacatatta tcatcaaact gtcaaaatca aagacaaaga   1020
attgtgaaat ctgccaagga aaagtgactc atcacacata agagatataa cataagattg   1080
tcacaggatt tctgaacaga cactttgcag gtcagaggga agtagggtga catattccag   1140
gtgctgaaag aagaaaacac cctgccaacc aagaatatgg catccagaaa aactttccta   1200
gaagaatgaa ggagaaattt agactttccc aaataaacaa aagctgaggg agttcattac   1260
taccagacct gctctgcaaa atgctaaaga gaaaccttca ggtgaaacaa aaagatgcta   1320
gacagtaaca caaaaccact cataaataac ttcttcagta aaaataatac atcgacaaat   1380
atggtaacct gtattaatac tggtgcacaa attcactttc aaattttata aataagaatt   1440
taaaggatga aaacatctaa aactaactat aaatctatat aatgaatata caatatataa   1500
aaaaatttgt gatcacaata acataaaatg ggggaggtag agctgtatag ggtagagct    1560
tttgtatgca attgaaatta ccatcagttt aaactgaact gttataacat taagatgttt   1620
tatgtaattg caatggtaac tatattctat agaatatatt aaaaagaaaa agaaaatagg   1680
aagggaatca aagcatgtcc ttgtaaaaaa gtcaatgaaa gcaaaagaaa ggcagaaaga   1740
```

-continued

```
gtgaaaagga ggaataaaaa gttataagac ataaaaaaaa tgaaaatagt aatagtcctg   1800
ccatatcagt aattacatta aatataaatg gattaaactc cctaatcaaa tcatagattg   1860
gtttgcaaga actaacttta caattaaaga cacacagctg acggtgaagg gagaaaaaaa   1920
acttccatgc agtgaccaaa atagaggagg gtggctgtat tactgtcaga caaaataaaa   1980
tttaagtcaa aaactgttac aagagtaaaa gaagggcatt atacagttaa aaaagtaaat   2040
tcgccaggca gacacaacaa ttataaatat caatacataa aaataagagc tcctaaatat   2100
atgcagcaaa cagacataat tgaagaaaga aataaatagc taaaatggta gaagacttta   2160
ataccccac ttacaataat gtataaaata acaagacaga atgtaaataa aaatgtagag    2220
aatttgagca acactgtaga ccaattggac ctaataaata tactcagaat aatccatcca   2280
accaaagcag aaacagaata tacattcttt tcaagtacac atttgacatt ctctgggatt   2340
aactacatgt tatgcaacaa acaagtctca acaatgttta aaagtctgat attacacaaa   2400
gtattgtttc tgatgacgat ggaaagaacc tagaagccaa tagcaaaaag aaaatagaaa   2460
atccacacat atgtggaaat taaactacat gcaattaagc aaagggccaa agaagaagaa   2520
gaaaaaagaa aacaccgtga aacaaataaa aacaaaaata cagcatatga aaatgcatgg   2580
gatgcagcaa aagtgatggt aagagaaatg tttatagtta taaatgcaaa ccttaaaaaa   2640
gaagaaagaa aacaaaaata ctcaaattaa caactttaca agtcaagaag gtagagaaaa   2700
aagaacaaac tataccaaaa gctaacacag aaagaaaaga ataaagatta aaaacaaaaa   2760
caatttaaaa aatagcagaa ctaaaagttg gttctttgaa aagatcaaca gaattgacaa   2820
tttcttagct acattaagaa aaatacaaga ctcaaataac acaaatcagt ggtgaaaggg   2880
ggtattataa ctgatgccac agaaatacaa aaggatcata agggactact acaaattgta   2940
tgacaacaaa ttgagtaacc taggatacct tgataaattc caaaaaatgc acaatatact   3000
gaatcatgaa tacatgaccc ttataaatca agactaaatc ataaagaaat agaaaatatc   3060
aacagaccaa taattagtaa ggagaataaa ctagtaatca gaaacctccc aacaaagaaa   3120
agcttaggac caaatggctt tactggagaa ttctaccaac cattaaaagg ataattaaga   3180
ccaatcttcc tcaaactttt aaaacaaatg ttaaagagga ggaaactctt tcaatctcat   3240
tcataaggtc agcattatcc ttataccaaa accagacaaa gacactatta aaaaaactta   3300
gaccaatatc cctgatgaat ttcgatgcaa gaatcctcag caaaatacta tcaaacaatt   3360
caacagcata cttaaatgat tatatgctgt aatcaagatg catttattct ttgaatgcaa   3420
gtgtaattca acacataaaa ttcaatcaat gtaatacacc acattaacag aatgagagac   3480
aaaaaccaca taattatatc aactgatgca gaaaaaaatc tgacacagtt caacaccttt   3540
tgtgataaaa acactcaaca aactaggaaa agaaggaaac aactttaaca catcatatgc   3600
tcactgatga aaatctacaa gttctttata aaagatcagg aacaagacaa taatctgcat   3660
tgttaccact tctattatac gtagtattgg aagttctaat cagagcaaat taggcaagaa   3720
aaataaataa aaggcatcca aagtggaaag gaagtaaaat aatctctttt tacagatgat   3780
ataaccttag aattagaaaa tcctaaaaat ttcacatacc aagaaaaagc gtgttaaaat   3840
taataagtaa attcagcaag ttgactgata caaaatcaac acagaaagct cagttgtgtg   3900
tctgtgtgtc tcatacacta acaatgaaca atctgaaaag gagattaaga aaacaatttc   3960
atttacaata gcatcaggaa aaaaaataaa tacttaggaa caaacttaac caaggggttg   4020
gaattcctgt atactgaaaa ctacaaatat tgccaaaaga aaataaagga gacacaaata   4080
agtgatatgt ttttaatatg tccacccaaa gtgatcttca gattcaatga aatccctatc   4140
```

```
aaagttataa tggcattttt ctgcaggaat gtaaaaattt atcctaaaat tcatatagaa   4200
tctctaggta ccctgagggc caaacaattt tgagaaaaaa aaaagaacaa aattggagga   4260
ctcacacttc cagattacaa gaatatttac aaattacata tttacaaaaa aaattacaaa   4320
gccacaataa tcaaaacaac gtgggatttg cataaaggca gatatataga ccagtggaat   4380
agtattgaga gtccagaaat aaacccttag gtatatcatc aaatgacatt tgacaaagtg   4440
ctggtaccac tcaatgggaa tgggacaatt tgttcaacaa atagagcaaa gaaaactaaa   4500
catccatgtg caaaagaata aatctggacc cttatattac actatagaca aaattaattc   4560
aaaatggatt aaagatctaa atgaaagatc taaaactata aaactcctag gagaaaacag   4620
aggaaaaatt tcatgctaat ttggcaacat tttgtgatgt gacaccaaaa gcagagtcaa   4680
taaaagcaaa aattagacag atggaaatcc atcatagttt ataacttttg gtcattaaag   4740
aacagtcaac agagtgaaaa ggcaatctat aaaatggggg aaaaacagaa aatatgtgca   4800
aatcacagat atctgatagg ggattcatat ccagaataaa taaagaactc ctatatctca   4860
acaacaaaaa atctaatcca atcaaaaaat gggccaaggg agtgaagata catttctcca   4920
aagatgttat acaaatggcc aggaagcata tgaaaagatg ttcaatgtca ctaatcatca   4980
gagaaatgca aatcaaaacc acagtgcaat atcacttcac attcattaga atggcttctg   5040
tcatgaacaa cagaaaataa caagtgttga tgagtgtgta gagaaattga gacctttata   5100
taattttggc agaaattcaa aatggtgcaa ccactataaa aaatgatatg gaggtcctca   5160
aaaaattaaa aatagaacta ccatatgatc cacaatccca cctctgggta catattcaaa   5220
agaattgaaa gcagggtgtt gaagatatat ttgcacactc tttatagcag cactgttcac   5280
aatagccaag agatgaaagt aacccaaagg ttcatgaagc aatgaataaa caaaatatat   5340
tatgtacata gagtaaaata ctgtgcagct ttaaagagaa aggaaatctt atactatgct   5400
acaacatgaa tggaacttta gggcattata gtaagtaaaa taagccagtt ttttttaaag   5460
gacaaataaa cactatacga ttctacttaa gtatttaatg ttgtcaaatt tataaatata   5520
gaatgtagaa tagtggttac cctgagctgg gggaaagggg caaaggggaa ttgttatttt   5580
aatgggtata gtttcagttc tgcaaaatga aaaggttctg gaaatctgtt tcacaatgtt   5640
gtaaatataa ttactctgaa attgtacact taaaaatggt taagatgaca aatagagttg   5700
tgatgtcttc ttttgttatt atatagaaaa actttttcat atgataatag tctttgtttt   5760
taagctgact ttgctgatat taatataatc cttccatttt tctttaaaat gctatatgct   5820
ttcacataat tttgctttac gttgatgtat ttatacataa ggtgggtttc ttatagatac   5880
cacgttgtgt gtcttttttta tctaagttga tagacttgcc ttttgttagg gtatttaaat   5940
aatttatatt taatgtaatt attgatatag ttgagtgtgt tgatttttgt tttctatttg   6000
ctccatctgt tgttggttct cattattcct ctgtttctac cttcttttgt actaattatt   6060
atattttatt atttttcatc tcaactgttg gcttattagc cacattgctt ttaaaatttt   6120
taatgattgc tctagggttt ataataaaca aaatgttagc attttctacc atcaaatatt   6180
tttacactat tcatgtatac ttcaatttct ttcttcccat cctttgaact atatcttcat   6240
acattttact ctacatttgt tataactcag tgctttgaaa gtcaattatt tttgtctttg   6300
acagtcaatg atttttaaag agtttaacag tgaaaaaaaa tggctttcat ctttttccat   6360
tagatttcat actccttctg cctgaagaat ttcttttaat agaccttgta ctgcgggtct   6420
caggcaagaa attctctcag cctttgttgg tttgaaaaac tgcttattac acctttgttt   6480
```

```
ttgaaagata ttttcactag gtatagaagt ctgggttgac agttctcatt gtttgtcaca   6540

gcatttttaa gatgcccatt caattgtctt gtcttgtata attttggatt agtctggtgt   6600

atttcttacc tttgttcctc tctgtgcaat gcttcaacca tcccacttca ggctgccttt   6660

aagatgtttt cttttccctt aatctttagt ttttagctgg ttgacagtga cgcatctaag   6720

tgtagtgtat gaggttgctt ttattgtcac tgttgttg                           6758
```

```
<210> SEQ ID NO 347
<211> LENGTH: 6758
<212> TYPE: DNA
<213> ORGANISM: Homo sapiens

<400> SEQUENCE: 347

agagtgggcc attgttctga ctagtctggg gctccccaaa gaactggtat ctgtctcacc     60

tgactcagaa caatgataag gctgtagatc tttttggaag tctatgaaaa caggcacaat    120

gaaggcagca tgttagagat ataattccac aggaagatgc caggtaaaac aaaagagaaa    180

aagcaggaac aagctgatta ggaaatttgt gatgactaaa agtatataca caagcccaaa    240

taagatactc caaagatgtt tgataggttc tagatctcta gatatactgc tcaatgaaag    300

tgtccccctg aacaaagcca gtctgcaaag actgggtgag atgatttttt ttaaatgtca    360

agtctcagca acaacaaaaa tgacaagaca tgcacagaag caagaaaata taacacaatc    420

aaagaaaaaa aagccacaga aatcagtcct agagaaaact gatctatgag ctgcctgama    480

ataattataa aataactatc ataaaaatgc ccagtgagat ataagaaaac acagacaact    540

aaatgaatca ggaaaatgat gcatgaacaa aatgggcata tcaacagaga tggaaatgac    600

aaagataaac aaacagaaat tttggagctt aaaaatacag taagtaaagt gaataattca    660

ctaaaaatat tcaatagcag actagatcag gcagaagaaa atatcaatga acttgaagac    720

agatcatcaa gtcagaggaa caacagcaac aaaaaagaat gaaaaaagtg aagacagcct    780

aagggactta ggagtcagta ccaaggaaat caatatatac gttatagatg tatcagaaga    840

aaaagggaga aaaatgaaaa gaaagcatat ttgaaaaaat aatagctgaa gaattctcaa    900

tttcaaagag agaaattgat atacaaattc aagaagttca aaagactcta gccataataa    960

atctaaagag actcacacta agacatatta tcatcaaact gtcaaaatca aagacaaaga   1020

attgtgaaat ctgccaagga aaagtgactc atcacacata agagatataa cataagattg   1080

tcacaggatt tctgaacaga cactttgcag gtcagaggga agtagggtga catattccag   1140

gtgctgaaag aagaaaacac cctgccaacc aagaatatgg catccagaaa aactttccta   1200

gaagaatgaa ggagaaattt agactttccc aaataaacaa aagctgaggg agttcattac   1260

taccagacct gctctgcaaa atgctaaaga gaaaccttca ggtgaaacaa aaagatgcta   1320

gacagtaaca caaaaccact cataaataac ttcttcagta aaaataatac atcgacaaat   1380

atggtaacct gtattaatac tggtgcacaa attcactttc aaattttata aataagaatt   1440

taaaggatga aaacatctaa aactaactat aaatctatat aatgaatata caatatataa   1500

aaaaatttgt gatcacaata acataaaatg ggggaggtag agctgtatag gggtagagct   1560

tttgtatgca attgaaatta ccatcagttt aaactgaact gttataacat taagatgttt   1620

tatgtaattg caatggtaac tatattctat agaatatatt aaaaagaaaa agaaaatagg   1680

aagggaatca aagcatgtcc ttgtaaaaaa gtcaatgaaa gcaaaagaaa ggcagaaaga   1740

gtgaaaagga ggaataaaaa gttataagac ataaaaaaaa tgaaaatagt aatagtcctg   1800

ccatatcagt aattacatta aatataaatg gattaaactc cctaatcaaa tcatagattg   1860
```

-continued gtttgcaaga actaacttta caattaaaga cacacagctg acggtgaagg gagaaaaaaa 1920
acttccatgc agtgaccaaa atagaggagg gtggctgtat tactgtcaga caaaataaaa 1980
tttaagtcaa aaactgttac aagagtaaaa gaagggcatt atacagttaa aaaagtaaat 2040
tcgccaggca gacacaacaa ttataaatat caatacataa aaataagagc tcctaaatat 2100
atgcagcaaa cagacataat tgaagaaaga aataaatagc taaaatggta gaagacttta 2160
atacccccac ttacaataat gtataaaata acaagacaga atgtaaataa aaatgtagag 2220
aatttgagca acactgtaga ccaattggac ctaataaata tactcagaat aatccatcca 2280
accaaagcag aaacagaata tacattcttt tcaagtacac atttgacatt ctctgggatt 2340
aactacatgt tatgcaacaa acaagtctca acaatgttta aaagtctgat attacacaaa 2400
gtattgtttc tgatgacgat ggaaagaacc tagaagccaa tagcaaaaag aaaatagaaa 2460
atccacacat atgtggaaat taaactacat gcaattaagc aaagggccaa agaagaagaa 2520
gaaaaaagaa aacaccgtga aacaaataaa aacaaaaata cagcatatga aaatgcatgg 2580
gatgcagcaa aagtgatggt aagagaaatg tttatagtta taaatgcaaa ccttaaaaaa 2640
gaagaaagaa aacaaaaata ctcaaattaa caactttaca agtcaagaag gtagagaaaa 2700
aagaacaaac tataccaaaa gctaacacag aaagaaaaga ataaagatta aaaacaaaaa 2760
caatttaaaa aatagcagaa ctaaaagttg gttctttgaa aagatcaaca gaattgacaa 2820
tttcttagct acattaagaa aaatacaaga ctcaaataac acaaatcagt ggtgaaaggg 2880
ggtattataa ctgatgccac agaaatacaa aaggatcata agggactact acaaattgta 2940
tgacaacaaa ttgagtaacc taggatacct tgataaattc caaaaaatgc acaatatact 3000
gaatcatgaa tacatgaccc ttataaatca agactaaatc ataaagaaat agaaaatatc 3060
aacagaccaa taattagtaa ggagaataaa ctagtaatca gaaacctccc aacaaagaaa 3120
agcttaggac caaatggctt tactggagaa ttctaccaac cattaaaagg ataattaaga 3180
ccaatcttcc tcaaactttt aaaacaaatg ttaaagagga ggaaactctt tcaatctcat 3240
tcataaggtc agcattatcc ttataccaaa accagacaaa gacactatta aaaaaactta 3300
gaccaatatc cctgatgaat ttcgatgcaa gaatcctcag caaaatacta tcaaacaatt 3360
caacagcata cttaaatgat tatatgctgt aatcaagatg catttattct ttgaatgcaa 3420
gtgtaattca acacataaaa ttcaatcaat gtaatacacc acattaacag aatgagagac 3480
aaaaaccaca taattatatc aactgatgca gaaaaaaatc tgacacagtt caacaccttt 3540
tgtgataaaa acactcaaca aactaggaaa agaaggaaac aactttaaca catcatatgc 3600
tcactgatga aaatctacaa gttctttata aaagatcagg aacaagacaa taatctgcat 3660
tgttaccact tctattatac gtagtattgg aagttctaat cagagcaaat taggcaagaa 3720
aaataaataa aaggcatcca aagtggaaag gaagtaaaat aatctctttt tacagatgat 3780
ataaccttag aattagaaaa tcctaaaaat ttcacatacc aagaaaaagc gtgttaaaat 3840
taataagtaa attcagcaag ttgactgata caaaatcaac acagaaagct cagttgtgtg 3900
tctgtgtgtc tcatacacta acaatgaaca atctgaaaag gagattaaga aaacaatttc 3960
atttacaata gcatcaggaa aaaaaataaa tacttaggaa caaacttaac caaggggttg 4020
gaattcctgt atactgaaaa ctacaaatat tgccaaaaga aaataaagga gacacaaata 4080
agtgatatgt ttttaatatg tccacccaaa gtgatcttca gattcaatga aatccctatc 4140
aaagttataa tggcattttt ctgcaggaat gtaaaaattt atcctaaaat tcatatagaa 4200

-continued

```
tctctaggta ccctgagggc caaacaattt tgagaaaaaa aaaagaacaa aattggagga   4260
ctcacacttc cagattacaa gaatatttac aaattacata tttacaaaaa aaattacaaa   4320
gccacaataa tcaaaacaac gtgggatttg cataaaggca gatatataga ccagtggaat   4380
agtattgaga gtccagaaat aaaccccttag gtatatcatc aaatgacatt tgacaaagtg   4440
ctggtaccac tcaatgggaa tgggacaatt tgttcaacaa atagagcaaa gaaaactaaa   4500
catccatgtg caaaagaata aatctggacc cttatattac actatagaca aaattaattc   4560
aaaatggatt aaagatctaa atgaaagatc taaaactata aaactcctag gagaaaacag   4620
aggaaaaatt tcatgctaat ttggcaacat tttgtgatgt gacaccaaaa gcagagtcaa   4680
taaaagcaaa aattagacag atggaaatcc atcatagttt ataacttttg gtcattaaag   4740
aacagtcaac agagtgaaaa ggcaatctat aaaatggggg aaaaacagaa aatatgtgca   4800
aatcacagat atctgatagg ggattcatat ccagaataaa taaagaactc ctatatctca   4860
acaacaaaaa atctaatcca atcaaaaaat gggccaaggg agtgaagata catttctcca   4920
aagatgttat acaaatggcc aggaagcata tgaaaagatg ttcaatgtca ctaatcatca   4980
gagaaatgca aatcaaaacc acagtgcaat atcacttcac attcattaga atggcttctg   5040
tcatgaacaa cagaaaataa caagtgttga tgagtgtgta gagaaattga gacctttata   5100
taattttggc agaaattcaa aatggtgcaa ccactataaa aaatgatatg gaggtcctca   5160
aaaaattaaa aatagaacta ccatatgatc cacaatccca cctctgggta catattcaaa   5220
agaattgaaa gcagggtgtt gaagatatat ttgcacactc tttatagcag cactgttcac   5280
aatagccaag agatgaaagt aacccaaagg ttcatgaagc aatgaataaa caaaatatat   5340
tatgtacata gagtaaaata ctgtgcagct ttaaagagaa aggaaatctt atactatgct   5400
acaacatgaa tggaacttta gggcattata gtaagtaaaa taagccagtt ttttttaaag   5460
gacaaataaa cactatacga ttctacttaa gtatttaatg ttgtcaaatt tataaatata   5520
gaatgtagaa tagtggttac cctgagctgg gggaaagggg caaaggggaa ttgttatttt   5580
aatgggtata gtttcagttc tgcaaaatga aaaggttctg gaaatctgtt tcacaatgtt   5640
gtaaatataa ttactctgaa attgtacact taaaaatggt taagatgaca aatagagttg   5700
tgatgtcttc ttttgttatt atatagaaaa actttttcat atgataatag tctttgtttt   5760
taagctgact ttgctgatat taatataatc cttccatttt tctttaaaat gctatatgct   5820
ttcacataat tttgctttac gttgatgtat ttatacataa ggtgggtttc ttatagatac   5880
cacgttgtgt gtctttttta tctaagttga tagacttgcc ttttgttagg gtatttaaat   5940
aatttatatt taatgtaatt attgatatag ttgagtgtgt tgatttttgt tttctatttg   6000
ctccatctgt tgttggttct cattattcct ctgtttctac cttcttttgt actaattatt   6060
atattttatt atttttcatc tcaactgttg gcttattagc cacattgctt ttaaaatttt   6120
taatgattgc tctagggttt ataataaaca aaatgttagc attttctacc atcaaatatt   6180
tttacactat tcatgtatac ttcaatttct ttcttcccat cctttgaact atatcttcat   6240
acattttact ctacatttgt tataactcag tgctttgaaa gtcaattatt tttgtctttg   6300
acagtcaatg atttttaaag agtttaacag tgaaaaaaaa tggctttcat ctttttccat   6360
tagatttcat actccttctg cctgaagaat ttcttttaat agaccttgta ctgcgggtct   6420
caggcaagaa attctctcag cctttgttgg tttgaaaaac tgcttattac acctttgttt   6480
ttgaaagata ttttcactag gtatagaagt ctgggttgac agttctcatt gtttgtcaca   6540
gcatttttaa gatgcccatt caattgtctt gtcttgtata attttggatt agtctggtgt   6600
```

atttcttacc tttgttcctc tctgtgcaat gcttcaacca tcccacttca ggctgccttt 6660
aagatgtttt cttttccctt aatctttagt ttttagctgg ttgacagtga cgcatctaag 6720
tgtagtgtat gaggttgctt ttattgtcac tgttgttg 6758

<210> SEQ ID NO 348
<211> LENGTH: 501
<212> TYPE: DNA
<213> ORGANISM: Homo sapiens

<400> SEQUENCE: 348
gaccatgtta tgacatttta gtgcttgcta agcagtaaat actgacttac tttcctgcta 60
cactcttcag agcagaaaga gaaatctaca aaaagggcaa tgtagttggg atccaccaca 120
gccttgagac tgggccatgt ttctacagct tacccacatt ttacccccac tttctctgag 180
aaacaatgca aactggagaa caaggtcaga gaagttatct tggatggtag aagagaagaa 240
aggagaagaa rggataagca gaaaatcaaa aagggcataa aaaaattact ggggaaaata 300
attcttagtc actcaccatt tcttatgttt gtgaaaacag aaacgaggag caagtgttgt 360
tgtaagaatt gttcttgccc ctccccctcc accacccaca tctgtcaagc tatccctgtt 420
tcactgtttc ctctgcactc tctattaact tctttgtcct cctcttttct tttcctacag 480
caaagacttt ttgtcatgtt t 501

<210> SEQ ID NO 349
<211> LENGTH: 501
<212> TYPE: DNA
<213> ORGANISM: Homo sapiens

<400> SEQUENCE: 349
tgacttactt tcctgctaca ctcttcagag cagaaagaga aatctacaaa aagggcaatg 60
tagttgggat ccaccacagc cttgagactg ggccatgttt ctacagctta cccacatttt 120
acccccactt tctctgagaa acaatgcaaa ctggagaaca aggtcagaga agttatcttg 180
gatggtagaa gagaagaaag gagaagaaag gataagcaga aaatcaaaaa gggcataaaa 240
aaattactgg rgaaaataat tcttagtcac tcaccatttc ttatgtttgt gaaaacagaa 300
acgaggagca agtgttgttg taagaattgt tcttgcccct ccccctccac cacccacatc 360
tgtcaagcta tccctgtttc actgtttcct ctgcactctc tattaacttc tttgtcctcc 420
tcttttcttt tcctacagca aagacttttt gtcatgtttt gtttcttttt ctattgtttc 480
tttccctttt ctaatccttg a 501

<210> SEQ ID NO 350
<211> LENGTH: 1148
<212> TYPE: DNA
<213> ORGANISM: Homo sapiens

<400> SEQUENCE: 350
tatgagattt aatgttaaga aataaaatgt aggatctaaa acgtaatcta tagcataatc 60
tcaaaaatgg tttagaaatg acataataat acagacattt gtgggtggta ggattatgca 120
tatttttata tatttttaaa tatatttttc aaaagcttcc tataaagaat gtaattcttt 180
cccaattcca aatctagctt aaacataatt ttacaaaaat tattctctca gaatgtaaac 240
tagtaccacc tctatggaaa acattatgga gatttcctaa agagttaaaa gtagatctac 300
catttgatcc agcaatctta atactgggta tctacccgga ggaaaagaag tcattgtatg 360

-continued

```
aaaaagacac ttgtacacat atgtttacag gaccacaatt cacaaatgca aagatgcaga    420

accaacctaa gtggccastg actaatgaga ggataaagaa gatgtggcat atatatatca    480

gggactacta ctcagccatt acaaggaaca aaataatgtc ttttgcaaca acttggatag    540

agctggaggc cattattcta agtaaagtaa ttcaggaatt ggaaaaccaa aaaccgtatg    600

ttctctctta taagtgggaa ctaagttagg aataagcaaa ggcacacaga gggacatatt    660

ggactttaga gactcacgag gaggagggta ataggggact agggattaaa agaaaaacta    720

gacattaggt acaaggtacc ctacttaagt gcactaaaat ctcagaattc accactacgt    780

aattcaacta agtaacaaga aaccacttgt accccaaaag ctactgaaat aaaaattatt    840

ctctcaaaaa ttttaagccc taaacttcag ttcctattgt ttatatttac taagaaaaac    900

aacagaaaac actgttttaa aaatggtgga ttttttaag gttaaaggta tataagacag    960

ctgcctaagg aaacgcagat acccctgtac cttgttgttg ttgttgtttt tcactttttt   1020

aaaaaacata gagatgggat ctccttatgc tgcccaggct tgtctcaaac tcctgagctc   1080

aagcaatcct ctgacctcag actctcaaag ttttgggact acaggcgaca gtcaccatgc   1140

cagccaat                                                            1148
```

```
<210> SEQ ID NO 351
<211> LENGTH: 1148
<212> TYPE: DNA
<213> ORGANISM: Homo sapiens

<400> SEQUENCE: 351

tatgagattt aatgttaaga aataaaatgt aggatctaaa acgtaatcta tagcataatc     60

tcaaaaatgg tttagaaatg acataataat acagacattt gtgggtggta ggattatgca    120

tatttttata tatttttaaa tatatttttc aaaagcttcc tataaagaat gtaattcttt    180

cccaattcca aatctagctt aaacataatt ttacaaaaat tattctctca gaatgtaaac    240

tagtaccacc tctatggaaa acattatgga gatttcctaa agagttaaaa gtagatctac    300

catttgatcc agcaatctta atactgggta tctacccgga ggaaaagaag tcattgtatg    360

aaaaagacac ttgtacacat atgtttacag gaccacaatt cacaaatgca aagatgcaga    420

accaacctaa gtggccactg actaatgaga ggataaagaa gatgtggcat atatayatca    480

gggactacta ctcagccatt acaaggaaca aaataatgtc ttttgcaaca acttggatag    540

agctggaggc cattattcta agtaaagtaa ttcaggaatt ggaaaaccaa aaaccgtatg    600

ttctctctta taagtgggaa ctaagttagg aataagcaaa ggcacacaga gggacatatt    660

ggactttaga gactcacgag gaggagggta ataggggact agggattaaa agaaaaacta    720

gacattaggt acaaggtacc ctacttaagt gcactaaaat ctcagaattc accactacgt    780

aattcaacta agtaacaaga aaccacttgt accccaaaag ctactgaaat aaaaattatt    840

ctctcaaaaa ttttaagccc taaacttcag ttcctattgt ttatatttac taagaaaaac    900

aacagaaaac actgttttaa aaatggtgga ttttttaag gttaaaggta tataagacag    960

ctgcctaagg aaacgcagat acccctgtac cttgttgttg ttgttgtttt tcactttttt   1020

aaaaaacata gagatgggat ctccttatgc tgcccaggct tgtctcaaac tcctgagctc   1080

aagcaatcct ctgacctcag actctcaaag ttttgggact acaggcgaca gtcaccatgc   1140

cagccaat                                                            1148

<210> SEQ ID NO 352
<211> LENGTH: 1148
```

<212> TYPE: DNA
<213> ORGANISM: Homo sapiens

<400> SEQUENCE: 352
tatgagattt aatgttaaga aataaaatgt aggatctaaa acgtaatcta tagcataatc 60
tcaaaaatgg tttagaaatg acataataat acagacattt gtgggtggta ggattatgca 120
tatttttata tatttttaaa tatatttttc aaaagcttcc tataaagaat gtaattcttt 180
cccaattcca aatctagctt aaacataatt ttacaaaaat tattctctca gaatgtaaac 240
tagtaccacc tctatggaaa acattatgga gatttcctaa agagttaaaa gtagatctac 300
catttgatcc agcaatctta atactgggta tctacccgga ggaaaagaag tcattgtatg 360
aaaaagacac ttgtacacat atgtttacag gaccacaatt cacaaatgca aagatgcaga 420
accaacctaa gtggccactg actaatgaga ggataaagaa gatgtggcat atatayatca 480
gggactacta ctcagccatt acaaggaaca aaataatgtc ttttgcaaca acttggatag 540
agctggaggc cattattcta agtaaagtaa ttcaggaatt ggaaaaccaa aaaccgtatg 600
ttctctctta taagtgggaa ctaagttagg aataagcaaa ggcacacaga gggacatatt 660
ggactttaga gactcacgag gaggagggta ataggggact agggattaaa agaaaaacta 720
gacattaggt acaaggtacc ctacttaagt gcactaaaat ctcagaattc accactacgt 780
aattcaacta agtaacaaga aaccacttgt accccaaaag ctactgaaat aaaaattatt 840
ctctcaaaaa ttttaagccc taaacttcag ttcctattgt ttatatttac taagaaaaac 900
aacagaaaac actgttttaa aaatggtgga ttttttaag gttaaaggta tataagacag 960
ctgcctaagg aaacgcagat acccctgtac cttgttgttg ttgttgtttt tcactttttt 1020
aaaaaacata gagatgggat ctccttatgc tgcccaggct tgtctcaaac tcctgagctc 1080
aagcaatcct ctgacctcag actctcaaag ttttgggact acaggcgaca gtcaccatgc 1140
cagccaat 1148

<210> SEQ ID NO 353
<211> LENGTH: 1148
<212> TYPE: DNA
<213> ORGANISM: Homo sapiens

<400> SEQUENCE: 353
tatgagattt aatgttaaga aataaaatgt aggatctaaa acgtaatcta tagcataatc 60
tcaaaaatgg tttagaaatg acataataat acagacattt gtgggtggta ggattatgca 120
tatttttata tatttttaaa tatatttttc aaaagcttcc tataaagaat gtaattcttt 180
cccaattcca aatctagctt aaacataatt ttacaaaaat tattctctca gaatgtaaac 240
tagtaccacc tctatggaaa acattatgga gatttcctaa agagttaaaa gtagatctac 300
catttgatcc agcaatctta atactgggta tctacccgga ggaaaagaag tcattgtatg 360
aaaaagacac ttgtacacat atgtttacag gaccacaatt cacaaatgca aagatgcaga 420
accaacctaa gtggccactg actaatgaga ggataaagaa gatgtggcat atatatatca 480
gggactactr ctcagccatt acaaggaaca aaataatgtc ttttgcaaca acttggatag 540
agctggaggc cattattcta agtaaagtaa ttcaggaatt ggaaaaccaa aaaccgtatg 600
ttctctctta taagtgggaa ctaagttagg aataagcaaa ggcacacaga gggacatatt 660
ggactttaga gactcacgag gaggagggta ataggggact agggattaaa agaaaaacta 720
gacattaggt acaaggtacc ctacttaagt gcactaaaat ctcagaattc accactacgt 780
aattcaacta agtaacaaga aaccacttgt accccaaaag ctactgaaat aaaaattatt 840
ctctcaaaaa ttttaagccc taaacttcag ttcctattgt ttatatttac taagaaaaac 900
aacagaaaac actgttttaa aaatggtgga ttttttttaag gttaaaggta tataagacag 960
ctgcctaagg aaacgcagat acccctgtac cttgttgttg ttgttgtttt tcactttttt 1020
aaaaaacata gagatgggat ctccttatgc tgcccaggct tgtctcaaac tcctgagctc 1080
aagcaatcct ctgacctcag actctcaaag ttttgggact acaggcgaca gtcaccatgc 1140
cagccaat 1148

<210> SEQ ID NO 354
<211> LENGTH: 611
<212> TYPE: DNA
<213> ORGANISM: Homo sapiens

<400> SEQUENCE: 354
caaaacctca accttccaga taagtctaag ggtgagaact tcacacaaga tgaataagaa 60
ccaatttctt ccagggcgat gttgaacctg gaaatgaaag ccaatctctc ttggaaggcc 120
tggtttgtag aaatgtcagt ctttgtttca agctgtggga gaatgagaag caagacttta 180
gggaaagagg aataaaatag atgtgcagaa ataacagagt gagaaagtct tcagggtgtc 240
gctagcccta attgcaggca tccctgaatc ctagaccttg gattgcaaga gactccttaa 300
tatcttccca tgtccacatt tgcttcacat agtttgaatg tggcttctat tatatacaga 360
tacaagattc aaatccaacc tctaygatga ctggtcttgt gaataagcag aagaggcact 420
aacaatatga cgtgagggat tcagggaaga gcactttctt gagcacatat cttccctggt 480
ctgccagctg tagtttatga aattccacaa tgaggatgaa atggaatcac catttacaga 540
gtactctcca gatgtctaac cctaagctag gtaccttcaa aatattatct agtttagata 600
atcaaccctt t 611

<210> SEQ ID NO 355
<211> LENGTH: 601
<212> TYPE: DNA
<213> ORGANISM: Homo sapiens

<400> SEQUENCE: 355
ttctctagtc caaagggttg attatctaaa ctagataata ttttgaaggt acctagctta 60
gggttagaca tctggagagt actctgtaaa tggtgattcc atttcatcct cattgtggaa 120
tttcataaac tacagctggc agaccaggga agatatgtgc tcaagaaagt gctcttccct 180
gaatccctca cgtcatattg ttagtgcctc ttctgcttat tcacaagacc agtcatcata 240
gaggttggat ttgaatcttg tatctgtata taatagaagc cacattcaaa ctatgtgaag 300
yaaatgtgga catgggaaga tattaaggag tctcttgcaa tccaaggtct aggattcagg 360
gatgcctgca attagggcta gcgacaccct gaagactttc tcactctgtt atttctgcac 420
atctatttta ttcctctttc cctaaagtct tgcttctcat tctcccacag cttgaaacaa 480
agactgacat ttctacaaac caggccttcc aagagagatt ggctttcatt tccaggttca 540
acatcgccct ggaagaaatt ggttcttatt catcttgtgt gaagttctca cccttagact 600
t 601

<210> SEQ ID NO 356
<211> LENGTH: 527
<212> TYPE: DNA
<213> ORGANISM: Homo sapiens

<400> SEQUENCE: 356
gctctagaat atggcattcc agaagtggga tgctacaaat agtctcattg agagtcaact 60
tgcacaatgt atcgtcctac ccttacatca atttctgaaa caacttctct ttgcacttcc 120
cctatagtta catgcataat aaattctgac aactcttatg aagtcatgga ataactttct 180
tcttatgttt cctatcaatg tcattagccc tttatcttgt ttgagtttcc atcagcaatg 240
ttttcaagtc ccaagatcat tcatgtatcc acaagcaatg atacgccaga tttggacaaa 300
taatactgaa tactatctta ttttcactgc catgatcaag gcagtgtgga ttgctgccaa 360
gtccaagaga agtgaggtca gcagctgcaa gccacctccg tcatttagaa aagcttcatg 420
atgtagtgtg tcgtttcgat gtgacactgt ctcacagagt taaaatgatg tgmaaggaac 480
tgttcaatgg aaatttagaa atttctcttt ttctcaattt tagtgta 527

<210> SEQ ID NO 357
<211> LENGTH: 601
<212> TYPE: DNA
<213> ORGANISM: Homo sapiens

<400> SEQUENCE: 357
gaacaagatt ttcctgcttt taaaaatact acattaaagc tgaaaattta ggccaaaatt 60
ttcaagtggt aatagttaca ggcaattcat ctttctggtc agaaaagggt gttactgcag 120
ctatttctgc ctgaaactgg gtggcactac tacttttttt tttttttttt taactgagca 180
gacattttcc ttacactaaa attgagaaaa agagaaattt ctaaatttcc attgaacagt 240
tccttgcaca tcattttaac tctgtgagac agtgtcacat cgaaacgaca cactacatca 300
ygaagctttt ctaaatgacg gaggtggctt gcagctgctg acctcacttc tcttggactt 360
ggcagcaatc cacactgcct tgatcatggc agtgaaaata agatagtatt cagtattatt 420
tgtccaaatc tggcgtatca ttgcttgtgg atacatgaat gatcttggga cttgaaaaca 480
ttgctgatgg aaactcaaac aagataaagg gctaatgaca ttgataggaa acataagaag 540
aaagttattc catgacttca taagagttgt cagaatttat tatgcatgta actacagggg 600
a 601

<210> SEQ ID NO 358
<211> LENGTH: 1001
<212> TYPE: DNA
<213> ORGANISM: Homo sapiens

<400> SEQUENCE: 358
gcttaatacc tgagtgatgg aatattctgt tcaacaaacc cctctgacat aggtttgcct 60
atataataaa cctgttcatg tactcctgaa cctaaaagtt taaaaaagat tatgtagaaa 120
acccaaagga atctataaaa agtctactag agctagagtg attttaacaa gatttcaata 180
cacaaattca aatgtctttc tatatattaa tgacaatcaa caataaaatt ttaaaacatt 240
attaaagtat aatgaaaata tcaactgttt agggagaaat gtaacaagaa tggtgaagga 300
cctatacact aaaaagcttc aatatgttgt tgagattaac tgaagaaggt ctaaatagat 360
ttttttttca tgtctcggaa gacttaatat gtgaagatac caattcttcc ccaaatgatc 420
aacaggtgaa atgcaatccc aatcaaaatc ccagcaatta ttttaagggg gaaattggca 480
atctgattct aaaattcata yggaaaaaaa caatggagtt agaataacta aaacaagtcc 540
gaaaaagaaa aagaaatgga ggactaatgc tacctgattt caagtcttat cgtataaatc 600

-continued

```
tacatcaata aaggacaagt tggtattggg ttaaagatag ataaatacat cagtggaata    660

gaatattgaa tccagaataa atccacacat atatggataa aaataccaga caattcagtg    720

gagatggttt tgtttttaca acaaatgtta ctggaacaaa ttgatatatg tattagtcag    780

atatggctgc cataacaaag aaccacaaac aggtggttta aataatggaa ataaatttcc    840

tcagaattct ggagtatgga agcccaagat caagttgctg ggaggattcg tttcttctga    900

gtgtctcttt ttttgatgac agatgactat cttttaccaa tgtcttcact tggttttccc    960

tctgtgtgtg cctaggtcct attctccaat tcctataagg a                       1001
```

<210> SEQ ID NO 359
<211> LENGTH: 1001
<212> TYPE: DNA
<213> ORGANISM: Homo sapiens

<400> SEQUENCE: 359

```
ctaaaagttt aaaaaagatt atgtagaaaa cccaaaggaa tctataaaaa gtctactaga     60

gctagagtga ttttaacaag atttcaatac acaaattcaa atgtctttct atatattaat    120

gacaatcaac aataaaattt taaaacatta ttaaagtata atgaaaatat caactgttta    180

gggagaaatg taacaagaat ggtgaaggac ctatacacta aaaagcttca atatgttgtt    240

gagattaact gaagaaggtc taaatagatt ttttttcat gtctcggaag acttaatatg     300

tgaagatacc aattcttccc caaatgatca acaggtgaaa tgcaatccca atcaaaatcc    360

cagcaattat tttaaggggg aaattggcaa tctgattcta aaattcatat ggaaaaaaac    420

aatggagtta gaataactaa aacaagtccg aaaaagaaaa agaaatggag gactaatgct    480

acctgatttc aagtcttatc rtataaatct acatcaataa aggacaagtt ggtattgggt    540

taaagataga taaatacatc agtggaatag aatattgaat ccagaataaa tccacacata    600

tatggataaa aataccagac aattcagtgg agatggtttt gtttttacaa caaatgttac    660

tggaacaaat tgatatatgt attagtcaga tatggctgcc ataacaaaga accacaaaca    720

ggtggtttaa ataatggaaa taaatttcct cagaattctg gagtatggaa gcccaagatc    780

aagttgctgg gaggattcgt ttcttctgag tgtctctttt tttgatgaca gatgactatc    840

ttttaccaat gtcttcactt ggttttccct ctgtgtgtgc ctaggtccta ttctccaatt    900

cctataagga aaccagtcat attggattag ggcccactct aatggcccca ttttacttgc    960

attatctctt taaagacact atctccagat gtagccacac t                       1001
```

<210> SEQ ID NO 360
<211> LENGTH: 1058
<212> TYPE: DNA
<213> ORGANISM: Homo sapiens

<400> SEQUENCE: 360

```
catgattagc tatgctactt tccactgctc ttagtatact gagaggcagc ataagtaaaa     60

ctaaaatatc tgaagatagc aatagactat ttaaagtaga agaagtatgc tatttttgtt    120

ttgttttcat ttcgaaggaa atatgcaaag gtttattgag tatttcagct tctcttacag    180

taggtttttt ttggattctt tctgtgtttg tctatgttga taaaacattg aaatgccata    240

tagctcaaag gtcattcact taagaaatct aagtactgat aacatcttag ccccgattct    300

tcataggcat tgttaagcct attataattt tggtwcagag agaaggtaaa ctatattcca    360

gacaggcata taaagcaatt tctcctataa ttggagttca cgaaaaattc acatatttct    420

ttttaatagt aactctcaca gcaagaacat atgtttgtaa ataatacatc acagaatctt    480
```

```
attggcagac aaggaaattc ctaaaatatt ttttactgcc acatcaatta agatatataa    540

aataccttat atagaagatg tttgcaccca ggccaaacaa atcaaacaag aatagaagca    600

ctgacagtct tatttcaaaa ttggtttaac ttgtatttac aggatattgt agtaccttat    660

aaagttgatt gctgattggc cgtcttttac agaattctgt cagattgtta ttatttcttg    720

taaagattga ttcaaacaaa taaaaattgt caggattgga tatgtcctat agtgaggtgt    780

agttatgtca catgagattt ttaattacaa agaaatggaa aataaaatga gaatagaatt    840

gagactcccc tgtcacctca caaatatgtt gaaatacaat gaaatttcca aagatgttaa    900

agcatataaa gttgaataat tcttattatg tattaaactt acagaaattt aatttcttta    960

ctttataaga ggtagtgaaa atataaaatt aattatgaag acagagtagt cttagtcaga   1020

catggcccta taaagcatat tcccattcgt tacatcaa                           1058
```

<210> SEQ ID NO 361
<211> LENGTH: 1058
<212> TYPE: DNA
<213> ORGANISM: Homo sapiens

<400> SEQUENCE: 361

```
catgattagc tatgctactt tccactgctc ttagtatact gagaggcagc ataagtaaaa     60

ctaaaatatc tgaagatagc aatagactat ttaaagtaga agaagtatgc tatttttgtt    120

ttgttttcat ttcgaaggaa atatgcaaag gtttattgag tatttcagct tctcttacag    180

taggtttttt ttggattctt tctgtgtttg tctatgttga taaaacattg aaatgccaya    240

tagctcaaag gtcattcact taagaaatct aagtactgat aacatcttag ccccgattct    300

tcataggcat tgttaagcct attataattt tggtacagag agaaggtaaa ctatattcca    360

gacaggcata taaagcaatt tctcctataa ttggagttca cgaaaaaattc acatatttct    420

ttttaatagt aactctcaca gcaagaacat atgtttgtaa ataatacatc acagaatctt    480

attggcagac aaggaaattc ctaaaatatt ttttactgcc acatcaatta agatatataa    540

aataccttat atagaagatg tttgcaccca ggccaaacaa atcaaacaag aatagaagca    600

ctgacagtct tatttcaaaa ttggtttaac ttgtatttac aggatattgt agtaccttat    660

aaagttgatt gctgattggc cgtcttttac agaattctgt cagattgtta ttatttcttg    720

taaagattga ttcaaacaaa taaaaattgt caggattgga tatgtcctat agtgaggtgt    780

agttatgtca catgagattt ttaattacaa agaaatggaa aataaaatga gaatagaatt    840

gagactcccc tgtcacctca caaatatgtt gaaatacaat gaaatttcca aagatgttaa    900

agcatataaa gttgaataat tcttattatg tattaaactt acagaaattt aatttcttta    960

ctttataaga ggtagtgaaa atataaaatt aattatgaag acagagtagt cttagtcaga   1020

catggcccta taaagcatat tcccattcgt tacatcaa                           1058
```

<210> SEQ ID NO 362
<211> LENGTH: 956
<212> TYPE: DNA
<213> ORGANISM: Homo sapiens

<400> SEQUENCE: 362

```
aaaacaagga acaaacaaac aaaaatgtta caaccgaaca acagactttt gagtcatgtt     60

tcaggccaag aggtgatgag ttactgtagt tgcttgagct ggttggtgaa atattacctg    120

gcaacaaaac tgaaatagaa ggtggcttag taaaatgcag attcagaatg agtgccttaa    180
```

```
ggttaaggca tataagacca aactgatttt ctttttcacg aggtcttcag gtaaggccat    240

tgtagaagat accttgtttg cgaacttcag taaattactt cacttgtctc atattttcat    300

tttcaggatg gaggcttgag attgaattgt agtgcaatta ggtaaatttt tacccatttt    360

aaatataata ttaaaatatt aattataaat taccttattt gaatctggaa taatatttat    420

tgcagggcat ataatctaag ctgtaaacgt cctgtyagaa gacaacatat tcatcttgct    480

aaggtataag ctatatgact ggcactgtgc tcaactcaga gtcattgaat gaacagtatt    540

tatttaatct atgaatgaga gcacttcaag tatacagaaa gatatctcaa aagattcagc    600

cttacattgc tcataacttc aatgacttag atgaaaacct cctgaacatt tttatcagtt    660

gtataggtac cccaaatcat aagggaatgt ttatcaatta gatgatgaaa tggggatgca    720

actacatcat ggcaggctaa agcaatagaa tgactttgac aagaggaaat tacatagagg    780

cacctgagtc tcctaaacca atttcaaagg tatgagaggg gggtgatata aataaatagt    840

tgatagatga aaaaactcag aagttatagt tgacagcaat tttaatataa tatgaaaaat    900

gtggttggac ttttagggaa aaaaacctaa taaaatctaa tggaaattag tggtcc        956
```

<210> SEQ ID NO 363
<211> LENGTH: 956
<212> TYPE: DNA
<213> ORGANISM: Homo sapiens

<400> SEQUENCE: 363

```
caaccgaaca acagactttt gagtcatgtt tcaggccaag aggtgatgag ttactgtagt     60

tgcttgagct ggttggtgaa atattacctg gcaacaaaac tgaaatagaa ggtggcttag    120

taaaatgcag attcagaatg agtgccttaa ggttaaggca tataagacca aactgatttt    180

ctttttcacg aggtcttcag gtaaggccat tgtagaagat accttgtttg cgaacttcag    240

taaattactt cacttgtctc atattttcat tttcaggatg gaggcttgag attgaattgt    300

agtgcaatta ggtaaatttt tacccatttt aaatataata ttaaaatatt aattataaat    360

taccttattt gaatctggaa taatatttat tgcagggcat ataatctaag ctgtaaacgt    420

cctgtcagaa gacaacatat tcatcttgct aaggtrtaag ctatatgact ggcactgtgc    480

tcaactcaga gtcattgaat gaacagtatt tatttaatct atgaatgaga gcacttcaag    540

tatacagaaa gatatctcaa aagattcagc cttacattgc tcataacttc aatgacttag    600

atgaaaacct cctgaacatt tttatcagtt gtataggtac cccaaatcat aagggaatgt    660

ttatcaatta gatgatgaaa tggggatgca actacatcat ggcaggctaa agcaatagaa    720

tgactttgac aagaggaaat tacatagagg cacctgagtc tcctaaacca atttcaaagg    780

tatgagaggg gggtgatata aataaatagt tgatagatga aaaaactcag aagttatagt    840

tgacagcaat tttaatataa tatgaaaaat gtggttggac ttttagggaa aaaaacctaa    900

taaaatctaa tggaaattag tggtccactc atttctccac ctaggatgtt aaaaat        956
```

<210> SEQ ID NO 364
<211> LENGTH: 601
<212> TYPE: DNA
<213> ORGANISM: Homo sapiens

<400> SEQUENCE: 364

```
gtaaaacaca tagatcgctg tatccttgtt cagtaagcta caacatactc gtatctcctg     60

aaatcctggg cttaaatcga ggtctcaaag gctttgtttt gttttgttgt atggttgtat    120

ggtgagtgtg tgtgtgtgtg tgtgtgtgtg tgtttattct cctgaaattc tcctcctcac    180
```

```
ttgacttaag ctaaaagata aacgtcctct tcctttcagc cacagatggt gatggataaa    240

ttgaatgtca ttcacattat tcccttaaaa taaactctct ccctcccctc tcccgtctca    300

wccttgtccc tttctttata taatgggtaa tgcgttaatg tcagcagaat agttttgggg    360

ccataatggc aagtatcacg tggatggttt agcattgttt ttagaatgct gtgaatttgg    420

gtatatgtga gttttgggga aagttttgca actatatgtt tgttaattaa atgaggacta    480

taaagtaata taaaattatg tttctggaac atattttgga agctataaag tcatctgtat    540

ttattatcca cagacataat gtcattgttc aggtcctgca accttcttat aatcaacata    600

c                                                                    601
```

<210> SEQ ID NO 365
<211> LENGTH: 601
<212> TYPE: DNA
<213> ORGANISM: Homo sapiens

<400> SEQUENCE: 365

```
agtaagctac aacatactcg tatctcctga aatcctgggc ttaaatcgag gtctcaaagg     60

ctttgttttg ttttgttgta tggttgtatg gtgagtgtgt gtgtgtgtgt gtgtgtgtgt    120

gtttattctc ctgaaattct cctcctcact tgacttaagc taaaagataa acgtcctctt    180

cctttcagcc acagatggtg atggataaat tgaatgtcat tcacattatt cccttaaaat    240

aaactctctc cctcccctct cccgtctcat ccttgtccct ttctttatat aatgggtaat    300

kcgttaatgt cagcagaata gttttggggc cataatggca agtatcacgt ggatggttta    360

gcattgtttt tagaatgctg tgaatttggg tatatgtgag ttttggggaa agttttgcaa    420

ctatatgttt gttaattaaa tgaggactat aaagtaatat aaaattatgt ttctggaaca    480

tattttggaa gctataaagt catctgtatt tattatccac agacataatg tcattgttca    540

ggtcctgcaa ccttcttata atcaacatac gtgggcccag ggattttatg tatcttcgcc    600

t                                                                    601
```

<210> SEQ ID NO 366
<211> LENGTH: 1079
<212> TYPE: DNA
<213> ORGANISM: Homo sapiens

<400> SEQUENCE: 366

```
gaatttatgg tctgatggag aagggaatca ttaaagttct atgtagtgag atatccccaa     60

ggggtgtatt aggcttacca ccactggaat ctggatagat gaagacagag tggcagggaa    120

gtcgtattaa ggttctgttt ctgctgggag ccacaggtcc tcaggaagca acaagtactg    180

ggcagattga tactgtagct rggctctagc tctatacctc tagaataaag gttacaaact    240

agcaacttga aagctaaacc tggcccacag atatgtttta tttggctctt acactgtttt    300

aaaaaatatt accaacattt aaaactggga agttttatga aaaaacccag acttctggat    360

tctgttgaaa aaaaaaatca gaagatctgg caatactgag ctgacattcc tatatgacaa    420

caattggctg gatctatgca gcttctctcc aaaaagcaaa gaatgtgttc ttgcttaaca    480

cagtccccac cactccctca tattctccaa tcctggacct gagcgtcatt tgctatgtat    540

cgccatttgc catgaagttt tacactctac agaaatataa ttttttgta gaagactatg    600

ctttaatcaa gatcaggata atataaagtg agatctgaaa gtggaaaaaa gataaatgtc    660

caacaatgat agactggatt aagaaaatgt ggcacatata caccgtggag tactatgcag    720
```

ccaaaaaaaa cgatgagttc atgtcctttg tagggacatg gatgaagctg gaaaccacca 780
ttctcagcaa actatcgcaa ggacaaaaaa ccaaacgccg catgttctca ctcataggtg 840
ggaattgaac aatgagaaca cttgggcaca ggaaggggaa catcacacac cgggccctgt 900
tgtggggtgg ggggaggagg gagggatagc atttggagat atacctaatg ttaaatgact 960
agtttctggg tgcagcacac catcatggca catgtataca tatgtaacta acctgcacat 1020
tgtgcacatg taccctaaaa cttaaagtat aatttttaaa aaaagatatt ttcttatct 1079

<210> SEQ ID NO 367
<211> LENGTH: 501
<212> TYPE: DNA
<213> ORGANISM: Homo sapiens

<400> SEQUENCE: 367
ataaattttc tcttccctca agaatttatg gtctgatgga gaagggaatc attaaagttc 60
tatgtagtga gatatcccca aggggtgtat taggcttacc accactggaa tctggataga 120
tgaagacaga gtggcaggga agtcgtatta aggttctgtt tctgctggga gccacaggtc 180
ctcaggaagc aacaagtact gggcagattg atactgtagc tgggctctag ctctatacct 240
ctagaataaa kgttacaaac tagcaacttg aaagctaaac ctggcccaca gatatgtttt 300
atttggctct tacactgttt taaaaaatat taccaacatt taaaactggg aagttttatg 360
aaaaaaccca gacttctgga ttctgttgaa aaaaaaaatc agaagatctg gcaatactga 420
gctgacattc ctatatgaca acaattggct ggatctatgc agcttctctc caaaaagcaa 480
agaatgtgtt cttgcttaac a 501

<210> SEQ ID NO 368
<211> LENGTH: 1001
<212> TYPE: DNA
<213> ORGANISM: Homo sapiens

<400> SEQUENCE: 368
tgaagaagcc gcctggcttc ttgtttcttc tcatagcaaa atgcaatgag aaagagataa 60
tttgagaaaa gaaccgttta aacaaaaaga aaccaagaca taatgatttt ggaaattctc 120
agtttattca gactgcaaaa gatattaaaa taaagaaact cagtaacagg gatagataat 180
ctaaagaaaa agcctaggac acggctgtag taaccttctg tttttatacc tcagcaattt 240
gctaatgcct caaaaagatc aaaagtactc aaatataaag ggctctttga agagattaga 300
tttcctcaat caaaccaaag agcatcgagg aagcttaagg ttactgtccc tcacatatct 360
cagcagaagg caaaaataga agactgatta tctaagaaag atctctgaaa gagtctcata 420
ttatggagtg aacccctgtg gcatacatgg gagacccact tggttcttga gaattttata 480
tcaggagaaa cactgtcagt ytgtattgaa aggaacagag aaaatacgaa attaaagaag 540
actattaaac ctccaaaatt ctggcaggaa agaagcttac acagctactc agttgcaaag 600
atctgccact tttcatatac atgaaaggac tcagaggagg aagccacagg tttagaagga 660
aaagctaaaa gcaacatcgt attagtcttg gatctaggaa cctaatttct ctagcagaat 720
ctagaaatgg cttgggacaa gtgattgttt ttttacctag gattttctcc ctcttgaaaa 780
caggactgtc tgtaactatt atcctatgcc tgccctacca tcatatttca gaaacaggta 840
acttatgttt tcactttcaa agattcacaa taaagagaaa ttgtacctca gaatggatta 900
taccagagct ttcctcatgc ataaattaaa taatttaggt tatgtgattt gaagcttttg 960
agtgggtgag gtgacatttt ggatgctgag ttggtgccgt a 1001

<210> SEQ ID NO 369
<211> LENGTH: 1001
<212> TYPE: DNA
<213> ORGANISM: Homo sapiens

<400> SEQUENCE: 369
tcttctcata gcaaaatgca atgagaaaga gataatttga gaaaagaacc gtttaaacaa 60
aaagaaacca agacataatg attttggaaa ttctcagttt attcagactg caaaagatat 120
taaaataaag aaactcagta acagggatag ataatctaaa gaaaaagcct aggacacggc 180
tgtagtaacc ttctgttttt atacctcagc aatttgctaa tgcctcaaaa agatcaaaag 240
tactcaaata taaagggctc tttgaagaga ttagatttcc tcaatcaaac caaagagcat 300
cgaggaagct taaggttact gtccctcaca tatctcagca gaaggcaaaa atagaagact 360
gattatctaa gaaagatctc tgaaagagtc tcatattatg gagtgaaccc ctgtggcata 420
catgggagac ccacttggtt cttgagaatt ttatatcagg agaaacactg tcagtctgta 480
ttgaaaggaa cagagaaaat rcgaaattaa agaagactat taaacctcca aaattctggc 540
aggaaagaag cttacacagc tactcagttg caaagatctg ccacttttca tatacatgaa 600
aggactcaga ggaggaagcc acaggtttag aaggaaaagc taaaagcaac atcgtattag 660
tcttggatct aggaacctaa tttctctagc agaatctaga aatggcttgg gacaagtgat 720
tgttttttta cctaggattt tctccctctt gaaaacagga ctgtctgtaa ctattatcct 780
atgcctgccc taccatcata tttcagaaac aggtaactta tgttttcact ttcaaagatt 840
cacaataaag agaaattgta cctcagaatg gattatacca gagctttcct catgcataaa 900
ttaaataatt taggttatgt gatttgaagc ttttgagtgg gtgaggtgac attttggatg 960
ctgagttggt gccgtagtga gtccagaatt ctgcggaact t 1001

<210> SEQ ID NO 370
<211> LENGTH: 601
<212> TYPE: DNA
<213> ORGANISM: Homo sapiens

<400> SEQUENCE: 370
ctctagactc ctcctgtatt ttaatttagc cacttttttta gggcctacaa ttttagatct 60
ccacagggct cttgaaactt cttgaacctc atcagtaaca tgtccattag tggcatgacc 120
caagagttct agaacatcta ttcagcaagt gtgtatctgg taagtgaata ttccttctat 180
gtgttccctt ttgcatcaaa ctacacactg tcattcctcc tttatctcca aaagcttgaa 240
aattcctcac ttgtatctca ttctttctct cttagaaaac tgatcacctc tgatgaatta 300
raacggaatg accaagcttt gggagaggca aaagaatctc ggtgttaaag actcagagtt 360
taagaagcaa caaaaagatt atacagatgt gaatatgtga ccttcctcca ccagggcatg 420
ttgccttgga gtaagataat ctaagcacac acttcatagc ctgagaacaa ttttggaagt 480
ctttgcttta tggatattta cataaagcaa atatggatat ttacctaaag gctggaccaa 540
ggcctaattc ctctagagcc ccttgatcat gaacaccatt cctgtcatga ttcttaaggt 600
c 601

<210> SEQ ID NO 371
<211> LENGTH: 601
<212> TYPE: DNA
<213> ORGANISM: Homo sapiens

<400> SEQUENCE: 371
acaagctcca gccatggacg caattccttc tagaagcaaa atttatctct agactcctcc 60
tgtattttaa tttagccact tttttagggc ctacaatttt agatctccac agggctcttg 120
aaacttcttg aacctcatca gtaacatgtc cattagtggc atgacccaag agttctagaa 180
catctattca gcaagtgtgt atctggtaag tgaatattcc ttctatgtgt tcccttttgc 240
atcaaactac acactgtcat tcctccttta tctccaaaag cttgaaaatt cctcacttgt 300
rtctcattct ttctctctta gaaaactgat cacctctgat gaattagaac ggaatgacca 360
agctttggga gaggcaaaag aatctcggtg ttaaagactc agagtttaag aagcaacaaa 420
aagattatac agatgtgaat atgtgacctt cctccaccag ggcatgttgc cttggagtaa 480
gataatctaa gcacacactt catagcctga gaacaatttt ggaagtcttt gctttatgga 540
tatttacata aagcaaatat ggatatttac ctaaaggctg gaccaaggcc taattcctct 600
a 601

<210> SEQ ID NO 372
<211> LENGTH: 701
<212> TYPE: DNA
<213> ORGANISM: Homo sapiens

<400> SEQUENCE: 372
gaagatgcac tctaatgttt tttcccagaa gctctgtagg tttagctttt acctttctgg 60
gtttgttttg ttttgttttt tgagatggag tcccactcgt gtcacccagg ctggagtaca 120
atggtgcaat ctcggttcac tgcaacctcc acctcccggg ttcaagcaat tcccctgtct 180
ccacctctcg agtagctggg atgggaggcg cctgccacca tacctggcta attttcatat 240
ttttagtaaa gatagggttt caccatgtta gccaggctgg tctcgaactc ctgacctcaa 300
gtgatccacc cgcctcagct tcccaaagtg ctgggattac aggcgtgagc cactgcgccc 360
agccctagct ttttggtcta tgattcctcc caaattaatt tctgtgaacc attaccttaa 420
gatgttgaga tttaatgtcc agaatctcat ttgttcacct ttgaaaatta agaaaccctg 480
gcacagtgtt gactggagcc wcttacctta atagaaaata aagctcacat atatccataa 540
tgaaaagcag agaccagcac aaccatagtc acctgacagt tttaaaatcc aaggccagga 600
tcttctcaac tcaggcccac tcacttactc cacaacatac ttcttctttc ctcagcatct 660
actacttgtg ctgggacctt ggtcttccca ttgttcatgt c 701

<210> SEQ ID NO 373
<211> LENGTH: 701
<212> TYPE: DNA
<213> ORGANISM: Homo sapiens

<400> SEQUENCE: 373
agatggagtc ccactcgtgt cacccaggct ggagtacaat ggtgcaatct cggttcactg 60
caacctccac ctcccgggtt caagcaattc ccctgtctcc acctctcgag tagctgggat 120
gggaggcgcc tgccaccata cctggctaat tttcatattt ttagtaaaga tagggtttca 180
ccatgttagc caggctggtc tcgaactcct gacctcaagt gatccacccg cctcagcttc 240
ccaaagtgct gggattacag gcgtgagcca ctgcgcccag ccctagcttt ttggtctatg 300
attcctccca aattaatttc tgtgaaccat taccttaaga tgttgagatt taatgtccag 360
aatctcattt gttcaccttt gaaaattaag aaaccctggc acagtgttga ctggagccac 420
ttaccttaat agaaaataaa gctcacatat atccataatg aaaagcagag accagcacaa 480

```
ccatagtcac ctgacagttt waaaatccaa ggccaggatc ttctcaactc aggcccactc    540

acttactcca caacatactt cttctttcct cagcatctac tacttgtgct gggaccttgg    600

tcttcccatt gttcatgtca ttcttttcct cacagttccc attcttttct ccctgaaata    660

aagaaatttc aaaatatacc atgtttcatg aaaaagacaa a                        701
```

<210> SEQ ID NO 374
<211> LENGTH: 701
<212> TYPE: DNA
<213> ORGANISM: Homo sapiens

<400> SEQUENCE: 374

```
gatttccacc ctcaggtgat ggggatggtt gaacatccaa cacctgaaac aggacagacg     60

atattgacag tacttgttag ttgcatataa tcacagacca gtggaaacag atgaaccaca    120

cagggccaca gcggggtttc actggggaac agagtgaaca atcaggaggt gtgggaggca    180

ggtttagtag tttaaagagg ttgaggtgtc cccctggatc ccatgggagg atcacattgg    240

ctcatttgaa ttatcatacg gactggcagg gaactgaaat cttctactca gggataagca    300

gaaactgtcc ctggtttcct tgataaaaag ggttgtttga taggggacct tatccatggg    360

aggaaagtga ggagggaaat ttgtggctaa gccattcaag gccctcccag ttttactaga    420

tgtcaaggca gcacacgtaa tattgggact taattttagc cacataacta ataaatttgt    480

aagtatgtgc aacggctcac rcttgcttcc agaatggcac ctaaaaaaca gatttacctc    540

tccccaaatt cagatatgga attaaatgta atgtcaggaa aattgtctaa gagttggaaa    600

tgggaaaaaa atgttctttt ggtggagtta tggactccag aggttatcag attctattga    660

ataacgtact tttgattgta tttgtaacaa ttaggctatt t                        701
```

<210> SEQ ID NO 375
<211> LENGTH: 1001
<212> TYPE: DNA
<213> ORGANISM: Homo sapiens

<400> SEQUENCE: 375

```
gcatataatc acagaccagt ggaaacagat gaaccacaca gggccacagc ggggtttcac     60

tggggaacag agtgaacaat caggaggtgt gggaggcagg tttagtagtt taaagaggtt    120

gaggtgtccc cctggatccc atgggaggat cacattggct catttgaatt atcatacgga    180

ctggcaggga actgaaatct tctactcagg gataagcaga aactgtccct ggtttccttg    240

ataaaaaggg ttgtttgata ggggacctta tccatgggag gaaagtgagg agggaaattt    300

gtggctaagc cattcaaggc cctcccagtt ttactagatg tcaaggcagc acacgtaata    360

ttgggactta attttagcca cataactaat aaatttgtaa gtatgtgcaa cggctcacac    420

ttgcttccag aatggcacct aaaaaacaga tttacctctc cccaaattca gatatggaat    480

taaatgtaat gtcaggaaaa ytgtctaaga gttggaaatg ggaaaaaaat gttcttttgg    540

tggagttatg gactccagag gttatcagat tctattgaat aacgtacttt tgattgtatt    600

tgtaacaatt aggctatttg tgaactcggt aggggtagaa atcgagttgt agaaaatgga    660

tggtaatgca agtgattttt gaccatatca atgcaaatga attctgttgg tagaaatatt    720

catttccaca ctgtagatga ccctaaacat atgtcattac attatatttt attgccttat    780

agactattaa ccaattttga atcatacagt agcaaattta tttcagcatt cttgtgtgta    840

tgtgtttata tatacacgtg catatgtatt taagatatat aattgtatat tcttcaaatt    900
```

cttctttgaa caggtttgaa cctcttatta gtttcctcat taaggaattt aataagacct 960
ttaatgcatg tttgtatttt catgagagtc attattttac c 1001

<210> SEQ ID NO 376
<211> LENGTH: 695
<212> TYPE: DNA
<213> ORGANISM: Homo sapiens

<400> SEQUENCE: 376
tgctccttca ttagtgcaat ggaacagcaa atcaggatac tttcacagtt ctcttaagtg 60
agcctagaag tggggagctg cttgttcaca aacttgaagc ctgaatatgt taatattctt 120
tcagtggccg gacgcggtgg ctcatgcctg taatcccaac actttgggag gccgaggtag 180
gcagatcaac ctgaagtcag gagttcgagg ccagcctggc caacatggtg aaaccccacc 240
tgttggtctg tactaaaaat agaaaaatta gctgggcatg gtggcgcatg cctgtaatcc 300
cagctactca ggaggctgtg gcagaagaat cgcctgcacc tgggaggcag aggttgcttt 360
gagttgatat cgtgtcactg cactccagcc tgggcaacag agtgagatcc tttcagaaac 420
ctgctgtctg tatttggata caattaaaaa aaaaaaaaag atgagacagg caggtgcgaa 480
agaaataaaa gtcamaactg atccagttgg gaaactcaga attgacagtt acgtgtcctt 540
tcatttattg atattttgag attcacaggg gtttaaactt tatttttcca agactgaata 600
gttcccacct cccttccata tataaaattt gagtagctgg ggagatttaa aagaggctcc 660
ccataaactc agaagttaaa agagacaagg gtccc 695

<210> SEQ ID NO 377
<211> LENGTH: 601
<212> TYPE: DNA
<213> ORGANISM: Homo sapiens

<400> SEQUENCE: 377
aaccccacct gttggtctgt actaaaaata gaaaaattag ctgggcatgg tggcgcatgc 60
ctgtaatccc agctactcag gaggctgtgg cagaagaatc gcctgcacct gggaggcaga 120
ggttgctttg agttgatatc gtgtcactgc actccagcct gggcaacaga gtgagatcct 180
ttcagaaacc tgctgtctgt atttggatac aattaaaaaa aaaaaaaaga tgagacaggc 240
aggtgcgaaa gaaataaaag tcacaactga tccagttggg aaactcagaa ttgacagtta 300
sgtgtccttt catttattga tattttgaga ttcacagggg tttaaacttt attcttccaa 360
gactgaatag ttcccacctc ccttccatat ataaaatttg agtagctggg gagatttaaa 420
agaggctccc cataaactca gaagttaaaa gagacaaggg tcccagtaaa tacaaaatga 480
ttggggttga ggaggcagat tttctgtcct cagtgaagtt tgttggttgg ttggttggtt 540
ggttggttaa ttggttggtt tttgagtcag ggtctcactt tgtcacccaa gctggagtgc 600
a 601

<210> SEQ ID NO 378
<211> LENGTH: 663
<212> TYPE: DNA
<213> ORGANISM: Homo sapiens

<400> SEQUENCE: 378
tgtagcaaca ggagggatga gacccaaagg tctgaaaagc cagtatttta agaagtcttg 60
gaaaatgtgg aggttgaaaa atctaacagg agtgcttgct tcagcagcaa tttagagtag 120
attagcatgg cctctgcgcc aggatgacat gcacattcct aaaagtgttc cgtgttttaa 180
aaaaaagaga gagacagaat ctaaggggat gtgtacattt gctagagcta ctataacaaa 240
gtaccagagg cagggtcact tcaacaacag aaatttattt ctcacagttc tggaggctag 300
acgtccaaga ttaaggtgtt gactgggttg aattcagccc ataacaggaa ataaggagtt 360
aaataaagca cttgcttcta ttgtttgtac ctaaacttaa cagaayacag taagtaacaa 420
gtcattggga tgcagaaaag aaaaaagaga gtgaaggaag gagagaaggt gaagggagaa 480
tggaagagag gaagggaggg aggaaagaaa agtttgatga atgattgcag tctaaactgg 540
ttcaaacaag agatcttgtt taattaagga attcatccca tctctgccta ttaggaggag 600
gaaaaagtct aaaatagaag atggtgaaag ttggatgacc ccaggcatta aggccattca 660
tct 663

<210> SEQ ID NO 379
<211> LENGTH: 662
<212> TYPE: DNA
<213> ORGANISM: Homo sapiens

<400> SEQUENCE: 379
ttaagaagtc ttggaaaatg tggaggttga aaaatctaac aggagtgctt gcttcagcag 60
caatttagag tagattagca tggcctctgc gccaggatga catgcacatt cctaaaagtg 120
ttccgtgttt taaaaaaaag agagagacag aatctaaggg gatgtgtaca tttgctagag 180
ctactataac aaagtaccag aggcagggtc acttcaacaa cagaaattta tttctcacag 240
ttctggaggc tagacgtcca agattaaggt gttgactggg ttgaattcag cccataacag 300
gaaataagga gttaaataaa gcacttgctt ctattgtttg tacctaaact taacagaaca 360
cagtaagtaa caagtcattg ggatgcagaa aagaaaaaag agagtgaagg aaggagaraa 420
ggtgaaggga gaatggaaga gaggaaggga gggaggaaag aaaagtttga tgaatgattg 480
cagtctaaac tggttcaaac aagagatctt gtttaattaa ggaattcatc ccatctctgc 540
ctattaggag gaggaaaaag tctaaaatag aagatggtga aagttggatg accccaggca 600
ttaaggccat tcatctttaa ctgttatgct tggatcatgc aaatgtgtct ggtagctaca 660
ag 662

<210> SEQ ID NO 380
<211> LENGTH: 615
<212> TYPE: DNA
<213> ORGANISM: Homo sapiens

<400> SEQUENCE: 380
ttccatacat tccttccaca ccattgccct taacctttca aattcctgct taaaactaat 60
cccattttta tggctgacct caccctgtat caaaaactcc gacatccctt tacgacagag 120
agcacaaact agtggtccaa aatgtcatgg gggtcttctc agagttgttt tttcaatcag 180
gaaatttcac ataaaaatat ggatttctga tttctctttt aaaaacagaa aaacgagcca 240
ccagtgggag cactgcaggt atctgtgtga gaccygtact tcacaactcc tgctttccct 300
ccataaagta gcttgcattt tccacattga ctttgcagtt ctttggtatc tgtattggtt 360
ttaagataat ttctactata tcacatatct cctcacagta caaagatatc attttctttc 420
ccttttcttt ttaaaaaatt tgtattttta atttttgtgg gtacacagta gatatttatg 480
gggcatatga ggtattttat aggcatataa tatgtactag ggtaagtggg gtattcatca 540
cctcaagcat ttatcctttc tttgtgtaaa atatagcatt ttctgaacac tatgaatact 600
taagtacaag gatca 615

<210> SEQ ID NO 381
<211> LENGTH: 994
<212> TYPE: DNA
<213> ORGANISM: Homo sapiens

<400> SEQUENCE: 381
tcaaagtgta acaaatttcc tttcctcata aactagcaga cattctatcc cctcattatt 60
gtaacacatt tctaatatct ttctcaaatt gtcttcctgt attacaatgc actcaccttg 120
gcttagaatg tctgagacaa gaaaatctat tcaccattcc cacagatgac tccctcactc 180
tcctcccaag tcttccatac attccttcca caccattgcc cttaaccttt caaattcctg 240
cttaaaacta atcccatttt tatggctgac ctcaccctgt atcaaaaact ccgacatccc 300
tttacgacag agagcacaaa ctagtggtcc aaaatgtcat gggggtcttc tcagagttgt 360
tttttcaatc aggaaatttc acataaaaat atggatttct gatttctctt ttaaaaacag 420
aaaaacgagc caccagtggg agcactgcag gtatctgtgt gagacctgta cttcacaact 480
cctgctttcc ctccataaag yagcttgcat tttccacatt gactttgcag ttctttggta 540
tctgtattgg ttttaagata atttctacta tatcacatat ctcctcacag tacaaagata 600
tcattttctt tccctttctt ttttaaaaaa tttgtatttt taatttttgt gggtacacag 660
tagatattta tggggcatat gaggtatttt ataggcatat aatatgtact agggtaagtg 720
gggtattcat cacctcaagc atttatcctt tctttgtgta aaatatagca ttttctgaac 780
actatgaata cttaagtaca aggatcaagt cataggattt ggaattgatt tttaaaatat 840
gttgaccaaa gtgctcttat catcaaactt aacatcacta atgaaggatg aacatcccaa 900
atctgaaaat ccaaaatcca aaatgctcca taatctaaaa cttgttgagc accaacatga 960
tgcttaaagg aaatgctcct ggagcatttc agat 994

<210> SEQ ID NO 382
<211> LENGTH: 1001
<212> TYPE: DNA
<213> ORGANISM: Homo sapiens

<400> SEQUENCE: 382
ctatgagaaa tatttttaaa gtggttagga acaattcata gcactgacat gttatcagta 60
aaaatagaag aaaataaatt aatattatga aatattaatt atatttcatt aattatgtaa 120
tatgaattat gttttagctc aaatatttcc caagggacaa ttaagtaaat gaaaaataca 180
cacagattaa aataataaat agagaaggag atattaatga ggtacaaaaa gaaaaaatac 240
atgtaatcac atgaaatgct attatttgaa agattaacaa aacttgtaaa ctacctgcta 300
acttgatcaa agaaaaaaat cgagaaacca tatgcgcaat taatagtaag agggaaataa 360
acattgaaac agaagacatt tgaaatacca tataagactg ggtttcagag ctctatgtac 420
gtaaattgat aatgtcctgg agaagtgcag atgaccaaaa tggacacctt tcaacttaga 480
aatcataaac agattcattt ycttaaagtt aatgaaaaga attaacagac cctcctcaaa 540
aaagacatat atgcggccta caatcatatg aaaaaaagtt caacattact gttcattaga 600
gaaatgcaaa tcaaaaccac aatgagatac catctcacac cagtcagaat ggctattatt 660
aagaagtcaa aaaataaaag atgctggcga ggttgtggag aaaaaagaat gcttttatac 720
acttggtggg aatgtaaatt agttcagtca ttgtggaaga ctttgatgat tcctagaaga 780
cctaaataca gaactactat ttgacccaac aatcccatta ctgggtatat actcaaatga 840
ctataaatca ttctattata aagacacatg catggatatg ttcattacag cactatgcac 900
aatagcaaag acttggaatc aacatgaatg tccatcaatg atagactaga taaagaaaat 960
gtggtacaca tataccatgg aatactatgc agccataaaa a 1001

<210> SEQ ID NO 383
<211> LENGTH: 1001
<212> TYPE: DNA
<213> ORGANISM: Homo sapiens

<400> SEQUENCE: 383
tcagtaaaaa tagaagaaaa taaattaata ttatgaaata ttaattatat ttcattaatt 60
atgtaatatg aattatgttt tagctcaaat atttcccaag ggacaattaa gtaaatgaaa 120
aatacacaca gattaaaata ataaatagag aaggagatat taatgaggta caaaaagaaa 180
aaatacatgt aatcacatga aatgctatta tttgaaagat taacaaaact tgtaaactac 240
ctgctaactt gatcaaagaa aaaaatcgag aaaccatatg cgcaattaat agtaagaggg 300
aaataaacat tgaaacagaa gacatttgaa ataccatata agactgggtt tcagagctct 360
atgtacgtaa attgataatg tcctggagaa gtgcagatga ccaaaatgga cacctttcaa 420
cttagaaatc ataaacagat tcatttcctt aaagttaatg aaaagaatta acagaccctc 480
ctcaaaaaag acatatatgc rgcctacaat catatgaaaa aaagttcaac attactgttc 540
attagagaaa tgcaaatcaa aaccacaatg agataccatc tcacaccagt cagaatggct 600
attattaaga agtcaaaaaa taaaagatgc tggcgaggtt gtggagaaaa aagaatgctt 660
ttatacactt ggtgggaatg taaattagtt cagtcattgt ggaagacttt gatgattcct 720
agaagaccta aatacagaac tactatttga cccaacaatc ccattactgg gtatatactc 780
aaatgactat aaatcattct attataaaga cacatgcatg gatatgttca ttacagcact 840
atgcacaata gcaaagactt ggaatcaaca tgaatgtcca tcaatgatag actagataaa 900
gaaaatgtgg tacacatata ccatggaata ctatgcagcc ataaaaatga aggagatcat 960
gccctttgca gggacacgaa tagaggtgga ggccattatc c 1001

<210> SEQ ID NO 384
<211> LENGTH: 501
<212> TYPE: DNA
<213> ORGANISM: Homo sapiens

<400> SEQUENCE: 384
agttgcttga aagcaaagtt ctcgcagtag ctctctatct agaaggaggc attttattta 60
tgtaaggaag tcacctaaaa gaaaattcat ttgttatggt gtggctttaa gagttactta 120
cttttaatgg aatcccccag ataataataa attctgaaaa aaaaaaatca gaatcatggc 180
atgttaaaac tggatacatt cctagaaata gatggaaact gctcttgcaa aaagcttagc 240
acatgttaaa rcattttaga aacaatttgc caaagtttat ttagtctagt gatttcgaca 300
ggttaaatgg accctttgag atcttttttc ctcaagtaca aaggctcact tgcttaatga 360
acacagtccc agaaaagcag gggctgaac cttggctcta ccatcttacc taagattcta 420
gagttagcaa agggtttcca caagcccaaa ttattatgtt taatcttttc aattatctgt 480
gaagcattag gttggtgcaa a 501

<210> SEQ ID NO 385
<211> LENGTH: 501
<212> TYPE: DNA

<213> ORGANISM: Homo sapiens

<400> SEQUENCE: 385
gaggcatttt atttatgtaa ggaagtcacc taaaagaaaa ttcatttgtt atggtgtggc 60
tttaagagtt acttactttt aatggaatcc cccagataat aataaattct gaaaaaaaaa 120
aatcagaatc atggcatgtt aaaactggat acattcctag aaatagatgg aaactgctct 180
tgcaaaaagc ttagcacatg ttaaagcatt ttagaaacaa tttgccaaag tttatttagt 240
ctagtgattt ygacaggtta aatggaccct ttgagatctt ttttcctcaa gtacaaaggc 300
tcacttgctt aatgaacaca gtcccagaaa agcagggggc tgaaccttgg ctctaccatc 360
ttacctaaga ttctagagtt agcaaagggt ttccacaagc ccaaattatt atgtttaatc 420
ttttcaatta tctgtgaagc attaggttgg tgcaaaagta actgcaggtt ttgacattaa 480
aactggcaaa aactgcaata a 501

<210> SEQ ID NO 386
<211> LENGTH: 703
<212> TYPE: DNA
<213> ORGANISM: Homo sapiens

<400> SEQUENCE: 386
gacaccagtt agcatattgt cgcgggggag aggggtggga aaggcgagag aacagcatgt 60
ggtccagagg ccatacccag atggaggctg cagtcagctc cccagtcaaa ggcaaagccc 120
aagtcaaagc catgcttccc tcttgcccac ctgctccaat gccacccaca gagagtgcgc 180
cacagctcac aggatgcagg tctggttgaa tcttaacaat aactttgtaa gggaggtgtc 240
attagctcca ttctcctggc aggaggatga ggctcaaggc agctaaaggc ttttgctgaa 300
catcaagtgg tgagccagga ctcaawgcca gatcttcttg tttccctgtt aggtgtatgt 360
agcacaactg gtatctgcag actatgctgc tggaagggct agccgtcact gttatcacag 420
cgactgctgc ctgagatatg ccaggtactg ctgcaagaag tttacaaata taagctcact 480
tgatcttcat aacatactac ctaggtacaa tcattatatt tatttgacag atacagagac 540
agaggggaca cagaaaggat tagtaacttg ccccaaacca cacagccagc aaggtgtaag 600
tgagcacctg cagtctagat gagacaccac tcaaaacgtc atttttctgg cagccccgtg 660
cagttaccac agtggtcacc ccagtggtca gctaaaggcc aag 703

<210> SEQ ID NO 387
<211> LENGTH: 704
<212> TYPE: DNA
<213> ORGANISM: Homo sapiens

<400> SEQUENCE: 387
gcatattgtc gcgggggaga ggggtgggaa aggcgagaga acagcatgtg gtccagaggc 60
catacccaga tggaggctgc agtcagctcc ccagtcaaag gcaaagccca agtcaaagcc 120
atgcttccct cttgcccacc tgctccaatg ccacccacag agagtgcgcc acagctcaca 180
ggatgcaggt ctggttgaat cttaacaata actttgtaag ggaggtgtca ttagctccat 240
tctcctggca ggaggatgag gctcaaggca gctaaaggct tttgctgaac atcaagtggt 300
gagccaggac tcaatgccag atcttcttgt ttccctgtta ggtgtwtgta gcacaactgg 360
tatctgcaga ctatgctgct ggaagggcta gccgtcactg ttatcacagc gactgctgcc 420
tgagatatgc caggtactgc tgcaagaagt ttacaaatat aagctcactt gatcttcata 480
acatactacc taggtacaat cattatattt atttgacaga tacagagaca gaggggacac 540
agaaaggatt agtaacttgc cccaaaccac acagccagca aggtgtaagt gagcacctgc 600
agtctagatg agacaccact caaaacgtca tttttctggc agccccgtgc agttaccaca 660
gtggtcaccc cagtggtcag ctaaaggcca agcccaccgt ttct 704

<210> SEQ ID NO 388
<211> LENGTH: 975
<212> TYPE: DNA
<213> ORGANISM: Homo sapiens

<400> SEQUENCE: 388
gacttaagac aagggggtct taatttgatt attttttttct gttttatatg atttctatga 60
aaactacaac aaaataaagt taattctatt taagtgactt tttaatgaat tgcctttgtt 120
agaaaaaaaa ttaagtgttt ttgtctcact ctgtcaccca ggctggagca cagtggtgtg 180
atcatggctt actgcagcca tgacctcccg ggctcaggtg atcctcccac ctcagcttcc 240
caaatagatg ggactacagt tgtgtgccac aacgcctggc taatttttgt atttttttgt 300
agagacaggg tctcaccagg ttgcccaggc tgatcttgaa ctccttggct caagcgatcc 360
acccacctca gcctccctga gtgctgggat tacaggcatg agccagcgca cccagccaga 420
attacatttt tttaaatggt actgtcctag aaaatccagg atgtgcagtg atcaygtatg 480
aatgcatgga cctgcacaca caggagtgaa caaaagaccc acccctgcca ggtcaccact 540
catatctcac cccagcccac gctagctcac actcctcccc acacaccact gacctcatca 600
ttgctaggta cccacttgac ttctcaacag gttcaagaca attggccttc ctcgtctctt 660
ctagaaacac cctcttttct gggctttgtg taacacctgg tctttctccc ctctctggcc 720
acttctcagc ttttcttttt ctttctttct tttttttttt tttttttttg ccacttcctc 780
ttcctctaca tcaagcttgt ccaacccaca gcccaggaca gctttgaatg cagcctaaca 840
caaattcgta agctttctta aaacattatg agatgtgtgt gtgtgtgtgt gtgtgtgtgt 900
gtgtgtgtgt gtgtgtgtgt gtttagctca tcagctatcg ttattgttag tgtattttat 960
gtgtggccca agaca 975

<210> SEQ ID NO 389
<211> LENGTH: 976
<212> TYPE: DNA
<213> ORGANISM: Homo sapiens

<400> SEQUENCE: 389
gactttttaa tgaattgcct ttgttagaaa aaaaattaag tgtttttgtc tcactctgtc 60
acccaggctg gagcacagtg gtgtgatcat ggcttactgc agccatgacc tcccgggctc 120
aggtgatcct cccacctcag cttcccaaat agatgggact acagttgtgt gccacaacgc 180
ctggctaatt tttgtatttt tttgtagaga cagggtctca ccaggttgcc caggctgatc 240
ttgaactcct tggctcaagc gatccaccca cctcagcctc cctgagtgct gggattacag 300
gcatgagcca gcgcacccag ccagaattac attttttttaa atggtactgt cctagaaaat 360
ccaggatgtg cagtgatcac gtatgaatgc atggacctgc acacacagga gtgaacaaaa 420
gacccacccc tgccaggtca ccactcatat ctcaccccag cccacgctag ctcacrctcc 480
tccccacaca ccactgacct catcattgct aggtacccac ttgacttctc aacaggttca 540
agacaattgg ccttcctcgt ctcttctaga aacaccctct tttctgggct ttgtgtaaca 600
cctggtcttt ctcccctctc tggccacttc tcagcttttc tttttctttc tttcttttt 660

-continued

```
tttttttttt ttttgccact tcctcttcct ctacatcaag cttgtccaac ccacagccca    720

ggacagcttt gaatgcagcc taacacaaat tcgtaagctt tcttaaaaca ttatgagatg    780

tgtgtgtgtg tgtgtgtgtg tgtgtgtgtg tgtgtgtgtg tgtgtgttta gctcatcagc    840

tatcgttatt gttagtgtat tttatgtgtg gcccaagaca tttcttcttc cagtgtggcc    900

cagggaagcc aaaagattgg acacccctgc tctacaacat ctcaatatag gcctttttca    960

tgtttcattc tagatt                                                    976
```

<210> SEQ ID NO 390
<211> LENGTH: 801
<212> TYPE: DNA
<213> ORGANISM: Homo sapiens

<400> SEQUENCE: 390

```
atccagacgg tgcccatact ccctgctctg tctagatggt gtccacattc cctgctccgt     60

ctagactgtg cccatattcg ctgctggctg caaatgcgag gagttgacag cagcctcccc    120

tttacaaggc aggaggtgcc actgttcgcc attgtctcca cctagggctt cacttgcttt    180

ctatctgcag acatcagagg gacccacatc tctctgttct gacacgctgt gtgttgatgg    240

cagagtttaa ttatccacat gcaatcttac tttccttatt cccaagtccg tggggctgcc    300

tcatcaaagc attgtaagaa ctgataacca tcttctagaa gtatcatagt gatattaaga    360

acacacatca cagatcatag taaatggctt taatttttta rcgaaatctc actactgcaa    420

atgcattgtt gtcctagcta atgaatgcat agagtattgc ctgcaaaata ataattgaga    480

ttctattttt aagaagctta gaacagtaca tggtgcatag caaagactct gtgtatgtga    540

agccagattt taaaatatgg taacaagtgt ctgaaaatat gtggctcaat ttgtctcccg    600

gttacttttc cctctccccc tttaaaatgt agaggaagga gaagaagaga taagaggttt    660

gtgagtgaag acaagggccc tttaaggcct gggaagacta acgccatagg gatctccctc    720

tgccttaaaa ggcacaggaa tcttagtggg gaaaaagaag tggtgataaa tagccagtcc    780

gtgtgcctgg aatatcaaag t                                              801
```

<210> SEQ ID NO 391
<211> LENGTH: 801
<212> TYPE: DNA
<213> ORGANISM: Homo sapiens

<400> SEQUENCE: 391

```
ccctgctccg tctagactgt gcccatattc gctgctggct gcaaatgcga ggagttgaca     60

gcagcctccc ctttacaagg caggaggtgc cactgttcgc cattgtctcc acctagggct    120

tcacttgctt tctatctgca gacatcagag ggacccacat ctctctgttc tgacacgctg    180

tgtgttgatg gcagagttta attatccaca tgcaatctta ctttccttat tcccaagtcc    240

gtggggctgc ctcatcaaag cattgtaaga actgataacc atcttctaga agtatcatag    300

tgatattaag aacacacatc acagatcata gtaaatggct ttaatttttt agcgaaatct    360

cactactgca aatgcattgt tgtcctagct aatgaatgca yagagtattg cctgcaaaat    420

aataattgag attctatttt taagaagctt agaacagtac atggtgcata gcaaagactc    480

tgtgtatgtg aagccagatt ttaaaatatg gtaacaagtg tctgaaaata tgtggctcaa    540

tttgtctccc ggttactttt ccctctcccc ctttaaaatg tagaggaagg agaagaagag    600

ataagaggtt tgtgagtgaa gacaagggcc ctttaaggcc tgggaagact aacgccatag    660

ggatctccct ctgccttaaa aggcacagga atcttagtgg ggaaaaagaa gtggtgataa    720
```

atagccagtc cgtgtgcctg gaatatcaaa gtcagtgcgt gccagggatc acactgcggg 780
tcacgtgcac tctgggtctc t 801

<210> SEQ ID NO 392
<211> LENGTH: 601
<212> TYPE: DNA
<213> ORGANISM: Homo sapiens

<400> SEQUENCE: 392
ttggcctggg gctgattcct ccaaagcaat gtgtctcttc gcagagtctc ttagagctgc 60
aaggcagtat gggatcatca gagaggatgc taggaagctt cagaaatgga ggtcctggta 120
gaaagggtcc tttggcgtgg cctctgaaga gtccaaatgt gggacaagac cctccgaaag 180
cggtggcctg gggagccaca ggtggggcag ccagcacgga agagggtggc tttgctacca 240
ttgggaaaac ttatcctcca catcctcatg aggcaaacac ctttcctacc ttaccgctcc 300
ycagtggcct ccctgttgcc ttcttattca agactaagac cctctagaat gttctttatc 360
ctgagtccag ctgattgtct atactaatat cagtacgggg tgtagatgag gacaaccagt 420
gtgcctggct gccaggcacc ccctccccaa accccaggag tttctggaac attccaactc 480
tgcttgaggg tatccatgca gcatctacta ctgtgagcag gtggtctgat ctgtggaaaa 540
cttctatgat tcacctgagg gtaactgccc tttgtgattt gaaagaatga tgctaacaga 600
a 601

<210> SEQ ID NO 393
<211> LENGTH: 601
<212> TYPE: DNA
<213> ORGANISM: Homo sapiens

<400> SEQUENCE: 393
gcagagtctc ttagagctgc aaggcagtat gggatcatca gagaggatgc taggaagctt 60
cagaaatgga ggtcctggta gaaagggtcc tttggcgtgg cctctgaaga gtccaaatgt 120
gggacaagac cctccgaaag cggtggcctg gggagccaca ggtggggcag ccagcacgga 180
agagggtggc tttgctacca ttgggaaaac ttatcctcca catcctcatg aggcaaacac 240
ctttcctacc ttaccgctcc tcagtggcct ccctgttgcc ttcttattca agactaagac 300
yctctagaat gttctttatc ctgagtccag ctgattgtct atactaatat cagtacgggg 360
tgtagatgag gacaaccagt gtgcctggct gccaggcacc ccctccccaa accccaggag 420
tttctggaac attccaactc tgcttgaggg tatccatgca gcatctacta ctgtgagcag 480
gtggtctgat ctgtggaaaa cttctatgat tcacctgagg gtaactgccc tttgtgattt 540
gaaagaatga tgctaacaga aagtgttgtc atttctgaac ttttctgaac tctgcagcga 600
g 601

<210> SEQ ID NO 394
<211> LENGTH: 1001
<212> TYPE: DNA
<213> ORGANISM: Homo sapiens

<400> SEQUENCE: 394
agatttggat ggggacacaa aaccaaacca tatcataggt taaattgtgt ctcccacccc 60
aaaaatgtgt atgttgaagt cctaaccttc agtactcaga atgtgacatt atttggaaat 120
agggtcattg cagatggagt tagttaagat gaggtcatta ggatgagtcc ctaatccaat 180

```
atgactggtg ctcttacaaa aaggggaagt ttggacacag agccatgcac atgggtggga    240
agaatcccaa atgaacggat aggcagaggg ttggagagat gcatcaacaa ggaacaccaa    300
agattgccag caacccccag aagctggggg agaggcctgg aacagattct ccctcacagc    360
ctgagaggaa ccaagctggc tgacaccttg atctcaggtt accggccttg agaactgaga    420
gaccctgggt ttctgttgtt taagcctctc agggtgcagc actttattat ggaagcctga    480
gctgactaat acaggtgtct ytatatctca ctgagggaaa gtgacaggaa agtaagaacc    540
atttatgtcc aagagtccag aggagtcaac cagattctgg gggaaaagaa ggtacaatgc    600
tggcctctcc atgcagccta gtccccaaca cttgtagggc ccagggcaag atctaaagca    660
ctctctcacc tatgcatcta tatgctgtaa ctcagataaa caaactatta aataatatat    720
gtgtcttgcc tctcaatctg acaattacac ctttataata gcaacatagg aaaataacta    780
aaactatggt ttttaggcaa ccaaatacca gcaaaatgta ataattccta ttattagata    840
tgtttaagtg ttctgctggt gggtcagcat ctttggtaga gtcataaaat taaaatgtac    900
ataattaatt aaatattata tgtttattcc ctaacattta tttctgtcat ttcttttttc    960
tttttttcag acagtctcac tcttttgccc aggccggagt g                       1001
```

<210> SEQ ID NO 395
<211> LENGTH: 1001
<212> TYPE: DNA
<213> ORGANISM: Homo sapiens

<400> SEQUENCE: 395

```
ttgtgtctcc caccccaaaa atgtgtatgt tgaagtccta accttcagta ctcagaatgt     60
gacattattt ggaaataggg tcattgcaga tggagttagt taagatgagg tcattaggat    120
gagtccctaa tccaatatga ctggtgctct tacaaaaagg ggaagtttgg acacagagcc    180
atgcacatgg gtgggaagaa tcccaaatga acggataggc agagggttgg agagatgcat    240
caacaaggaa caccaaagat tgccagcaac ccccagaagc tgggggagag gcctggaaca    300
gattctccct cacagcctga gaggaaccaa gctggctgac accttgatct caggttaccg    360
gccttgagaa ctgagagacc ctgggtttct gttgtttaag cctctcaggg tgcagcactt    420
tattatggaa gcctgagctg actaatacag gtgtctctat atctcactga gggaaagtga    480
caggaaagta agaaccattt rtgtccaaga gtccagagga gtcaaccaga ttctggggga    540
aaagaaggta caatgctggc ctctccatgc agcctagtcc ccaacacttg tagggcccag    600
ggcaagatct aaagcactct ctcacctatg catctatatg ctgtaactca gataaacaaa    660
ctattaaata atatatgtgt cttgcctctc aatctgacaa ttacaccttt ataatagcaa    720
cataggaaaa taactaaaac tatggttttt aggcaaccaa ataccagcaa aatgtaataa    780
ttcctattat tagatatgtt taagtgttct gctggtgggt cagcatcttt ggtagagtca    840
taaaattaaa atgtacataa ttaattaaat attatatgtt tattccctaa catttatttc    900
tgtcatttct tttttctttt tttcagacag tctcactctt ttgcccaggc cggagtgcag    960
tggcgtgatc tcagctcact gcaacctccg cctcccaggt t                       1001
```

<210> SEQ ID NO 396
<211> LENGTH: 1218
<212> TYPE: DNA
<213> ORGANISM: Homo sapiens

<400> SEQUENCE: 396

```
gataaagaaa ggtcatcctc aatttcaatt tactttatat attctttgag aggtaaccgt     60
```

```
gtcttatctc cccccaaaat tccttttaaa aggaaatttc caaagatgct ctattctgtg    120
aataaagcat tgtgccacag ccgagaggat ccagcaatga acatgagatt gcccttgatt    180
cataaggtct acaagctagt aaggatagag aacactttaa aataaaaaaa aatagttttt    240
ggtatattta tattgtgtat ttggtataat tgagttttct acattctcat atatgtattt    300
catattttga agaatatgca gaaaataatc aagcttccaa ataaacattt tttttaaga     360
actgcacaag tgagaattta ggagaacaga agatcagagg gctgcacrgg ctaaactaga    420
caatgagccc atgcaagtaa gttaagagga gaagcgggta agtatgcacc tgctttgtct    480
aggtgaccag caagcattta gcaatagtct tttcaaaaca acagctcctt atattgtcaa    540
atctcaagaa gtaatattta tggttaaaaa aatctcagac ccaacagaaa atccatgagg    600
gagatggttt tggaaacgca gaattttcag ctatgatatc cttttataaa caagcagata    660
ctttccccaa atataattca atgcctcagt ctacctcctg ctgaaaccac taacaccacc    720
actaaagctc gactatatgg gaaaatttag gtgtcacttt caaaatatgt cctagcataa    780
aggcaattaa aaaatgtaaa gcaccaaaga tgcaagagag acataaatga ataaaatatc    840
tggcacgaaa gttttcaaaa gcttgggaat ctgattcaaa aaaaaataaa atcagccaag    900
cagtgttagt aagttagcca atcaggtttc aagaaggcag aaagacaaaa tcaacatcac    960
cagcatttga caccgctact gggggaaaaa agggggatgg agttcgttta tggccttttt   1020
aaaaatgcca ttacttggac aagagtcata acagagaagc actgcttatt tcagttctgt   1080
taactgtaaa tatcagagcc aacacccaga aaaagttcac cattagccaa ttggttttgc   1140
ctggccaatt ggagatggta ataggcctgc tatggatgac attctttctg atataagttg   1200
tttcttgctt tttctccc                                                 1218
```

<210> SEQ ID NO 397
<211> LENGTH: 1218
<212> TYPE: DNA
<213> ORGANISM: Homo sapiens

<400> SEQUENCE: 397

```
gataaagaaa ggtcatcctc aatttcaatt tactttatat attctttgag aggtaaccgt     60
gtcttatctc cccccaaaat tccttttaaa aggaaatttc caaagatgct ctattctgtg    120
aataaagcat tgtgccacag ccgagaggat ccagcaatga acatgagatt gcccttgatt    180
cataaggtct acaagctagt aaggatagag aacactttaa aataaaaaaa aatagttttt    240
ggtatattta tattgtgtat ttggtataat tgagttttct acattctcat atatgtattt    300
catattttga agaatatgca gaaaataatc aagcttccaa ataaacattt tttttaaga     360
actgcacaag tgagaattta ggagaacaga agatcagagg gctgcacggg ctaaactaga    420
caatgagccc atgcaagtaa gttaagagga gaagcgggta agtatgcacc tgctttgtct    480
aggwgaccag caagcattta gcaatagtct tttcaaaaca acagctcctt atattgtcaa    540
atctcaagaa gtaatattta tggttaaaaa aatctcagac ccaacagaaa atccatgagg    600
gagatggttt tggaaacgca gaattttcag ctatgatatc cttttataaa caagcagata    660
ctttccccaa atataattca atgcctcagt ctacctcctg ctgaaaccac taacaccacc    720
actaaagctc gactatatgg gaaaatttag gtgtcacttt caaaatatgt cctagcataa    780
aggcaattaa aaaatgtaaa gcaccaaaga tgcaagagag acataaatga ataaaatatc    840
tggcacgaaa gttttcaaaa gcttgggaat ctgattcaaa aaaaaataaa atcagccaag    900
```

-continued

```
cagtgttagt aagttagcca atcaggtttc aagaaggcag aaagacaaaa tcaacatcac    960

cagcatttga caccgctact gggggaaaaa agggggatgg agttcgttta tggccttttt   1020

aaaaatgcca ttacttggac aagagtcata acagagaagc actgcttatt tcagttctgt   1080

taactgtaaa tatcagagcc aacacccaga aaaagttcac cattagccaa ttggttttgc   1140

ctggccaatt ggagatggta ataggcctgc tatggatgac attctttctg atataagttg   1200

tttcttgctt tttctccc                                                 1218
```

<210> SEQ ID NO 398
<211> LENGTH: 1072
<212> TYPE: DNA
<213> ORGANISM: Homo sapiens

<400> SEQUENCE: 398

```
cacttaaaag ctctggaaac ctacgagatt atctttaaaa tcgtggggac caaatggctg     60

gccaaggact tgtttctgta caggtgcgat tgcttctctg ctgtgttcct ttttattacc    120

caagtaaccg gtatttcagc tcacaagatg agaaaatgac aaacaggcaa aataagcgta    180

gggctgtgtg tgcaacagtt watcataaag ccatcaccag gagacgtcac tgggcgcctt    240

ctggagtcta tccgtcctaa ctttgctttc tttctttttt tttttaaatt taagttctag    300

ggtacatatg cacaacgtgc aggtttgtca cacatgtata catgtgccat gttggtgtgc    360

tgcacccatt aactcgtcat ttacattagg tgtatctcct agtgctatcc ctccccactc    420

ccccgacccc atgacaggcc ccagtgtgtg atgttcccct tcctgtgtcc aagtgttctc    480

attgttcaat ccccacctat gagtgagaac atgccatgtt tggtttttttg tccttgcgat    540

agtttgctga gaatgatggt ttccagcttc atccatgtcc ctacaaagga catgaactca    600

tcctttttta tggctacata gtattccatg gtgtatatgt gccacatttt cttaatccag    660

tctatcatcg atggacattt gggttggttc caagtctttg ctattgtgac tagtgttgca    720

ataaatatac gtgtggatgt gtctttatag cagtttgatt tataatcctt tgggtatata    780

cccagtaacg ggatggctgg gtcaaatggt atttctagtt ctagatcctt gaggaatcgc    840

cacactgact tccacaatgg ttgaactagt taacagtccc accaacagtg tgaaagtgtt    900

cctatttctc cacatcctct ccagcacccc attttgactt tgctataagg gaactttagc    960

atctgaacgt gcggacagct tcattgctgg cttgttacgt aacagtgttt tgtgaccatc   1020

tcatgtcata cccacacatc gaaaccagca gtttaaatgg ccagctgttt gc           1072
```

<210> SEQ ID NO 399
<211> LENGTH: 1072
<212> TYPE: DNA
<213> ORGANISM: Homo sapiens

<400> SEQUENCE: 399

```
agattatctt taaaatcgtg gggaccaaat ggctggccaa ggacttgttt ctgtacaggt     60

gcgattgctt ctctgctgtg ttccttttta ttacccaagt aaccggtatt tcagctcaca    120

agatgagaaa atgacaaaca ggcaaaataa gcgtagggct gtgtgtgcaa cagtttatca    180

taaagccatc accaggagac rtcactgggc gccttctgga gtctatccgt cctaactttg    240

ctttctttct tttttttttt aaatttaagt tctagggtac atatgcacaa cgtgcaggtt    300

tgtcacacat gtatacatgt gccatgttgg tgtgctgcac ccattaactc gtcatttaca    360

ttaggtgtat ctcctagtgc tatccctccc cactcccccg accccatgac aggccccagt    420

gtgtgatgtt ccccttcctg tgtccaagtg ttctcattgt tcaatcccca cctatgagtg    480
```

agaacatgcc atgtttggtt ttttgtcctt gcgatagttt gctgagaatg atggtttcca 540
gcttcatcca tgtccctaca aaggacatga actcatcctt ttttatggct acatagtatt 600
ccatggtgta tatgtgccac attttcttaa tccagtctat catcgatgga catttgggtt 660
ggttccaagt ctttgctatt gtgactagtg ttgcaataaa tatacgtgtg gatgtgtctt 720
tatagcagtt tgatttataa tcctttgggt atatacccag taacgggatg gctgggtcaa 780
atggtatttc tagttctaga tccttgagga atcgccacac tgacttccac aatggttgaa 840
ctagttaaca gtcccaccaa cagtgtgaaa gtgttcctat ttctccacat cctctccagc 900
accccatttt gactttgcta taagggaact ttagcatctg aacgtgcgga cagcttcatt 960
gctggcttgt tacgtaacag tgttttgtga ccatctcatg tcatacccac acatcgaaac 1020
cagcagttta aatggccagc tgtttgcttg tgaaaactcc cctcggctgg ct 1072

<210> SEQ ID NO 400
<211> LENGTH: 948
<212> TYPE: DNA
<213> ORGANISM: Homo sapiens

<400> SEQUENCE: 400
aaattttctt tgctgaagtg tcttttcaaa tttttgcctt ttaaaaaaat tgagttgtct 60
taatattgag tcgtaaggtt ctttatatat tctggctata tgtcctttgt cagatatatg 120
tcttgcaaat attttctccc agtctgtggc ttaccttttc cattttttaaa ctgtgtttta 180 taaaaaaaag aagttttttt agatcaaagt ccattttaat catttttttct tttatagttc 240 atgcttttttg tgtctcattt aagaaatctt tccctactcc aatgtcacaa atatattctc 300
tgagaagctt aacagttttt gcaactaaat ttaggtctat gatccgtttt gacttaattt 360
ttccatatgg tgtcatgtaa cagttgagat tttttttccta tgcaggcaga tattcaatgg 420
ttcaagtacc atttattgaa atggctatct tttctccact gaatgacctt ggcactttta 480
tcaaacatca actggccaca yacaggtgag tctacttctg gacacttacc ctgttccatt 540
catctgtata tctctatcct tacaccaaca cgcatagtct tgaatactag ggcaagttaa 600
ttttaagatg tctcctggat atgtaaaaat tatatctgag ttgaactaca gtttatttat 660
atatccaggc agcaaataaa tgtgagaatc tggaggtgag ggaagagatc agagatacca 720
ccttggaaac catcaattta gagatgattc ttaaggcagg ggactaaggg acactctgta 780
ggacacagac atagagaagg gaaggggctg cggcctgaac accccacctg catgctcact 840
cacatacttt cgtcggcctg tgttaacgaa gtgctgggtc tccccagcct ctctcatctg 900
taagcagtgc caacaacgtc caacacagtt ccatccaatt tggatctg 948

<210> SEQ ID NO 401
<211> LENGTH: 920
<212> TYPE: DNA
<213> ORGANISM: Homo sapiens

<400> SEQUENCE: 401
aatttttgcc ttttaaaaaa attgagttgt cttaatattg agtcgtaagg ttctttatat 60
attctggcta tatgtccttt gtcagatata tgtcttgcaa atattttctc ccagtctgtg 120
gcttaccttt tccattttta aactgtgttt tataaaaaaa agaagttttt ttagatcaaa 180
gtccatttta atcatttttt cttttatagt tcatgctttt tgtgtctcat ttaagaaatc 240
tttccctact ccaatgtcac aaatatattc tctgagaagc ttaacagttt ttgcaactaa 300

```
atttaggtct atgatccgtt ttgacttaat ttttccatat ggtgtcatgt aacagttgag    360
atttttttcc tatgcaggca gatattcaat ggttcaagta ccatttattg aaatggctat    420
cttttctcca ctgaatgacc ttggcacttt tatcaaacat caactggcca cacacaggtg    480
agtctacttc tggacactta ycctgttcca ttcatctgta tatctctatc cttacaccaa    540
cacgcatagt cttgaatact agggcaagtt aattttaaga tgtctcctgg atatgtaaaa    600
attatatctg agttgaacta cagtttattt atatatccag gcagcaaata aatgtgagaa    660
tctggaggtg agggaagaga tcagagatac caccttggaa accatcaatt tagagatgat    720
tcttaaggca ggggactaag ggacactctg taggacacag acatagagaa gggaaggggc    780
tgcggcctga acaccccacc tgcatgctca ctcacatact ttcgtcggcc tgtgttaacg    840
aagtgctggg tctccccagc ctctctcatc tgtaagcagt gccaacaacg tccaacacag    900
ttccatccaa tttggatctg                                                920
```

<210> SEQ ID NO 402
<211> LENGTH: 701
<212> TYPE: DNA
<213> ORGANISM: Homo sapiens

<400> SEQUENCE: 402

```
tgtgctgctt ccattccata ggcacctgat cctaagtgtt aaccaatccc agaactctcc     60
ccttatttct tgctgcatgt tttgaattga tgtgataaac aatgtgattc gagcgtctta    120
actcagccta tgagcctctc tattctgtga ctgctggaat aggctgcttg gccatgttct    180
tggaagctac caccatatca rggtaatttc ccacacaaca ttccagcccc tgctttcccc    240
tctggcctta tctagggcca ttccccaact caggtgaatg cagactccaa atgtactgag    300
ctgtgtgcag gggccaggtg caaatgcttt ctgtgcatct gcacatgctg ttctacctgg    360
gaagtccttt cctcctttca cctattttta ccttaaacct cagacatcat ctaccctgga    420
aagtccttcc tgacctcacg catctaagta ggtccccccc ataatcccta tccatgcctt    480
ctatagtact taacatggtg acctttaatt gttcatttac ttagctctct gctctcccac    540
actgtgaact ccttacaaac agggaatgtc atctctgaat gaatctttca tctccatgta    600
acacatgcct ccaaccctac ctagcacaca atctggcata taacaggcac tcaataaacc    660
ttcaatgaat gccttgatca agtacaagga acataagcaa a                        701
```

<210> SEQ ID NO 403
<211> LENGTH: 701
<212> TYPE: DNA
<213> ORGANISM: Homo sapiens

<400> SEQUENCE: 403

```
ttaaccaatc ccagaactct ccccttattt cttgctgcat gttttgaatt gatgtgataa     60
acaatgtgat tcgagcgtct taactcagcc tatgagcctc tctattctgt gactgctgga    120
ataggctgct tggccatgtt cttggaagct accaccatat cagggtaatt tcccacacaa    180
cattccagcc cctgctttcc yctctggcct tatctagggc cattccccaa ctcaggtgaa    240
tgcagactcc aaatgtactg agctgtgtgc aggggccagg tgcaaatgct ttctgtgcat    300
ctgcacatgc tgttctacct gggaagtcct ttcctccttt cacctatttt taccttaaac    360
ctcagacatc atctaccctg gaaagtcctt cctgacctca cgcatctaag taggtccccc    420
ccataatccc tatccatgcc ttctatagta cttaacatgg tgacctttaa ttgttcattt    480
acttagctct ctgctctccc acactgtgaa ctccttacaa acagggaatg tcatctctga    540
```

atgaatcttt catctccatg taacacatgc ctccaaccct acctagcaca caatctggca 600
tataacaggc actcaataaa ccttcaatga atgccttgat caagtacaag gaacataagc 660
aaatttcctg tggaaaaaaa gaattgtatt aagttctttg g 701

<210> SEQ ID NO 404
<211> LENGTH: 601
<212> TYPE: DNA
<213> ORGANISM: Homo sapiens

<400> SEQUENCE: 404
atgttcactt acacatcttt ctttcactta attgaatcct ttatttttgt cttagaatct 60
tctgaatatt gaaaacagag aactatactg gaagaacata gtgtattaag actcatggag 120
agggagatgt gatactgtgt cactgaggtc gttccagtca taggagaaat gttaccactg 180
gattgaggtc tggtacattt taaaagatga tttaattcta tgatatgtgt tcaacttgca 240
ctaggatagt ttttactttc acctttgttc catgcaccgc gcaaatacct gggaaccctt 300
rttgcccaac tcaagagcca gagtcctctg tcatcatttt gcctctctcc taagtgacag 360
gactgagtgc agacttggtg tttgtgggtg aggcatgtgg actgacaggc aggcttcagt 420
ttatttagcg agtgtgagcc ctggcaggaa gattctcttt ctctgcttgc caggttgagg 480
aggcctcatt aagcagtttg aacttgtggt tttggcgtgt ctagtcctgg tgcaggtggc 540
ttggtatcct cacaggcatt tctttggcct caccctttggg gtgactgttc acttgtgttt 600
g 601

<210> SEQ ID NO 405
<211> LENGTH: 601
<212> TYPE: DNA
<213> ORGANISM: Homo sapiens

<400> SEQUENCE: 405
tcttctgaat attgaaaaca gagaactata ctggaagaac atagtgtatt aagactcatg 60
gagagggaga tgtgatactg tgtcactgag gtcgttccag tcataggaga aatgttacca 120
ctggattgag gtctggtaca ttttaaaaga tgatttaatt ctatgatatg tgttcaactt 180
gcactaggat agtttttact ttcacctttg ttccatgcac cgcgcaaata cctgggaacc 240
cttgttgccc aactcaagag ccagagtcct ctgtcatcat tttgcctctc tcctaagtga 300
saggactgag tgcagacttg gtgtttgtgg gtgaggcatg tggactgaca ggcaggcttc 360
agtttattta gcgagtgtga gccctggcag gaagattctc tttctctgct tgccaggttg 420
aggaggcctc attaagcagt ttgaacttgt ggttttggcg tgtctagtcc tggtgcaggt 480
ggcttggtat cctcacaggc atttctttgg cctcaccctt ggggtgactg ttcacttgtg 540
tttgagcggc tgggactcag taggttcact ggagtaggta tttctttaga gccactggcg 600
g 601

<210> SEQ ID NO 406
<211> LENGTH: 701
<212> TYPE: DNA
<213> ORGANISM: Homo sapiens

<400> SEQUENCE: 406
cagctccttg gcaagcctgc tccttcccca gcaaatggaa acaccattct gaacacctgg 60
gcattgtctc tgatgtccct tttcatctcc ctactctcac acaatccagc tgcctctctg 120

-continued

```
ccttccacgg atattaagaa cgtccaccat ctcctgagtc caagcccttc tcactcacct    180

ctttcttgaa ctaatttctt yctgtttttt tccagtcctc ccttctgttc atgtctctcc    240

tctgcacact tccattttct ggttcagaaa atgtcaccgt cccagtcaca cttgccttat    300

ggctgttgtg tcataaatac agttgacact tgaacaacat gggtttgaac tgcatggatt    360

cacttataca catatttttt caatacaaat atatttaaaa attttggaga tttgcaacaa    420

tttgaaaaaa cttgcagatg aacagcatag catagaaata ttgaaaaatt aagaaaaagg    480

tatgtcatga atgcataaaa catatgcaga tactagtcta ttttaacctt tactgccata    540

aaatatacac aaatctatta taaaaggtta aagtttatca aagcttatgc acacaaacac    600

ttatagacca tatagggagc cattcagtag agagaaatgt aagcgaacgt aaaggtgtgc    660

tatttaatca caactgcata cacactgtac cactgcacta a                        701
```

<210> SEQ ID NO 407
<211> LENGTH: 701
<212> TYPE: DNA
<213> ORGANISM: Homo sapiens

<400> SEQUENCE: 407

```
gggcattgtc tctgatgtcc cttttcatct ccctactctc acacaatcca gctgcctctc     60

tgccttccac ggatattaag aacgtccacc atctcctgag tccaagccct tctcactcac    120

ctctttcttg aactaatttc tttctgtttt tttccagtcc tcccttctgt tcatgtctct    180

cctctgcaca cttccatttt stggttcaga aaatgtcacc gtcccagtca cacttgcctt    240

atggctgttg tgtcataaat acagttgaca cttgaacaac atgggtttga actgcatgga    300

ttcacttata cacatatttt ttcaatacaa atatatttaa aaattttgga gatttgcaac    360

aatttgaaaa aacttgcaga tgaacagcat agcatagaaa tattgaaaaa ttaagaaaaa    420

ggtatgtcat gaatgcataa aacatatgca gatactagtc tattttaacc tttactgcca    480

taaaatatac acaaatctat tataaaaggt taaagtttat caaagcttat gcacacaaac    540

acttatagac catataggga gccattcagt agagagaaat gtaagcgaac gtaaaggtgt    600

gctatttaat cacaactgca tacacactgt accactgcac taatttcaga gccacctcct    660

gttgtgattg tggtgagccc aagtgttgtg aggatctgct t                        701
```

<210> SEQ ID NO 408
<211> LENGTH: 501
<212> TYPE: DNA
<213> ORGANISM: Homo sapiens

<400> SEQUENCE: 408

```
caggtagggt aagcaaatga acacaaattc aaactcggaa ttcaaaacca gcctctgtgt     60

attcctgagg accatactgt ctgctaagtg tagagaaagg cacatcctgg ttcaacagca    120

gagaaagcaa acaggaggca ctttctgtga gtcatctcca ccacagggcc ctctcttttg    180

tgatccagcg atacttgttc acagtcaaag cccaggaaga gtggaaagat taacctttgt    240

gagccaaacc rtgtgacact tgattacttg acagaactaa tccttctgtc ctgatgacag    300

aaattcaact acacaggtac atgcaagcta atatctgttg taatgcctcc cagtttctct    360

ggagaattcc ttagtttcct ggacatctct gaaatgcaaa gttttggcaa cgagtctctg    420

aattaacctc tgaaaatctc acccagccaa gatggccttc ttgagaagac tgaagaacat    480

ggttggtttc aggctgagct g                                              501
```

<210> SEQ ID NO 409
<211> LENGTH: 604
<212> TYPE: DNA
<213> ORGANISM: Homo sapiens

<400> SEQUENCE: 409
cactttctgt gagtcatctc caccacaggg ccctctcttt tgtgatccag cgatacttgt 60
tcacagtcaa agcccaggaa gagtggaaag attaaccttt gtgagccaaa ccgtgtgaca 120
cttgattact tgacagaact aatccttctg tcctgatgac agaamttcaa ctacacaggt 180
acatgcaagc taatatctgt tgtaatgcct cccagtttct ctggagaatt ccttagtttc 240
ctggacatct ctgaaatgca aagttttggc aacgagtctc tgaattaacc tctgaaaatc 300
tcacccagcc aagatggcct tcttgagaag actgaagaac atggttggtt tcaggctgag 360
ctggaagtgg tttacctccc aggagaggtt ccccacagtg gtgtttaagg catggggtgg 420
accaacacca ggaagactca gacatcacac cacccacctt caactcagtc acatccacct 480
acattttctg aaaacaaaag gcagtctccc caaaaagcac tgagactctt gtgtaggtaa 540
tctgagcaga caccaacttc ccagggcttc cttttatcca ggagagcttg gctgttcttt 600
ttaa 604

<210> SEQ ID NO 410
<211> LENGTH: 701
<212> TYPE: DNA
<213> ORGANISM: Homo sapiens

<400> SEQUENCE: 410
ctccttccgc catggttgta agtttcctga cgcctcccag tcatgcttcc cgtacagcct 60
gcagaactgc gagtcaatga aatccctttt ctccacaaat tacccagtct caggtagttc 120
cttacagcag cgtgggaaca gactcaagag ctgaagcaag caaggccgtt agcaaggagc 180
gggctgggga gagcactcca ggcagaggga acagccaggg ccagggcctt gagacagacg 240
tgagccagga tatctgagga acagcagaga agccagtgtg gccgcagcta aatgaggaac 300
aatgtgtgag ttccctgggg cggccaaaac aaacaccacg gacgggggcc ttcaaccaca 360
gacaccgatt tcctcacagc tctggaggcg aaaagtccaa gaaaactgca cggagtatct 420
atgaggccct gatggagacc tgacctggtc cacacccatg gcctggcaag ctagatgggg 480
tgaattttca cctgccacag ycgcaagtca aagccaccgg cttctctctt ctccctccca 540
ttgctcctga cagccagggt taatattttg cctcatgtaa acagggaggc atccacccga 600
gaatctcccc tcagcccaca taagctctgc agagagggct gtgttgctcc agttcccacc 660
tggacatgag cactttgaag ggcagcttcc ctcccggggt c 701

<210> SEQ ID NO 411
<211> LENGTH: 612
<212> TYPE: DNA
<213> ORGANISM: Homo sapiens

<400> SEQUENCE: 411
gggctgggga gagcactcca ggcagaggga acagccaggg ccagggcctt gagacagacg 60
tgagccagga tatctgagga acagcagaga agccagtgtg gccgcagcta aatgaggaac 120
aatgtgtgag ttccctgggg cggccaaaac aaacaccacg gacgggggcc ttcaaccaca 180
gacaccgatt tcctcacagc tctggaggcg aaaagtccaa gaaaactgca cggagtatct 240
atgaggccct gatggagacc tgacctggtc cacacccatg gcctggcaag ctagatgggg 300

-continued

```
tgaattttca cctgccacag tcgcaagtca aagccaccgg cttctctctt ctccctccca    360

ttgctcctga cagccagggt taatattttg cctcatgtaa acagggaggc ayccacccga    420

gaatctcccc tcagcccaca taagctctgc agagagggct gtgttgctcc agttcccacc    480

tggacatgag cactttgaag ggcagcttcc ctcccggggt ctggctgagc tcagggtagg    540

cgtcagtctg catggattgg atggaggaag gctgtgcgtg gcaggagatg acactgccct    600

tgggctgtgt gg                                                        612


<210> SEQ ID NO 412
<211> LENGTH: 1001
<212> TYPE: DNA
<213> ORGANISM: Homo sapiens

<400> SEQUENCE: 412

ttggggaagg aagcactggg gggaaggaag cactgggctt gggacagggc tgggcgctgc     60

ctcttcactg gaccatgaca aggttgttac ctcaccaagg agaggtgcaa aaagcttagg    120

ggcttggatt tctagatttc agtgccaact atgccactta ctggctttat ccttggggaa    180

tttatctact ctgtgaccct cagttttttt atcttaatta ttaatacata cctcataatg    240

tgactgtgag gattcactta ataatatatg gaaaaccata gaatagtgcc cagcatctag    300

gaagtgccac agccccccttc agaagctagt gaaacctgca gaccactttt cagagtgata    360

ttattatttt tttctaggtt tactgagtta taattgaaaa aataaaaatg gaatatagat    420

gtacaacatg aagctctgat gcatatatcc attgtgaaat gatgaccaca atcaagctaa    480

ttaatgttat ctatcacttc wcatagttca accttttttt gtggtgagag tactgaagat    540

ctactctctt agcaatttc aaatctaaaa tacattatta ttaacacagt cactgtgccg    600

tacgttagct ctgaggacct tattcatttt atacctaaaa gtctgtatcc tttaaccaac    660

ctctcctaat ttcccactgt catccctact gccacctctg gtaaccagcc ttctgctctg    720

tttctgagtc caaccttctt agattccaca tatgagtgag atcatgctgt gcagtgtttg    780

tttttctgtg tctggcttgc tttcacttag cataatgtcc tccaggtcca cccatgttgt    840

tgcaaatggc agaatcttct tcttgttaaa gactgaataa tatccctgtg tgtgcgtgca    900

tgtgtgtgtg tgtttgtgtg tgtgtgtgta tcacattttc ttcatccatt catccatcaa    960

tggacactaa gcactaaggt tgattccgta tcttggctat t                       1001


<210> SEQ ID NO 413
<211> LENGTH: 2480
<212> TYPE: DNA
<213> ORGANISM: Homo sapiens

<400> SEQUENCE: 413

aacattactt ggggaaggaa gcactggggg gaaggaagca ctgggcttgg gacagggctg     60

ggcgctgcct cttcactgga ccatgacaag gttgttacct caccaaggag aggtgcaaaa    120

agcttagggg cttggatttc tagatttcag tgccaactat gccacttact ggctttatcc    180

ttggggaatt tatctactct gtgaccctca gtttttttat cttaattatt aatacatacc    240

tcataatgtg actgtgagga ttcacttaat aatatatgga aaaccataga atagtgccca    300

gcatctagga agtgccacag ccccccttcag aagctagtga aacctgcaga ccacttttca    360

gagtgatatt attatttttt tctaggttta ctgagttata attgaaaaaa taaaaatgga    420

atatagatgt acaacatgaa gctctgatgc atatatccat tgtgaaatga tgaccacaat    480

caagctaatt aatgttatct atcacttcac atagttcaac cttttttttgt ggtgagagta    540
```

ctgaagatct actctcttag caattttcaa atctaaaata cattattatt aacacagtca 600
ctgtgccrta cgttagctct gaggacctta ttcattttat acctaaaagt ctgtatcctt 660
taaccaacct ctcctaattt cccactgtca tccctactgc cacctctggt aaccagcctt 720
ctgctctgtt tctgagtcca accttcttag attccacata tgagtgagat catgctgtgc 780
agtgtttgtt tttctgtgtc tggcttgctt tcacttagca taatgtcctc caggtccacc 840
catgttgttg caaatggcag aatcttcttc ttgttaaaga ctgaataata tccctgtgtg 900
tgcgtgcatg tgtgtgtgtg tttgtgtgtg tgtgtgtatc acattttctt catccattca 960
tccatcaatg gacactaagc actaaggttg attccgtatc ttggctattg tgaataatgc 1020
tgcaataaac atatgagtcc agatacctct tcaagatact gatttcattt cctttaaata 1080
tatgcccaga agtgggattg ctggatcata tggtagttct atatttagta tcttgaggaa 1140
tttccatact gtttttcata atgattgtag caatctatat tcccatcaac agtgtacaag 1200
ggttccattt tctacatggc cttaccaacg tttgttatca cttatctttt tgataataga 1260
tattctagca ggtgtgaggt ggtatctcat tgtggtttta atttgcattt tcctgatgat 1320
tagtggtgta gagcatcttt tcatattccc attggtaatt cgtatatctt cctttgagaa 1380
atatttattc agatcttttg cccattgtta gctgagttat atgtgagttg gttttggttt 1440
gttgttgttt tttgtttttg ctattgagct gagttccttg tatattttgg atattaaatc 1500
cttctcagct gtatggttga cagatacatt cttgcattct gtaagttgca tctgtaggtt 1560
gcaacagagt ctctttactc tgttgattgc ttgctttact gtgtgaaagc tttttttagct 1620 tgatgtaatt gtgtttgtct atttttgctt ttgttgcttg tacttttagt gtcatatcca 1680
aaaagttatt gcccagacca gtgtcatccc ctatgttttc ttctagtaat tttaaagttt 1740
caggtcttat gtctatgtct ttaatccatt ttgagttaat ttttgtgtag ggtttaagat 1800
aagaatccaa ttttattttt attttttgta tatggatatc caatttcccc aacaccattt 1860
attgaaaatt ctatcctttc tttgttgtgt attaacatca gaataatatt tttaaataca 1920
taaaattcag aagatgacaa aggaaaccaa ttacattgaa atgcatacag agttataatt 1980
ctgaaagagc aatatatgtg cctctttgta aacacatcat atatcaaact gcagtgaccg 2040
ttctaacaac tattgcaatt tcaaagtcat gttgagtagg aggagtactt tgagattctg 2100
aaacaacgtt cttgtgctat gaaatatcca tgattttgat tggtgatggt atcccaggtc 2160
ttgttaatgc tgctgtaatc tgttgcttcc attccatagt tgaataaaat gcttgatatc 2220
tgttggaaat tagtaaaaat aaaaacgtat ttttttccat ccaagttcat tctcagaccc 2280
tgaagagtca cttctctgga ttctgcagca aagttcccag ctggggcagc aagatttagg 2340
caattgaaaa gaacatacac cttgttctca gtggcaaacc acatggaaag ctttaaatgt 2400
cagagaagaa ttctgccatt ttgctgactt ttttgtagtt ctcctaataa acaagtgtta 2460
agtgacaagc ttttcagagg 2480

<210> SEQ ID NO 414
<211> LENGTH: 601
<212> TYPE: DNA
<213> ORGANISM: Homo sapiens

<400> SEQUENCE: 414
cccccccccc ccccgcagat ctcaggtggg catttttgaa cttaactaga taacaaaaca 60
cagctaagac aagtcctttt ctccagcaaa gatggcaatg ctctaataac tctgagcata 120

-continued ttaaagattc tccaagactc tagcctctgc tgcaaaaaca catacaaata cctactacta 180
ctgctgctgt gatgatgatg atgacagcaa tagtgagaat attttaaata tgccaggcac 240
ggtggcaact gctttccaaa tattatcata tttaatctga tcattgccct atgaggtagg 300
ragtattctg attcccattt tataaataag gaacccgagg cttagagagc atcggtgact 360
tgttcaaggt cacccacagc tgtcaagtga cagaacttcg ataaaaatcc agactccttt 420
aatggagtat ggagggaggt cagaaaacat aggaagtaag ggattgtgat tgacaatgtg 480
tccttgcaaa gggacaggtt aagagacaca agggcagctg tctgaggtgt gccattcacc 540
agcttcagga gagaagtggc aggctacctc cagctatcca gccctatcca gccaaggaag 600
c 601

<210> SEQ ID NO 415
<211> LENGTH: 601
<212> TYPE: DNA
<213> ORGANISM: Homo sapiens

<400> SEQUENCE: 415
caaaacacag ctaagacaag tccttttctc cagcaaagat ggcaatgctc taataactct 60
gagcatatta aagattctcc aagactctag cctctgctgc aaaaacacat acaaatacct 120
actactactg ctgctgtgat gatgatgatg acagcaatag tgagaatatt ttaaatatgc 180
caggcacggt ggcaactgct ttccaaatat tatcatattt aatctgatca ttgccctatg 240
aggtagggag tattctgatt cccattttat aaataaggaa cccgaggctt agagagcatc 300
rgtgacttgt tcaaggtcac ccacagctgt caagtgacag aacttcgata aaaatccaga 360
ctcctttaat ggagtatgga gggaggtcag aaaacatagg aagtaaggga ttgtgattga 420
caatgtgtcc ttgcaaaggg acaggttaag agacacaagg gcagctgtct gaggtgtgcc 480
attcaccagc ttcaggagag aagtggcagg ctacctccag ctatccagcc ctatccagcc 540
aaggaagctt gggagacatg ttagttcccg ccttcatttc catcagcaac ctcaaagcca 600
c 601

<210> SEQ ID NO 416
<211> LENGTH: 5823
<212> TYPE: DNA
<213> ORGANISM: Homo sapiens

<400> SEQUENCE: 416
tatttcaggc tttcttcttt ctatggataa gaaagctcct caggtggcaa caaaggccat 60
ttctttggaa gcaggcatgg catgtgacga aaaaaagaca tctcagaaaa gagccaagaa 120
taagactgga gagccactgt cagagaacag aaactgggct taatcaagga acatctcttg 180
ttcccagagt aggaggctgg caatattttc tcactgaaat ttcagaattg ttatggacca 240
gtgactgctc tatgtgttca atttgttccc ttttcaaatg gaagcattta ttgcagacga 300
cctgcctctg tcccaccatt gtgtattagg tttgtagagy gtagacaact tgccttttta 360
gtttgtaggt ttctgtatca agagaagatg tgtgtgggcc taacctagat tacaggatcc 420
tggacttcaa gtctgatata atgactggat gagactttga ctgtcctaga attgggatga 480
acatattttg ccggtgggag ggcgtgagta attgcggtta gagggcagac tgtccctcac 540
acctattcct tttcatggtg ccttcccaaa ctgcctctgg aggtggccac acaaatggct 600
ttggccattg tgaccatggg aaacttgatg cagaggctgg aaaaagcact tgcatgtttc 660
tgtctcctct cttgttcctc tacaatcaca agaaatgtct aggcaggtct gagcaggccc 720

-continued

```
aggctcatct gccatggaag aagaatggca catggaagag ggtcacattg tcccaaccaa    780
gacgatccta gaccagccag gccccagttc atggttcaag acacatgaac atagttgcac    840
gaaccaagat tagttgtgta tggcccagac tagcagcagc acccatccaa cctacagact    900
ctgagaaata aatactagtt gtcttaagct tccaagtttc agtgtgagca ttaggtagta    960
acagttaatg aataagacag ataatcattt tatctgtctg gatacttata caatgatttc   1020
tatttttat tgatacataa tattttacat attgctgggg tacatgtgac attttgctac   1080
atacatagaa tgtgtaatga tccagtcagg atatctgagg tgtccatcac tttgagaatt   1140
tctcacttct gtgtgttggg aacaattcaa gtcgtctctt ctagttattt taaaatatac   1200
aatacattgt taactgtagt ctttttatt gaatgacagg acttgtacct tttatctaac   1260
tgtatgtttg tatctattaa gctagttctc tttatccctg ccccctccta cccactcact   1320
cttcccaacc tctaacatgt atcatcctat tctatatctc catgagatca acttctttag   1380
ctcccacata tgagcaaaaa catatgatgt ttgtctttct gtgcccggtt tatttcactt   1440
atgacctcca tttccatcca tgttactata aatgacagga tttcattctt tttgtggcca   1500
aacagtattt cattgtgtat atatactaca ttttctttat ccattcatcc attgatgaac   1560
acttacgttg attccatatc tttgctattg tgaatggtgc tgcaataaac atgcacgtgc   1620
agttatccct ttgatacact gatttatttt cctttggata aatacccagt agtgagattg   1680
ctggatcata cggtagttct acttttagtt tttgagacat ttccatactt ttccagtgtt   1740
tgtattaatt tacattccca tcaacaatgt ataagatttc cctttcctcc acatcctcac   1800
cagcatctgc tattttttgt ctttttaata atagtcattc taactggggt gagaggatat   1860
ctcgctatgg ttttgatttg catttccctg atatttaatg atattgagca tttcttcata   1920
taacctattg gccatttgtg tgtctttttt tttttttttt ttttttttga gaattgtcta   1980
ctcattttg gctttttaaa agatttattt tttgttgttg ttgagtttag tgcatatcct   2040
ggatattagt ctcttatctg atgaagagtt tgccaatatt ttctcccatt caacaggttg   2100
tctcttcatt ctgttgactg tttcctttgc tgtgcagaag cactttatat acagtcccat   2160
ttgtctattt tttagtagtc tatgcattta aggtctcagc cacaaaatct ttgcctagac   2220
cagtcctaaa gtgtttcccc tatattttct tctagtagtt ttattgtttc atgtcttata   2280
tttaagtcta taatccattg tgagttgatt tttgtatatg gtgagatagg ggccttgttt   2340
cattcctctg catatagata tttaattttc tcagcaccat ttattgaagg tgtccttccc   2400
tattgtatgt tcttggtgcc tttgtcaaaa ttcagttggc tataaatatg tgaatttatt   2460
tctgggttct ctatgtggtt ccattagtct atgtgtctat ttttatacca atatcatgct   2520
gttttgatta ccatagcctt gtaatatatt ttgaagtcag gtagtgtgat gcctccagct   2580
ttgttctttt tgctcaggat tgctgtgcat actctggctt tttggttaca tacaaatttc   2640
aggattttttg tatttctgtg aaaaatggca ttagtatttt gataggaatt gcactggatc   2700
tgtatattgt cctggacaac atggtcattt taacaatatt aattcttcta atctatgagt   2760
atgagacgtc ttcccacttg tttgtgtcct cttcaatttc tttcattggt gtttcataat   2820
ctcccttcta caggcctttc acctccttgg ttaaattaat tcctaggtat ttttttgtag   2880
ctactgtaaa tgggactgcc ttctttctca gctagttcat ttttggtgca tagaaaccct   2940
atttttgtat gttcattttc tatcctgcaa cattaccaaa tttgcttatc agctttaagt   3000
gtgtattttg ctttgcttgt agagtcttct ggtttctcta aatgtaagac gatgtcatct   3060
```

-continued

```
gcaaacgggg acaatttgac ttcctcttaa aaatctgtat gccttttatt cctttctctt   3120
gcctgattgc tctggctcta cctccagtac tatactgaat aaaagtggta aaagtgagca   3180
tccttccttg tcttgctcta gttcttagag gaaatacttt cagtttttcc ccactcagta   3240
tgatgttagc tgtgggtcat atatagcctt tattatgtta agatatgttt cttctgtacc   3300
tggtttgttg acagcttttt atcataaaag gatgtagaat tttatcaaat gtttttctg    3360
catctgttga gataatcata tggtttttgt cattccttct actgttgtga tgtatcatgt   3420
ttattgattt gtgtatgtta aaccatcctt gtgtccttgg tataaattat acttggtcat   3480
ggtgtattat ctttttggca tcctgtcgaa ttgtttgcta gctttttgtt ttgttctttt   3540
tgagaatttt tatgtctagg ttccttagaa acactggcct gtagttctct ttttgtgtgt   3600
gtgtccttgt ctagtttggt gtcagggaaa tggtggtctt gtagaatgag ttgtttttc    3660
tttgattttt ttgcaagagt ttgaggagaa tgggtattag ttcttcttta tgtggttggt   3720
caaattggca gtgaattcat tcagtcatga gcttttcttt ttttgggagg gttctcatta   3780
ctgagttaat cacactgctc attactgatc tgttcagatt ttctatttct tctggaatct   3840
cagtagttgt atgtttccag caatttatcc atttcctcta ggttttctag tttggtagta   3900
tatagctatt cataatagtc tctgatgatc ttttgtattt ctgtgatatc agttgtaatg   3960
tctttttcat ttcctatttt atttgggtct tttcttgttt agtctagcaa ggggtttatc   4020
tattttatct ttttgaagaa ccaacttttt gtttcattga ccctttctac gtctttagtc   4080
tttatttcat ttagatttgc tctgaacttt actatgtctt tccttctaat tttgggtttg   4140
gtttgttctt ttctagttcc ttgaggtgca tcattgaatt gtttctttga tatctatcta   4200
ctcatttgat gtaggtgttt attgctatac actctcccct cctagagctc cttttgttgt   4260
gtcccatagg tcttggtatg ttgtttctat tttcatttgt ttcaaacatt ttatttccat   4320
attaattttt atcattcagg aggagcatat tatttaattc ccatgtattt gtatagtttc   4380
caaagttcct cttatttcta tttttactcc attgtggtct gagaagatac ttcatatgat   4440
ttcaattttt aaaaatttgt caagacttgt tttttgtcct aacatatggt ctatcctgga   4500
gaatgttcca tgtgctgatg agaaaaatgt gtactcagca gttgttgagt aacatgttct   4560
acaaatatct gttagatcca tttggtctaa agtctagttt aaatccaatg agtttttgtt   4620
aattttgtct agatgatcat gatctgagac tgaggtgaag tccccaacaa ttatcgtgtt   4680
ggagtctacc tctcttttta aatctagaaa tatttgcttt ataaatccgg gtggtctagt   4740
gttgggtgca tatatttagt tgttatttcc tcattagatt gatctcttta ctattatata   4800
ataactgttt actgcttctg gcataaagtc tgttttatgt aagtacagcc attcctgctt   4860
gagtttagta ccatgttgac aaagggatgc atagagagtt ggtaaagcat gatttctggg   4920
tgtctgtgtg aaggtgtttt gagaagagtt tagcatgagt ctgtggagtg agtgggaaga   4980
ttctccctca atgtcagcag gaaccatcca tccactgggg gcccaggtag aaaaagatga   5040
agaaatggtg aattctctct ctctcctgga gctgggtcac ccttcttctg cccttgaaca   5100
ggacatcaca actccaggct ctccagcctt tggactccaa gactgacacc agtgcccctc   5160
cccaattacc ccaggccctc aggcctttgg cctaggattg agacttacac catcagcttc   5220
cctggttctg aggcttctgg acttgcactg ggccatacta ccagcatccc agggtctcca   5280
gcttgcagag agcctgttgt gggacttttc agcctccata atcaagtaag ccaatttccc   5340
tggtatctat atagatatac aatcatgttt tgcttaccag cctgaaaaat gtatcgctag   5400
atgagtctgt cattgcataa acatcatagt gtacttacac aaacctagat tctatagcct   5460
```

actacacacc tagtctataa acatgtacag catgttactg tactgaatat tgtaggcaac 5520
tgtaacacaa tggtgaatat ttgcatattt aaacatatct tatcattaaa aagatacagt 5580
aaacataagg tataaaagac aaaaaaccggc acacctatat agggcactta ccataaatgc 5640
agcttgcagg actagaagtc actcagggtg agtcagtgag cgaacgtgaa ggcctaggtt 5700
attactgtcc actacggtag actttatcaa cactgtacac aggctacact aaatttattt 5760
tttaaaaatt tgctctccaa taataaatta atcttcgcat ccttttttttg ttgttcactg 5820 tgg 5823

<210> SEQ ID NO 417
<211> LENGTH: 5823
<212> TYPE: DNA
<213> ORGANISM: Homo sapiens

<400> SEQUENCE: 417
tatttcaggc tttcttcttt ctatggataa gaaagctcct caggtggcaa caaaggccat 60
ttctttggaa gcaggcatgg catgtgacga aaaaaagaca tctcagaaaa gagccaagaa 120
taagactgga gagccactgt cagagaacag aaactgggct taatcaagga acatctcttg 180
ttcccagagt aggaggctgg caatattttc tcactgaaat ttcagaattg ttatggacca 240
gtgactgctc tatgtgttca atttgttccc ttttcaaatg gaagcattta ttgcagacga 300
cctgcctctg tcccaccatt gtgtattagg tttgtagagt gtagacaact tgccttttta 360
gtttgtaggt ttctgtatca agagaagatg tgtgtrggcc taacctagat tacaggatcc 420
tggacttcaa gtctgatata atgactggat gagactttga ctgtcctaga attgggatga 480
acatattttg ccggtgggag ggcgtgagta attgcggtta gagggcagac tgtccctcac 540
acctattcct tttcatggtg ccttcccaaa ctgcctctgg aggtggccac acaaatggct 600
ttggccattg tgaccatggg aaacttgatg cagaggctgg aaaaagcact tgcatgtttc 660
tgtctcctct cttgttcctc tacaatcaca agaaatgtct aggcaggtct gagcaggccc 720
aggctcatct gccatggaag aagaatggca catggaagag ggtcacattg tcccaaccaa 780
gacgatccta gaccagccag gccccagttc atggttcaag acacatgaac atagttgcac 840
gaaccaagat tagttgtgta tggcccagac tagcagcagc acccatccaa cctacagact 900
ctgagaaata aatactagtt gtcttaagct tccaagtttc agtgtgagca ttaggtagta 960
acagttaatg aataagacag ataatcattt tatctgtctg gatacttata caatgatttc 1020
tattttttat tgatacataa tattttacat attgctgggg tacatgtgac attttgctac 1080
atacatagaa tgtgtaatga tccagtcagg atatctgagg tgtccatcac tttgagaatt 1140
tctcacttct gtgtgttggg aacaattcaa gtcgtctctt ctagttattt taaaatatac 1200
aatacattgt taactgtagt ctttttttatt gaatgacagg acttgtacct tttatctaac 1260
tgtatgtttg tatctattaa gctagttctc tttatccctg ccccctccta cccactcact 1320
cttcccaacc tctaacatgt atcatcctat tctatatctc catgagatca acttctttag 1380
ctcccacata tgagcaaaaa catatgatgt ttgtctttct gtgcccggtt tatttcactt 1440
atgacctcca tttccatcca tgttactata aatgacagga tttcattctt tttgtggcca 1500
aacagtattt cattgtgtat atatactaca ttttctttat ccattcatcc attgatgaac 1560
acttacgttg attccatatc tttgctattg tgaatggtgc tgcaataaac atgcacgtgc 1620
agttatccct ttgatacact gatttatttt cctttggata aatacccagt agtgagattg 1680

-continued

```
ctggatcata cggtagttct acttttagtt tttgagacat ttccatactt ttccagtgtt   1740
tgtattaatt tacattccca tcaacaatgt ataagatttc cctttcctcc acatcctcac   1800
cagcatctgc tattttttgt ctttttaata atagtcattc taactggggt gagaggatat   1860
ctcgctatgg ttttgatttg catttccctg atatttaatg atattgagca tttcttcata   1920
taacctattg gccatttgtg tgtctttttt tttttttttt ttttttttga gaattgtcta   1980
ctcatttttg gctttttaaa agatttattt tttgttgttg ttgagtttag tgcatatcct   2040
ggatattagt ctcttatctg atgaagagtt tgccaatatt ttctcccatt caacaggttg   2100
tctcttcatt ctgttgactg tttcctttgc tgtgcagaag cactttatat acagtcccat   2160
ttgtctattt tttagtagtc tatgcattta aggtctcagc cacaaaatct ttgcctagac   2220
cagtcctaaa gtgtttcccc tatattttct tctagtagtt ttattgtttc atgtcttata   2280
tttaagtcta taatccattg tgagttgatt tttgtatatg gtgagatagg ggccttgttt   2340
cattcctctg catatagata tttaattttc tcagcaccat ttattgaagg tgtccttccc   2400
tattgtatgt tcttggtgcc tttgtcaaaa ttcagttggc tataaatatg tgaatttatt   2460
tctgggttct ctatgtggtt ccattagtct atgtgtctat ttttatacca atatcatgct   2520
gttttgatta ccatagcctt gtaatatatt ttgaagtcag gtagtgtgat gcctccagct   2580
ttgttctttt tgctcaggat tgctgtgcat actctggctt tttggttaca tacaaatttc   2640
aggattttg tatttctgtg aaaaatggca ttagtatttt gataggaatt gcactggatc   2700
tgtatattgt cctggacaac atggtcattt taacaatatt aattcttcta atctatgagt   2760
atgagacgtc ttcccacttg tttgtgtcct cttcaatttc tttcattggt gtttcataat   2820
ctcccttcta caggcctttc acctccttgg ttaaattaat tcctaggtat ttttttgtag   2880
ctactgtaaa tgggactgcc ttctttctca gctagttcat ttttggtgca tagaaaccct   2940
atttttgtat gttcattttc tatcctgcaa cattaccaaa tttgcttatc agctttaagt   3000
gtgtattttg ctttgcttgt agagtcttct ggtttctcta aatgtaagac gatgtcatct   3060
gcaaacgggg acaatttgac ttcctcttaa aaatctgtat gcctttttatt cctttctctt   3120
gcctgattgc tctggctcta cctccagtac tatactgaat aaaagtggta aaagtgagca   3180
tccttccttg tcttgctcta gttcttagag gaaatacttt cagtttttcc ccactcagta   3240
tgatgttagc tgtgggtcat atatagcctt tattatgtta agatatgttt cttctgtacc   3300
tggtttgttg acagcttttt atcataaaag gatgtagaat tttatcaaat gtttttttctg   3360
catctgttga gataatcata tggtttttgt cattccttct actgttgtga tgtatcatgt   3420
ttattgattt gtgtatgtta aaccatcctt gtgtccttgg tataaattat acttggtcat   3480
ggtgtattat ctttttggca tcctgtcgaa ttgtttgcta gctttttgtt ttgttctttt   3540
tgagaatttt tatgtctagg ttccttagaa acactggcct gtagttctct ttttgtgtgt   3600
gtgtccttgt ctagtttggt gtcagggaaa tggtggtctt gtagaatgag ttgtttttttc   3660
tttgattttt ttgcaagagt ttgaggagaa tgggtattag ttcttcttta tgtggttggt   3720
caaattggca gtgaattcat tcagtcatga gcttttcttt ttttgggagg gttctcatta   3780
ctgagttaat cacactgctc attactgatc tgttcagatt ttctatttct tctggaatct   3840
cagtagttgt atgtttccag caatttatcc atttcctcta ggttttctag tttggtagta   3900
tatagctatt cataatagtc tctgatgatc ttttgtattt ctgtgatatc agttgtaatg   3960
tctttttcat ttcctatttt atttgggtct tttcttgttt agtctagcaa ggggtttatc   4020
tattttatct ttttgaagaa ccaacttttt gtttcattga ccctttctac gtctttagtc   4080
```

```
tttatttcat ttagatttgc tctgaacttt actatgtctt tccttctaat tttgggtttg   4140
gtttgttctt ttctagttcc ttgaggtgca tcattgaatt gtttctttga tatctatcta   4200
ctcatttgat gtaggtgttt attgctatac actctcccct cctagagctc cttttgttgt   4260
gtcccatagg tcttggtatg ttgtttctat tttcatttgt ttcaaacatt ttatttccat   4320
attaattttt atcattcagg aggagcatat tatttaattc ccatgtattt gtatagtttc   4380
caaagttcct cttatttcta tttttactcc attgtggtct gagaagatac ttcatatgat   4440
ttcaattttt aaaaatttgt caagacttgt tttttgtcct aacatatggt ctatcctgga   4500
gaatgttcca tgtgctgatg agaaaaatgt gtactcagca gttgttgagt aacatgttct   4560
acaaatatct gttagatcca tttggtctaa agtctagttt aaatccaatg agtttttgtt   4620
aattttgtct agatgatcat gatctgagac tgaggtgaag tccccaacaa ttatcgtgtt   4680
ggagtctacc tctcttttta aatctagaaa tatttgcttt ataaatccgg gtggtctagt   4740
gttgggtgca tatatttagt tgttatttcc tcattagatt gatctcttta ctattatata   4800
ataactgttt actgcttctg gcataaagtc tgttttatgt aagtacagcc attcctgctt   4860
gagtttagta ccatgttgac aaagggatgc atagagagtt ggtaaagcat gatttctggg   4920
tgtctgtgtg aaggtgtttt gagaagagtt tagcatgagt ctgtggagtg agtgggaaga   4980
ttctccctca atgtcagcag gaaccatcca tccactgggg gcccaggtag aaaaagatga   5040
agaaatggtg aattctctct ctctcctgga gctgggtcac ccttcttctg cccttgaaca   5100
ggacatcaca actccaggct ctccagcctt tggactccaa gactgacacc agtgcccctc   5160
cccaattacc ccaggccctc aggcctttgg cctaggattg agacttacac catcagcttc   5220
cctggttctg aggcttctgg acttgcactg ggccatacta ccagcatccc agggtctcca   5280
gcttgcagag agcctgttgt gggacttttc agcctccata atcaagtaag ccaatttccc   5340
tggtatctat atagatatac aatcatgttt tgcttaccag cctgaaaaat gtatcgctag   5400
atgagtctgt cattgcataa acatcatagt gtacttacac aaacctagat tctatagcct   5460
actacacacc tagtctataa acatgtacag catgttactg tactgaatat tgtaggcaac   5520
tgtaacacaa tggtgaatat ttgcatattt aaacatatct tatcattaaa aagatacagt   5580
aaacataagg tataaaagac aaaaaccggc acacctatat agggcactta ccataaatgc   5640
agcttgcagg actagaagtc actcagggtg agtcagtgag cgaacgtgaa ggcctaggtt   5700
attactgtcc actacggtag actttatcaa cactgtacac aggctacact aaatttattt   5760
tttaaaaatt tgctctccaa taataaatta atcttcgcat ccttttttttg ttgttcactg   5820
tgg                                                                  5823
```

<210> SEQ ID NO 418
<211> LENGTH: 707
<212> TYPE: DNA
<213> ORGANISM: Homo sapiens

<400> SEQUENCE: 418

```
aacggtgtca gctggagtga actcctgtgt gtgcaaggcc tgggtctcct ggtcagacta     60
ctttctatgg gaaaggcata gtgtatagtc tatatactat acataggggt gctgggagga    120
actggggttt tcacagccag ctttggtttt cattaggttt gtttagtttc cattgcttca    180
ggggtgttag ttttgtgttc mcaactagat tataaactcc tcttgcattc ctgatggcag    240
tgacttgaag gcatttattt gaagaataat agacatacag aaaggggcgc atgtcataaa    300
```

```
ggtacagctg gacgactttt cacaaagtga gcacatttgt atgatcgatg ttgagaccaa    360

gagcattcag tggacaactc ctttccagtt actccacccc actcccagtg accatcattc    420

tgacttctaa ctgtgtagac atgttttgct tgttttgtac tttacaaaca tatctactct    480

attttaggtg gctagacaat gtgttttaca atgctggcca tgacagtgtt tgaaagaata    540

aaatggaatc aaatagaatg ggcagtatca gagtgtgttg cctgcctaag aaatgttttg    600

tgacattttg gctttgggtc tatttacaca ttaaatctaa gagcaccaga atgtggtgtc    660

aaaatgtgtt tggggatgaa gatattctaa agtcctgtag taagcaa                 707


<210> SEQ ID NO 419
<211> LENGTH: 712
<212> TYPE: DNA
<213> ORGANISM: Homo sapiens

<400> SEQUENCE: 419

cagactactt tctatgggaa aggcatagtg tatagtctat atactataca taggggtgct     60

gggaggaact ggggttttca cagccagctt tggttttcat taggtttgtt tagtttccat    120

tgcttcaggg gtgttagttt tgtgttccca actagattat aaactcctct tgcattcctg    180

atggcagtga cttgaaggca tttatttgaa gaataataga catacagaaa ggggcrcatg    240

tcataaaggt acagctggac gacttttcac aaagtgagca catttgtatg atcgatgttg    300

agaccaagag cattcagtgg acaactcctt tccagttact ccaccccact cccagtgacc    360

atcattctga cttctaactg tgtagacatg ttttgcttgt tttgtacttt acaaacatat    420

ctactctatt ttaggtggct agacaatgtg ttttacaatg ctggccatga cagtgtttga    480

aagaataaaa tggaatcaaa tagaatgggc agtatcagag tgtgttgcct gcctaagaaa    540

tgttttgtga cattttggct ttgggtctat ttacacatta aatctaagag caccagaatg    600

tggtgtcaaa atgtgtttgg ggatgaagat attctaaagt cctgtagtaa gcaatgcaaa    660

acgttctgga ggtgtttatt aaacatttgt ttgtagaatg gagaggaaga ca            712


<210> SEQ ID NO 420
<211> LENGTH: 1210
<212> TYPE: DNA
<213> ORGANISM: Homo sapiens

<400> SEQUENCE: 420

aaagcagcac tgctctgcat tcagccttgc tacgtctcct tcagatgggc gcactagata     60

ctgagtgatg atcatgcctt gtctaggatc tcaccaagac agttcatgaa agagacagtg    120

cagctcatgg aggagatggt gcagctcaca gagaggatgg tgccatcatg gaaagcatgg    180

ggcagtcatg gagatgacgg rgtagctcat ggagaatata atgccatcat ggaaggcata    240

gtgcagtcat ggagatgatg gtgcagctca tggagaagat ggtgccatca tggaaggcat    300

ggtgcaatca tggagtagac agtgcagctg ggccaagatt ctccctgact aagctcttct    360

caggcacctc tgagccgtcg tcttaactag gcctccagct tggcttgtga aaactgcaga    420

ctctcagcac aaatgatttg cctcctacat taagagactt aaataaacac ttgcatggct    480

gtgtttattt aaacagctca aggctgtgtc cctgggatga caatgactcc agcccctaaa    540

attcctgctt gtgaaagctc attgctgaca gaaggatcta ccatttgttc cagccaacac    600

ctggtggcag gcagataggc cctgagcccc atttaagagc agttccttta gaaagcttgc    660

aattgtaaat cttttctctg cccatttgag atgtaaatct tctaccacct agaactgtct    720

tctcaaggac ctgtgagctg actcactgaa atgcaaacat tcagggagat aactccactc    780
```

```
ctgtccccat gcgacggcga ggccctgact ttggtgggca ccttgctctt atttgcacca    840

ccacctcctg tcctaaagac atgagacgtt tgtctctcct ctggataagt gcctattaac    900

caacccaggt gtcctggtca catgaaccag tccagcctag cacctggcac tgcctttccc    960

tcagcacact ccagtctgta aaagtctcct tatggttgtt ttggcaaagt tgagcttagt   1020

taatgctaga ccccttctct actgcaatag ttactgctga ataaagtcta tccttaccac   1080

tttaactagt gttgggcttt gtttctcttt cataagctca tggagaagac aatgcagttc   1140

catcaagttt ctggctctta cactgctaac agtcagctct ggggtccctg agagggacag   1200

actcacacca                                                          1210
```

```
<210> SEQ ID NO 421
<211> LENGTH: 1194
<212> TYPE: DNA
<213> ORGANISM: Homo sapiens

<400> SEQUENCE: 421

gcattcagcc ttgctacgtc tccttcagat gggcgcacta gatactgagt gatgatcatg     60

ccttgtctag gatctcacca agacagttca tgaaagagac agtgcagctc atggaggaga    120

tggtgcagct cacagagagg atggtgccat catggaaagc atggggcagt catggagatg    180

acggagtagc tcatggagaa kataatgcca tcatggaagg catagtgcag tcatggagat    240

gatggtgcag ctcatggaga agatggtgcc atcatggaag gcatggtgca atcatggagt    300

agacagtgca gctgggccaa gattctccct gactaagctc ttctcaggca cctctgagcc    360

gtcgtcttaa ctaggcctcc agcttggctt gtgaaaactg cagactctca gcacaaatga    420

tttgcctcct acattaagag acttaaataa acacttgcat ggctgtgttt atttaaacag    480

ctcaaggctg tgtccctggg atgacaatga ctccagcccc taaaattcct gcttgtgaaa    540

gctcattgct gacagaagga tctaccattt gttccagcca acacctggtg gcaggcagat    600

aggccctgag ccccatttaa gagcagttcc tttagaaagc ttgcaattgt aaatcttttc    660

tctgcccatt tgagatgtaa atcttctacc acctagaact gtcttctcaa ggacctgtga    720

gctgactcac tgaaatgcaa acattcaggg agataactcc actcctgtcc ccatgcgacg    780

gcgaggccct gactttggtg ggcaccttgc tcttatttgc accaccacct cctgtcctaa    840

agacatgaga cgtttgtctc tcctctggat aagtgcctat taaccaaccc aggtgtcctg    900

gtcacatgaa ccagtccagc ctagcacctg gcactgcctt tccctcagca cactccagtc    960

tgtaaaagtc tccttatggt tgttttggca aagttgagct tagttaatgc tagacccctt   1020

ctctactgca atagttactg ctgaataaag tctatcctta ccactttaac tagtgttggg   1080

ctttgtttct ctttcataag ctcatggaga agacaatgca gttccatcaa gtttctggct   1140

cttacactgc taacagtcag ctctggggtc cctgagaggg acagactcac acca         1194
```

```
<210> SEQ ID NO 422
<211> LENGTH: 1194
<212> TYPE: DNA
<213> ORGANISM: Homo sapiens

<400> SEQUENCE: 422

gcattcagcc ttgctacgtc tccttcagat gggcgcacta gatactgagt gatgatcatg     60

ccttgtctag gatctcacca agacagttca tgaaagagac agtgcagctc atggaggaga    120

tggtgcagct cacagagagg atggtgccat catggaaagc atggggcagt catggagatg    180
```

```
acggagtagc tcatggagaa kataatgcca tcatggaagg catagtgcag tcatggagat    240
gatggtgcag ctcatggaga agatggtgcc atcatggaag gcatggtgca atcatggagt    300
agacagtgca gctgggccaa gattctccct gactaagctc ttctcaggca cctctgagcc    360
gtcgtcttaa ctaggcctcc agcttggctt gtgaaaactg cagactctca gcacaaatga    420
tttgcctcct acattaagag acttaaataa acacttgcat ggctgtgttt atttaaacag    480
ctcaaggctg tgtccctggg atgacaatga ctccagcccc taaaattcct gcttgtgaaa    540
gctcattgct gacagaagga tctaccattt gttccagcca acacctggtg gcaggcagat    600
aggccctgag ccccatttaa gagcagttcc tttagaaagc ttgcaattgt aaatcttttc    660
tctgcccatt tgagatgtaa atcttctacc acctagaact gtcttctcaa ggacctgtga    720
gctgactcac tgaaatgcaa acattcaggg agataactcc actcctgtcc ccatgcgacg    780
gcgaggccct gactttggtg ggcaccttgc tcttatttgc accaccacct cctgtcctaa    840
agacatgaga cgtttgtctc tcctctggat aagtgcctat taaccaaccc aggtgtcctg    900
gtcacatgaa ccagtccagc ctagcacctg gcactgcctt tccctcagca cactccagtc    960
tgtaaaagtc tccttatggt tgttttggca aagttgagct tagttaatgc tagacccctt   1020
ctctactgca atagttactg ctgaataaag tctatcctta ccactttaac tagtgttggg   1080
ctttgtttct ctttcataag ctcatggaga agacaatgca gttccatcaa gtttctggct   1140
cttacactgc taacagtcag ctctggggtc cctgagaggg acagactcac acca         1194
```

<210> SEQ ID NO 423
<211> LENGTH: 1118
<212> TYPE: DNA
<213> ORGANISM: Homo sapiens

<400> SEQUENCE: 423

```
accaagacag ttcatgaaag agacagtgca gctcatggag gagatggtgc agctcacaga     60
gaggatggtg ccatcatgga aagcatgggg cagtcatgga gatgacggag tagctcatgg    120
agaagataat gccatcatgg aaggcatagt gcagtcatgg agatgatggt gcagctcatg    180
gagaagatgg tgccatcatg raaggcatgg tgcaatcatg gagtagacag tgcagctggg    240
ccaagattct ccctgactaa gctcttctca ggcacctctg agccgtcgtc ttaactaggc    300
ctccagcttg gcttgtgaaa actgcagact ctcagcacaa atgatttgcc tcctacatta    360
agagacttaa ataaacactt gcatggctgt gtttatttaa acagctcaag gctgtgtccc    420
tgggatgaca atgactccag cccctaaaat tcctgcttgt gaaagctcat tgctgacaga    480
aggatctacc atttgttcca gccaacacct ggtggcaggc agataggccc tgagccccat    540
ttaagagcag ttcctttaga aagcttgcaa ttgtaaatct tttctctgcc catttgagat    600
gtaaatcttc taccacctag aactgtcttc tcaaggacct gtgagctgac tcactgaaat    660
gcaaacattc agggagataa ctccactcct gtccccatgc gacggcgagg ccctgacttt    720
ggtgggcacc ttgctcttat ttgcaccacc acctcctgtc ctaaagacat gagacgtttg    780
tctctcctct ggataagtgc ctattaacca acccaggtgt cctggtcaca tgaaccagtc    840
cagcctagca cctggcactg cctttccctc agcacactcc agtctgtaaa agtctcctta    900
tggttgtttt ggcaaagttg agcttagtta atgctagacc ccttctctac tgcaatagtt    960
actgctgaat aaagtctatc cttaccactt taactagtgt tgggctttgt ttctctttca   1020
taagctcatg gagaagacaa tgcagttcca tcaagtttct ggctcttaca ctgctaacag   1080
tcagctctgg ggtccctgag agggacagac tcacacca                           1118
```

<210> SEQ ID NO 424
<211> LENGTH: 601
<212> TYPE: DNA
<213> ORGANISM: Homo sapiens

<400> SEQUENCE: 424

```
gtaggggcac tgtctatact ggctgcactc tggccagtgc tgtcccaacg ctgacccctc     60
tggaagctaa tctggcttat aatgaggatg ctttctttag aggggactct ccatgcacag    120
cagaaaatcc caatggagtg gttcttccct atgtccccaa gggactggga atattctttc    180
agtaacaatg gcccattggg ggaagaagga tgaaagtggg gtgagagacg tgaaatttgg    240
agaggtccct caaagattgt gatgtgcctc tcttgttcca atcacaggac aggggtataa    300
yggctttcct ttgaaacacg gggatgaatt taactattca cttcccaggt agattcatca    360
gggtctagag cttcagctaa cagcatgagg aagattccaa atgtgccccc atcagcatag    420
gaactgggta tgttgagtct atggtctcat aaaaccagaa gaaggacaag ggattgtggc    480
tccaggcttg ggagcacctt ttccttacca tgggctacag tatttattta gggtaaagga    540
aggaaactcc tgaggtgcta tggggtgcca gcaatttgga gcatcagtaa ttcaatgtcc    600
c                                                                    601
```

<210> SEQ ID NO 425
<211> LENGTH: 601
<212> TYPE: DNA
<213> ORGANISM: Homo sapiens

<400> SEQUENCE: 425

```
acgctgaccc ctctggaagc taatctggct tataatgagg atgctttctt tagaggggac     60
tctccatgca cagcagaaaa tcccaatgga gtggttcttc cctatgtccc caagggactg    120
ggaatattct ttcagtaaca atggcccatt gggggaagaa ggatgaaagt ggggtgagag    180
acgtgaaatt tggagaggtc cctcaaagat tgtgatgtgc ctctcttgtt ccaatcacag    240
gacaggggta taacggcttt cctttgaaac acggggatga atttaactat tcacttccca    300
rgtagattca tcagggtcta gagcttcagc taacagcatg aggaagattc caaatgtgcc    360
cccatcagca taggaactgg gtatgttgag tctatggtct cataaaacca gaagaaggac    420
aagggattgt ggctccaggc ttgggagcac cttttcctta ccatgggcta cagtatttat    480
ttagggtaaa ggaaggaaac tcctgaggtg ctatggggtg ccagcaattt ggagcatcag    540
taattcaatg tcccttcagc catgtgtatt caactcctgc tgtgggtgtg gacttggtgc    600
a                                                                    601
```

<210> SEQ ID NO 426
<211> LENGTH: 701
<212> TYPE: DNA
<213> ORGANISM: Homo sapiens

<400> SEQUENCE: 426

```
ttcctgggca tcgtcatatt ctgtaaaaca aggaagctca gcccagtgtg ttctaacatg     60
acctcctttc tacatcctta ggtgttgtta tgcgtgaatc acgtcccccc aaaagacatg    120
ttcatgtcct aacccccagg acctcagaat gtgtgatctg gtttggaaat aaggtcatca    180
cagatgaaat tagctaagac aaggtcatat tggaataggg ttggccctta atccactgtg    240
actggtgtcc ttttaagaag aggacacaga cacaggaggg gagagggcca tgggatgatg    300
```

-continued

```
caggtggaga ctggagtgct acagctgcaa gcaaatacat ttctgtgctg tgaagccacc    360

catttggtgg tactacgtta aaacagctct aggaaattaa tacagatgtt gcctgtattt    420

ttgtttctca tattactact cattgtttta atgatgactg ttttattcat taagttgaaa    480

gctcctaaag cagagggacc rtatttttat gtcccaactc tccttaaggc cttgcctatg    540

atagcacatc tcttcaatag aattgtccta actttaacag agacaacttg ggttatttaa    600

tatggagaac aaagggttaa gctggtgcca gatgggtttc attttctcta aatctggaac    660

caaaggcagc aagtctatgg ggtggacgga gttcttagct c                        701


<210> SEQ ID NO 427
<211> LENGTH: 701
<212> TYPE: DNA
<213> ORGANISM: Homo sapiens

<400> SEQUENCE: 427

caaggaagct cagcccagtg tgttctaaca tgacctcctt tctacatcct taggtgttgt     60

tatgcgtgaa tcacgtcccc ccaaaagaca tgttcatgtc ctaaccccca ggacctcaga    120

atgtgtgatc tggtttggaa ataaggtcat cacagatgaa attagctaag acaaggtcat    180

attggaatag ggttggccct taatccactg tgactggtgt ccttttaaga agaggacaca    240

gacacaggag gggagagggc catgggatga tgcaggtgga gactggagtg ctacagctgc    300

aagcaaatac atttctgtgc tgtgaagcca cccatttggt ggtactacgt taaaacagct    360

ctaggaaatt aatacagatg ttgcctgtat ttttgtttct catattacta ctcattgttt    420

taatgatgac tgttttattc attaagttga aagctcctaa agcagaggga ccatattttt    480

atgtcccaac tctccttaag sccttgccta tgatagcaca tctcttcaat agaattgtcc    540

taactttaac agagacaact tgggttattt aatatggaga acaaagggtt aagctggtgc    600

cagatgggtt tcattttctc taaatctgga accaaaggca gcaagtctat ggggtggacg    660

gagttcttag ctcaaccctt tggtgaggta agaagaagga t                        701
```

SIMULTANEOUS DETERMINATION OF ANEUPLOIDY AND FETAL FRACTION

CROSS REFERENCE

This application is a continuation of, and claims priority to, U.S. patent application Ser. No. 13/365,240 entitled "Simultaneous Determination of Aneuploidy and Fetal Fraction", filed on Feb. 2, 2012, which is a continuation of U.S. patent application Ser. No. 12/958,356 entitled "Simultaneous Determination of Aneuploidy and Fetal Fraction", filed on Dec. 1, 2010, which claims priority to U.S. Provisional Application Ser. No. 61/296,358 entitled "Methods for Determining Fraction of Fetal Nucleic Acids in Maternal Samples", filed on Jan. 19, 2010; U.S. Provisional Application Ser. No. 61/360,837 entitled "Methods for Determining Fraction of Fetal Nucleic Acids in Maternal Samples", filed on Jul. 1, 2010; U.S. Provisional Application Ser. No. 61/407,017 entitled "Method for Determining Copy Number Variations", filed on Oct. 26, 2010; and U.S. Provisional Application Ser. No. 61/455,849 entitled "Simultaneous determination of Aneuploidy and Fetal Fraction", filed on Oct. 26, 2010; which are incorporated herein by reference in their entirety.

SEQUENCE LISTING

The sequence listing submitted via EFS, in compliance with C.F.R. §1.52(e), is incorporated herein by reference. The sequence listing text file submitted via EFS, in U.S. patent application Ser. No. 13/365,240, contains the file "Seq_List_0119_301.txt" created on Mar. 7, 2012, which is 238,557 bytes in size.

FIELD OF THE INVENTION

The invention relates generally to the field of diagnostics, and provides a method that is applicable to the practice of noninvasive prenatal diagnostics.

BACKGROUND OF THE INVENTION

Prenatal diagnosis to determine potential fetal abnormalities provides an opportunity for necessary care and management during pregnancy, the neonatal period and delivery. Imaging techniques such as ultrasonography, magnetic resonance imaging and fetal echocardiography are useful for the identification of structural abnormalities of the fetus. Amniocentesis, chronic villus sampling and fetal blood sampling provide fetal cells and tissues for the analysis of chromosomal, genetic and biochemical abnormalities, but are invasive and pose great risk to the pregnancy.

The existence of circulating cell-free DNA in maternal blood (Lo et al., Lancet 350:485-487 [1997]) is being exploited for developing noninvasive processes that use fetal nucleic acids from a maternal peripheral blood sample to determine fetal chromosomal abnormalities (Fan H C and Quake S R Anal Chem 79:7576-7579 [2007]; Fan et al., Proc Natl Acad Sci 105:16266-16271 [2008]).

These methods provide a paradigm shift in prenatal diagnosis, as they could effectively pronounce the end of invasive procedures. However, the sensitivity of fetal aneuploidy determination largely depends on the fetal DNA fraction, which has been determined to be <10% of the total circulating cell-free DNA (cfDNA) (Lo et al., *Am J Hum Genet* 62:768-775 [1998]). Given the relatively low concentration of fetal circulating nucleic acids, false negative results can arise if there is insufficient starting nucleic acid for analysis. Accordingly, assays for the noninvasive determination of fetal DNA fraction have been developed, but typically rely on comparing the amount of fetal-specific locus (such as the SRY locus on chromosome Y in male pregnancies) to that of a locus on any autosome that is common to both the mother and the fetus (Dahllan et al., Lancet 369:474-481 [2007], Li et al., Clin Chem 1002-1011 [2004]; Fan et al., Proc Natl Acad Sci 105:16266-16271 [2008]). In addition, the assays used for quantifying fetal fraction are performed independently of the assays being developed for determining the presence or absence of aneuploidies in circulating cfDNA.

Therefore, it would be desirable to provide a prenatal test that affords an internal control to measure the adequacy of input fetal nucleic acids and avoid incorrect diagnoses of fetal chromosomal abnormalities.

The present invention provides compositions and methods that enable the simultaneous determination of fetal fraction and the determination of the presence or absence of aneuploidy from a single diagnostic sequencing process. The method allows for determining fetal fraction in a gender-independent manner, which relies on quantification of alleles on multiple chromosomes. The noninvasive diagnostic method encompasses the use of next generation sequencing (NGS) technology that can be implemented in a streamlined and cost-effective process to provide noninvasive prenatal diagnoses of fetal aneuploidies with greater confidence.

SUMMARY OF THE INVENTION

The invention provides compositions and methods for simultaneously determining the presence or absence of fetal aneuploidy and the relative amount of fetal nucleic acids in a sample obtained from a pregnant female. The method encompasses the use of sequencing technologies and exploits the occurrence of polymorphisms to provide a streamlined noninvasive process applicable to the practice of prenatal diagnostics.

In one embodiment, a method is provided for simultaneously determining aneuploidy and fetal fraction in a maternal sample comprising a mixture of fetal and maternal nucleic acid molecules, the method comprising: (a) enriching said mixture for a plurality of polymorphic target nucleic acids; (b) sequencing at least a portion of the enriched mixture obtained in step (a), wherein sequencing comprises providing a plurality of sequence tags; and (c) based on the sequencing, simultaneously determining the fetal fraction and the presence or absence of the fetal aneuploidy.

In another embodiment, a method is provided for simultaneously determining aneuploidy and fetal fraction in a maternal sample comprising a mixture of fetal and maternal nucleic acid molecules, the method comprising: (a) enriching said mixture for a plurality of polymorphic target nucleic acids; wherein enriching comprises amplifying a plurality of polymorphic target nucleic acids in a portion of said mixture; (b) sequencing at least a portion of the enriched mixture obtained in step (a), wherein sequencing comprises providing a plurality of sequence tags; and (c) based on the sequencing, simultaneously determining the fetal fraction and the presence or absence of the fetal aneuploidy.

In another embodiment, a method is provided for simultaneously determining aneuploidy and fetal fraction in a maternal sample comprising a mixture of fetal and maternal nucleic acid molecules, the method comprising: (a) enriching said mixture for a plurality of polymorphic target nucleic acids; wherein enriching comprises amplifying a plurality of polymorphic target nucleic acids in a portion of a purified mixture of fetal and maternal nucleic acids; (b) sequencing at least a portion of the enriched mixture obtained in step (a), wherein sequencing comprises providing a plurality of sequence tags; and (c) based on the sequencing, simultaneously determining the fetal fraction and the presence or absence of the fetal aneuploidy.

In another embodiment, a method is provided for simultaneously determining aneuploidy and fetal fraction in a maternal sample comprising a mixture of fetal and maternal nucleic acid molecules, the method comprising: (a) enriching said mixture for a plurality of polymorphic target nucleic acids; wherein enriching comprises combining at least a portion of a first sequencing library of said mixture of fetal and maternal nucleic acid molecules with at least a portion of a second sequencing library of amplified polymorphic target nucleic acids; (b) sequencing at least a portion of the enriched mixture obtained in step (a), wherein sequencing comprises providing a plurality of sequence tags; and (c) based on the sequencing, simultaneously determining the fetal fraction and the presence or absence of the fetal aneuploidy.

In one embodiment, a method is provided for simultaneously determining aneuploidy and fetal fraction in a maternal sample comprising a mixture of fetal and maternal nucleic acid molecules, the method comprising: (a) enriching said mixture for a plurality of polymorphic target nucleic acids; wherein each of the plurality of polymorphic target nucleic acids comprises at least one single nucleotide polymorphism (SNP); (b) sequencing at least a portion of the enriched mixture obtained in step (a), wherein sequencing comprises providing a plurality of sequence tags; and (c) based on the sequencing, simultaneously determining the fetal fraction and the presence or absence of the fetal aneuploidy. In some embodiments, the at least one SNP, is a single SNP selected from each of said plurality of polymorphic target nucleic acids comprises a SNP selected from rs560681, rs1109037, rs9866013, rs13182883, rs13218440, rs7041158, rs740598, rs10773760, rs4530059, rs7205345, rs8078417, rs576261, rs2567608, rs430046, rs9951171, rs338882, rs10776839, rs9905977, rs1277284, rs258684, rs1347696, rs508485, rs9788670, rs8137254, rs3143, rs2182957, rs3739005, and rs530022. Alternatively, the at least one SNP is a set of two tandem SNPs selected from sets rs7277033-rs2110153; rs2822654-rs1882882; rs368657-rs376635; rs2822731-rs2822732; rs1475881-rs7275487; rs1735976-rs2827016; rs447340-rs2824097; rs418989-rs13047336; rs987980-rs987981; rs4143392-rs4143391; rs1691324-rs13050434; rs11909758-rs9980111; rs2826842-rs232414; rs1980969-rs1980970; rs9978999-rs9979175; rs1034346-rs12481852; rs7509629-rs2828358; rs4817013-rs7277036; rs9981121-rs2829696; rs455921-rs2898102; rs2898102-rs458848; rs961301-rs2830208; rs2174536-rs458076; rs11088023-rs11088024; rs1101734-rs1011733; rs2831244-rs9789838; rs8132769-rs2831440; rs8134080-rs2831524; rs4817219-rs4817220; rs2250911-rs2250997; rs2831899-rs2831900; rs2831902-rs2831903; rs11088086-rs2251447; rs2832040-rs11088088; rs2832141-rs2246777; rs2832959-rs9980934; rs2833734-rs2833735; rs933121-rs933122; rs2834140-rs12626953; rs2834485-rs3453; rs9974986-rs2834703; rs2776266-rs2835001; rs1984014-rs1984015; rs7281674-rs2835316; rs13047304-rs13047322; rs2835545-rs4816551; rs2835735-rs2835736; rs13047608-rs2835826; rs2836550-rs2212596; rs2836660-rs2836661; rs465612-rs8131220; rs9980072-rs8130031; rs418359-rs2836926; rs7278447-rs7278858; rs385787-rs367001; rs367001-rs386095; rs2837296-rs2837297; and rs2837381-rs4816672.

In one embodiment, a method is provided for simultaneously determining aneuploidy and fetal fraction in a maternal sample comprising a mixture of fetal and maternal nucleic acid molecules, the method comprising: (a) enriching said mixture for a plurality of polymorphic target nucleic acids; wherein each of the plurality of polymorphic target nucleic acids comprises at least one single nucleotide polymorphism (SNP); (b) sequencing at least a portion of the enriched mixture obtained in step (a), wherein sequencing comprises providing a plurality of sequence tags; and (c) based on the sequencing, simultaneously determining the fetal fraction and the presence or absence of the fetal aneuploidy. The step of enriching comprises amplifying a plurality of polymorphic target nucleic acids in a portion of said mixture. In some embodiments, the at least one SNP, is a single SNP selected from each of said plurality of polymorphic target nucleic acids comprises a SNP selected from rs560681, rs1109037, rs9866013, rs13182883, rs13218440, rs7041158, rs740598, rs10773760, rs4530059, rs7205345, rs8078417, rs576261, rs2567608, rs430046, rs9951171, rs338882, rs10776839, rs9905977, rs1277284, rs258684, rs1347696, rs508485, rs9788670, rs8137254, rs3143, rs2182957, rs3739005, and rs530022. Alternatively, the at least one SNP is a set of two tandem SNPs selected from sets rs7277033-rs2110153; rs2822654-rs1882882; rs368657-rs376635; rs2822731-rs2822732; rs1475881-rs7275487; rs1735976-rs2827016; rs447340-rs2824097; rs418989-rs13047336; rs987980-rs987981; rs4143392-rs4143391; rs1691324-rs13050434; rs11909758-rs9980111; rs2826842-rs232414; rs1980969-rs1980970; rs9978999-rs9979175; rs1034346-rs12481852; rs7509629-rs2828358; rs4817013-rs7277036; rs9981121-rs2829696; rs455921-rs2898102; rs2898102-rs458848; rs961301-rs2830208; rs2174536-rs458076; rs11088023-rs11088024; rs1011734-rs1011733; rs2831244-rs9789838; rs8132769-rs2831440; rs8134080-rs2831524; rs4817219-rs4817220; rs2250911-rs2250997; rs2831899-rs2831900; rs2831902-rs2831903; rs11088086-rs2251447; rs2832040-rs11088088; rs2832141-rs2246777; rs2832959-rs9980934; rs2833734-rs2833735; rs933121-rs933122; rs2834140-rs12626953; rs2834485-rs3453; rs9974986-rs2834703; rs2776266-rs2835001; rs1984014-rs1984015; rs7281674-rs2835316; rs13047304-rs13047322; rs2835545-rs4816551; rs2835735-rs2835736; rs13047608-rs2835826; rs2836550-rs2212596; rs2836660-rs2836661; rs465612-rs8131220; rs9980072-rs8130031; rs418359-rs2836926; rs7278447-rs7278858; rs385787-rs367001; rs367001-rs386095; rs2837296-rs2837297; and rs2837381-rs4816672.

In one embodiment, a method is provided for simultaneously determining aneuploidy and fetal fraction in a maternal sample comprising a mixture of fetal and maternal nucleic acid molecules, the method comprising: (a) enriching said mixture for a plurality of polymorphic target nucleic acids; wherein each of the plurality of polymorphic target nucleic acids comprises at least one single nucleotide polymorphism (SNP); (b) sequencing at least a portion of the enriched mixture obtained in step (a), wherein sequencing comprises providing a plurality of sequence tags; and (c) based on the sequencing, simultaneously determining the fetal fraction and the presence or absence of the fetal aneuploidy. The step of enriching comprises amplifying a plurality of polymorphic target nucleic acids in a portion of a purified mixture of fetal and maternal nucleic acids. In some embodiments, the at least one SNP, is a single SNP selected from rs560681, rs1109037, rs9866013, rs13182883, rs13218440, rs7041158, rs740598, rs10773760, rs 4530059, rs7205345, rs8078417, rs576261, rs2567608, rs430046, rs9951171, rs338882, rs10776839, rs9905977, rs1277284, rs258684, rs1347696, rs508485, rs9788670, rs8137254, rs3143, rs2182957, rs3739005, and rs530022. Alternatively, the at least one SNP is a set of two tandem SNPs selected from sets rs7277033-rs2110153; rs2822654-rs1882882; rs368657-rs376635; rs2822731-rs2822732; rs1475881-rs7275487; rs1735976-rs2827016; rs447340-rs2824097; rs418989-rs13047336; rs987980-rs987981; rs4143392-rs4143391; rs1691324-rs13050434; rs11909758-rs9980111; rs2826842-rs232414; rs1980969-rs1980970; rs9978999-rs9979175; rs1034346-rs12481852; rs7509629-rs2828358; rs4817013-rs7277036; rs9981121-rs2829696; rs455921-rs2898102; rs2898102-rs458848; rs961301-rs2830208; rs2174536-rs458076; rs11088023-rs11088024; rs1011734-rs1011733; rs2831244-rs9789838; rs8132769-rs2831440; rs8134080-rs2831524; rs4817219-rs4817220; rs2250911-rs2250997; rs2831899-rs2831900; rs2831902-rs2831903; rs11088086-rs2251447; rs2832040-rs11088088; rs2832141-rs2246777; rs2832959-rs9980934; rs2833734-rs2833735; rs933121-rs933122; rs2834140-rs12626953; rs2834485-rs3453; rs9974986-rs2834703; rs2776266-rs2835001; rs1984014-rs1984015; rs7281674-rs2835316; rs13047304-rs13047322; rs2835545-rs4816551; rs2835735-rs2835736; rs13047608-rs2835826; rs2836550-rs2212596; rs2836660-rs2836661; rs465612-rs8131220; rs9980072-rs8130031; rs418359-rs2836926; rs7278447-rs7278858; rs385787-rs367001; rs367001-rs386095; rs2837296-rs2837297; and rs2837381-rs4816672.

In one embodiment, a method is provided for simultaneously determining aneuploidy and fetal fraction in a maternal sample comprising a mixture of fetal and maternal nucleic acid molecules, the method comprising: (a) enriching said mixture for a plurality of polymorphic target nucleic acids; wherein each of the plurality of polymorphic target nucleic acids comprises at least one single nucleotide polymorphism (SNP); (b) sequencing at least a portion of the enriched mixture obtained in step (a), wherein sequencing comprises providing a plurality of sequence tags; and (c) based on the sequencing, simultaneously determining the fetal fraction and the presence or absence of the fetal aneuploidy. The step of enriching comprises combining at least a portion of a first sequencing library of said mixture of fetal and maternal nucleic acid molecules with at least a portion of a second sequencing library of amplified polymorphic target nucleic acids. In some embodiments, the at least one SNP, is a single SNP selected from each of said plurality of polymorphic target nucleic acids comprises a SNP selected from rs560681, rs1109037, rs9866013, rs13182883, rs13218440, rs7041158, rs740598, rs10773760, rs4530059, rs7205345, rs8078417, rs576261, rs2567608, rs430046, rs9951171, rs338882, rs10776839, rs9905977, rs1277284, rs258684, rs1347696, rs508485, rs9788670, rs8137254, rs3143, rs2182957, rs3739005, and rs530022. Alternatively, the at least one SNP is a set of two tandem SNPs selected from sets rs7277033-rs2110153; rs2822654-rs1882882; rs368657-rs376635; rs2822731-rs2822732; rs1475881-rs7275487; rs1735976-rs2827016 rs447340-rs2824097; rs418989-rs13047336; rs987980-rs987981; rs4143392-rs4143391; rs1691324-rs13050434; rs11909758-rs9980111; rs2826842-rs232414; rs1980969-rs1980970; rs9978999-rs9979175; rs1034346-rs12481852; rs7509629-rs2828358; rs4817013-rs7277036; rs9981121-rs2829696; rs455921-rs2898102; rs2898102-rs458848; rs961301-rs2830208; rs2174536-rs458076; rs11088023-rs11088024; rs1011734-rs1011733; rs2831244-rs9789838; rs8132769-rs2831440; rs8134080-rs2831524; rs4817219-rs4817220; rs2250911-rs2250997; rs2831899-rs2831900; rs2831902-rs2831903; rs11088086-rs2251447; rs2832040-rs11088088; rs2832141-rs2246777; rs2832959-rs9980934; rs2833734-rs2833735; rs933121-rs933122; rs2834140-rs12626953; rs2834485-rs3453; rs9974986-rs2834703; rs2776266-rs2835001; rs1984014-rs1984015; rs7281674-rs2835316; rs13047304-rs13047322; rs2835545-rs4816551; rs2835735-rs2835736; rs13047608-rs2835826; rs2836550-rs2212596; rs2836660-rs2836661; rs465612-rs8131220; rs9980072-rs8130031; rs418359-rs2836926; rs7278447-rs7278858; rs385787-rs367001; rs367001-rs386095; rs2837296-rs2837297; and rs2837381-rs4816672.

In another embodiment, a method is provided for simultaneously determining aneuploidy and fetal fraction in a maternal sample comprising a mixture of fetal and maternal nucleic acid molecules, the method comprising: (a) enriching said mixture for a plurality of polymorphic target nucleic acids, wherein each of the plurality of polymorphic target nucleic acids comprises at least one short tandem repeat (STR); (b) sequencing at least a portion of the enriched mixture obtained in step (a), wherein sequencing comprises providing a plurality of sequence tags; and (c) based on the sequencing, simultaneously determining the fetal fraction and the presence or absence of the fetal aneuploidy. In some embodiments, the at least one STR is less than about 200 base pairs. In other embodiments, each of said plurality of polymorphic target nucleic acids comprises an STR selected from CSF1PO, FGA, TH01, TPOX, vWA, D3S1358, D5S818, D7S820, D8S1179, D13S317, D16S539, D18S51, D21S11, D2S1338, Penta D, Penta E, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627 and D1GATA113.

In another embodiment, a method is provided for simultaneously determining aneuploidy and fetal fraction in a maternal sample comprising a mixture of fetal and maternal nucleic acid molecules, the method comprising: (a) enriching said mixture for a plurality of polymorphic target nucleic acids, wherein each of the plurality of polymorphic target nucleic acids comprises at least one short tandem repeat (STR); (b) sequencing at least a portion of the enriched mixture obtained in step (a), wherein sequencing comprises providing a plurality of sequence tags; and (c) based on the sequencing, simultaneously determining the fetal fraction and the presence or absence of the fetal aneuploidy. The step of enriching comprises amplifying a plurality of polymorphic target nucleic acids in a portion of the mixture. In some embodiments, the at least one STR is less than about 200 base pairs. In other embodiments, each of said plurality of polymorphic target nucleic acids comprises an STR selected from CSF1PO, FGA, TH01, TPOX, vWA, D3S1358, D5S818, D7S820, D8S1179, D13S317, D16S539, D18S51, D21S11, D2S1338, Penta D, Penta E, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627 and D1GATA113.

In another embodiment, a method is provided for simultaneously determining aneuploidy and fetal fraction in a maternal sample comprising a mixture of fetal and maternal nucleic acid molecules, the method comprising: (a) enriching said mixture for a plurality of polymorphic target nucleic acids, wherein each of the plurality of polymorphic target nucleic acids comprises at least one short tandem repeat (STR); (b) sequencing at least a portion of the enriched mixture obtained in step (a), wherein sequencing comprises providing a plurality of sequence tags; and (c) based on the sequencing, simultaneously determining the fetal fraction and the presence or absence of the fetal aneuploidy. The step of enriching comprises amplifying a plurality of polymorphic target nucleic acids in a portion of a purified mixture of fetal and maternal nucleic acids. In some embodiments, the at least one STR is less than about 200 base pairs. In other embodiments, each of said plurality of polymorphic target nucleic acids comprises an STR selected from CSF1PO, FGA, TH01, TPOX, vWA, D3S1358, D5S818, D7S820, D8S1179, D13S317, D16S539, D18S51, D21S11, D2S1338, Penta D, Penta E, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627 and D1GATA113.

In another embodiment, a method is provided for simultaneously determining aneuploidy and fetal fraction in a maternal sample comprising a mixture of fetal and maternal nucleic acid molecules, the method comprising: (a) enriching said mixture for a plurality of polymorphic target nucleic acids, wherein each of the plurality of polymorphic target nucleic acids comprises at least one short tandem repeat (STR); (b) sequencing at least a portion of the enriched mixture obtained in step (a), wherein sequencing comprises providing a plurality of sequence tags; and (c) based on the sequencing, simultaneously determining the fetal fraction and the presence or absence of the fetal aneuploidy. The step of enriching comprises combining at least a portion of a first sequencing library of said mixture of fetal and maternal nucleic acid molecules with at least a portion of a second sequencing library of amplified polymorphic target nucleic acids. In some embodiments, the at least one STR is less than about 200 base pairs. In other embodiments, each of said plurality of polymorphic target nucleic acids comprises an STR selected from CSF1PO, FGA, TH01, TPOX, vWA, D3S1358, D5S818, D7S820, D8S1179, D13S317, D16S539, D18S51, D21S11, D2S1338, Penta D, Penta E, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627 and D1GATA113.

In the embodiments of the method summarized above and described in further detail below, the maternal sample is a biological sample that can be chosen from but is not limited to blood, plasma, serum, urine and saliva. Preferably, the fetal and maternal nucleic acid molecules in the maternal sample are cell-free DNA (cfDNA) molecules. The polymorphic target nucleic acids can be on the same or on different chromosomes.

In the embodiments of the method summarized above and described in further detail below, the aneuploidy that is determined can be a chromosomal or a partial aneuploidy. In some embodiments, the aneuploidy is a chromosomal aneuploidy that is selected from trisomy 8, trisomy 13, trisomy 15, trisomy 16, trisomy 18, trisomy 21, trisomy 22, monosomy X, and XXX. In some embodiments, determining the aneuploidy comprises calculating a chromosome dose based on the number of said sequence tags for a chromosome of interest and for a normalizing chromosome, and comparing said dose to a threshold value, while determining the fetal fraction comprises identifying at least one informative polymorphic site in said enriched mixture, and calculating the fetal fraction from the amount of fetal and maternal polymorphic sites in said enriched sample.

In the embodiments of the method summarized above and described in further detail below, sequencing that can be used for the simultaneous determination is performed using next generation (NGS) sequencing. In some embodiments, sequencing is massively parallel sequencing using sequencing-by-synthesis with reversible dye terminators. In other embodiments, sequencing is sequencing-by-ligation. In yet other embodiments, sequencing is single molecule sequencing. The sequencing of the enriched mixture can further comprise an amplification.

In another embodiment, a composition comprising at least one set of primers for amplifying at least one SNP in a maternal sample e.g. a plasma sample, comprising a mixture of nucleic acid molecules is provided. Nucleic acid molecules can be cfDNA molecules. In one embodiment, the composition comprises at least one set of primers for amplifying at least one SNP selected from rs560681, rs1109037, rs9866013, rs13182883, rs13218440, rs7041158, rs740598, rs10773760, rs4530059, rs7205345, rs8078417, rs576261, rs2567608, rs430046, rs9951171, rs338882, rs10776839, rs9905977, rs1277284, rs258684, rs1347696, rs508485, rs9788670, rs8137254, rs3143, rs2182957, rs3739005, and rs530022. In one embodiment, the at least one set of primers is selected from primer sets of SEQ ID NOs:57-112.

In another embodiment, a composition comprising at least one set of primers for amplifying at least one STR in a maternal sample e.g. a plasma sample, comprising a mixture of nucleic acid molecules is provided. Nucleic acid molecules can be cfDNA molecules. In one embodiment, the composition comprises at least one set of primers for amplifying at least one STR selected from CSF1PO, FGA, TH01, TPOX, vWA, D3S1358, D5S818, D7S820, D8S1179, D13S317, D16S539, D18S51, D21S11, D2S1338, Penta D, Penta E, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627 and D1GATA113. In one embodiment, the at least one set of STR primers is selected from primer sets of SEQ ID NOs:113-1%.

In another embodiment, a kit for preparing a sequencing library for massively parallel sequencing of fetal and maternal nucleic acid molecules in a maternal sample is provided. In some embodiments, the maternal sample is a plasma sample. The kit comprises a composition comprising at least one set of primers for amplifying at least one polymorphic nucleic acid in the mixture of fetal and maternal nucleic acid molecules. The polymorphic nucleic acid sequences each comprise at least one SNP or an STR. Sequences comprising tandem SNPs are encompassed in the kit of the invention. In some embodiments, sequencing is single molecule sequencing. In some embodiments, the massively parallel sequencing is sequencing-by-synthesis with reversible dye terminators. In other embodiments, the massively parallel sequencing is sequencing-by-ligation.

Preferably, the fetal and maternal nucleic acid molecules are cfDNA molecules. In some embodiments, the maternal sample is a plasma sample. The kit comprises a composition comprising at least one set of primers for amplifying at least one polymorphic nucleic acid comprised in the fetal and maternal nucleic acid molecules. In some embodiments, the polymorphic nucleic acid comprises a SNP. In other embodiment, the polymorphic nucleic acid comprises an STR.

INCORPORATION BY REFERENCE

All patents, patent applications, and other publications, including all sequences disclosed within these references, referred to herein are expressly incorporated by reference, to the same extent as if each individual publication, patent or patent application was specifically and individually indicated to be incorporated by reference. All documents cited are, in relevant part, incorporated herein by reference. However, the citation of any document is not to be construed as an admission that it is prior art with respect to the present invention.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
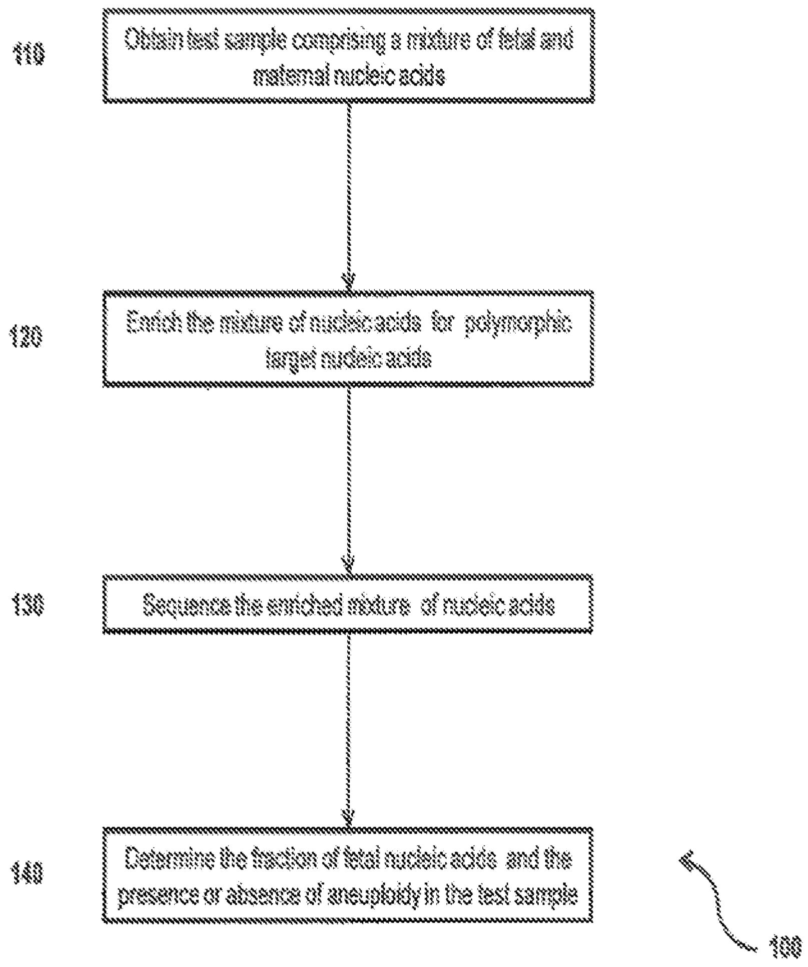
FIG. 1 is a flowchart of a method 100 for simultaneously determining the presence or absence of aneuploidy and the fetal fraction in a maternal test sample comprising a mixture of fetal and maternal nucleic acids.
Figure 2:
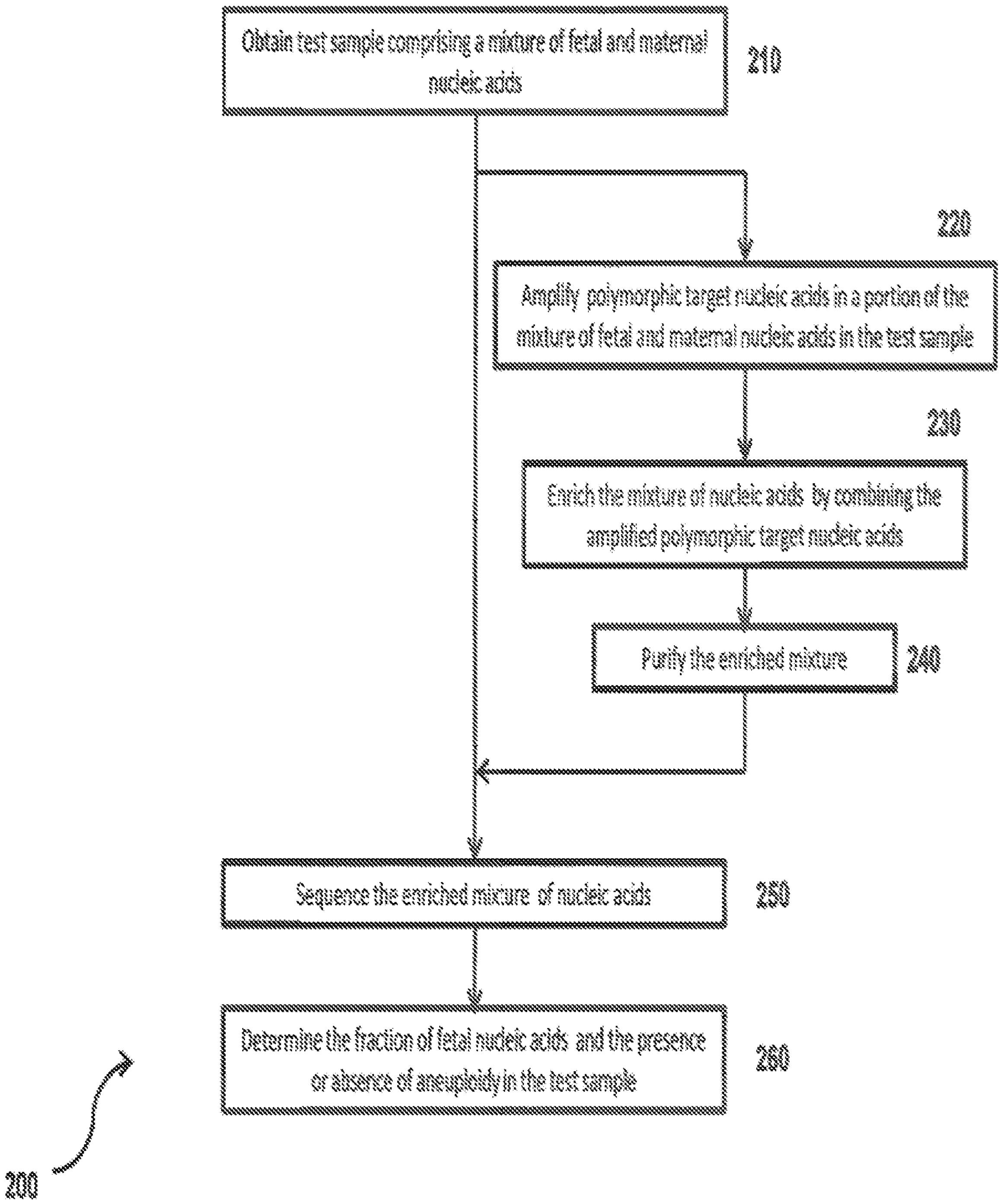
FIG. 2 is a flowchart of a method 200 for simultaneously determining the presence or absence of fetal aneuploidy and the fetal fraction in a maternal plasma test sample enriched for polymorphic nucleic acids.
Figure 3:
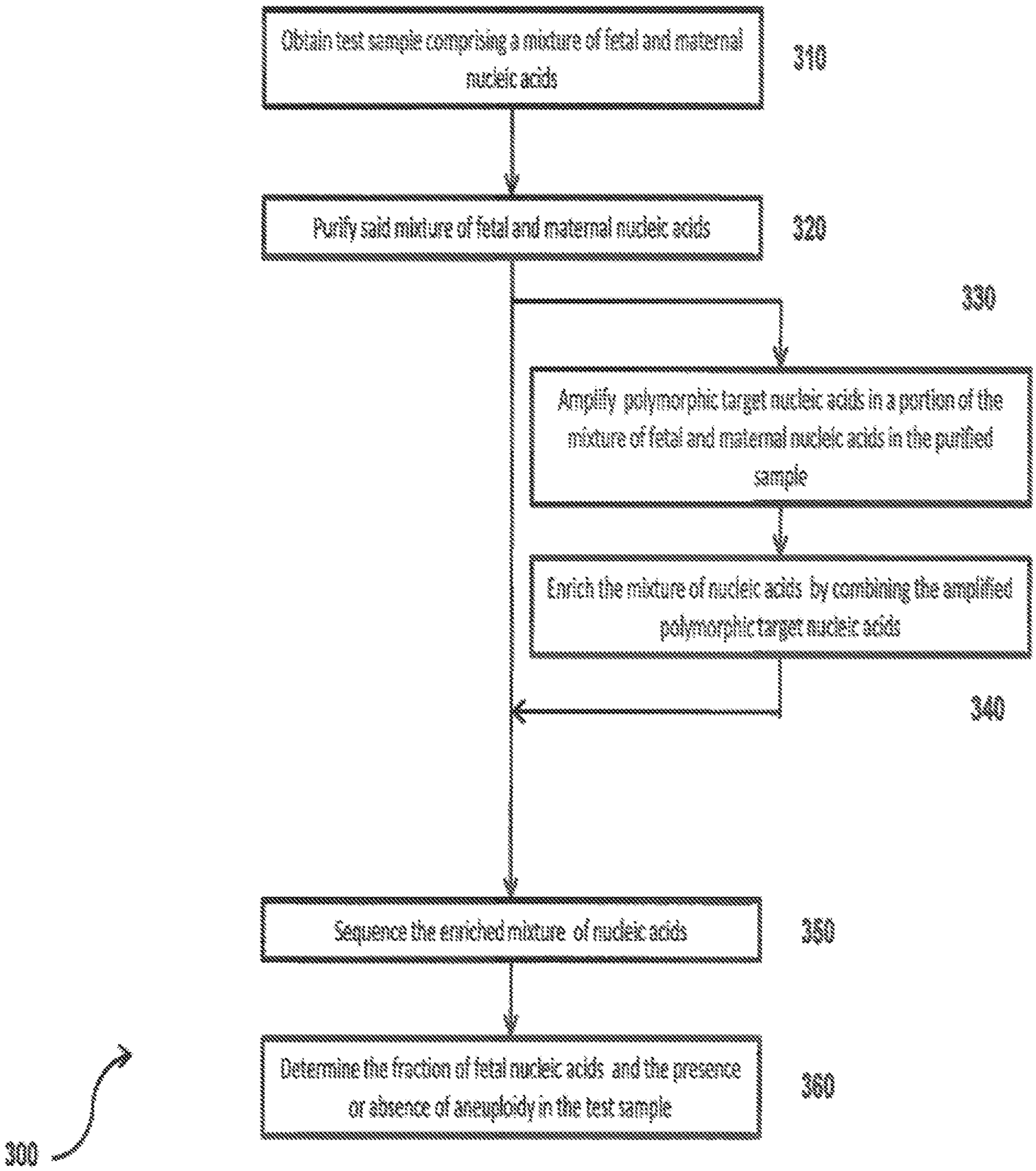
FIG. 3 is a flowchart of a method 300 for simultaneously determining the presence or absence of fetal aneuploidy and the fetal fraction in a maternal purified cfDNA test sample that has been enriched with polymorphic nucleic acids.

The invention provides compositions and methods for simultaneously determining the presence or absence of fetal aneuploidy and the relative amount of fetal nucleic acids in a sample obtained from a pregnant female. The method encompasses the use of sequencing technologies e.g. next generation sequencing, and exploits the occurrence of polymorphisms to provide a streamlined noninvasive process applicable to the practice of prenatal diagnostics.

Unless otherwise indicated, the practice of the present invention involves conventional techniques commonly used in molecular biology, microbiology, protein purification, protein engineering, protein and DNA sequencing, and recombinant DNA fields, which are within the skill of the art. Such techniques are known to those of skill in the art and are described in numerous standard texts and reference works. All patents, patent applications, articles and publications mentioned herein are hereby expressly incorporated herein by reference in their entirety.

Numeric ranges are inclusive of the numbers defining the range. It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The headings provided herein are not limitations of the various aspects or embodiments of the invention which can be had by reference to the Specification as a whole. Accordingly, as indicated above, the terms defined immediately below are more fully defined by reference to the specification as a whole.

Unless defined otherwise herein, all technical and scientific terms used herein have the same meaning as commonly understood by one of ordinary skill in the art to which this invention belongs. Various scientific dictionaries that include the terms included herein are well known and available to those in the art. Although any methods and materials similar or equivalent to those described herein find use in the practice or testing of the present invention, some preferred methods and materials are described. Accordingly, the terms defined immediately below are more fully described by reference to the Specification as a whole. It is to be understood that this invention is not limited to the particular methodology, protocols, and reagents described, as these may vary, depending upon the context they are used by those of skill in the art.

Definitions

As used herein, the singular terms "a". "an," and "the" include the plural reference unless the context clearly indicates otherwise. Unless otherwise indicated, nucleic acids are written left to right in 5' to 3' orientation and amino acid sequences are written left to right in amino to carboxy orientation, respectively.

The term "assessing" herein refers to characterizing the status of a chromosomal aneuploidy by one of three types of calls: "normal". "affected", and "no-call". For example, in the presence of trisomy the "normal" call is determined by the value of a parameter e.g. a test chromosome dose that is below a user-defined threshold of reliability, the "affected" call is determined by a parameter e.g. a test chromosome dose, that is above a user-defined threshold of reliability, and the "no-call" result is determined by a parameter e.g. a test chromosome dose, that lies between the a user-defined thresholds of reliability for making a "normal" or an "affected" call.

The term "copy number variation" herein refers to variation in the number of copies of a nucleic acid sequence that is 1 kb or larger present in a test sample in comparison with the copy number of the nucleic acid sequence present in a qualified sample. A "copy number variant" refers to the 1 kb or larger sequence of nucleic acid in which copy-number differences are found by comparison of a sequence of interest in test sample with that present in a qualified sample. Copy number variants/variations include deletions, including microdeletions, insertions, including microinsertions, duplications, multiplications, inversions, translocations and complex multi-site variants. CNV encompass chromosomal aneuploidies and partial aneuplodies.

The term "aneuploidy" herein refers to an imbalance of genetic material caused by a loss or gain of a whole chromosome, or part of a chromosome.

The term "chromosomal aneuploidy" herein refers to an imbalance of genetic material caused by a loss or gain of a whole chromosome, and includes germline aneuploidy and mosaic aneuploidy.

The term "partial aneuploidy" herein refers to an imbalance of genetic material caused by a loss or gain of part of a chromosome e.g. partial monosomy and partial trisomy, and encompasses imbalances resulting from translocations, deletions and insertions.

The term "tandem SNPs" herein refers to two or more SNPs that are present within a polymorphic target nucleic acid sequence.

The terms "polymorphic target nucleic acid", "polymorphic sequence", "polymorphic target nucleic acid sequence" and "polymorphic nucleic acid" are used interchangeably herein to refer to a nucleic acid sequence e.g. a DNA sequence, that comprises one or more polymorphic sites.

The term "polymorphic site" herein refers to a single nucleotide polymorphism (SNP), a small-scale multi-base deletion or insertion, a Multi-Nucleotide Polymorphism (MNP) or a Short Tandem Repeat (STR).

The term "plurality" is used herein in reference to a number of nucleic acid molecules or sequence tags that is sufficient to identify significant differences in copy number variations (e.g. chromosome doses) in test samples and qualified samples using in the methods of the invention. In some embodiments, at least about $3\times10^6$ sequence tags, at least about $5\times10^6$ sequence tags, at least about $8\times10^6$ sequence tags, at least about $10\times10^6$ sequence tags, at least about $15\times10^6$ sequence tags, at least about $20\times10^6$ sequence tags, at least about $30\times10^6$ sequence tags, at least about $40\times10^6$ sequence tags, or at least about $50\times10^6$ sequence tags comprising between 20 and 40 bp reads are obtained for each test sample.

The terms "polynucleotide", "nucleic acid" and "nucleic acid molecules" are used interchangeably and refer to a covalently linked sequence of nucleotides (i.e., ribonucleotides for RNA and deoxyribonucleotides for DNA) in which the 3' position of the pentose of one nucleotide is joined by a phosphodiester group to the 5' position of the pentose of the next, include sequences of any form of nucleic acid, including, but not limited to RNA, DNA and cfDNA molecules. The term "polynucleotide" includes, without limitation, single- and double-stranded polynucleotide.

The term "portion" when used in reference to the amount of sequence information of fetal and maternal nucleic acid molecules in a biological sample herein refers to the amount of sequence information of fetal and maternal nucleic acid molecules in a biological sample that in sum amount to less than the sequence information of <1 human genome.

The term "test sample" herein refers to a sample comprising a mixture of nucleic acids comprising at least one nucleic acid sequence whose copy number is suspected of having undergone variation. Nucleic acids present in a test sample are referred to as "test nucleic acids".

The term "qualified sample" herein refers to a sample comprising a mixture of nucleic acids that are present in a known copy number to which the nucleic acids in a test sample are compared, and it is a sample that is normal i.e. not aneuploid, for the sequence of interest e.g. a qualified sample used for identifying a normalizing chromosome for chromosome 21 is a sample that is not a trisomy 21 sample.

The term "enrich" herein refers to the process of amplifying polymorphic target nucleic acids contained in a portion of a maternal sample, and combining the amplified product with the remainder of the maternal sample from which the portion was removed.

The term "qualified nucleic acid" is used interchangeably with "qualified sequence" is a sequence against which the amount of a test sequence or test nucleic acid is compared. A qualified sequence is one present in a biological sample preferably at a known representation i.e. the amount of a qualified sequence is known. A "qualified sequence of interest" is a qualified sequence for which the amount is known in a qualified sample, and is a sequence that is associated with a difference in sequence representation in an individual with a medical condition.

The term "sequence of interest" herein refers to a nucleic acid sequence that is associated with a difference in sequence representation in healthy versus diseased individuals. A sequence of interest can be a sequence on a chromosome that is misrepresented i.e. over- or under-represented, in a disease or genetic condition. A sequence of interest may also be a portion of a chromosome, or a chromosome. For example, a sequence of interest can be a chromosome that is over-represented in an aneuploidy condition, or a gene encoding a tumor-suppressor that is under-represented in a cancer. Sequences of interest include sequences that are over- or under-represented in the total population, or a subpopulation of cells of a subject. A "qualified sequence of interest" is a sequence of interest in a qualified sample. A "test sequence of interest" is a sequence of interest in a test sample.

The term "plurality of polymorphic target nucleic acids" herein refers to a number of nucleic acid sequences each comprising at least one polymorphic site e.g. one SNP, such that at least 1, 2, 3, 4, 5, 6, 7, 8, 9, 10, 15, 20, 25, 30, 40 or more different polymorphic sites are amplified from the polymorphic target nucleic acids to identify and/or quantify fetal alleles present in maternal samples comprising fetal and maternal nucleic acids.

The term "normalizing sequence" herein refers to a sequence that displays a variability in the number of sequence tags that are mapped to it among samples and sequencing runs that best approximates that of the sequence of interest for which it is used as a normalizing parameter, and/or that can best differentiate an affected sample from one or more unaffected samples. A "normalizing chromosome" is an example of a "normalizing sequence".

The term "differentiability" herein refers to the characteristic of a normalizing chromosome that enables to distinguish one or more unaffected i.e. normal, samples from one or more affected i.e. aneuploid, samples.

The term "group of chromosomes" herein refers to two or more chromosomes.

The term "sequence dose" herein refers to a parameter that relates the sequence tag density of a sequence of interest to the tag density of a normalizing sequence. A "test sequence dose" is a parameter that relates the sequence tag density of a sequence of interest e.g. chromosome 21, to that of a normalizing sequence e.g. chromosome 9, determined in a test sample. Similarly, a "qualified sequence dose" is a parameter that relates the sequence tag density of a sequence of interest to that of a normalizing sequence determined in a qualified sample.

The term "sequence tag density" herein refers to the number of sequence reads that are mapped to a reference genome sequence e.g. the sequence tag density for chromosome 21 is the number of sequence reads generated by the sequencing method that are mapped to chromosome 21 of the reference genome. The term "sequence tag density ratio" herein refers to the ratio of the number of sequence tags that are mapped to a chromosome of the reference genome e.g. chromosome 21, to the length of the reference genome chromosome 21.

The term "parameter" herein refers to a numerical value that characterizes a quantitative data set and/or a numerical relationship between quantitative data sets. For example, a ratio (or function of a ratio) between the number of sequence tags mapped to a chromosome and the length of the chromosome to which the tags are mapped, is a parameter.

The terms "threshold value" and "qualified threshold value" herein refer to any number that is calculated using a qualifying data set and serves as a limit of diagnosis of a copy number variation e.g. an aneuploidy, in an organism. If a threshold is exceeded by results obtained from practicing the invention a subject can be diagnosed with a copy number variation e.g. trisomy 21.

The term "read" refers to a DNA sequence of sufficient length (e.g., at least about 30 bp) that can be used to identify a larger sequence or region, e.g. that can be aligned and specifically assigned to a chromosome or genomic region or gene.

The term "sequence tag" is herein used interchangeably with the term "mapped sequence tag" to refer to a sequence read that has been specifically assigned i.e. mapped, to a larger sequence e.g. a reference genome, by alignment. Mapped sequence tags are uniquely mapped to a reference genome i.e. they are assigned to a single location to the reference genome. Tags that can be mapped to more than one location on a reference genome i.e. tags that do not map uniquely, are not included in the analysis.

The terms "aligned", "alignment", or "aligning" refer to one or more sequences that are identified as a match in terms of the order of their nucleic acid molecules to a known sequence from a reference genome. Such alignment can be done manually or by a computer algorithm, examples including the Efficient Local Alignment of Nucleotide Data (ELAND) computer program distributed as part of the Illumina Genomics Analysis pipeline. The matching of a sequence read in aligning can be a 100% sequence match or less than 100% (non-perfect match).

The term "reference genome" refers to any particular known genome sequence, whether partial or complete, of any organism or virus which may be used to reference identified sequences from a subject. For example, a reference genome used for human subjects as well as many other organisms is found at the National Center for Biotechnology Information at www.ncbi.nlm.nih.gov. A "genome" refers to the complete genetic information of an organism or virus, expressed in nucleic acid sequences.

The term "artificial target sequences genome" herein refers to a grouping of known sequences that encompass alleles of known polymorphic sites. For example, a "SNP reference genome" is an artificial target sequences genome comprising a grouping of sequences that encompass alleles of known SNPs.

The term "clinically-relevant sequence" herein refers to a nucleic acid sequence that is known or is suspected to be associated or implicated with a genetic or disease condition. Determining the absence or presence of a clinically-relevant sequence can be useful in determining a diagnosis or confirming a diagnosis of a medical condition, or providing a prognosis for the development of a disease.

The term "derived" when used in the context of a nucleic acid or a mixture of nucleic acids, herein refers to the means whereby the nucleic acid(s) are obtained from the source from which they originate. For example, in one embodiment, a mixture of nucleic acids that is derived from two different genomes means that the nucleic acids e.g. cfDNA, were naturally released by cells through naturally occurring processes such as necrosis or apoptosis. In another embodiment, a mixture of nucleic acids that is derived from two different genomes means that the nucleic acids were extracted from two different types of cells from a subject.

The term "maternal sample" herein refers to a biological sample obtained from a pregnant subject e.g. a woman.

The term "original maternal sample" herein refers to a biological sample obtained from a pregnant subject e.g. a woman, who serves as the source from which a portion is removed to amplify polymorphic target nucleic acids. The "original sample" can be any sample obtained from a pregnant subject and the processed fractions thereof e.g. a purified cfDNA sample extracted from a maternal plasma sample.

The term "biological fluid" herein refers to a liquid taken from a biological source and includes, for example, blood, serum, plasma, sputum, lavage fluid, cerebrospinal fluid, urine, semen, sweat, tears, saliva, and the like. As used herein, the terms "blood," "plasma" and "serum" expressly encompass fractions or processed portions thereof. Similarly, where a sample is taken from a biopsy, swab, smear, etc., the "sample" expressly encompasses a processed fraction or portion derived from the biopsy, swab, smear, etc.

The terms "maternal nucleic acids" and "fetal nucleic acids" herein refer to the nucleic acids of a pregnant female subject and the nucleic acids of the fetus being carried by the pregnant female, respectively.

The term "corresponding to" herein refers to a nucleic acid sequence e.g. a gene or a chromosome, that is present in the genome of different subjects, and which does not necessarily have the same sequence in all genomes, but serves to provide the identity rather than the genetic information of a sequence of interest e.g. a gene or chromosome.

The term "substantially cell free" herein refers to preparations of the desired sample from which components that are normally associated with it are removed. For example, a plasma sample is rendered essentially cell free by removing blood cells e.g. white blood cells, which are normally associated with it. In some embodiments, substantially free samples are processed to remove cells that would otherwise contribute to the desired genetic material that is to be tested for an aneuploidy.

As used herein, the term "fetal fraction" refers to the fraction of fetal nucleic acids present in a sample comprising fetal and maternal nucleic acid.

As used herein the term "chromosome" refers to the heredity-bearing gene carrier of a living cell which is derived from chromatin and which comprises DNA and protein components (especially histones). The conventional internationally recognized individual human genome chromosome numbering system is employed herein.

As used herein, the term "polynucleotide length" refers to the absolute number of nucleic acid molecules (nucleotides) in a sequence or in a region of a reference genome. The term "chromosome length" refers to the known length of the chromosome given in base pairs e.g. provided in the NCBI36/hg18 assembly of the human chromosome found on the world wide web at genome.ucsc.edu/cgi-bin/hgTracks?hgsid=167155613&chromInfoPage=

The term "subject" herein refers to a human subject as well as a non-human subject such as a mammal, an invertebrate, a vertebrate, a fungus, a yeast, a bacteria, and a virus. Although the examples herein concern human cells and the language is primarily directed to human concerns, the concept of this invention is applicable to genomes from any plant or animal, and is useful in the fields of veterinary medicine, animal sciences, research laboratories and such.

The term "condition" herein refers to "medical condition" as a broad term that includes all diseases and disorders, but can include injuries and normal health situations, such as pregnancy, that might affect a person's health, benefit from medical assistance, or have implications for medical treatments.

DESCRIPTION

The method described herein is a sequencing method that enables the simultaneous determination of the fraction of the minor fetal nucleic acid component in a sample comprising a mixture of fetal and maternal nucleic acids. In particular, the method enables the determination of the fraction of cfDNA contributed by a fetus to the mixture of fetal and maternal cfDNA in a maternal sample e.g. a plasma sample. The difference between the maternal and fetal fraction is determined by the relative contribution of a polymorphic allele derived from the fetal genome to the contribution of the corresponding polymorphic allele derived from the maternal genome. Polymorphic sequences can be used in conjunction with clinically-relevant diagnostic tests as a positive control for the presence of cfDNA in order to highlight false-negative or false-positive results stemming from low levels of cfDNA below the identification limit. The method described is useful across a range of gestational ages.

Exemplary embodiments of the method of the invention are illustrated in FIGS. 1-4 as follows.

FIG. 1 provides a flow diagram of one embodiment of method of the invention 100 for simultaneously determining a fetal aneuploidy and the fraction of fetal nucleic acids in a maternal biological sample. In step 110 a test sample comprising a mixture of fetal and maternal nucleic acids is obtained from a subject. The sample is a maternal sample that is obtained from a pregnant female, for example a pregnant woman. Any maternal biological sample can be used a source of fetal and maternal nucleic acids which are contained in cells or that are "cell-free". In some embodiments, it is advantageous to obtain a maternal sample that comprises cell-free nucleic acids e.g. cfDNA. Preferably, the maternal biological sample is a biological fluid sample. A biological fluid includes, as non-limiting examples, blood, plasma, serum, sweat, tears, sputum, urine, sputum, ear flow, lymph, saliva, cerebrospinal fluid, ravages, bone marrow suspension, vaginal flow, transcervical lavage, brain fluid, ascites, milk, secretions of the respiratory, intestinal and genitourinary tracts, and leukophoresis samples. In some embodiments, the biological fluid sample is a sample that is easily obtainable by non-invasive procedures e.g. blood, plasma, serum, sweat, tears, sputum, urine, sputum, ear flow, and saliva. In some embodiments, the biological sample is a peripheral blood sample, or the plasma and/or the serum fractions thereof. In another embodiment, the sample is a mixture of two or more biological samples e.g. a biological sample can comprise two or more of a biological fluid samples. As used herein, the terms "blood," "plasma" and "serum" expressly encompass fractions or processed portions thereof. In some embodiments, the biological sample is processed to obtain a sample fraction e.g. plasma, that contains the mixture of fetal and maternal nucleic acids. In some embodiments, the mixture of fetal and maternal nucleic acids is further processed from the sample fraction e.g. plasma, to obtain a sample comprising a purified mixture of fetal and maternal nucleic acids e.g. cfDNA. Cell-free nucleic acids, including cell-free DNA, can be obtained by various methods known in the art from biological samples including but not limited to plasma, serum and urine (Fan et al., Proc Natl Acad Sci 105:16266-16271 [2008]; Koide et al., Prenatal Diagnosis 25:604-607 [2005]; Chen et al., Nature Med. 2: 1033-1035 [1996]; Lo et al., Lancet 350: 485-487 [1997). To separate cfDNA from cells, fractionation, centrifugation (e.g., density gradient centrifugation). DNA-specific precipitation, or high-throughput cell sorting and/or separation methods can be used. Commercially available kits for manual and automated separation of cfDNA are available (Roche Diagnostics, Indianapolis, Ind., Qiagen, Valencia, Calif., Macherey-Nagel, Duren, Del.). In some instances, it can be advantageous to fragment the nucleic acid molecules in the nucleic acid sample. Fragmentation can be random, or it can be specific, as achieved, for example, using restriction endonuclease digestion. Methods for random fragmentation are well known in the art, and include, for example, limited DNAse digestion, alkali treatment and physical shearing. In one embodiment, sample nucleic acids are obtained from as cfDNA, which is not subjected to fragmentation. In other embodiments, the sample nucleic acids are obtained as genomic DNA, which is subjected to fragmentation into fragments of approximately 500 or more base pairs, and to which NGS methods can be readily applied.

In step 120 (FIG. 1) the mixture of nucleic acids present in the sample is enriched for polymorphic target nucleic acids each comprising a polymorphic site. In some embodiments, the nucleic acids that are enriched are cfDNA. Target nucleic acids are segments of genetic material that are known to comprise at least one polymorphic site. In some embodiments, the target nucleic acids comprise a SNP. In other embodiments, the target nucleic acid comprises an STR. Enrichment of a mixture of fetal and maternal nucleic acids comprises amplifying target sequences from a portion of nucleic acids contained in the original maternal sample, and combining part or the entire amplified product with the remainder of the original maternal sample. In step 130, at least a portion of the enriched mixture is sequenced, sequence differences stemming from the polymorphic nature of the target sequences are identified, and the relative contribution of polymorphic sequences derived from the fetal genome i.e. the fetal fraction, is determined in step 140. In some embodiments, the original maternal sample is a biological fluid sample e.g. plasma. In other embodiments, the original maternal sample is a processed fraction of plasma comprising purified fetal and maternal cfDNA.

Polymorphic sites that are contained in the target nucleic acids include without limitation single nucleotide polymorphisms (SNPs), tandem SNPs, small-scale multi-base deletions or insertions, called IN-DELS (also called deletion insertion polymorphisms or DIPs), Multi-Nucleotide Polymorphisms (MNPs) and Short Tandem Repeats (STRs). The polymorphic sites that are encompassed by the method of the invention are located on autosomal chromosomes, thereby enabling the determination of fetal fraction independently of sex of the fetus. Any polymorphic site that can be encompassed by the reads generated by the sequencing methods described herein can be used to determine simultaneously the fetal fraction and the presence or absence of an aneuploidy in a maternal sample.

In one embodiment, the mixture of fetal and maternal nucleic acids in the sample is enriched for target nucleic acids that comprise at least one SNP. In some embodiments, each target nucleic acid comprises a single i.e. one SNP. Target nucleic acid sequences comprising SNPs are available from publicly accessible databases including, but not limited to Human SNP Database at world wide web address wi.mit.edu, NCBI dbSNP Home Page at world wide web address ncbi.nlm.nih.gov, world wide web address lifesciences.perkinelmer.com, Celera Human SNP database at world wide web address celera.com, the SNP Database of the Genome Analysis Group (GAN) at world wide web address gan.iarc.fr. In one embodiment, the SNPs chosen for enriching the fetal and maternal cfDNA are selected from the group of 92 individual identification SNPs (IISNPs) described by Pakstis et al. (Pakstis et al. Hum Genet 127: 315-324 [2010]), which have been shown to have a very small variation in frequency across populations ($F_a$<0.06), and to be highly informative around the world having an average heterozygosity ≥0.4. SNPs that are encompassed by the method of the invention include linked and unlinked SNPs. Each target nucleic acid comprises at least one polymorphic site e.g. a single SNP, that differs from that present on another target nucleic acid to generate a panel of polymorphic sites e.g. SNPs, that contain a sufficient number of polymorphic sites of which at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40 or more are informative. For example, a panel of SNPs can be configured to comprise at least one informative SNP. In one embodiment, the SNPs that are targeted for amplification are selected from rs560681, rs1109037, rs9866013, rs13182883, rs13218440, rs7041158, rs740598, rs10773760, rs4530059, rs7205345, rs8078417, rs576261, rs2567608, rs430046, rs9951171, rs338882, rs10776839, rs9905977, rs1277284, rs258684, rs1347696, rs508485, rs9788670, rs8137254, rs3143, rs2182957, rs3739005, and rs530022.

In other embodiments, each target nucleic acid comprises two or more SNPs i.e. each target nucleic acid comprises tandem SNPs. Preferably, each target nucleic acid comprises two tandem SNPs. The tandem SNPs are analyzed as a single unit as short haplotypes, and are provided herein as sets of two SNPs. To identify suitable tandem SNP sequences, the International HapMap Consortium database can be searched (The International HapMap Project, Nature 426:789-796 [2003]). The database is available on the world wide web at hapmap.org. In one embodiment, tandem SNPs that are targeted for amplification are selected from the following sets of tandem pairs of SNPS rs7277033-rs2110153; rs2822654-rs1882882; rs368657-rs376635; rs2822731-rs2822732; rs1475881-rs7275487; rs1735976-rs2827016; rs447340-rs2824097; rs418989-rs13047336; rs987980-rs987981; rs4143392-rs4143391; rs1691324-rs13050434; rs1909758-rs9980111; rs2826842-rs232414; rs1980969-rs980970; rs9978999-rs9979175; rs1034346-rs12481852; rs7509629-rs2828358; rs4817013-rs7277036; rs9981121-rs28296%; rs455921-rs2898102; rs2898102-rs458848; rs961301-rs2830208; rs2174536-rs458076; rs11088023-rs11088024; rs1011734-rs1011733; rs2831244-rs9789838; rs8132769-rs2831440; rs8134080-rs2831524; rs4817219-rs4817220; rs2250911-rs2250997; rs2831899-rs2831900; rs2831902-rs2831903; rs11088086-rs2251447; rs2832040-rs11088088; rs2832141-rs2246777; rs2832959-rs9980934; rs2833734-rs2833735; rs933121-rs933122; rs2834140-rs12626953; rs2834485-rs3453; rs9974986-rs2834703; rs2776266-rs2835001; rs1984014-rs1984015; rs7281674-rs2835316; rs13047304-rs13047322; rs2835545-rs4816551; rs2835735-rs2835736; rs13047608-rs2835826; rs2836550-rs22125%; rs2836660-rs2836661; rs465612-rs8131220; rs9980072-rs8130031; rs418359-rs2836926; rs7278447-rs7278858; rs385787-rs367001; rs367001-rs386095; rs2837296-rs2837297; and rs2837381-rs4816672.

In another embodiment, the mixture of fetal and maternal nucleic acids in the sample is enriched for target nucleic acids that comprise at least one STR. STR loci are found on almost every chromosome in the genome and may be amplified using a variety of polymerase chain reaction (PCR) primers. Tetranucleotide repeats have been preferred among forensic scientists due to their fidelity in PCR amplification, although some tri- and pentanucleotide repeats are also in use. A comprehensive listing of references, facts and sequence information on STRs, published PCR primers, common multiplex systems, and related population data are compiled in STRBase, which may be accessed via the World Wide Web at ibm4.carb.nist.gov:8800/dna/home.htm. Sequence information from GenBank® (http://www2.ncbi.nlm.nih.gov/cgi-bin/genbank) for commonly used STR loci is also accessible through STRBase. The polymorphic nature of tandem repeated DNA sequences that are widespread throughout the human genome have made them important genetic markers for gene mapping studies, linkage analysis, and human identity testing. Because of the high polymorphism of STRs, most individuals will be heterozygous i.e. most people will possess two alleles (versions) of each—one inherited from each parent—with a different number of repeats. Therefore, the non-maternally inherited fetal STR sequence will differ in the number of repeats from the maternal sequence. Amplification of these STR sequences will result in two major amplification products corresponding to the maternal alleles (and the maternally inherited fetal allele) and one minor product corresponding to the non-maternally inherited fetal allele. This technique was first reported in 2000 (Pertl et al., Human Genetics 106:45-49 [2002]) and has subsequently been developed using simultaneous identification of multiple different STR regions using real-time PCR (Liu et al., Acta Obset Gyn Scand 86:535-541 [2007]). Thus, the fraction of fetal nucleic acid in a maternal sample can also be determined by sequencing polymorphic target nucleic acids comprising STRs, which vary among individuals in the number of tandem repeated units between alleles. In one embodiment, simultaneous determination of aneuploidy and fetal fraction comprises sequencing at least a portion of fetal and maternal nucleic acids present in a maternal sample that has been enriched for polymorphic sequences comprising STRs. Given that the size of fetal cfDNA is between X and Y bp, the polymorphic sequences comprise miniSTR, which can be amplified to generate amplicons that are of lengths about the size of the circulating fetal DNA fragments. The method can use one or a combination of any number of informative miniSTRs to determine the fraction of fetal nucleic acid. For example, any one or a combination of any number of miniSTRs, for example the miniSTRs disclosed in Table 15, can be used. In one embodiment, the fraction of fetal nucleic acid in a maternal sample is performed using a method that includes determining the number of copies of the maternal and fetal nucleic acid present in the maternal sample by amplifying at least one autosomal miniSTR chosen from CSF1PO, FGA, TH01, TPOX, vWA, D3S1358, D5S818, D7S820, D8S1179, D13S317, D16S539, D18S51, D21S11, Penta D, Penta E, D2S1338, D1S1677, D2S441, D4S2364, D10S1248, D14S1434, D22S1045, D22S1045, D20S1082, D20S482, D18S853, D17S1301, D17S974, D14S1434, D12ATA63, D11S4463, D10S1435, D10S1248, D9S2157, D9S1122, D8S115, D6S1017, D6S474, D5S2500, D5S2500, D4S2408, D4S2364, D3S4529, D3S3053, D2S1776, D2S441, D1S1677, D1S1627, and D1GATA113. In another embodiment, the at least one autosomal miniSTR is the group of miniSTRs CSF1PO, FGA, D13S317, D16S539, D18S51, D2S1338, D21S11 and D7S820.

Enrichment of the sample for the target nucleic acids is accomplished by methods that comprise specifically amplifying target nucleic acid sequences that comprise the polymorphic site. Amplification of the target sequences can be performed by any method that uses PCR or variations of the method including but not limited to asymmetric PCR, helicase-dependent amplification, hot-start PCR, qPCR, solid phase PCR, and touchdown PCR. Alternatively, replication of target nucleic acid sequences can be obtained by enzyme-independent methods e.g. chemical solid-phase synthesis using the phosphoramidites. Amplification of the target sequences is accomplished using primer pairs each capable of amplifying a target nucleic acid sequence comprising the polymorphic site e.g. SNP, in a multiplex PCR reaction. Multiplex PCR reactions include combining at least 2, at least three, at least 3, at least 5, at least 10, at least 15, at least 20, at least 25, at least 30, at least 35, at least 40 or more sets of primers in the same reaction to quantify the amplified target nucleic acids comprising at least two, at least three, at least 5, at least 10, at least 15, at least 20, at least 25, at least 30, at least 35, at least 40 or more polymorphic sites in the same sequencing reaction. Any panel of primer sets can be configured to amplify at least one informative polymorphic sequence.

Amplification of SNPs

A number of nucleic acid primers are already available to amplify DNA fragments containing the SNP polymorphisms and their sequences can be obtained, for example, from the above-identified databases. Additional primers can also be designed, for example, using a method similar to that published by Vieux, E. F., Kwok, P-Y and Miller. R. D. in BioTechniques (June 2002) Vol. 32. Supplement: "SNPs: Discovery of Marker Disease, pp. 28-32. In one embodiment, at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40 or more sets of primers is chosen to amplify a target nucleic acid comprising at least one informative SNPs in a portion of a mixture of fetal and maternal cfDNA. In one embodiment, the sets are of primers comprise forward and reverse primers that encompass at least one informative SNP selected from rs560681, rs1109037, rs9866013, rs13182883, rs13218440, rs7041158, rs740598, rs10773760, rs4530059, rs7205345, rs8078417, rs576261, rs2567608, rs430046, rs9951171, rs338882, rs10776839, rs9905977, rs1277284, rs258684, rs1347696, rs508485, rs9788670, rs8137254, rs3143, rs2182957, rs3739005, and rs530022. Exemplary sets of primers that are used to amplify the tandem SNPs provided in Example 5 (Tables 5 and 6) and disclosed herein as SEQ ID NOs:57-112 to amplify a target nucleic acid comprising at least one informative SNP in a portion of a mixture of fetal and maternal cfDNA. In another embodiment, the group of 13 sets of primers SEQ ID NOs:1-26 is used to amplify a target nucleic acid each comprising at least one SNP e.g. a single SNP, in a portion of a mixture of fetal and maternal cfDNA.

In yet another embodiment, at least one set of primers is used to amplify a target nucleic acid each comprising at least one SNP e.g. a set of two tandem SNPs, in a portion of a mixture of fetal and maternal cfDNA. In one embodiment, the sets are of primers comprise forward and reverse primers that encompass at least one informative tandem SNP selected from rs7277033-rs2110153; rs2822654-rs1882882;

rs368657-rs376635; rs2822731-rs2822732; rs1475881-rs7275487; rs1735976-rs2827016; rs447340-rs2824097; rs418989-rs13047336; rs987980-rs987981; rs4143392-rs4143391; rs1691324-rs13050434; rs1909758-rs9980111; rs2826842-rs232414; rs1980969-rs1980970; rs9978999-rs9979175; rs1034346-rs12481852; rs7509629-rs2828358; rs4817013-rs7277036; rs9981121-rs2829696; rs455921-rs2898102; rs2898102-rs458848; rs961301-rs2830208; rs2174536-rs458076; rs11088023-rs11088024; rs1011734-rs1011733; rs2831244-rs9789838; rs8132769-rs2831440; rs8134080-rs2831524; rs4817219-rs4817220; rs2250911-rs2250997; rs2831899-rs2831900; rs2831902-rs2831903; rs1088086-rs2251447; rs2832040-rs11088088; rs2832141-rs2246777; rs2832959-rs9980934; rs2833734-rs2833735; rs933121-rs933122; rs2834140-rs12626953; rs2834485-rs3453; rs9974986-rs2834703; rs2776266-rs2835001; rs1984014-rs1984015; rs7281674-rs2835316; rs13047304-rs13047322; rs2835545-rs4816551; rs2835735-rs2835736; rs13047608-rs2835826; rs2836550-rs2212596; rs2836660-rs2836661; rs465612-rs8131220; rs9980072-rs8130031; rs418359-rs2836926; rs7278447-rs7278858; rs385787-rs367001; rs367001-rs386095; rs2837296-rs2837297; and rs2837381-rs4816672.

The primers used for amplifying the target sequences comprising the tandem SNPs are designed to encompass both SNP sites. Exemplary sets of primers that are used to amplify the tandem SNPs disclosed herein are provided in Example 10 and disclosed as SEQ ID Nos:197-310.

Amplification of the target nucleic acids is performed using sequence-specific primers that allow for sequence specific amplification. For example, the PCR primers are designed to discriminate against the amplification of similar genes or paralogs that are on other chromosomes by taking advantage of sequence differences between the target nucleic acid and any paralogs from other chromosomes. The forward or reverse PCR primers are designed to anneal close to the SNP site and to amplify a nucleic acid sequence of sufficient length to be encompassed in the reads generated by massively parallel sequencing methods. In some embodiments, some massively parallel sequencing methods require that nucleic acid sequence have a minimum length (bp) to enable bridging amplification that may optionally be used prior to sequencing. Thus, the PCR primers used for amplifying target nucleic acids are designed to amplify sequences that are of sufficient length to be bridge amplified and to identify SNPs that are encompassed by the sequence reads. In some embodiments, the first of two primers in the primer set comprising the forward and the reverse primer for amplifying the target nucleic acid is designed to identify a single SNP present within a sequence read of about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, or about 500 bp. It is expected that technological advances in massively parallel sequencing technologies will enable single-end reads of greater than 500 bp. In one embodiment, one of the PCR primers is designed to amplify SNPs that are encompassed in sequence reads of 36 bp. The second primer is designed to amplify the target nucleic acid as an amplicon of sufficient length to allow for bridge amplification. In one embodiment, the exemplary PCR primers are designed to amplify target nucleic acids that contain a single SNP selected from SNPs rs560681, rs1109037, rs9866013, rs13182883, rs13218440, rs7041158, rs740598, rs10773760, rs4530059, rs7205345, rs8078417, rs576261, rs2567608, rs430046, rs9951171, rs338882, rs10776839, rs9905977, rs1277284, rs258684, rs1347696, rs508485, rs9788670, rs8137254, rs3143, rs2182957, rs3739005 and rs530022. In other embodiments, the forward and reverse primers are each designed for amplifying target nucleic acids each comprising a set of two tandem SNPs, each being present within a sequence read of about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, or about 500 bp. In one embodiment, at least one of the primers is designed to amplify the target nucleic acid comprising a set of two tandem SNPs as an amplicon of sufficient length to allow for bridge amplification.

The SNPs, single or tandem SNPs, are contained in amplified target nucleic acid amplicons of at least about 100 bp, at least about 150 bp, at least about 200 bp, at least about 250 bp, at least about 300 bp, at least about 350 bp, or at least about 400 bp. In one embodiment, target nucleic acids comprising a polymorphic site e.g. a SNP, are amplified as amplicons of at least about 110 bp, and that comprise a SNP within 36 bp from the 3' or 5' end of the amplicon. In another embodiment, target nucleic acids comprising two or more polymorphic sites e.g. two tandem SNPs, are amplified as amplicons of at least about 110 bp, and that comprise the first SNP within 36 bp from the 3' end of the amplicon, and/or the second SNP within 36 bp from the 5' end of the amplicon.

Amplification of STRs

A number of nucleic acid primers are already available to amplify DNA fragments containing the STRs and their sequences can be obtained, for example, from the above-identified databases. Various sized PCR amplicons have been used to discern the respective size distributions of circulating fetal and maternal DNA species, and have shown that the fetal DNA molecules in the plasma of pregnant women are generally shorter than maternal DNA molecules (Chan et al., Clin Chem 50:8892 [2004]). Size fractionation of circulating fetal DNA has confirmed that the average length of circulating fetal DNA fragments is <300 bp, while maternal DNA has been estimated to be between about 0.5 and 1 Kb (Li et al., Clin Chem, 50: 1002-1011 [2004]). These findings are consistent with those of Fan et al., who determined using NGS that fetal cfDNA is rarely >340 bp (Fan et al., Clin Chem 56:1279-1286 [2010]). The method of the invention encompasses determining the fraction of fetal nucleic acid in a maternal sample that has been enriched with target nucleic acids each comprising one miniSTR comprising quantifying at least one fetal and one maternal allele at a polymorphic miniSTR, which can be amplified to generate amplicons that are of lengths about the size of the circulating fetal DNA fragments.

In one embodiment, the method comprises determining the number of copies of at least one fetal and at least one maternal allele at least at one polymorphic miniSTR that is amplified to generate amplicons that are less than about 300 bp, less than about 250 bp, less than about 200 bp, less than about 150 bp, less than about 100 bp, or less than about 50 bp. In another embodiment, the amplicons that are generated by amplifying the miniSTRs are less than about 300 bp. In another embodiment, the amplicons that are generated by amplifying the miniSTRs are less than about 250 bp. In another embodiment, the amplicons that are generated by amplifying the miniSTRs are less than about 200 bp. Amplification of the informative allele includes using miniSTR primers, which allow for the amplification of reduced-size amplicons to discern STR alleles that are less than about 500 bp, less than about 450 bp, less than about 400 bp, less than about 350 bp, less than about 300 base pairs (bp), less than about 250 bp, less than about 200 bp, less than about 150 bp, less than about 100 bp, or less than about 50 bp. The reduced-size amplicons generated using the miniSTR primers are known as miniSTRs that are identified according to the marker name corresponding to the locus to which they have been mapped. In one embodiment, the miniSTR primers include mini STR primers that have permitted the maximum size reduction in amplicon size for all 13 CODIS STR loci in addition to the D2S1338, Penta D, and pentaE found in commercially available STR kits (Butler et al., J Forensic Sci 48:1054-1064 [2003]), miniSTR loci that are unlinked to the CODIS markers as described by Coble and Butler (Coble and Butler, J Forensic Sci 50:43-53 [2005]), and other minSTRs that have been characterized at NIST. Information regarding the miniSTRs characterized at NIST is accessible via the world wide web at cstl.nist.gov/biotech/strbase/newSTRs.htm. Any one pair or a combination of two or more pairs of miniSTR primers can be used to amplify at least one miniSTR. For example, at least one set of primers is selected from set CSF1PO_F (SEQ ID NO:81) and CSF1PO_R (SEQ ID NO:82), set FGA_F (SEQ ID NO:83) and FGA_R (SEQ ID NO:84), set TH01_F (SEQ ID NO:85) and TH01_R (SEQ ID NO:86), set TPOX_F (SEQ ID NO:87) and TPOX_R (SEQ ID NO:88), set vWA_F (SEQ ID NO:89) and vWA_R (SEQ ID NO:90), set D3S1358_F (SEQ ID NO:91) and D3S1358_R (SEQ ID NO:92), set D5S818_F (SEQ ID NO:93) and D5S818_R (SEQ ID NO:94), set D7S820_F (SEQ ID NO:95) and D7S820_R (SEQ ID NO:96), set D7S820_F (SEQ ID NO:97) and D7S820_R (SEQ ID NO:98), set D13S317_F (SEQ ID NO:99) and D13S317_R (SEQ ID NO: 100), set D16S539_F (SEQ ID NO:101) and D16S539_R (SEQ ID NO:102), set D18S51_F (SEQ ID NO:103) and D18S51_R (SEQ ID NO:104), set D21S11_F (SEQ ID NO:105) and D21S11_R (SEQ ID NO:106), set D2S1338_F (SEQ ID NO:107) and D2S1338_R (SEQ ID NO: 108), set Penta D_F (SEQ ID NO: 109) and Penta D_R (SEQ ID NO: 110), set Penta E_F (SEQ ID NO: 111) and Penta E_R (SEQ ID NO:112), set (D22S1045_F; SEQ ID NO:113) and D22S1045_ F (SEQ ID NO:114), set D20S1082_R (SEQ ID NO: 115) and D20S1082_F (SEQ ID NO: 116), set D20S482_R (SEQ ID NO: 117) and D20S482_F (SEQ ID NO:118), set D18S853_R (SEQ ID NO: 119) and D18S853_F (SEQ ID NO: 120), set D17S1301_F (SEQ ID NO:121) and D17S1301_R (SEQ ID NO:122), set D17S974_F (SEQ ID NO:123) and D17S974_R (SEQ ID NO:124), set D14S1434_F (SEQ ID NO:125) and D14S1434_R (SEQ ID NO:126), set D12ATA63_F (SEQ ID NO:127) and D12ATA63_R (SEQ ID NO:128), D11S4463_F (SEQ ID NO:129) and D11S4463_R(SEQ ID NO:130), set D10S1435_F (SEQ ID NO:131) and D10S1435_R (SEQ ID NO:132), set D10S1248_F (SEQ ID NO:133) and D10S1248_R (SEQ ID NO:134), set D9S2157_F (SEQ ID NO:135) and D9S2157_R (SEQ ID NO:136), set D9S1122_F (SEQ ID NO:137) and D9S1122_R (SEQ ID NO:138), set D8S1115_F (SEQ ID NO:139) and D8S1115_R (SEQ ID NO:140), set D6S1017_F (SEQ ID NO:141) and D6S1017_R (SEQ ID NO:142), D6S474_F (SEQ ID NO:143) and D6S474_R (SEQ ID NO: 144), set D5S2500_F (SEQ ID NO: 145) and D5S2500_R (SEQ ID NO:146), set D4S2408_F (SEQ ID NO: 147) and D4S2408_R (SEQ ID NO: 148), set D4S2364U_F (SEQ ID NO: 149) and D4S2364U_R (SEQ ID NO: 150), set D3S452_F (SEQ ID NO:151) and D3S452_R (SEQ ID NO:152), set D3S3053_F (SEQ ID NO:153) and D3S3053_R (SEQ ID NO:154), set D2S1776_F (SEQ ID NO:155) and D2S1776_R (SEQ ID NO:156), set D2S441_F (SEQ ID NO:157) and D2S441_R (SEQ ID NO:158), set D1S1677_F (SEQ ID NO:159) and D1S1677_R (SEQ ID NO:160), set D1S1627_F (SEQ ID NO:161) and D1S1627_R (SEQ ID NO:162), and set D1GATA113_F (SEQ ID NO:163) and D1GATA113_R (SEQ ID NO:164).

Enrichment of the sample is obtained by amplifying target nucleic acids contained in a portion of the mixture of fetal and maternal nucleic acids in the original sample, and combining at least a portion or all of the amplified product with the remainder of the original unamplified sample. Enrichment comprises amplifying the target nucleic acids that are contained in a portion of biological fluid sample. In one embodiment, the sample that is enriched is the plasma fraction of a blood sample (See FIG. 2). For example, a portion of an original maternal plasma sample is used for amplifying target nucleic acid sequences. Subsequently, some or all of the amplified product is combined with the remaining unamplified original plasma sample thereby enriching it (see Example 8). In another embodiment, the sample that is enriched is the sample of purified cfDNA that is extracted from plasma (See FIG. 3). For example, enrichment comprises amplifying the target nucleic acids that are contained in a portion of an original sample of purified mixture of fetal and maternal nucleic acids e.g. cfDNA that has been purified from a maternal plasma sample, and subsequently combining some or all of the amplified product with the remaining unamplified original purified sample (see Example 7). In yet another embodiment, the sample that is enriched is a sequencing library sample prepared from a purified mixture of fetal and maternal nucleic acids (see FIG. 4). For example, enrichment comprises amplifying the target nucleic acids that are contained in a portion of an original sample of purified mixture of fetal and maternal nucleic acids e.g. cfDNA that has been purified from a maternal plasma sample, preparing a first sequencing library of unamplified nucleic acid sequences, preparing a second sequencing library of amplified polymorphic target nucleic acids, and subsequently combining some or all of the second sequencing library with some or all of the first sequencing library (see Example 6). The amount of amplified product that is used to enrich the original sample is selected to obtain sufficient sequencing information for determining both the presence or absence of aneuploidy and the fetal fraction from the same sequencing run. At least about 3%, at least about 5%, at least about 70%, at least about 10%, at least about 15%, at least about 20%, at least about 25%, at least about 30% or more of the total number of sequence tags obtained from sequencing are mapped to determine the fetal fraction.

In step 130 (FIG. 1), the enriched mixture of fetal and maternal nucleic acids is sequenced. Sequence information that is needed for the simultaneous determination of aneuploidy and fetal fraction can be obtained using any of the known DNA sequencing methods. In one embodiment, the method described herein employs next generation sequencing technology (NGS) in which clonally amplified DNA templates or single DNA molecules are sequenced in a massively parallel fashion within a flow cell (e.g. as described in Volkerding et al. Clin Chem 55:641-658 [2009];

Metzker M Nature Rev 11:31-46 [2010]). In addition to high-throughput sequence information, NGS provides digital quantitative information, in that each sequence read is a countable "sequence tag" representing an individual clonal DNA template or a single DNA molecule. This quantification allows NGS to expand the digital concept of counting cell-free DNA molecules (Fan et al., Proc Natl Acad Sci USA 105:16266-16271 [2008]; Chiu et al, Proc Natl Acad Sci USA 2008; 105:20458-20463 [2008]). The sequencing technologies of NGS include pyrosequencing, sequencing-by-synthesis with reversible dye terminators, sequencing by oligonucleotide probe ligation and real time sequencing.

Some of the sequencing technologies are available commercially, such as the sequencing-by-hybridization platform from Affymetrix Inc. (Sunnyvale, Calif.) and the sequencing-by-synthesis platforms from 454 Life Sciences (Bradford. Conn.). Illumina/Solexa (Hayward, Calif.) and Helicos Biosciences (Cambridge, Mass.), and the sequencing-by-ligation platform from Applied Biosystems (Foster City, Calif.), as described below. In addition to the single molecule sequencing performed using sequencing-by-synthesis of Helicos Biosciences, other single molecule sequencing technologies are encompassed by the method of the invention and include the SMRT™ technology of Pacific Biosciences, the Ion Torrent™ technology, and nanopore sequencing being developed for example, by Oxford Nanopore Technologies.

While the automated Sanger method is considered as a 'first generation' technology. Sanger sequencing including the automated Sanger sequencing, can also be employed by the method of the invention. Additional sequencing methods that comprise the use of developing nucleic acid imaging technologies e.g. atomic force microscopy (AFM) or transmission electron microscopy (TEM), are also encompassed by the method of the invention. Exemplary sequencing technologies are described below.

In one embodiment, the DNA sequencing technology that is used in the method of the invention is the Helicos True Single Molecule Sequencing (tSMS) (e.g. as described in Harris T. D. et al., Science 320:106-109 [2008]). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. The templates can be at a density of about 100 million templates/$cm^2$. The flow cell is then loaded into an instrument, e.g., HeliScope™ sequencer, and a laser illuminates the surface of the flow cell revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are discerned by imaging the flow cell surface. After imaging, a cleavage step removes the fluorescent label, and the process is repeated with other fluorescently labeled nucleotides until the desired read length is achieved. Sequence information is collected with each nucleotide addition step.

In one embodiment, the DNA sequencing technology that is used in the method of the invention is the 454 sequencing (Roche) (e.g. as described in Margulies, M. et al. Nature 437:376-380 [2005]). 454 sequencing involves two steps. In the first step, DNA is sheared into fragments of approximately 300-800 base pairs, and the fragments are blunt-ended. Oligonucleotide adaptors are then ligated to the ends of the fragments. The adaptors serve as primers for amplification and sequencing of the fragments. The fragments can be attached to DNA capture beads. e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (pico-liter sized). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is discerned and analyzed.

In one embodiment, the DNA sequencing technology that is used in the method of the invention is the SOLiD™ technology (Applied Biosystems). In SOLiD™ sequencing-by-ligation, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is cleaved and removed and the process is then repeated.

In one embodiment, the DNA sequencing technology that is used in the method of the invention is the single molecule, real-time (SMRT™) sequencing technology of Pacific Biosciences. In SMRT sequencing, the continuous incorporation of dye-labeled nucleotides is imaged during DNA synthesis. Single DNA polymerase molecules are attached to the bottom surface of individual zero-mode wavelength identifiers (ZMW identifiers) that obtain sequence information while phospolinked nucleotides are being incorporated into the growing primer strand. A ZMW is a confinement structure which enables observation of incorporation of a single nucleotide by DNA polymerase against the background of fluorescent nucleotides that rapidly diffuse in an out of the ZMW (in microseconds). It takes several milliseconds to incorporate a nucleotide into a growing strand. During this time, the fluorescent label is excited and produces a fluorescent signal, and the fluorescent tag is cleaved off. Identification of the corresponding fluorescence of the dye indicates which base was incorporated. The process is repeated.

In one embodiment, the DNA sequencing technology that is used in the method of the invention is nanopore sequencing (e.g. as described in Soni G V and Meller A. Clin Chem 53: 1996-2001 [2007]). Nanopore sequencing DNA analysis techniques are being industrially developed by a number of companies, including Oxford Nanopore Technologies (Oxford, United Kingdom). Nanopore sequencing is a single-molecule sequencing technology whereby a single molecule of DNA is sequenced directly as it passes through a nanopore. A nanopore is a small hole, of the order of 1 nanometer in diameter. Immersion of a nanopore in a conducting fluid and application of a potential (voltage) across it results in a slight electrical current due to conduction of ions through the nanopore. The amount of current which flows is sensitive to the size and shape of the nanopore. As a DNA molecule passes through a nanopore, each nucleotide on the DNA molecule obstructs the nanopore to a different degree, changing the magnitude of the current through the nanopore in different degrees. Thus, this change in the current as the DNA molecule passes through the nanopore represents a reading of the DNA sequence.

In one embodiment, the DNA sequencing technology that is used in the method of the invention is the chemical-sensitive field effect transistor (chemFET) array (e.g., as described in U.S. Patent Application Publication No. 20090026082). In one example of the technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be discerned by a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

In one embodiment, the DNA sequencing technology that is used in the method of the invention is the Halcyon Molecular's method that uses transmission electron microscopy (TEM). The method, termed Individual Molecule Placement Rapid Nano Transfer (IMPRNT), comprises utilizing single atom resolution transmission electron microscope imaging of high-molecular weight (150 kb or greater) DNA selectively labeled with heavy atom markers and arranging these molecules on ultra-thin films in ultra-dense (3 nm strand-to-strand) parallel arrays with consistent base-to-base spacing. The electron microscope is used to image the molecules on the films to determine the position of the heavy atom markers and to extract base sequence information from the DNA. The method is further described in PCT patent publication WO 2009/046445. The method allows for sequencing complete human genomes in less than ten minutes.

In one embodiment, the DNA sequencing technology is the Ion Torrent single molecule sequencing, which pairs semiconductor technology with a simple sequencing chemistry to directly translate chemically encoded information (A, C, G, T) into digital information (0, 1) on a semiconductor chip. In nature, when a nucleotide is incorporated into a strand of DNA by a polymerase, a hydrogen ion is released as a byproduct. Ion Torrent uses a high-density array of micro-machined wells to perform this biochemical process in a massively parallel way. Each well holds a different DNA molecule. Beneath the wells is an ion-sensitive layer and beneath that an ion sensor. When a nucleotide, for example a C, is added to a DNA template and is then incorporated into a strand of DNA, a hydrogen ion will be released. The charge from that ion will change the pH of the solution, which can be identified by Ion Torrent's ion sensor. The sequencer—essentially the world's smallest solid-state pH meter—calls the base, going directly from chemical information to digital information. The Ion personal Genome Machine (PGM™) sequencer then sequentially floods the chip with one nucleotide after another. If the next nucleotide that floods the chip is not a match. No voltage change will be recorded and no base will be called. If there are two identical bases on the DNA strand, the voltage will be double, and the chip will record two identical bases called. Direct identification allows recordation of nucleotide incorporation in seconds.

Other sequencing methods include digital PCR and sequencing by hybridization. Digital polymerase chain reaction (digital PCR or dPCR) can be used to directly identify and quantify nucleic acids in a sample. Digital PCR can be performed in an emulsion. Individual nucleic acids are separated, e.g., in a microfluidic chamber device, and each nucleic can is individually amplified by PCR. Nucleic acids can be separated such there is an average of approximately 0.5 nucleic acids/well, or not more than one nucleic acid/well. Different probes can be used to distinguish fetal alleles and maternal alleles. Alleles can be enumerated to determine copy number. In sequencing by hybridization, the hybridization comprises contacting the plurality of polynucleotide sequences with a plurality of polynucleotide probes, wherein each of the plurality of polynucleotide probes can be optionally tethered to a substrate. The substrate might be flat surface comprising an array of known nucleotide sequences. The pattern of hybridization to the array can be used to determine the polynucleotide sequences present in the sample. In other embodiments, each probe is tethered to a bead, e.g., a magnetic bead or the like. Hybridization to the beads can be identified and used to identify the plurality of polynucleotide sequences within the sample.

In one embodiment, the method employs massively parallel sequencing of millions of DNA fragments using Illumina's sequencing-by-synthesis and reversible terminator-based sequencing chemistry (e.g. as described in Bentley et al., Nature 6:53-59 [2009]). Template DNA can be genomic DNA e.g. cfDNA. In some embodiments, genomic DNA from isolated cells is used as the template, and it is fragmented into lengths of several hundred base pairs. In other embodiments, cfDNA is used as the template, and fragmentation is not required as cfDNA exists as short fragments. For example fetal cfDNA circulates in the bloodstream as fragments of <300 bp, and maternal cfDNA has been estimated to circulate as fragments of between about 0.5 and 1 Kb (Li et al., Clin Chem. 50: 1002-1011 [2004]). Illumina's sequencing technology relies on the attachment of fragmented genomic DNA to a planar, optically transparent surface on which oligonucleotide anchors are bound. Template DNA is end-repaired to generate 5'-phosphorylated blunt ends, and the polymerase activity of Klenow fragment is used to add a single A base to the 3' end of the blunt phosphorylated DNA fragments. This addition prepares the DNA fragments for ligation to oligonucleotide adapters, which have an overhang of a single T base at their 3' end to increase ligation efficiency. The adapter oligonucleotides are complementary to the flow-cell anchors. Under limiting-dilution conditions, adapter-modified, single-stranded template DNA is added to the flow cell and immobilized by hybridization to the anchors. Attached DNA fragments are extended and bridge amplified to create an ultra-high density sequencing flow cell with hundreds of millions of clusters, each containing ~1,000 copies of the same template. In one embodiment, the randomly fragmented genomic DNA e.g. cfDNA, is amplified using PCR before it is subjected to cluster amplification. Alternatively, an amplification-free genomic library preparation is used, and the randomly fragmented genomic DNA e.g. cfDNA is enriched using the cluster amplification alone (Kozarewa et al., Nature Methods 6:291-295 [2009]). The templates are sequenced using a robust four-color DNA sequencing-by-synthesis technology that employs reversible terminators with removable fluorescent dyes. High-sensitivity fluorescence identification is achieved using laser excitation and total internal reflection optics. Short sequence reads of about 20-40 bp e.g. 36 bp, are aligned against a repeat-masked reference genome and genetic differences are called using specially developed data analysis pipeline software. After completion of the first read, the templates can be regenerated in situ to enable a second read from the opposite end of the fragments. Thus, either single-end or paired end sequencing of the DNA fragments is used according to the method. Partial sequencing of DNA fragments present in the sample is performed, and sequence tags comprising reads of predetermined length e.g. 36 bp, that are mapped to a known reference genome are counted. In one embodiment, the reference genome sequence is the NCBI36/hg18 sequence, which is available on the world wide web at genome.ucsc.edu/cgi-bin/hgGateway?org=Human&db=hg18&hgsid=166260105). Other sources of public sequence information include GenBank, dbEST, dbSTS, EMBL (the European Molecular Biology Laboratory), and the DDBJ (the DNA Databank of Japan). A number of computer algorithms are available for aligning sequences, including without limitation BLAST (Altschul et al., 1990), BLITZ (MPsrech) (Sturrock & Collins, 1993). FASTA (Person & Lipman, 1988). BOWTIE (Langmead et al., Genome Biology 10:R25.1-R25.10 [2009]), or ELAND (Illumina, Inc., San Diego, Calif. USA). In one embodiment, one end of the clonally expanded copies of the plasma cfDNA molecules is sequenced and processed by bioinformatic alignment analysis for the Illumina Genome Analyzer, which uses the Efficient Large-Scale Alignment of Nucleotide Databases (ELAND) software.

The length of the sequence read is associated with the particular sequencing technology. NGS methods provide sequence reads that vary in size from tens to hundreds of base pairs. In some embodiments of the method described herein, the sequence reads are about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, or about 500 bp. It is expected that technological advances will enable single-end reads of greater than 500 bp enabling for reads of greater than about 1000 bp when paired end reads are generated. In one embodiment, the sequence reads are 36 bp. Other sequencing methods that can be employed by the method of the invention include the single molecule sequencing methods that can sequence nucleic acids molecules >5000 bp. The massive quantity of sequence output is transferred by an analysis pipeline that transforms primary imaging output from the sequencer into strings of bases. A package of integrated algorithms performs the core primary data transformation steps: image analysis, intensity scoring, base calling, and alignment.

In one embodiment, partial sequencing of DNA fragments present in the sample is performed, and sequence tags comprising reads of predetermined length e.g. 36 bp, that map to a known reference genome are counted. Only sequence reads that uniquely align to the reference genome are counted as sequence tags. In one embodiment, the reference genome is the human reference genome NCBI36/hg18 sequence, which is available on the world wide web at genome.ucsc.edu/cgi-bin/hgGateway?org=Human&db=hg18&hgsid=166260105). Other sources of public sequence information include GenBank, dbEST, dbSTS, EMBL (the European Molecular Biology Laboratory), and the DDBJ (the DNA Databank of Japan). In another embodiment, the reference genome comprises the human reference genome NCBI36/hg18 sequence and an artificial target sequences genome, which includes the target polymorphic sequences e.g. a SNP genome. Mapping of the sequence tags is achieved by comparing the sequence of the tag with the sequence of the reference genome to determine the chromosomal origin of the sequenced nucleic acid (e.g. cfDNA) molecule, and specific genetic sequence information is not needed. A number of computer algorithms are available for aligning sequences, including without limitation BLAST (Altschul et al., 1990), BLITZ (MPsrch) (Sturrock & Collins, 1993). FASTA (Person & Lipman, 1988), BOWTIE (Langmead et al., Genome Biology 10:R25.1-R25.10 [2009]), or ELAND (Illumina, Inc., San Diego, Calif., USA). In one embodiment, one end of the clonally expanded copies of the plasma cfDNA molecules is sequenced and processed by bioinformatic alignment analysis for the Illumina Genome Analyzer, which uses the Efficient Large-Scale Alignment of Nucleotide Databases (ELAND) software. Analysis of sequencing information for the determination of aneuploidy may allow for a small degree of mismatch (0-2 mismatches per sequence tag) to account for minor polymorphisms that may exist between the reference genome and the genomes in the mixed sample. Analysis of sequencing information for the determination of fetal fraction may allow for a small degree of mismatch depending on the polymorphic sequence. For example, a small degree of mismatch may be allowed if the polymorphic sequence is an STR. In cases when the polymorphic sequence is a SNP, all sequence that match exactly to either of the two alleles at the SNP site are counted first and filtered from the remaining reads, for which a small degree of mismatch may be allowed.

In step 140, the sequencing information obtained in step 130 is analyzed and the simultaneous determination of the fetal fraction and determination of the presence or absence of aneuploidy is made.

A plurality of sequence tags are obtained per sample. In some embodiments, at least about $3\times10^6$ sequence tags, at least about $5\times10^6$ sequence tags, at least about $8\times10^6$ sequence tags, at least about $10\times10^6$ sequence tags, at least about $15\times10^6$ sequence tags, at least about $20\times10^6$ sequence tags, at least about $30\times10^6$ sequence tags, at least about $40\times10^6$ sequence tags, or at least about $50\times10^6$ sequence tags comprising between 20 and 40 bp reads are obtained from mapping the reads to the reference genome per sample. In one embodiment, all the sequence reads are mapped to all regions of the reference genome. In one embodiment, the tags comprising reads that have been mapped to all regions e.g. all chromosomes, of the human reference genome are counted, and the fetal aneuploidy i.e. the over- or under-representation of a sequence of interest e.g. a chromosome or portion thereof, in the mixed DNA sample is determined, and the tags comprising reads that are mapped to the artificial target sequences genome are counted to determine the fetal fraction. The method does not require differentiation between the maternal and fetal genomes.

Determination of Aneuploidy

Figure 5:
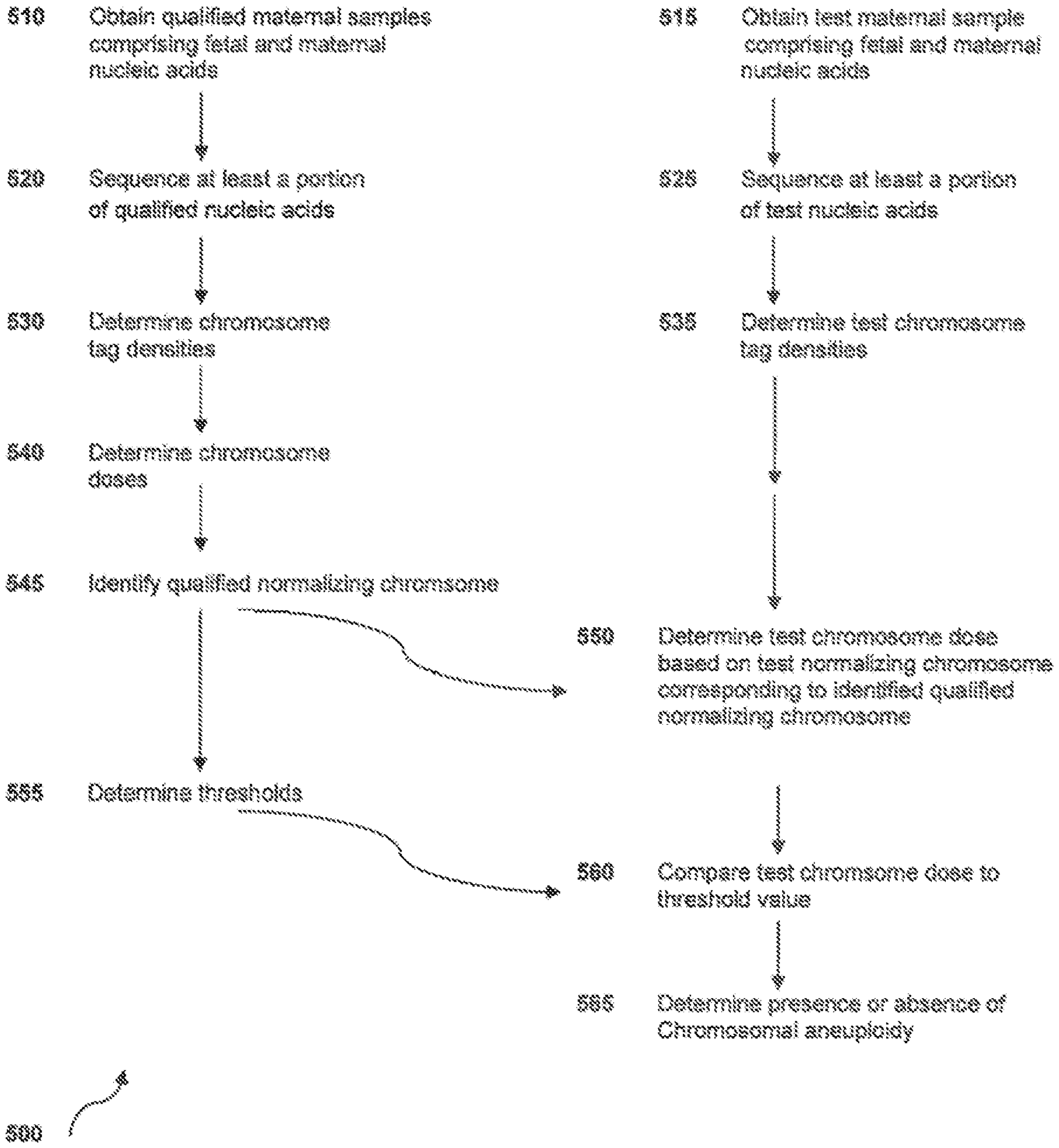
FIG. 5 is a flowchart of a method 500 for determining the presence or absence of a copy number variation in a test sample comprising a mixture of nucleic acids.

The accuracy required for correctly determining whether an aneuploidy is present or absent in a sample, is predicated in part on the variation of the number of sequence tags that map to the reference genome among samples within a sequencing run (inter-chromosomal variability), and the variation of the number of sequence tags that map to the reference genome in different sequencing runs (inter-sequencing variability). For example, the variations can be particularly pronounced for tags that map to GC-rich or GC-poor reference sequences. In one embodiment, the method uses sequencing information to calculate chromosome dose, which intrinsically account for the accrued variability stemming from interchromosomal, inter-sequencing and platform-dependent variability. Chromosome doses are determined from sequencing information i.e. the number of sequence tags, for the sequence of interest e.g. chromosome 21, and the number of sequence tags for a normalizing sequence. Identification of a normalizing sequence is performed in a set of qualified samples known not to contain an aneuploidy of the sequence of interest. The flow chart provided in FIG. 5 shows the process 500 whereby normalizing sequences e.g. normalizing chromosomes, are identified, and the presence or absence of an aneuploidy is determined. In step 510, a set of qualified maternal samples is obtained to identify qualified normalizing sequences e.g. normalizing chromosomes, and to provide variance values for use in determining statistically meaningful identification of an aneuploidy in test samples. In step 510, a plurality of biological qualified samples are obtained from a plurality of subjects known to comprise cells having a normal copy number for any one sequence of interest e.g. a chromosome of interest such as a chromosome associated with an aneuploidy. In one embodiment, the qualified samples are obtained from mothers pregnant with a fetus that has been confirmed using cytogenetic means to have a normal copy number of chromosomes relative to the chromosome of interest. The biological qualified maternal samples may be biological fluid samples e.g. plasma samples, or any suitable sample as described above that contains a mixture of fetal and maternal cfDNA molecules.

In step 520, at least a portion of each of all the qualified nucleic acids contained in the qualified maternal samples are sequenced to generate sequence reads of between 20 and 40 bp e.g. 36 bp, which are aligned to a reference genome, e.g. hg18. In some embodiments, the sequence reads comprise about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, or about 500 bp. It is expected that technological advances will enable single-end reads of greater than 500 bp enabling for reads of greater than about 1000 bp when paired end reads are generated. In one embodiment, the sequence reads comprise 36 bp. Sequence reads are aligned to a human reference genome, and the reads that are uniquely mapped to the human reference genome are counted as sequence tags. In one embodiment, at least about $3\times10^6$ qualified sequence tags, at least about $5\times10^6$ qualified sequence tags, at least about $8\times10^6$ qualified sequence tags, at least about $10\times10^6$ qualified sequence tags, at least about $15\times10^6$ qualified sequence tags, at least about $20\times10^6$ qualified sequence tags, at least about $30\times10^6$ qualified sequence tags, at least about $40\times10^6$ qualified sequence tags, or at least about $50\times10^6$ qualified sequence tags comprising between 20 and 40 bp reads are obtained from reads that map uniquely to a reference genome.

In step 530, all the tags obtained from sequencing the nucleic acids in the qualified maternal samples are counted to determine a qualified sequence tag density. In one embodiment the sequence tag density is determined as the number of qualified sequence tags mapped to the sequence of interest on the reference genome. In another embodiment, the qualified sequence tag density is determined as the number of qualified sequence tags mapped to a sequence of interest normalized to the length of the qualified sequence of interest to which they are mapped. Sequence tag densities that are determined as a ratio of the tag density relative to the length of the sequence of interest are herein referred to as tag density ratios. Normalization to the length of the sequence of interest is not required, and may be included as a step to reduce the number of digits in a number to simplify it for human interpretation. As all qualified sequence tags are mapped and counted in each of the qualified samples, the sequence tag density for a sequence of interest e.g. chromosome of interest, in the qualified samples is determined, as are the sequence tag densities for additional sequences from which normalizing sequences e.g. chromosomes, are identified subsequently. In one embodiment, the sequence of interest is a chromosome that is associated with a chromosomal aneuploidy e.g. chromosome 21, and the qualified normalizing sequence is a chromosome that is not associated with a chromosomal aneuploidy and whose variation in sequence tag density best approximates that of chromosome 21. For example, a qualified normalizing sequence is a sequence that has the smallest variability. In some embodiments, the normalizing sequence is a sequence that best distinguishes one or more qualified, samples from one or more affected samples i.e. the normalizing sequence is a sequence that has the greatest differentiability. The level of differentiability can be determined as a statistical difference between the chromosome doses in a population of qualified samples and the chromosome dose(s) in one or more test samples. In another embodiment, the sequence of interest is a segment of a chromosome associated with a partial aneuploidy, e.g. a chromosomal deletion or insertion, or unbalanced chromosomal translocation, and the normalizing sequence is a chromosomal segment that is not associated with the partial aneuploidy and whose variation in sequence tag density best approximates that of the chromosome segment associated with the partial aneuploidy.

In step 540, based on the calculated qualified tag densities, a qualified sequence dose for a sequence of interest is determined as the ratio of the sequence tag density for the sequence of interest and the qualified sequence tag density for additional sequences from which normalizing sequences are identified subsequently. In one embodiment, doses for the chromosome of interest e.g. chromosome 21, is determined as a ratio of the sequence tag density of chromosome 21 and the sequence tag density for each of all the remaining chromosomes i.e. chromosomes 1-20, chromosome 22, chromosome X, and chromosome Y.

In step 545, a normalizing sequence e.g. a normalizing chromosome, is identified for a sequence of interest e.g. chromosome 21, in a qualified sample based on the calculated sequence doses. The method identifies sequences that inherently have similar characteristics and that are prone to similar variations among samples and sequencing runs, and which are useful for determining sequence doses in test samples. In some embodiments, the normalizing sequence is one that best differentiates an affected sample i.e. an aneuploid sample, from one or more qualified samples. In other embodiments, a normalizing sequence is a sequence that displays a variability in the number of sequence tags that are mapped to it among samples and sequencing runs that best approximates that of the sequence of interest for which it is used as a normalizing parameter, and/or that can best differentiate an affected sample from one or more unaffected samples.

In some embodiments, more than one normalizing sequence is identified. For example, the variation e.g. coefficient of variation, in chromosome dose for chromosome of interest 21 is least when the sequence tag density of chromosome 14 is used. In other embodiments, two, three, four, five, six, seven, eight or more normalizing sequences are identified for use in determining a sequence dose for a sequence of interest in a test sample.

In one embodiment, the normalizing sequence for chromosome 21 is selected from chromosome 9, chromosome 1, chromosome 2, chromosome 3, chromosome 4, chromosome 5, chromosome 6, chromosome 7, chromosome 8, chromosome 10, chromosome 11, chromosome 12, chromosome 13, chromosome 14, chromosome 15, chromosome 16, and chromosome 17. Preferably, the normalizing sequence for chromosome 21 is selected from chromosome 9, chromosome 1, chromosome 2, chromosome 11, chromosome 12, and chromosome 14. Alternatively, the normalizing sequence for chromosome 21 is a group of chromosomes selected from chromosome 9, chromosome 1, chromosome 2, chromosome 3, chromosome 4, chromosome 5, chromosome 6, chromosome 7, chromosome 8, chromosome 10, chromosome 11, chromosome 12, chromosome 13, chromosome 14, chromosome 15, chromosome 16, and chromosome 17. In other embodiments, the normalizing sequence for chromosome 21 is a group of chromosomes selected from chromosome 9, chromosome 1, chromosome 2, chromosome 11, chromosome 12, and chromosome 14.

In one embodiment, the normalizing sequence for chromosome 18 is selected from chromosome 8, chromosome 2, chromosome 3, chromosome 4, chromosome 5, chromosome 6, chromosome 7, chromosome 9, chromosome 10, chromosome 11, chromosome 12, chromosome 13, and chromosome 14. Preferably, the normalizing sequence for chromosome 18 is selected chromosome 8, chromosome 2, chromosome 3, chromosome 5, chromosome 6, chromosome 12, and chromosome 14. Alternatively, the normalizing sequence for chromosome 18 is a group of chromosomes selected from chromosome 8, chromosome 2, chromosome 3, chromosome 4, chromosome 5, chromosome 6, chromosome 7, chromosome 9, chromosome 10, chromosome 11, chromosome 12, chromosome 13, and chromosome 14. In other embodiments, the normalizing sequence for chromosome 18 is a group of chromosomes selected from chromosome 8, chromosome 2, chromosome 3, chromosome 5, chromosome 6, chromosome 12, and chromosome 14.

In one embodiment, the normalizing sequence for chromosome X is selected from chromosome 1, chromosome 2, chromosome 3, chromosome 4, chromosome 5, chromosome 6, chromosome 7, chromosome 8, chromosome 9, chromosome 10, chromosome 11, chromosome 12, chromosome 13, chromosome 14, chromosome 15, and chromosome 16. Preferably, the normalizing sequence for chromosome X is selected from chromosome 2, chromosome 3, chromosome 4, chromosome 5, chromosome 6, and chromosome 8. Alternatively, the normalizing sequence for chromosome X is a group of chromosomes selected from chromosome 1, chromosome 2, chromosome 3, chromosome 4, chromosome 5, chromosome 6, chromosome 7, chromosome 8, chromosome 9, chromosome 10, chromosome 11, chromosome 12, chromosome 13, chromosome 14, chromosome 15, and chromosome 16. In other embodiments, the normalizing sequence for chromosome X is a group of chromosomes selected from chromosome 2, chromosome 3, chromosome 4, chromosome 5, chromosome 6, and chromosome 8

In one embodiment, the normalizing sequence for chromosome 13 is a chromosome selected from chromosome 2, chromosome 3, chromosome 4, chromosome 5, chromosome 6, chromosome 7, chromosome 8, chromosome 9, chromosome 10, chromosome 11, chromosome 12, chromosome 14, chromosome 18, and chromosome 21. Preferably, the normalizing sequence for chromosome 13 is selected from chromosome 2, chromosome 3, chromosome 4, chromosome 5, chromosome 6, and chromosome 8. In another embodiment, the normalizing sequence for chromosome 13 is a group of chromosomes selected from chromosome 2, chromosome 3, chromosome 4, chromosome 5, chromosome 6, chromosome 7, chromosome 8, chromosome 9, chromosome 10, chromosome 11, chromosome 12, chromosome 14, chromosome 18, and chromosome 21. In other embodiments, the normalizing sequence for chromosome 13 is a group of chromosomes selected from chromosome 2, chromosome 3, chromosome 4, chromosome 5, chromosome 6, and chromosome 8.

The variation in chromosome dose for chromosome Y is greater than 30 independently of which normalizing chromosome is used in determining the chromosome Y dose. Therefore, any one chromosome, or a group of two or more chromosomes selected from chromosomes 1-22 and chromosome X can be used as the normalizing sequence for chromosome Y. In one embodiment, the at least one normalizing chromosome is a group of chromosomes consisting of chromosomes 1-22, and chromosome X. In another embodiment, the at least one normalizing chromosome is a group of chromosomes selected from chromosome 2, chromosome 3, chromosome 4, chromosome 5 and chromosome 6.

Based on the identification of the normalizing sequence(s) in qualified samples, a sequence dose is determined for a sequence of interest in a test sample comprising a mixture of nucleic acids derived from genomes that differ in one or more sequences of interest.

In step 515, a test sample e.g. plasma sample, comprising fetal and maternal nucleic acids e.g. cfDNA, is obtained from a pregnant subject e.g. a pregnant woman, for which the presence or absence of a fetal aneuploidy needs to be determined.

In step 525, at least a portion of the test nucleic acids in the test sample is sequenced to generate millions of sequence reads comprising between 20 and 500 bp e.g. 36 bp. As in step 520, the reads generated from sequencing the nucleic acids in the test sample are uniquely mapped to a human reference genome and are counted. As described in step 520, at least about $3\times10^6$ qualified sequence tags, at least about $5\times10^6$ qualified sequence tags, at least about $8\times10^6$ qualified sequence tags, at least about $10\times10^6$ qualified sequence tags, at least about $15\times10^6$ qualified sequence tags, at least about $20\times10^6$ qualified sequence tags, at least about $30\times10^6$ qualified sequence tags, at least about $40\times10^6$ qualified sequence tags, or at least about $50\times10^{6}$ qualified sequence tags comprising between 20 and 40 bp reads are obtained from reads that map uniquely to the human reference genome.

In step 535, all the tags obtained from sequencing the nucleic acids in the test samples are counted to determine a test sequence tag density. In one embodiment the number of test sequence tags mapped to a sequence of interest is normalized to the known length of a sequence of interest to which they are mapped to provide a test sequence tag density. As described for the qualified samples, normalization to the known length of a sequence of interest is not required, and may be included as a step to reduce the number of digits in a number to simplify it for human interpretation. As all the mapped test sequence tags are counted in the test sample, the sequence tag density for a sequence of interest e.g. a clinically-relevant sequence such as chromosome 21, in the test samples is determined, as are the sequence tag densities for additional sequences that correspond to at least one normalizing sequence identified in the qualified samples.

In step 550, based on the identity of at least one normalizing sequence in the qualified samples, a test sequence dose is determined for a sequence of interest in the test sample. The sequence dose e.g. chromosome dose, for a sequence of interest in a test sample is a ratio of the sequence tag density determined for the sequence of interest in the test sample and the sequence tag density of at least one normalizing sequence determined in the test sample, wherein the normalizing sequence in the test sample corresponds to the normalizing sequence identified in the qualified samples for the particular sequence of interest. For example, if the normalizing sequence identified for chromosome 21 in the qualified samples is determined to be chromosome 14, then the test sequence dose for chromosome 21 (sequence of interest) is determined as the ratio of the sequence tag density for chromosome 21 in and the sequence tag density for chromosome 14 each determined in the test sample. Similarly, chromosome doses for chromosomes 13, 18, X, Y, and other chromosomes associated with chromosomal aneuploidies are determined. As described previously, a sequence of interest can be part of a chromosome e.g. a chromosome segment. Accordingly, the dose for a chromosome segment can be determined as the ratio of the sequence tag density determined for the segment in the test sample and the sequence tag density for the normalizing chromosome segment in the test sample, wherein the normalizing segment in the test sample corresponds to the normalizing segment identified in the qualified samples for the particular segment of interest.

In step 555, threshold values are derived from standard deviation values established for a plurality of qualified sequence doses. Accurate classification depends on the differences between probability distributions for the different classes i.e. type of aneuploidy. Preferably, thresholds are chosen from empirical distribution for each type of aneuploidy e.g. trisomy 21. Possible threshold values that were established for classifying trisomy 13, trisomy 18, trisomy 21, and monosomy X aneuploidies as described in the Examples, which describe the use of the method for determining chromosomal aneuploidies by sequencing cfDNA extracted from a maternal sample comprising a mixture of fetal and maternal nucleic acids.

In step 560, the copy number variation of the sequence of interest e.g. chromosomal or partial aneuploidy, is determined in the test sample by comparing the test sequence dose for the sequence of interest to at least one threshold value established from the qualified sequence doses.

In step 560, the calculated dose for a test sequence of interest is compared to that set as the threshold values that are chosen according to a user-defined threshold of reliability to classify the sample as a "normal" an "affected" or a "no call" in step 565. The "no call" samples are samples for which a definitive diagnosis cannot be made with reliability.

Another embodiment of the invention provides a method for providing prenatal diagnosis of a fetal chromosomal aneuploidy in a biological sample comprising fetal and maternal nucleic acid molecules. The diagnosis is made based on receiving the data from sequencing at least a portion of the mixture of the fetal and maternal nucleic acid molecules derived from a biological test sample e.g. a maternal plasma sample, computing from the sequencing data a normalizing chromosome dose for one or more chromosomes of interest, determining a statistically significant difference between the normalizing chromosome dose for the chromosome of interest in the test sample and a threshold value established in a plurality of qualified (normal) samples, and providing the prenatal diagnosis based on the statistical difference. As described in step 565 of the method, a diagnosis of normal or affected is made. A "no call" is provided in the event that the diagnosis for normal or affected cannot be made with confidence.

Quantification of the number of sequence reads aligning to each chromosome for determining chromosomal aneuploidies can also be achieved by normalizing the median number of sequence tags for a chromosome of interest to the median number of tags for each of the other autosomes (Fan et al., Proc Natl Acad Sci 105:16266-16271 [2008]). Alternatively, the number of unique reads aligning to each chromosome is compared to the total number of reads aligning to all chromosomes to derive a percent genomic representation for each chromosome. A "z score" is generated to represent the difference between the percent genomic representation of the chromosome of interest and the mean percent representation for the same chromosome between a euploid control group, divided by the standard deviation (Chiu et al., Clin Chem 56:459-463 [2010]).

Determination of Fetal Fraction

The determination of the fetal fraction is based on the total number of tags that map to the first allele and the total number of tags that map to second allele at an informative polymorphic site e.g. a SNP, contained in a reference genome. For example, the reference genome is the human reference genome NCBI36/hg18 sequence, or the reference genome comprises the human reference genome NCBI36/hg18 sequence and an artificial target sequences genome, which includes the target polymorphic sequences. For example, the artificial target genome encompasses polymorphic sequences that comprise SNPs rs560681, rs109037, rs9866013, rs13182883, rs13218440, rs7041158, rs740598, rs10773760, rs4530059, rs7205345, rs8078417, rs576261, rs2567608, rs430046, rs9951171, rs338882, rs10776839, rs9905977, rs1277284, rs258684, rs1347696, rs508485, rs9788670, rs8137254, rs3143, rs2182957, rs3739005, and rs530022. In another example, the artificial genome includes the polymorphic target sequences of SEQ ID NOs:1-56 (see Example 5). In another example, the artificial genome comprises polymorphic sequences that comprise tandem SNPs rs7277033-rs2110153; rs2822654-rs1882882; rs368657-rs376635; rs2822731-rs2822732; rs1475881-rs7275487; rs1735976-rs2827016; rs447340-rs2824097; rs418989-rs13047336; rs987980-rs987981; rs4143392-rs4143391; rs1691324-rs13050434; rs11909758-rs9980111;

rs2826842-rs232414; rs1980969-rs1980970; rs9978999-rs9979175; rs1034346-rs12481852; rs7509629-rs2828358; rs4817013-rs7277036; rs9981121-rs2829696; rs455921-rs2898102; rs2898102-rs458848; rs961301-rs2830208; rs2174536-rs458076; rs11088023-rs1088024; rs1011734-rs1011733; rs2831244-rs9789838; rs8132769-rs2831440; rs8134080-rs2831524; rs4817219-rs4817220; rs2250911-rs2250997; rs2831899-rs2831900; rs2831902-rs2831903; rs11088086-rs2251447; rs2832040-rs11088088; rs2832141-rs2246777; rs2832959-rs9980934; rs2833734-rs2833735; rs933121-rs933122; rs2834140-rs12626953; rs2834485-rs3453; rs9974986-rs2834703; rs2776266-rs2835001; rs1984014-rs1984015; rs7281674-rs2835316; rs13047304-rs13047322; rs2835545-rs4816551; rs2835735-rs2835736; rs13047608-rs2835826; rs2836550-rs2212596; rs2836660-rs2836661; rs465612-rs8131220; rs9980072-rs8130031; rs418359-rs2836926; rs7278447-rs7278858; rs385787-rs367001; rs367001-rs386095; rs2837296-rs2837297; and rs2837381-rs4816672. In another example, the artificial target genome encompasses polymorphic sequences that comprise STRs selected from CSF1PO, FGA, TH01. TPOX, vWA, D3S1358, D5S818, D7S820, D8S1179, D13S317, D16S539, D18S51, D21S11. Penta D, Penta E, D2S1338, D1S1677, D2S441, D4S2364, D10S1248, D14S1434, D22S1045, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D5S2500, D4S2408, D4S2364, D3S4529, D3S3053, D2S1776, D2S441, D1S1677, D1S1627, and D1GATA113. The composition of the artificial target sequences genome will vary depending on the polymorphic sequences that are used for determining the fetal fraction. Accordingly, an artificial target sequences genome is not limited to the SNP or STR sequences exemplified herein.

Figure 6:
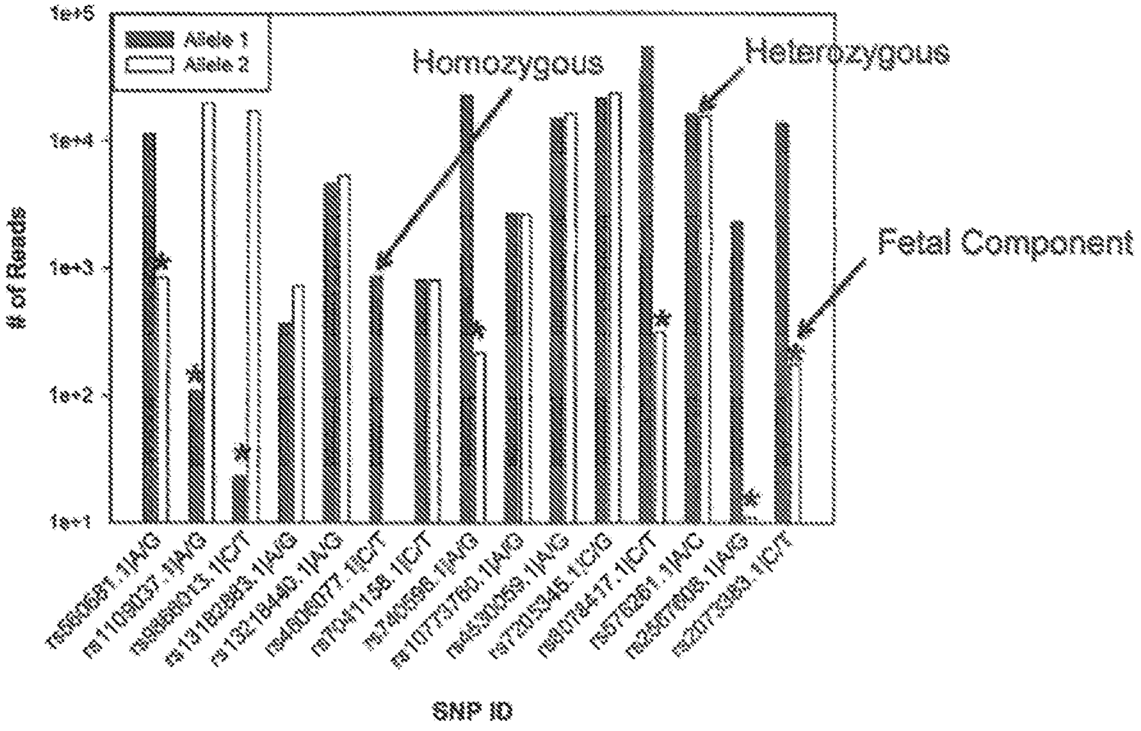
FIG. 6 is a bar diagram showing the identification of fetal and maternal polymorphic sequences (SNPs) used to determine fetal fraction in a test sample. The total number of sequence reads (Y-axis) mapped to the SNP sequences identified by rs numbers (X-axis), and the relative level of fetal nucleic acids (*) are shown.
Figure 7A:
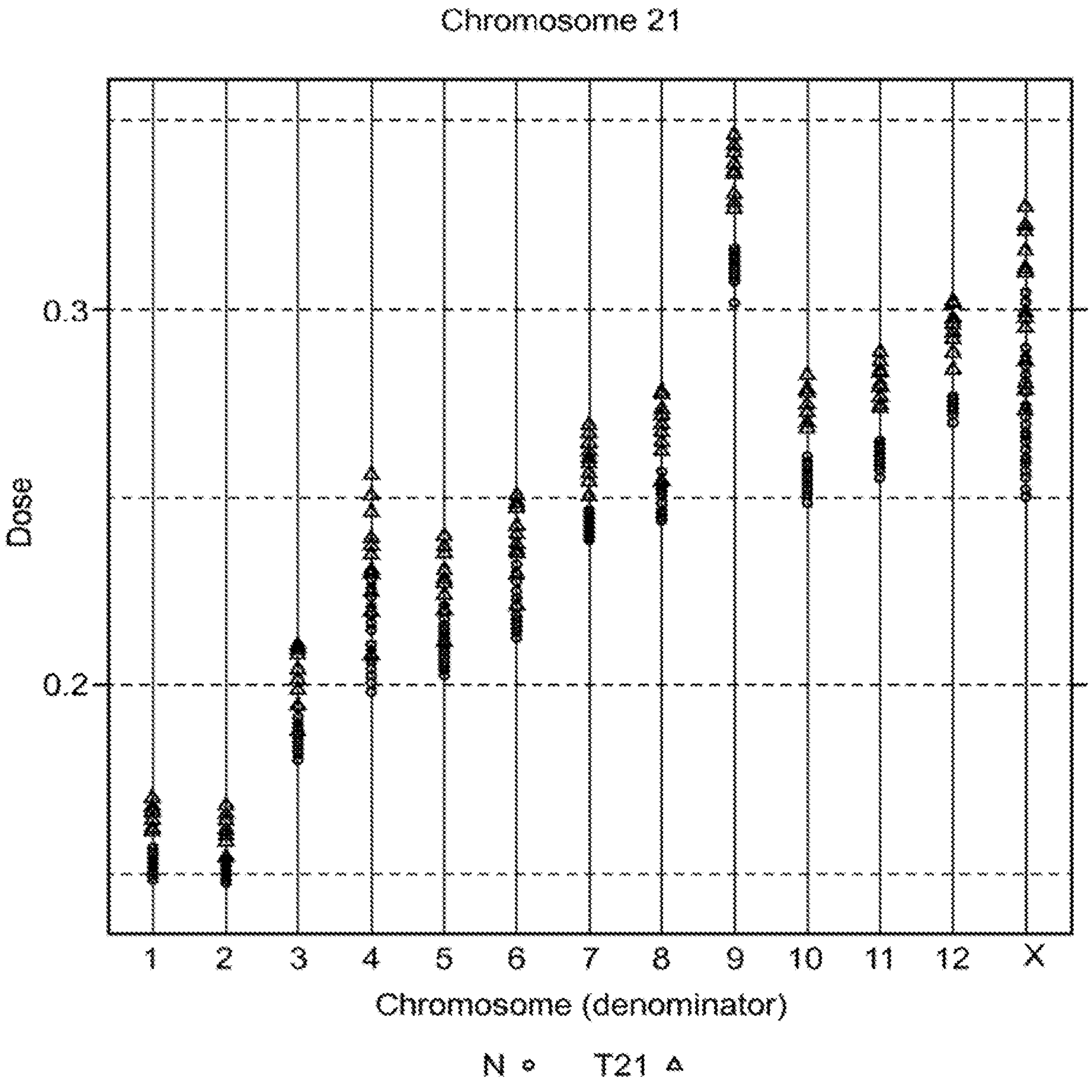
FIGS. 7A and 7B illustrate the distribution of the chromosome dose for chromosome 21 determined from sequencing cfDNA extracted from a set of 48 blood samples obtained from human subjects pregnant with male or female fetuses. Chromosome 21 doses for qualified i.e. normal for chromosome 21 (O), and trisomy 21 test samples are shown (Δ) for chromosomes 1-12 and X (FIG. 7A), and for chromosomes 1-22 and X (FIG. 7B).
Figure 7B:
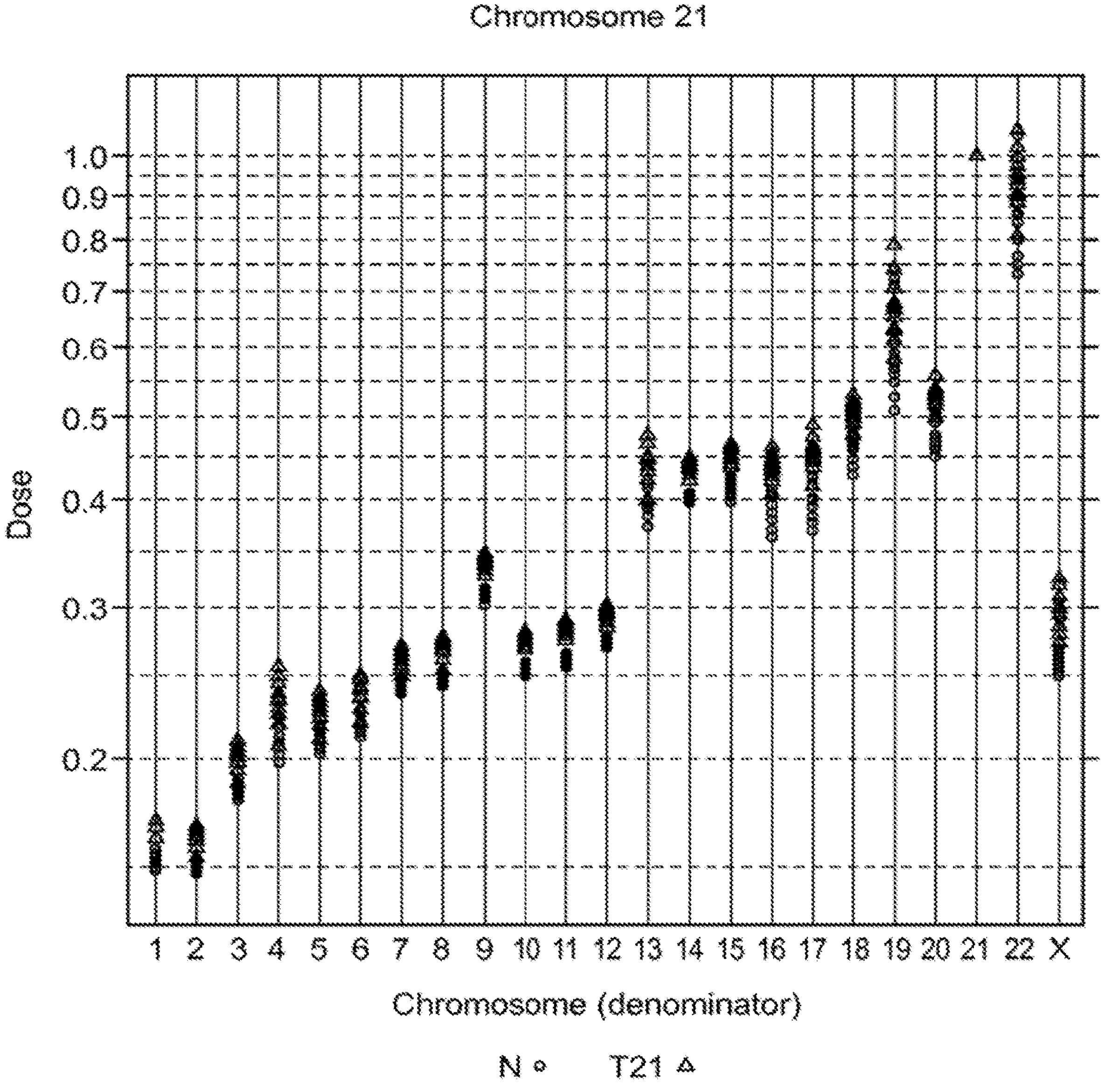
Figure 8A:
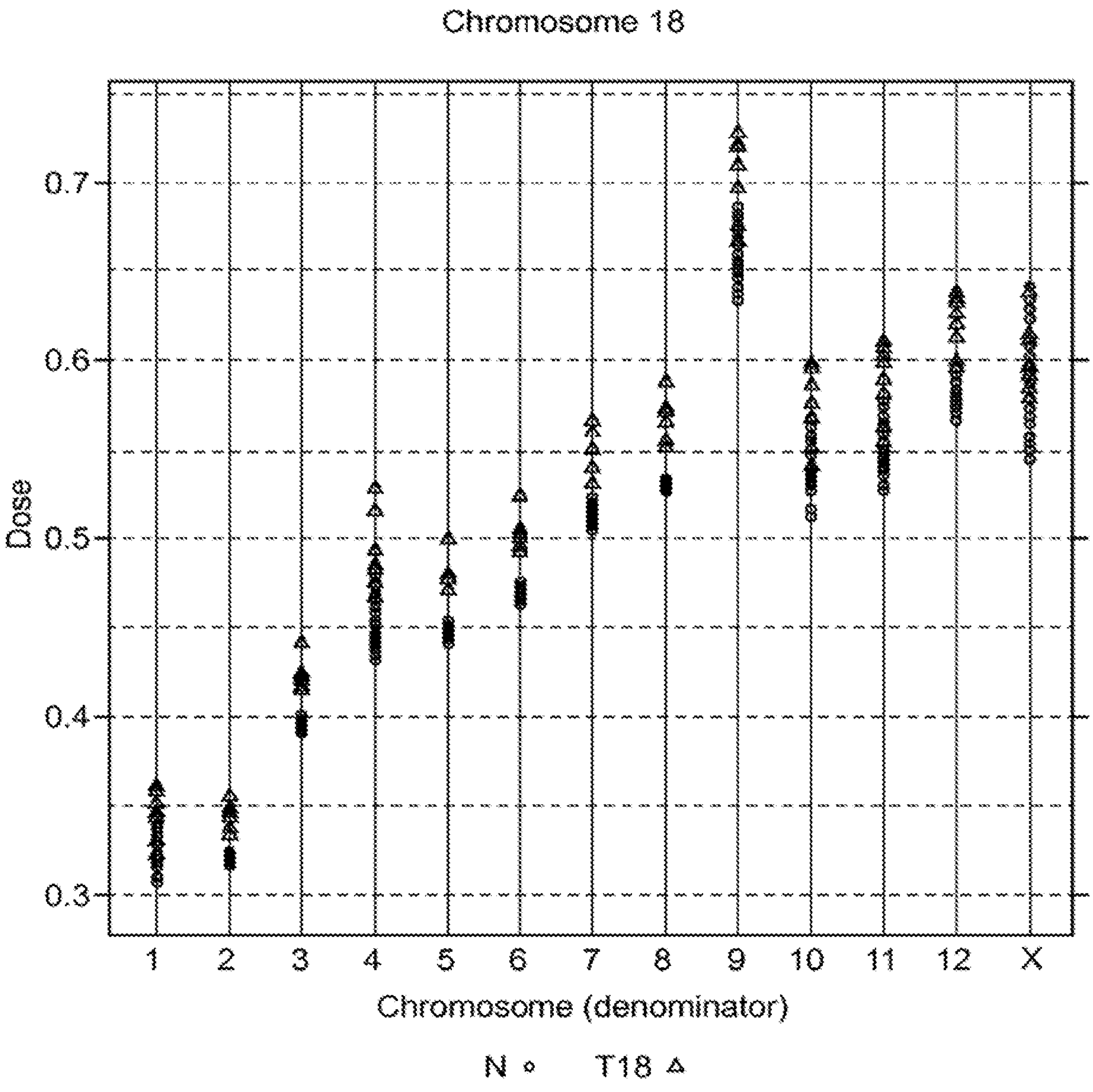
FIGS. 8A and 8B illustrate the distribution of the chromosome dose for chromosome 18 determined from sequencing cfDNA extracted from a set of 48 blood samples obtained from human subjects pregnant with male or female fetuses. Chromosome 18 doses for qualified i.e. normal for chromosome 18 (O), and trisomy 18 (Δ) test samples are shown for chromosomes 1-12 and X (FIG. 8A), and for chromosomes 1-22 and X (FIG. 8B).
Figure 8B:
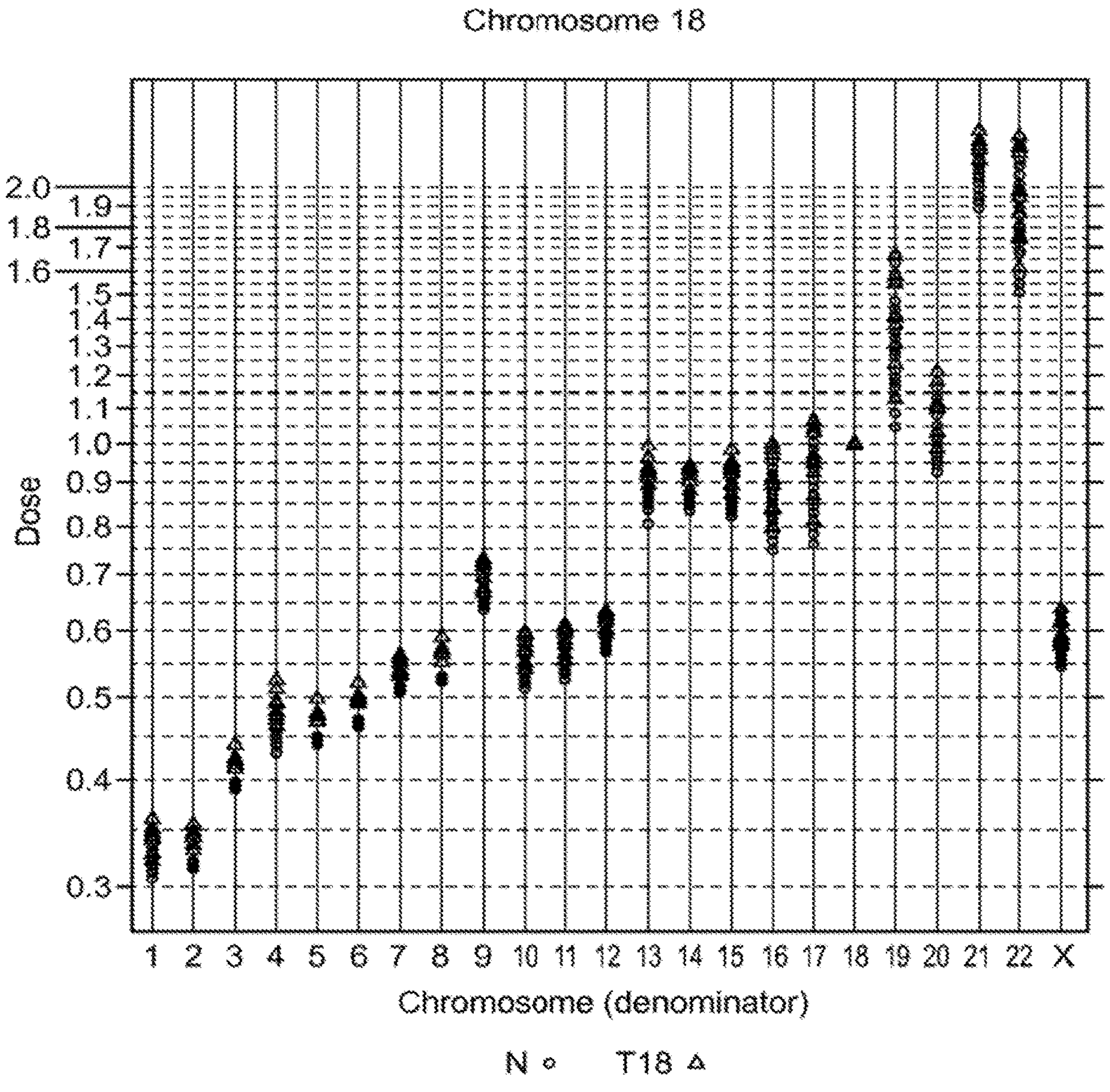
Figure 9A:
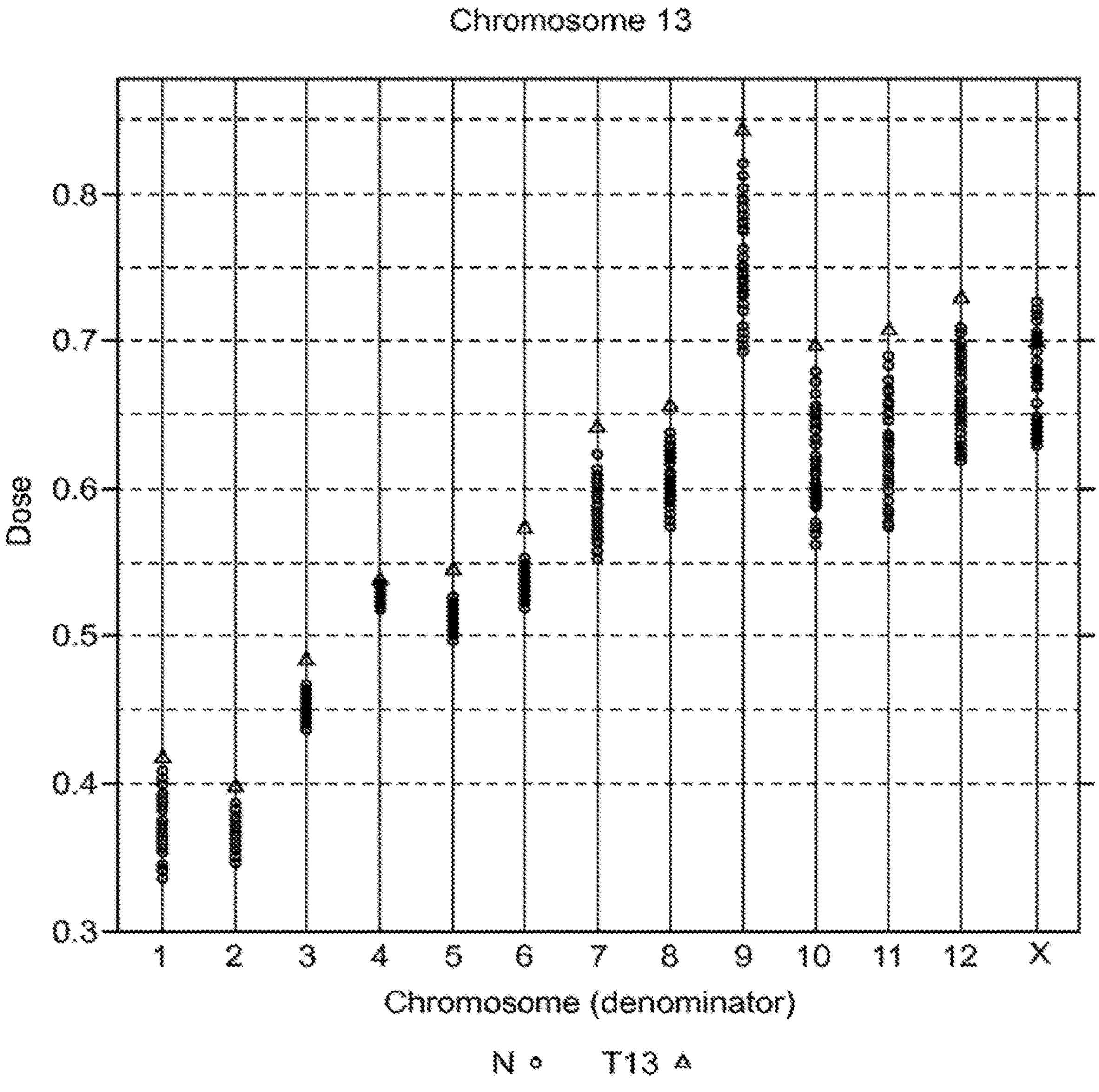
FIGS. 9A and 9B illustrate the distribution of the chromosome dose for chromosome 13 determined from sequencing cDNA extracted from a set of 48 blood samples obtained from human subjects pregnant with male or female fetuses. Chromosome 13 doses for qualified i.e. normal for chromosome 13 (O), and trisomy 13 (Δ) test samples are shown for chromosomes 1-12 and X (FIG. 9A), and for chromosomes 1-22 and X (FIG. 9B).
Figure 9B:
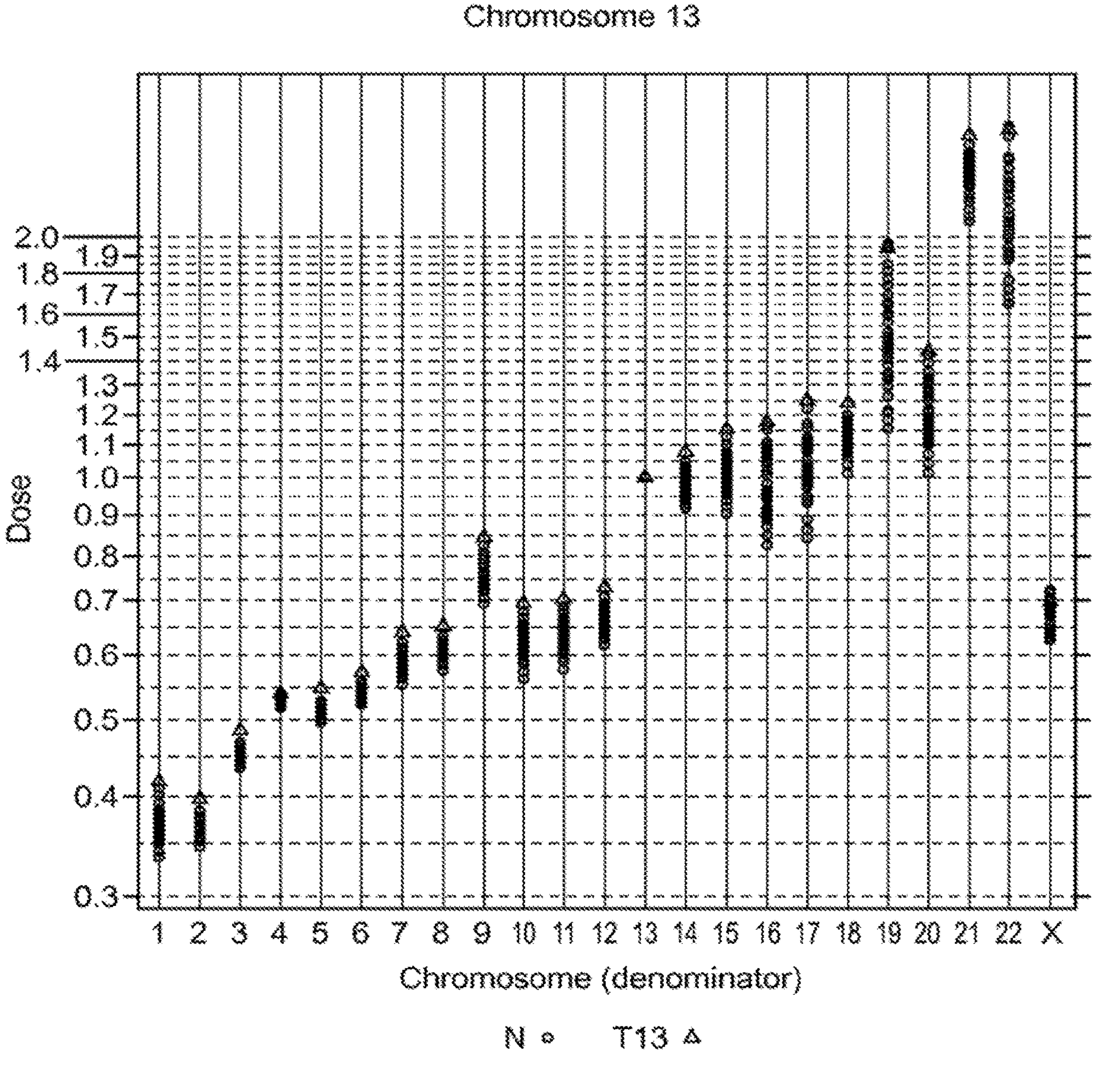
Figure 10A:
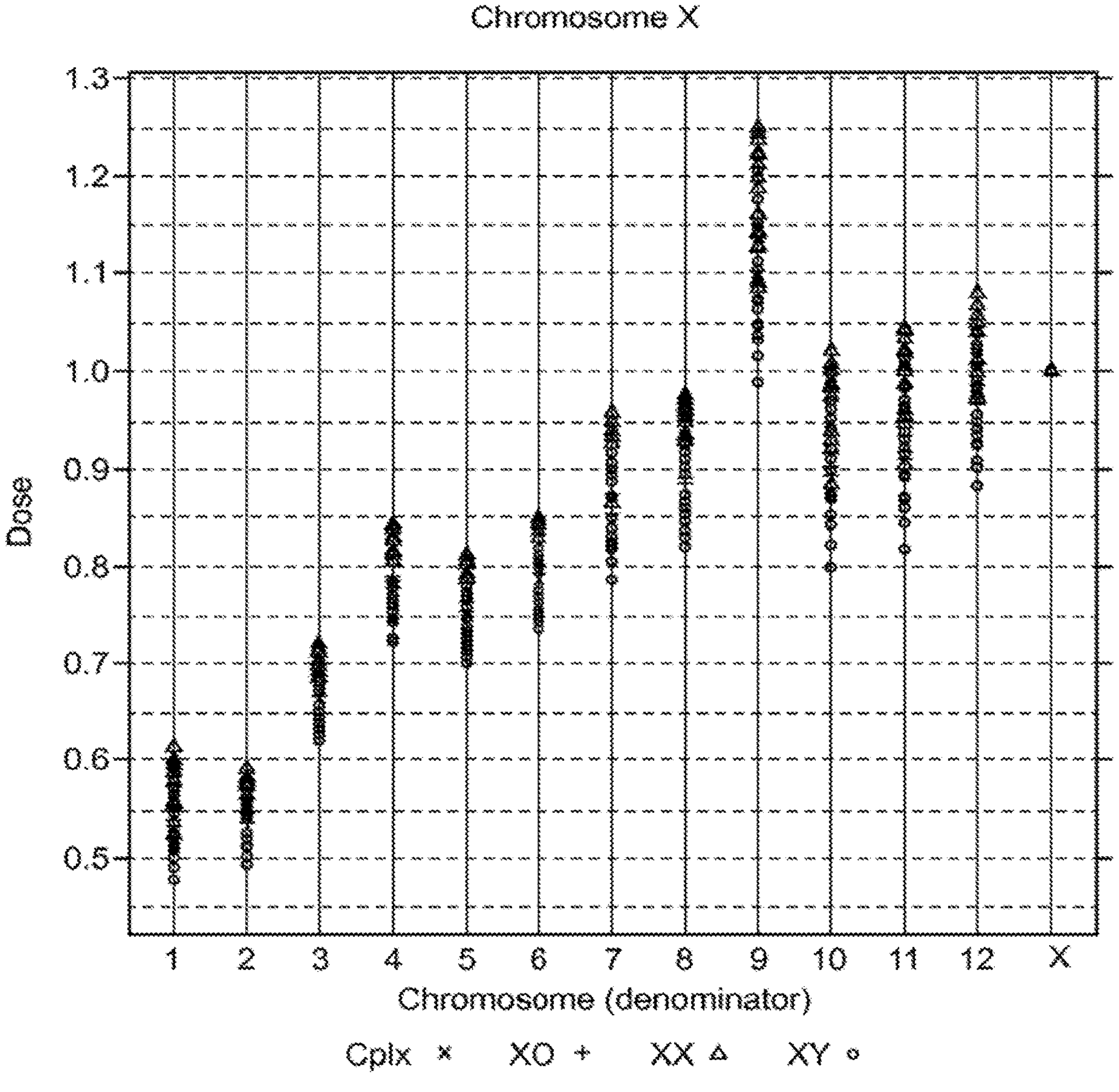
FIGS. 10A and 10B illustrate the distribution of the chromosome doses for chromosome X determined from sequencing cDNA extracted from a set of 48 test blood samples obtained from human subjects pregnant with either male or female fetuses. Chromosome X doses for males (46,XY; (O)), females (46,XX; (Δ)); monosomy X (45,X; (+)), and complex karyotypes (Cplx (X)) samples are shown for chromosomes 1-12 and X (FIG. 10A), and for chromosomes 1-22 and X (FIG. 10B).
Figure 10B:
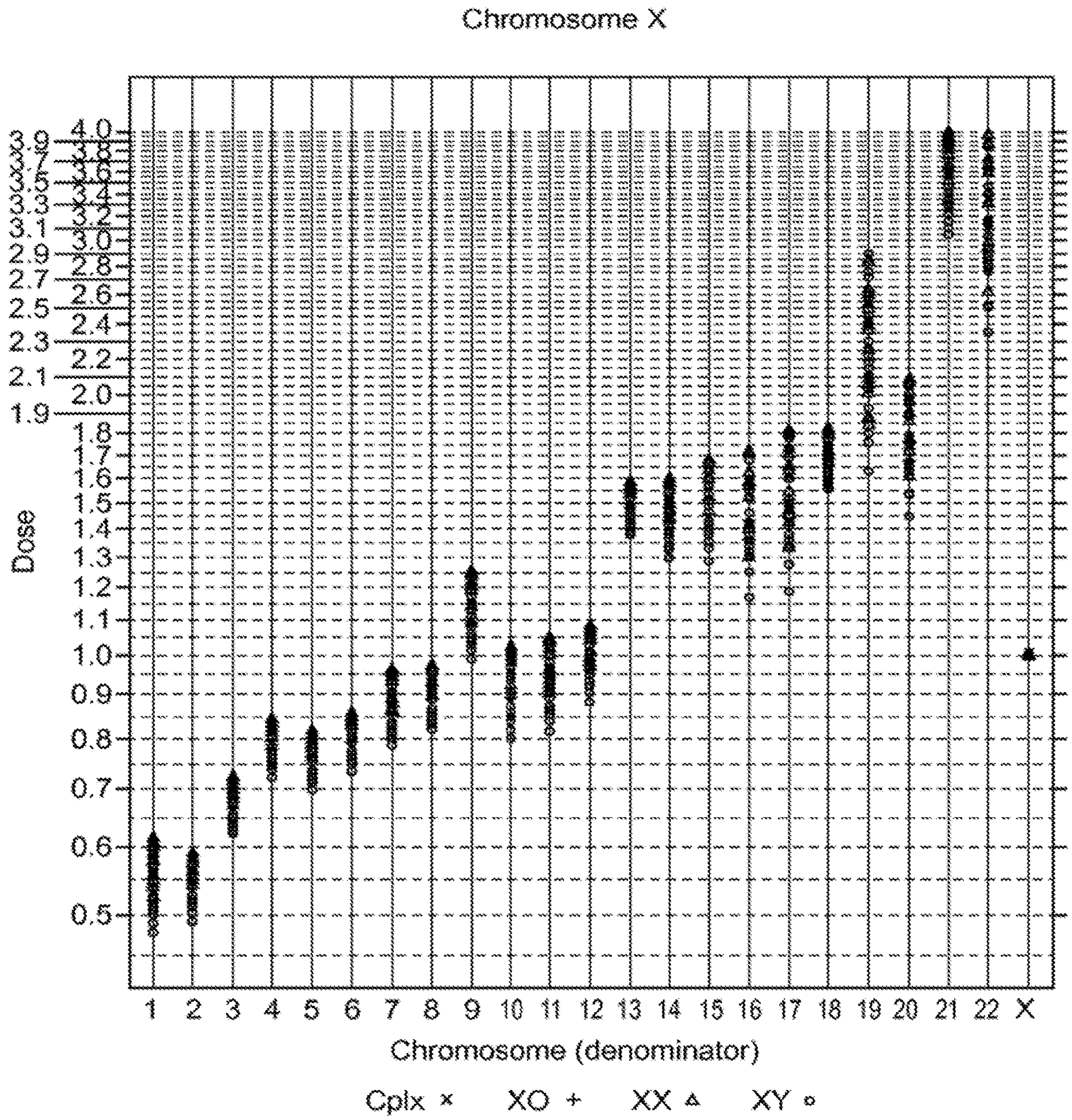
Figure 11A:
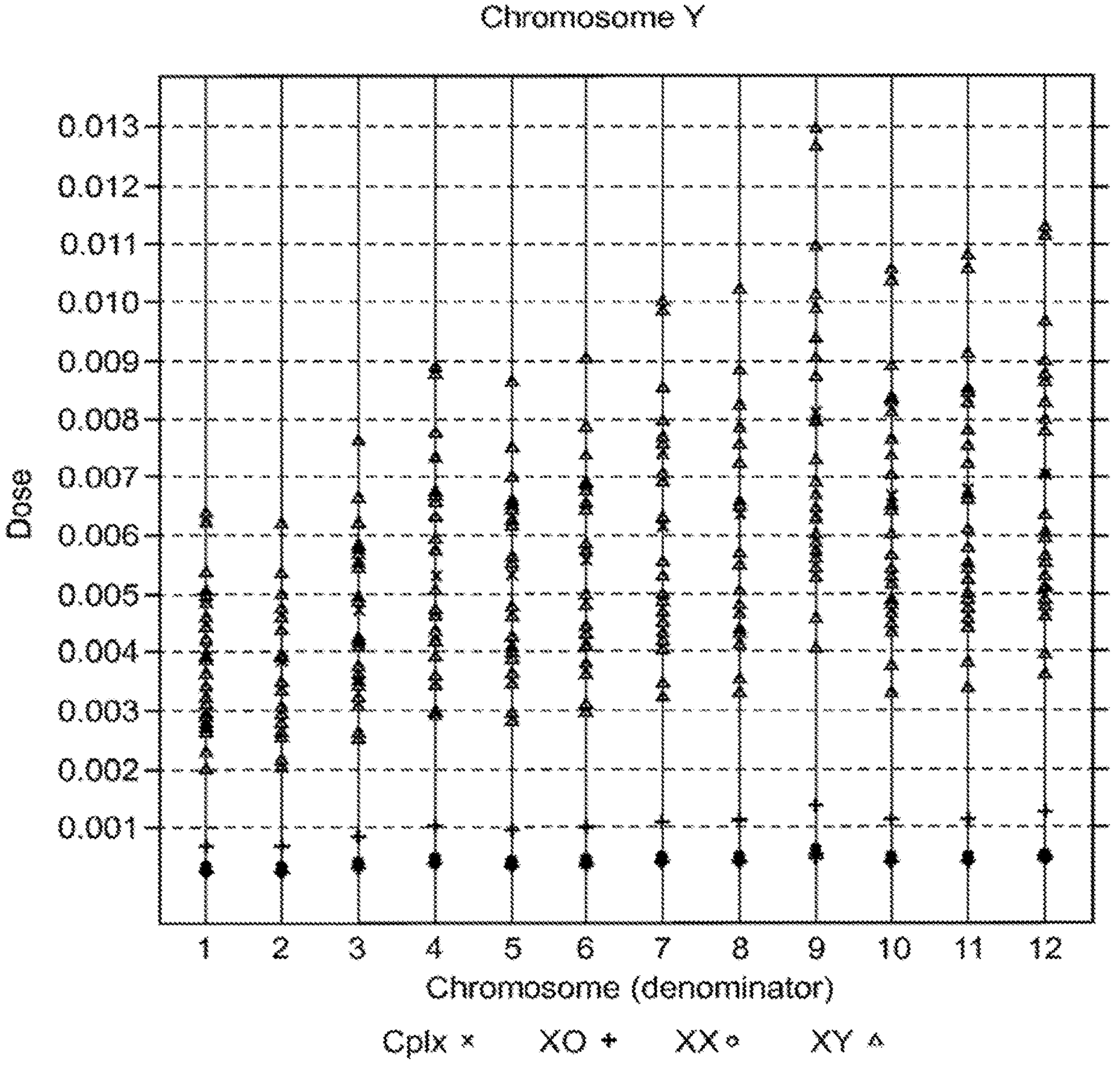
FIGS. 11A and 11B illustrate the distribution of the chromosome doses for chromosome Y determined from sequencing cfDNA extracted from a set of 48 test blood samples obtained from human subjects pregnant with either male or female fetuses. Chromosome Y doses for males (46,XY; (Δ)), females (46,XX; (O)); monosomy X (45,X; (+)), and complex karyotypes (Cplx (X)) samples are shown for chromosomes 1-12 (FIG. 11A), and for chromosomes 1-22 (FIG. 11B).
Figure 11B:
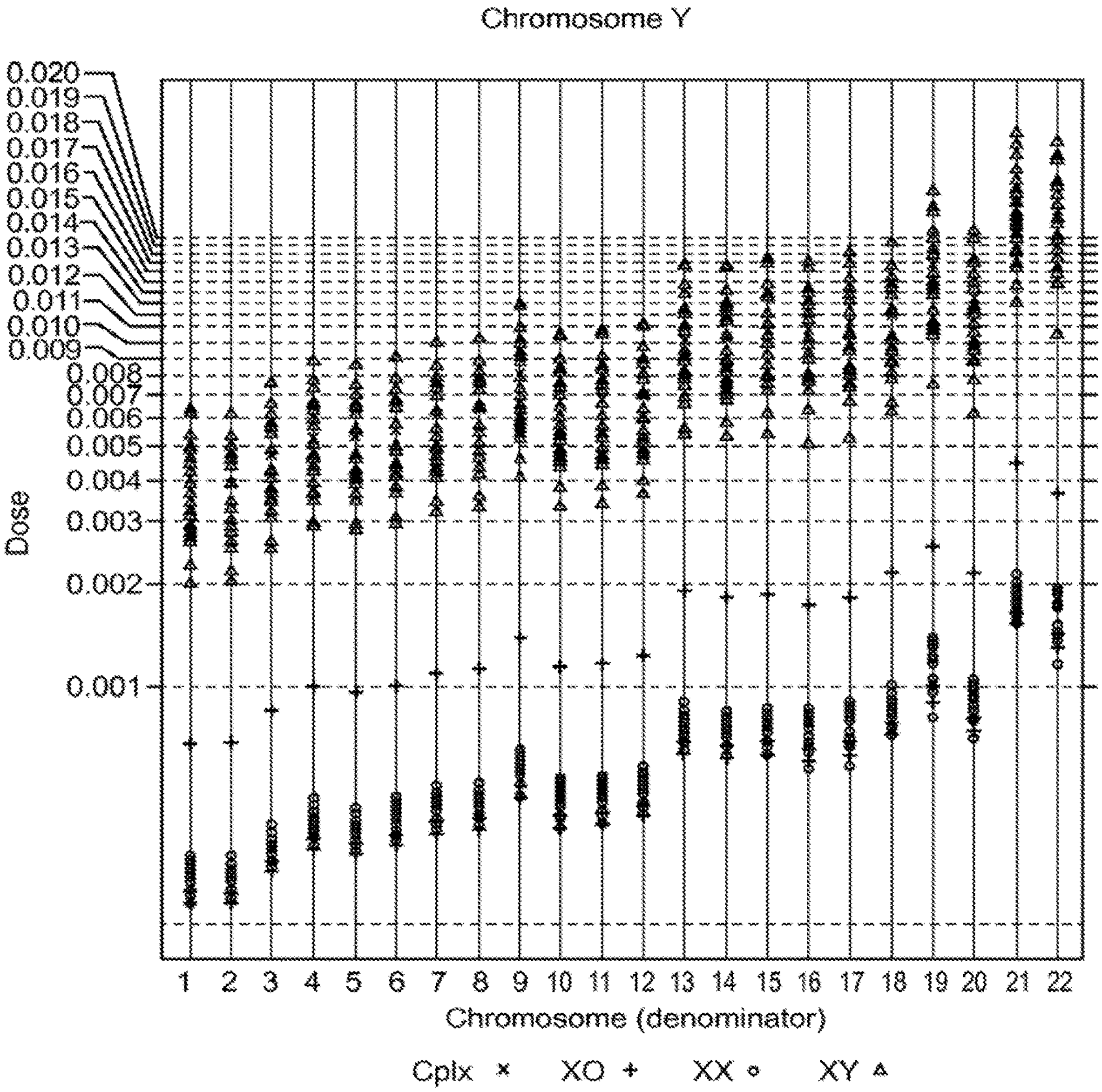

The informative polymorphic site e.g. SNP, is identified by the difference in the allelic sequences and the amount of each of the possible alleles. Fetal cfDNA is present at a concentration that is <10% of the maternal cfDNA. Thus, the presence of a minor contribution of an allele to the mixture of fetal and maternal nucleic acids relative to the major contribution of the maternal allele can be assigned to the fetus. Alleles that are derived from the maternal genome are herein referred to as major alleles, and alleles that are derived from the fetal genome are herein referred to as minor alleles. Alleles that are represented by similar levels of mapped sequence tags represent maternal alleles. The results of an exemplary multiplex amplification of target nucleic acids comprising SNPs and derived from a maternal plasma sample is shown in FIG. 6. Informative SNPs are discerned from the single nucleotide change at a predetermined polymorphic site, and fetal alleles are discerned by their relative minor contribution to the mixture of fetal and maternal nucleic acids in the sample when compared to the major contribution to the mixture by the maternal nucleic acids. Accordingly, the relative abundance of fetal cfDNA in the maternal sample is determined as a parameter of the total number of unique sequence tags mapped to the target nucleic acid sequence on a reference genome for each of the two alleles of the predetermined polymorphic site. In one embodiment, the fraction of fetal nucleic acids in the mixture of fetal and maternal nucleic acids is calculated for each of the informative allele (alleles) as follows:

% fetal fraction allele$_x$=((ΣFetal sequence tags for allele$_x$)/(ΣMaternal sequence tags for allele$_x$))×100 and fetal fraction for the sample is calculated as the average of the fetal fraction of all of the informative alleles. Optionally, the fraction of fetal nucleic acids in the mixture of fetal and maternal nucleic acids is calculated for each of the informative allele (allele) as follows:

% fetal fraction allele$_x$=((2×ΣFetal sequence tags for allele$_x$)/(ΣMaternal sequence lags for allele$_x$))×100, to compensate for the presence of 2 fetal alleles, one being masked by the maternal background.

The percent fetal fraction is calculated for at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40 or more informative alleles. In one embodiment, the fetal fraction is the average fetal fraction determined for at least 3 informative alleles.

In one embodiment, the step of enriching the mixture of fetal and maternal nucleic acids for polymorphic target nucleic acids comprises amplifying the target nucleic acids in a portion of a test sample e.g. a plasma test sample, and combining all or a portion of the amplified product with the remaining plasma test sample. The embodiment of the method 200 is depicted in flowchart provided in FIG. 2. In step 210, a test sample e.g. a biological fluid sample such as a blood sample, is obtained from a pregnant woman, and in step 220 a portion of the cfDNA contained in the plasma fraction of the blood sample is used for amplifying target nucleic acids comprising polymorphic sites e.g. SNPs. In one embodiment, at least about 1%, at least about 1.5%, at least about 2% at least about 10% of the maternal plasma was used to amplify the target nucleic acids. In step 230, a portion or all of the amplified target nucleic acids is combined with the mixture of fetal and maternal cfDNA present in the maternal sample, and the combined cfDNA and amplified nucleic acids are purified in step 240, and used for preparing a library that was sequenced in step 250. The library was prepared from purified cfDNA and comprising at least about 10%, at least about 15%, at least about 20%, at least about 25%, at least about 30%, at least about 35%, at least about 40%, at least about 45%, or at least about 50% amplified product. In step 260, the data from the sequencing runs is analyzed and the simultaneous determination of the fetal fraction and presence or absence of aneuploidy is made.

In one embodiment, the step of enriching the mixture of fetal and maternal nucleic acids for polymorphic target nucleic acids comprises a plurality of polymorphic target nucleic acids in a portion of a mixture of fetal and maternal nucleic acids purified from a maternal test sample. In one embodiment, a portion of a mixture of fetal and maternal nucleic acids e.g. cfDNA, purified from a maternal plasma sample is used for amplifying polymorphic nucleic acid sequences, and a portion of the amplified product is combined with the unamplified mixture of purified fetal and maternal nucleic acids e.g. cfDNA (see FIG. 3). The embodiment of the method 300 is depicted in flowchart provided in FIG. 3. In step 310, a test sample e.g. a biological fluid sample such as a blood sample, comprising a mixture of fetal and maternal nucleic acids is obtained from a pregnant woman, and the mixture of fetal and maternal nucleic acids is purified from the plasma fraction in step 320. As described above, methods for the separation of cell-free DNA from plasma are well-known. In step 330, a portion of the cfDNA contained in the purified sample is used for amplifying target nucleic acids comprising polymorphic sites e.g. SNPs. At least about 50%, at least about 10%, at least about 15%, at least about 20%, at least about 25%, at least about 30%, at least about 35%, at least about 40%, at least about 45%, or at least about 50% of purified cfDNA is used for amplifying the target nucleic acids. Preferably, amplification of the target sequences can be performed by any method that uses PCR or variations of the method including but not limited to asymmetric PCR, helicase-dependent amplification, hot-start PCR, qPCR, solid phase PCR, and touchdown PCR. In step 340, a portion e.g. at least about 0.01% of the amplified product is combined with the unamplified purified cfDNA sample, and the mixture of amplified and unamplified fetal and maternal nucleic acids is sequenced in step 350. In one embodiment, sequencing is performed using any one of the NGS technologies. In step 360, the data from the sequencing runs is analyzed and the simultaneous determination of the fetal fraction and presence or absence of aneuploidy is made as described in step 140 of the embodiment depicted in FIG. 1.

Figure 4:
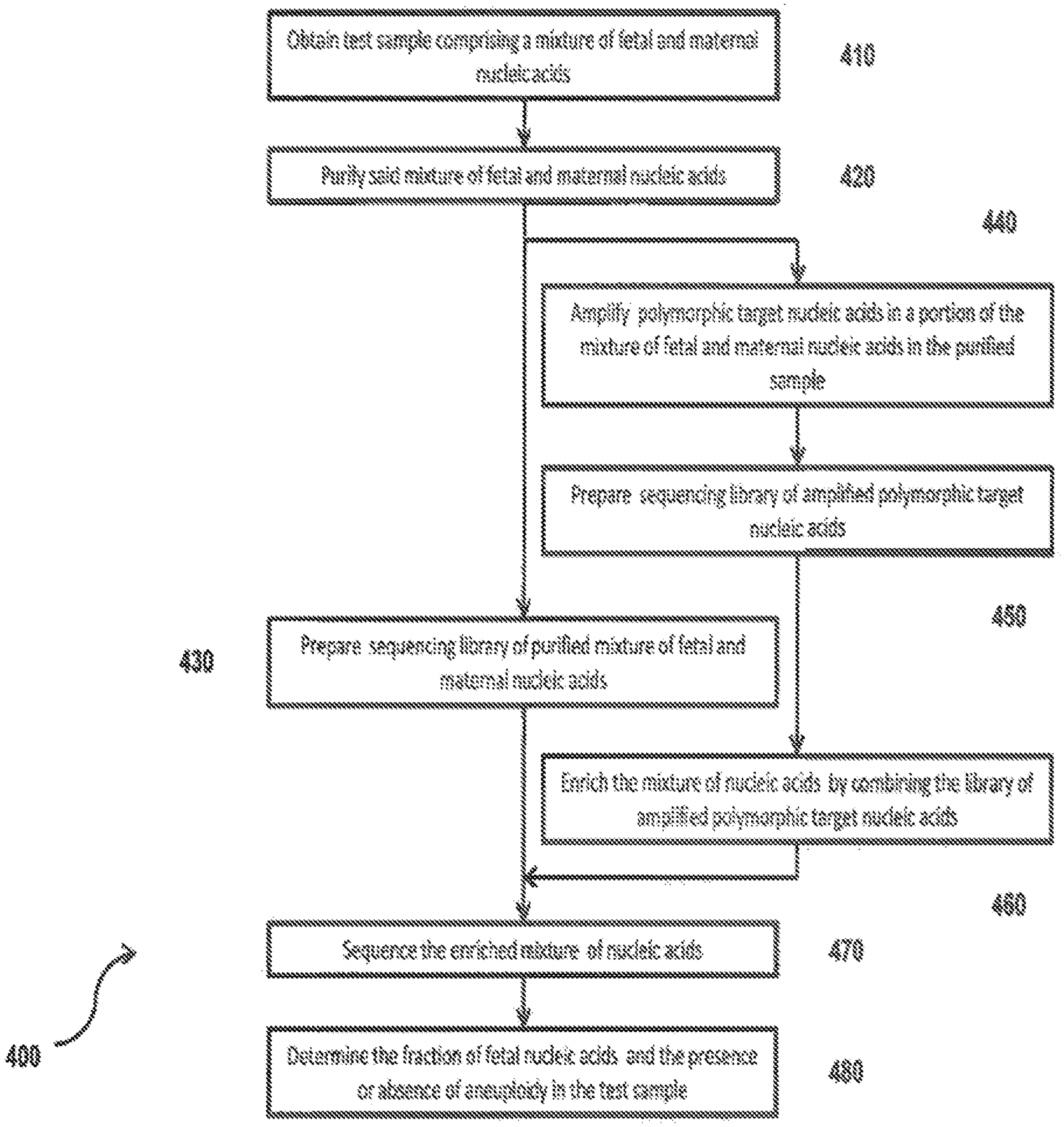
FIG. 4 is a flowchart of a method 400 for simultaneously determining the presence or absence of fetal aneuploidy and the fetal fraction in a sequencing library constructed from fetal and maternal nucleic acids derived from a maternal test sample and enriched with polymorphic nucleic acids.

In another embodiment, the step 120 of enriching the mixture of fetal and maternal nucleic acids for polymorphic target nucleic acids comprises combining at least a portion of a first sequencing library of unamplified fetal and maternal nucleic acid molecules with at least a portion of a second sequencing library of amplified polymorphic target nucleic acids. Thus, the sample that is enriched is the library sample that is prepared for sequencing (FIG. 4). Enrichment of the library sample for the target nucleic acids is accomplished by methods that comprise specifically amplifying the nucleic acid sequences that comprise the polymorphic site. In step 410, a test sample e.g. a biological fluid sample such as a blood sample, comprising a mixture of fetal and maternal nucleic acids is obtained from a pregnant woman, and the mixture of fetal and maternal nucleic acids is purified from the plasma fraction in step 420. In step 430, a portion of the cfDNA contained in the purified sample is used for amplifying target nucleic acids comprising polymorphic sites e.g. SNPs. At least about 5%, at least about 10%, at least about 15%, at least about 20%, at least about 25%, or at least about 30% of the purified cfDNA is used for amplifying target nucleic acid sequences. Preferably, amplification of the target sequences can be performed by any method that uses PCR or variations of the method including but not limited to asymmetric PCR, helicase-dependent amplification, hot-start PCR, qPCR, solid phase PCR, and touchdown PCR. In step 440, the amplified target nucleic acids comprising the polymorphic sites e.g. SNPs, are used to prepare a target nucleic acid sequencing library. Similarly, the portion of purified unamplified cfDNA is used to prepare a primary sequencing library in step 450. In step 460, a portion of the target library is combined with the primary library generated from the unamplified mixture of nucleic acids, and the mixture of fetal and maternal nucleic acids comprised in the two libraries is sequenced in step 470. The enriched library comprises at least about 50%, at least about 10%, at least about 15%, at least about 20%, or at least about 25% of the target library. In step 480, the data from the sequencing runs is analyzed and the simultaneous determination of the fetal fraction and presence or absence of aneuploidy is made as described in step 140 of the embodiment depicted in FIG. 1.

Determination of Aneuploidies for Prenatal Diagnoses

Cell-free fetal DNA and RNA circulating in maternal blood can be used for the early non-invasive prenatal diagnosis (NIPD) of an increasing number of genetic conditions, both for pregnancy management and to aid reproductive decision-making. The presence of cell-free DNA circulating in the bloodstream has been known for over 50 years. More recently, presence of small amounts of circulating fetal DNA was discovered in the maternal bloodstream during pregnancy (Lo et al., Lancet 350:485-487 [1997]). Thought to originate from dying placental cells, cell-free fetal DNA (cfDNA) has been shown to consists of short fragments typically fewer than 200 bp in length (Chan et al., Clin Chem 50:88-92 [2004]), which can be discerned as early as 4 weeks gestation (Illanes et al., Early Human Dev 83:563-566 [2007]), and known to be cleared from the maternal circulation within hours of delivery (Lo et al., Am J Hum Genet 64:218-224 [1999]). In addition to cfDNA, fragments of cell-free fetal RNA (cfRNA) can also be discerned in the maternal bloodstream, originating from genes that are transcribed in the fetus or placenta. The extraction and subsequent analysis of these fetal genetic elements from a maternal blood sample offers novel opportunities for NIPD.

The present method is a polymorphism-independent method that for use in NIPD and that does not require that the fetal cfDNA be distinguished from the maternal cfDNA to enable the determination of a fetal aneuploidy. In some embodiments, the aneuploidy is a complete chromosomal trisomy or monosomy, or a partial trisomy or monosomy. Partial aneuploidies are caused by loss or gain of part of a chromosome, and encompass chromosomal imbalances resulting from unbalanced translocations, unbalanced inversions, deletions and insertions. By far, the most common known aneuploidy compatible with life is trisomy 21 i.e. Down Syndrome (DS), which is caused by the presence of part or all of chromosome 21. Rarely, DS can be cause by an inherited or sporadic defect whereby an extra copy of all or part of chromosome 21 becomes attached to another chromosome (usually chromosome 14) to form a single aberrant chromosome. DS is associated with intellectual impairment, severe learning difficulties and excess mortality caused by long-term health problems such as heart disease. Other aneuploidies with known clinical significance include Edward syndrome (trisomy 18) and Patau Syndrome (trisomy 13), which are frequently fatal within the first few months of life. Abnormalities associated with the number of sex chromosomes are also known and include monosomy X e.g. Turner syndrome (XO), and triple X syndrome (XXX) in female births and Kleinefelter syndrome (XXY) and XYY syndrome in male births, which are all associated with various phenotypes including sterility and reduction in intellectual skills. The method of the invention can be used to diagnose these and other chromosomal abnormalities prenatally.

According to embodiments of the present invention the trisomy determined by the present invention is selected from trisomy 21 (T21; Down Syndrome), trisomy 18 (T18; Edward's Syndrome), trisomy 16 (T16), trisomy 22 (T22; Cat Eye Syndrome), trisomy 15 (T15; Prader Willi Syndrome), trisomy 13 (T13; Patau Syndrome), trisomy 8 (T8; Warkany Syndrome) and the XXY (Kleinefelter Syndrome), XYY, or XXX trisomies. It will be appreciated that various other trisomies and partial trisomies can be determined in fetal cfDNA according to the teachings of the present invention. These include, but not limited to, partial trisomy 1q32-44, trisomy 9 p, trisomy 4 mosaicism, trisomy 17p, partial trisomy 4q26-qter, trisomy 9, partial 2p trisomy, partial trisomy 1q, and/or partial trisomy 6p/monosomy 6q.

The method of the present invention can be also used to determine chromosomal monosomy X, and partial monosomies such as, monosomy 13, monosomy 15, monosomy 16, monosomy 21, and monosomy 22, which are known to be involved in pregnancy miscarriage. Partial monosomy of chromosomes typically involved in complete aneuploidy can also be determined by the method of the invention. Monosomy 18p is a rare chromosomal disorder in which all or part of the short arm (p) of chromosome 18 is deleted (monosomic). The disorder is typically characterized by short stature, variable degrees of mental retardation, speech delays, malformations of the skull and facial (craniofacial) region, and/or additional physical abnormalities. Associated craniofacial defects may vary greatly in range and severity from case to case. Conditions caused by changes in the structure or number of copies of chromosome 15 include Angelman Syndrome and Prader-Willi Syndrome, which involve a loss of gene activity in the same part of chromosome 15, the 15q11-q13 region. It will be appreciated that several translocations and microdeletions can be asymptomatic in the carrier parent, yet can cause a major genetic disease in the offspring. For example, a healthy mother who carries the 15q11-q13 microdeletion can give birth to a child with Angelman syndrome, a severe neurodegenerative disorder. Thus, the present invention can be used to identify such a deletion in the fetus. Partial monosomy 13q is a rare chromosomal disorder that results when a piece of the long arm (q) of chromosome 13 is missing (monosomic). Infants born with partial monosomy 13q may exhibit low birth weight, malformations of the head and face (craniofacial region), skeletal abnormalities (especially of the hands and feet), and other physical abnormalities. Mental retardation is characteristic of this condition. The mortality rate during infancy is high among individuals born with this disorder. Almost all cases of partial monosomy 13q occur randomly for no apparent reason (sporadic). 22q11.2 deletion syndrome, also known as DiGeorge syndrome, is a syndrome caused by the deletion of a small piece of chromosome 22. The deletion (22 q11.2) occurs near the middle of the chromosome on the long arm of one of the pair of chromosome. The features of this syndrome vary widely, even among members of the same family, and affect many parts of the body. Characteristic signs and symptoms may include birth defects such as congenital heart disease, defects in the palate, most commonly related to neuromuscular problems with closure (velo-pharyngeal insufficiency), learning disabilities, mild differences in facial features, and recurrent infections. Microdeletions in chromosomal region 22q11.2 are associated with a 20 to 30-fold increased risk of schizophrenia. In one embodiment, the method of the invention is used to determine partial monosomies including but not limited to monosomy 18p, partial monosomy of chromosome 15 (15q11-q13), partial monosomy 13q, and partial monosomy of chromosome 22 can also be determined using the method.

The method of the invention can be also used to determine any aneuploidy if one of the parents is a known carrier of such abnormality. These include, but not limited to, mosaic for a small supernumerary marker chromosome (SMC); t(11;14)(p15;p13) translocation; unbalanced translocation t(8;11)(p23.2;p15.5); 11q23 microdeletion; Smith-Magenis syndrome 17p11.2 deletion; 22q13.3 deletion; Xp22.3 microdeletion; 10p14 deletion; 20p microdeletion. DiGeorge syndrome [del(22)(q11.2q11.23)], Williams syndrome (7q11.23 and 7q36 deletions); 1p36 deletion; 2p microdeletion; neurofibromatosis type 1 (17q11.2 microdeletion), Yq deletion; Wolf-Hirschhorn syndrome (WHS, 4p16.3 microdeletion); 1p36.2 microdeletion; 11q14 deletion; 19q13.2 microdeletion; Rubinstein-Taybi (16 p13.3 microdeletion); 7p21 microdeletion; Miller-Dieker syndrome (17p13.3), 17p11.2 deletion; and 2q37 microdeletion.

Compositions and Kits

Compositions comprising primers for amplifying polymorphic sites are provided to enable the quantification of fetal fraction and aneuploidy by sequencing mixtures of fetal and maternal nucleic acids e.g. cfDNA, present in a sample. Preferably, the sample is a maternal blood plasma sample. In one embodiment, the composition includes primers for amplifying polymorphic target nucleic acids that each comprise at least one SNP. The at least one SNP is selected from SNPs rs560681, rs1109037, rs9866013, rs13182883, rs13218440, rs7041158, rs740598, rs10773760, rs4530059, rs7205345, rs8078417, rs576261, rs2567608, rs430046, rs9951171, rs338882, rs10776839, rs9905977, rs1277284, rs258684, rs1347696, rs508485, rs9788670, rs8137254, rs3143, rs2182957, rs3739005, and rs530022. The corresponding sets of primers for amplifying the SNPs are PROVIDED IN Example 3 and disclosed as SEQ ID NOs: 57-112.

In another embodiment, the composition includes primers for amplifying polymorphic target nucleic acids that each comprise at least one tandem SNP. In one embodiment, the composition includes primers for amplifying the exemplary tandem SNPs disclosed herein, and the composition comprises the corresponding exemplary primers of SEQ ID NOS:57-112.

In another embodiment, the composition includes primers for amplifying polymorphic target nucleic acids that each comprise at least one STR. Exemplary STRs include CSF1PO, FGA, TH01, TPOX, vWA, D3S1358, D5S818, D7S820, D8S1179, D13S317, D16S539, D18S51, D21S11, D2S1338. Penta D, Penta E, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627 and D1GATA1.13, which can be amplified by the corresponding sets of primers provided in Example 5 (Tables 5 and 6) and disclosed as SEQ ID NOs: 113-196.

The compositions of the invention can be included in kits for massively parallel sequencing mixtures of fetal and maternal nucleic acid molecules e.g. cfDNA, present in a maternal sample e.g. a plasma sample. The kits comprise a composition comprising at least one set of primers for amplifying at least one polymorphic target nucleic acid in said fetal and maternal nucleic acid molecules. Polymorphic nucleic acids can comprise a SNP or an STR. Sequencing methods are NGS methods of single nucleic acid molecules or clonally amplified nucleic acid molecules. The NGS methods are massively parallel sequencing methods including pyrosequencing, sequencing by synthesis with reversible dye terminators, real-time sequencing, or sequencing by oligonucleotide probe ligation.

The present invention is described in further detail in the following Examples which are not in any way intended to limit the scope of the invention as claimed. The attached Figures are meant to be considered as integral parts of the specification and description of the invention. The following examples are offered to illustrate, but not to limit the claimed invention.

EXPERIMENTAL

Example 1

Sample Processing and cfDNA Extraction

Peripheral blood samples were collected from pregnant women in their first or second trimester of pregnancy and who were deemed at risk for fetal aneuploidy. Informed consent was obtained from each participant prior to the blood draw. Blood was collected before amniocentesis or chorionic villus sampling. Karyotype analysis was performed using the chorionic villus or amniocentesis samples to confirm fetal karyotype.

Peripheral blood drawn from each subject was collected in ACD tubes. One tube of blood sample (approximately 6-9 mL/tube) was transferred into one 15-mL low speed centrifuge tube. Blood was centrifuged at 2640 rpm, 4° C. for 10 min using Beckman Allegra 6 R centrifuge and rotor model GA 3.8.

For cell-free plasma extraction, the upper plasma layer was transferred to a 15-ml high speed centrifuge tube and centrifuged at 16000×g, 4° C. for 10 min using Beckman Coulter Avanti J-E centrifuge, and JA-14 rotor. The two centrifugation steps were performed within 72 h after blood collection. Cell-free plasma comprising cfDNA was stored at −80° C. and thawed only once before amplification of plasma cfDNA or for purification of cfDNA.

Purified cell-free DNA (cfDNA) was extracted from cell-free plasma using the QIAamp Blood DNA Mini kit (Qiagen) essentially according to the manufacturer's instruction. One milliliter of buffer AL and 100 μl of Protease solution were added to 1 ml of plasma. The mixture was incubated for 15 minutes at 56° C. One milliliter of 100% ethanol was added to the plasma digest. The resulting mixture was transferred to QIAamp mini columns that were assembled with VacValves and VacConnectors provided in the QIAvac 24 Plus column assembly (Qiagen). Vacuum was applied to the samples, and the cfDNA retained on the column filters was washed under vacuum with 750 μl of buffer AW1, followed by a second wash with 750 μl of buffer AW24. The column was centrifuged at 14,000 RPM for 5 minutes to remove any residual buffer from the filter. The cfDNA was eluted with buffer AE by centrifugation at 14.000 RPM, and the concentration determined using Qubit™ Quantitation Platform (Invitrogen).

Example 2

Preparation and Sequencing of Primary and Enriched Sequencing Libraries a. Preparation of Sequencing Libraries All sequencing libraries i.e. primary and enriched libraries, were prepared from approximately 2 ng of purified cfDNA that was extracted from maternal plasma. Library preparation was performed using reagents of the NEBNext™ DNA Sample Prep DNA Reagent Set 1 (Part No. E6000L; New England Biolabs, Ipswich, Mass.), for Illumina® as follows. Because cell-free plasma DNA is fragmented in nature, no further fragmentation by nebulization or sonication was done on the plasma DNA samples. The overhangs of approximately 2 ng purified cfDNA fragments contained in 40 μl were converted into phosphorylated blunt ends according to the NEBNext® End Repair Module by incubating in a 1.5 ml microfuge tube the cfDNA with 5 μl 10× phosphorylation buffer, 2 μl deoxynucleotide solution mix (10 mM each dNTP), 1 μl of a 1:5 dilution of DNA Polymerase I, 1 μl T4 DNA Polymerase and 1 μl T4 Poly nucleotide Kinase provided in the NEBNext™ DNA Sample Prep DNA Reagent Set 1 for 15 minutes at 20° C. The enzymes were then heat inactivated by incubating the reaction mixture at 75° C. for 5 minutes. The mixture was cooled to 4° C., and dA tailing of the blunt-ended DNA was accomplished using 10 μl of the dA-tailing master mix containing the Klenow fragment (3' to 5' exo minus) (NEBNext™ DNA Sample Prep DNA Reagent Set 1), and incubating for 15 minutes at 37° C. Subsequently, the Klenow fragment was heat inactivated by incubating the reaction mixture at 75° C. for 5 minutes. Following the inactivation of the Klenow fragment, 1 μl of a 1:5 dilution of Illumina Genomic Adaptor Oligo Mix (Part No. 1000521; Illumina Inc., Hayward, Calif.) was used to ligate the Illumina adaptors (Non-Index Y-Adaptors) to the dA-tailed DNA using 4 μl of the T4 DNA ligase provided in the NEBNext™ DNA Sample Prep DNA Reagent Set 1, by incubating the reaction mixture for 15 minutes at 25° C. The mixture was cooled to 4° C., and the adaptor-ligated cfDNA was purified from unligated adaptors, adaptor dimers, and other reagents using magnetic beads provided in the Agencourt AMPure XP PCR purification system (Part No. A63881; Beckman Coulter Genomics, Danvers, Mass.). Eighteen cycles of PCR were performed to selectively enrich adaptor-ligated cfDNA (2511) using Phusion® High-Fidelity Master Mix (25 μl; Finnzymes, Woburn, Mass.) and Illumina's PCR primers (0.5 μM each) complementary to the adaptors (Part No. 1000537 and 1000537). The adaptor-ligated DNA was subjected to PCR (98° C. for 30 seconds; 18 cycles of 98° C. for 10 seconds, 65° C. for 30 seconds, and 72° C. for 30; final extension at 72° C. for 5 minutes, and hold at 4° C.) using Illumina Genomic PCR Primers (Part Nos. 100537 and 1000538) and the Phusion HF PCR Master Mix provided in the NEBNext™ DNA Sample Prep DNA Reagent Set 1, according to the manufacturer's instructions. The amplified product was purified using the Agencourt AMPure XP PCR purification system (Agencourt Bioscience Corporation, Beverly, Mass.) according to the manufacturer's instructions available at www.beckmangenomics.com/products/AMPureXPPmtocol_000387v001.pdf. The purified amplified product was eluted in 40 μl of Qiagen EB Buffer, and the concentration and size distribution of the amplified libraries was analyzed using the Agilent DNA 1000 Kit for the 2100 Bioanalyzer (Agilent technologies Inc., Santa Clara, Calif.).

b. Sequencing

Sequencing of library DNA was performed using the Genome Analyzer II (Illumina Inc., San Diego, Calif., USA) according to standard manufacturer protocols. Copies of the protocol for whole genome sequencing using Illumina/Solexa technology may be found at BioTechniques® Protocol Guide 2007 Published December 2006: p 29, and on the world wide web at biotechniques.com/defaultasp?page=protocol&subsection=article_display&id=112378. The DNA library was diluted to 1 nM and denatured. Library DNA (5 pM) was subjected to cluster amplification according to the procedure described in Illumina's Cluster Station User Guide and Cluster Station Operations Guide, available on the world wide web at illumina.com/systems/genome_analyzer/cluster_station-.ilmn. The amplified DNA was sequenced using Illumina's Genome Analyzer II to obtain single-end reads of 36 bp. Only about 30 bp of random sequence information are needed to identify a sequence as belonging to a specific human chromosome. Longer sequences can uniquely identify more particular targets. In the present case, a large number of 36 bp reads were obtained, covering approximately 10% of the genome.

Example 3

Analysis of Sequencing Data for the Determination of Aneuploidy and Fetal Fraction a. Analysis of Sequencing Data for the Determination of Aneuploidy Upon completion of sequencing of the sample, the Illumina "Sequencer Control Software" transferred image and base call files to a Unix server running the Illumina "Genome Analyzer Pipeline" software version 1.51. The Illumina "Gerald" program was run to align sequences i.e. 36 bp reads, to the hg18 reference human genome provided by National Center for Biotechnology Information (NCBI36/hg18, available on the world wide web at genome.ucsc.edu/cgi-bin/hgGateway?org=Human&db=hg18&hgsid=166260105). The sequence data generated from the above procedure that uniquely aligned to the genome was read from Gerald output (export.txt files) by a program (c2c.pl) running on a computer running the Linux operating system. Sequence alignments with base mis-matches were allowed and included in alignment counts only if they aligned uniquely to the genome. Sequence alignments with identical start and end coordinates (duplicates) were excluded.

Between about 15 and 25 million 36 bp tags with 2 or less mismatches were mapped uniquely to the human genome for each sample. All mapped tags were counted and included in the calculation of chromosome doses in both test and qualifying samples. Regions extending from base 0 to base $2\times10^6$, base $10\times10^6$ (to base $13\times10^6$, and base $23\times10^6$ to the end of chromosome Y, were specifically excluded from the analysis because tags derived from either male or female fetuses map to these regions of the Y-chromosome.

b. Analysis of Sequencing Data for the Determination of Fetal Fraction

Concomitant to the analysis for determining aneuploidy, the sequencing data was analyzed to determine the fetal fraction. Following the transfer of the image and base call files to the Unix server running the Illumina "Genome Analyzer Pipeline" software version 1.51 as described in a., the 36 bp reads were aligned to a 'SNP genome' using the BOWTIE program. The SNP genome was identified as the grouping of the 30 DNA sequences i.e. SEQ ID NOS: 1-30, that encompass the alleles of the 15 SNP disclosed in Table 5 in Example 5. Only reads that mapped uniquely to the SNP genome were used for the analysis of fetal fraction. Reads that matched perfectly to the SNP genome were counted as tags and filtered. Of the remaining reads, only reads having one or two mismatches were counted as tags and included in the analysis. Tags mapped to each of the SNP alleles were counted, and the fetal fraction was determined as described in Example 6.

Example 4

Identification of Normalizing Chromosomes for Determining Aneuploidy

To identify normalizing chromosomes to be used in determining chromosome doses and subsequent presence or absence of aneuploidy, plasma cfDNA was obtained from peripheral blood of 48 volunteer pregnant as described in Example 1, and sequenced as described in Example 2. The sequencing data provided in this example was obtained from sequencing a library constructed from fetal and maternal cfDNA that had been enriched for target nucleic acids comprised in a second sequencing library that had been constructed from amplified sequences containing SNPs as described below.

The total number of sequence tags that were mapped to each chromosome in the reference genome (sequence tag density) was determined. Alternatively, the number of mapped sequence tags may be normalized to the length of the chromosome to generate a sequence tag density ratio. The normalization to chromosome length is not a required step, and can be performed solely to reduce the number of digits in a number to simplify it for human interpretation. Chromosome lengths that can be used to normalize the sequence tags counts can be the lengths provided on the world wide web at genome.ucsc.edu/goldenPath/stats.html#hg18.

Table 1 provides the computed ratio for chromosomes X, and Y, and autosomes 1-22 in an exemplary cfDNA sample (11351; 46,XY).

TABLE 1

Sequence Tag Density for Chromosomes 1-22, X and Y (n = 1; sample 11351, 46 XY)

| Chromosome Name | Sequence Tag Density |
|---|---|
| chr1 | 1,857,858 |
| chr2 | 1,910,676 |
| chr3 | 1,562,572 |
| chr4 | 1,376,498 |
| chr5 | 1,383,453 |
| chr6 | 1,317,821 |
| chr7 | 1,192,136 |
| chr8 | 1,162,856 |
| chr9 | 914,624 |
| chr10 | 1,112,763 |
| chr11 | 1,093,028 |
| chr12 | 1,051,209 |
| chr13 | 717,684 |
| chr14 | 710,878 |
| chr15 | 675,596 |
| chr16 | 683,529 |
| chr17 | 647,571 |
| chr18 | 615,140 |
| chr19 | 432,191 |
| chr20 | 557,068 |
| chr21 | 284,701 |
| chr22 | 305,365 |
| chrX | 1,060,456 |
| chrY | 5380 |

Figure 12:
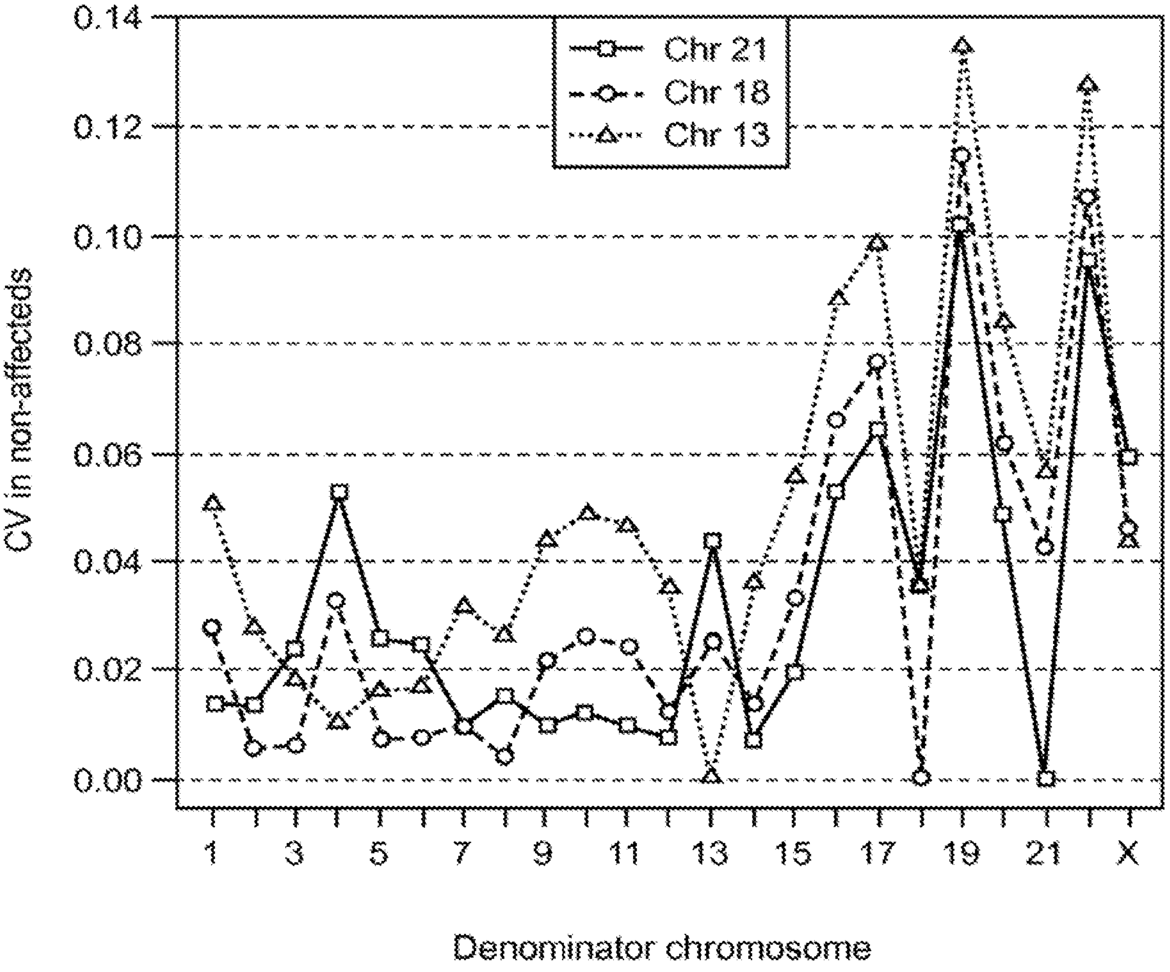
FIG. 12 shows the coefficient of variation (CV) for chromosomes 21 (□), 18 (O) and 13 (Δ) that was determined from the chromosome doses of qualified i.e. non-affected, samples shown in FIGS. 7, 8, and 9, respectively.
Figure 13:
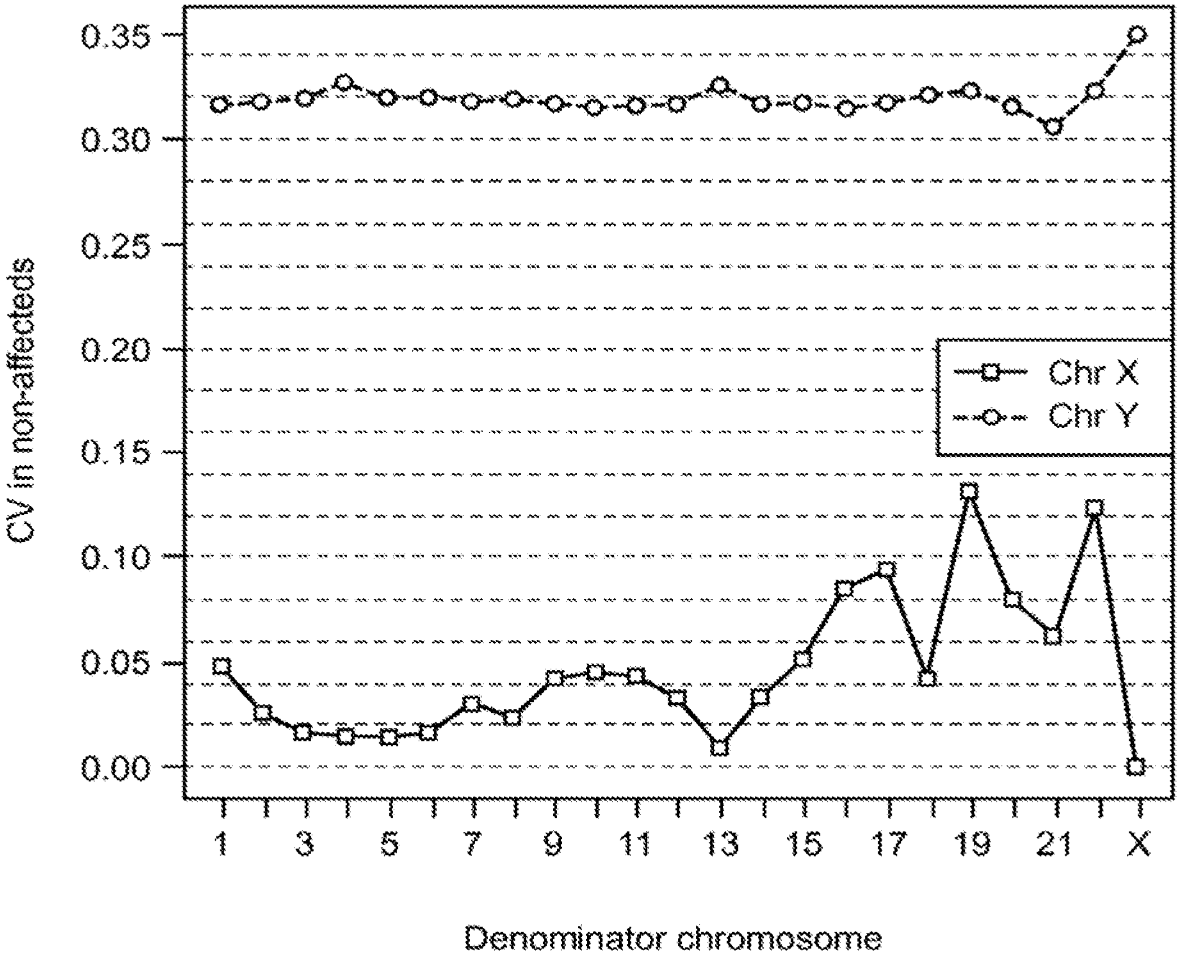
FIG. 13 shows the coefficient of variation (CV) for chromosomes X (□) and Y (O) that was determined from the chromosome doses of qualified i.e. non-affected, samples shown in FIGS. 10 and 11, respectively.

The resulting sequence tag density for each chromosome was related to the sequence tag density of each of the remaining chromosomes to derive a qualified chromosome dose, which was calculated as the ratio of the sequence tag density for the chromosome of interest e.g. chromosome 21, and the sequence tag density of each of the remaining chromosomes i.e. chromosomes 1-20, 22 and X. Chromosomes doses were determined for all chromosomes in all samples, and the average doses for chromosomes of interest 13, 18, 21, X and Y in the qualified samples are provided in Table 2, and depicted in FIGS. 7A-11B. FIGS. 7A-11B also depict the chromosome doses for the test samples. The chromosome doses for each of the chromosomes of interest in the qualified samples provides a measure of the variation in the total number of mapped sequence tags for each chromosome of interest relative to that of each of the remaining chromosomes. Thus, qualified chromosome doses can identify the chromosome or a group of chromosomes i.e. normalizing chromosome, that has a variation among samples that is closest to the variation of the chromosome of interest, and that would serve as ideal sequences for normalizing values for further statistical evaluation. FIGS. 12 and 13 depict the calculated average chromosome doses determined in a population of qualified samples for chromosomes 13, 18, and 21, and chromosomes X and Y.

In some instances, the best normalizing chromosome, may not have the least variation, but may have a distribution of qualified doses that best distinguishes a test sample or samples from the qualified samples i.e. the best normalizing chromosome may not have the lowest variation, but may have the greatest differentiability. Thus, differentiability accounts for the variation in chromosome dose and the distribution of the doses in the qualified samples.

Tables 3 and 4 provide the coefficient of variation as the measure of variability, and student t-test values as a measure of differentiability for chromosomes 18, 21, X and Y, wherein the smallest the T-test value, the greatest the differentiability. The differentiability for chromosome 13 was determined as the ratio of difference between the mean chromosome dose in the qualified samples and the dose for chromosome 13 in the only T13 test sample, and the standard deviation of mean of the qualified dose.

The qualified chromosome doses also serve as the basis for determining threshold values when identifying aneuploidies in test samples as described in the following.

TABLE 2

Qualified Chromosome Dose for Chromosomes 13, 18, 21, X and Y (n = 1; sample 11351, 46 XY)

| Chromosome | chr 21 | chr 18 | chr 13 | chr X | chrY |
|---|---|---|---|---|---|
| chr1 | 0.153242 | 0.331102 | 0.386296 | 0.570795 | 0.002896 |
| chr2 | 0.149005 | 0.321949 | 0.375618 | 0.555016 | 0.002816 |
| chr3 | 0.1822 | 0.393671 | 0.459297 | 0.678661 | 0.003443 |
| chr4 | 0.20683 | 0.446888 | 0.521384 | 0.770401 | 0.003908 |
| chr5 | 0.20579 | 0.444641 | 0.518763 | 0.766528 | 0.003889 |
| chr6 | 0.216039 | 0.466786 | 0.544599 | 0.804704 | 0.004082 |
| chr7 | 0.238816 | 0.515998 | 0.602015 | 0.889543 | 0.004513 |
| chr8 | 0.244829 | 0.528991 | 0.617174 | 0.911941 | 0.004627 |
| chr9 | 0.311277 | 0.672561 | 0.784677 | 1.159445 | 0.005882 |
| chr10 | 0.255851 | 0.552804 | 0.644957 | 0.952994 | 0.004835 |
| chr11 | 0.26047 | 0.562785 | 0.656602 | 0.9702 | 0.004922 |
| chr12 | 0.270832 | 0.585174 | 0.682722 | 1.008797 | 0.005118 |
| chr13 | 0.396694 | 0.857118 | 1 | 1.477609 | 0.007496 |
| chr14 | 0.400492 | 0.865324 | 1.009574 | 1.491755 | 0.007568 |
| chr15 | 0.421407 | 0.910515 | 1.062298 | 1.56966 | 0.007963 |
| chr16 | 0.416516 | 0.899947 | 1.049969 | 1.551443 | 0.007871 |
| chr17 | 0.439644 | 0.949919 | 1.108271 | 1.63759 | 0.008308 |
| chr18 | 0.462823 | 1 | 1.1667 | 1.723926 | 0.008746 |
| chr19 | 0.658739 | 1.423306 | 1.660571 | 2.453674 | 0.012448 |
| chr20 | 0.51107 | 1.104246 | 1.288324 | 1.903638 | 0.009658 |
| chr21 | 1 | 2.160653 | 2.520834 | 3.724806 | 0.018897 |
| chr22 | 0.93233 | 2.014442 | 2.35025 | 3.472749 | 0.017618 |
| chrX | 0.26847 | 0.580071 | 0.676769 | 1 | 0.005073 |
| chrY | 52.9184 | 114.3383 | 133.3985 | 197.1108 | 1 |

TABLE 3

Qualified Chromosome Dose, Variance and Differentiability for chromosomes 21 and 18

| | 21 (n = 35) | | | | 18 (n = 40) | | | |
|---|---|---|---|---|---|---|---|---|
| | Avg | Stdev | CV | T Test | Avg | Stdev | CV | T Test |
| chr1 | 0.15332 | 0.002129 | 1.39 | 1.06E−10 | 0.32451 | 0.008954 | 2.76 | 2.74E−03 |
| chr2 | 0.15106 | 0.002053 | 1.36 | 8.52E−08 | 0.31984 | 0.001783 | 0.56 | 5.32E−05 |
| chr3 | 0.18654 | 0.004402 | 2.36 | 8.07E−07 | 0.39511 | 0.002364 | 0.60 | 1.93E−05 |
| chr4 | 0.21578 | 0.011174 | 5.18 | 1.47E−04 | 0.45714 | 0.014794 | 3.24 | 1.37E−03 |
| chr5 | 0.21068 | 0.005332 | 2.53 | 1.08E−06 | 0.44626 | 0.003250 | 0.73 | 3.18E−05 |
| chr6 | 0.22112 | 0.005453 | 2.47 | 1.74E−06 | 0.46818 | 0.003434 | 0.73 | 2.24E−05 |
| chr7 | 0.24233 | 0.002314 | 0.96 | 2.39E−08 | 0.51341 | 0.005289 | 1.03 | 1.24E−04 |
| chr8 | 0.24975 | 0.003772 | 1.51 | 1.06E−07 | 0.52898 | 0.002161 | 0.41 | 6.32E−05 |
| chr9 | 0.31217 | 0.003050 | 0.98 | 1.60E−09 | 0.66100 | 0.014413 | 2.18 | 8.17E−04 |
| chr10 | 0.25550 | 0.003164 | 1.24 | 2.42E−11 | 0.54091 | 0.013953 | 2.58 | 2.26E−03 |
| chr11 | 0.26053 | 0.002596 | 1.00 | 1.32E−10 | 0.55158 | 0.013283 | 2.41 | 1.29E−03 |
| chr12 | 0.27401 | 0.002061 | 0.75 | 1.40E−08 | 0.58032 | 0.007198 | 1.24 | 1.57E−04 |
| chr13 | 0.41039 | 0.017637 | 4.30 | 3.09E−05 | 0.86961 | 0.021614 | 2.49 | 2.36E−04 |
| chr14 | 0.40482 | 0.002908 | 0.72 | 1.10E−08 | 0.85732 | 0.011748 | 1.37 | 2.16E−04 |
| chr15 | 0.41821 | 0.008238 | 1.97 | 1.24E−10 | 0.88503 | 0.029199 | 3.30 | 5.72E−03 |
| chr16 | 0.40668 | 0.021232 | 5.22 | 2.91E−05 | 0.86145 | 0.056245 | 6.53 | 1.04E−01 |
| chr17 | 0.42591 | 0.027001 | 6.34 | 5.85E−04 | 0.90135 | 0.068151 | 7.56 | 1.24E−01 |
| chr18 | 0.46529 | 0.016239 | 3.49 | 8.02E−09 | | | | |
| chr19 | 0.63003 | 0.063272 | 10.04 | 3.30E−02 | 1.33522 | 0.150794 | 11.29 | 3.04E−01 |
| chr20 | 0.49925 | 0.023907 | 4.79 | 1.65E−05 | 1.05648 | 0.064440 | 6.10 | 7.98E−02 |
| chr21 | | | | | 2.06768 | 0.087175 | 4.22 | 5.10E−05 |
| chr22 | 0.88726 | 0.083330 | 9.39 | 3.43E−02 | 1.87509 | 0.198316 | 10.58 | 2.43E−01 |
| chrX | 0.27398 | 0.016109 | 5.88 | 1.16E−04 | 0.58665 | 0.027280 | 4.65 | 7.50E−02 |

TABLE 4

Qualified Chromosome Dose, Variance and Differentiability for chromosomes 13, X and Y

| | 13 (n = 47) | | | | X (n = 20) | | | |
|---|---|---|---|---|---|---|---|---|
| | Avg | Stdev | CV | Diff | Avg | Stdev | CV | T Test |
| chr1 | 0.37213 | 0.018589 | 5.00 | 2.41 | 0.58035 | 0.02706 | 4.66 | 5.68E−05 |
| chr2 | 0.36707 | 0.010067 | 2.74 | 3.03 | 0.57260 | 0.01432 | 2.50 | 1.53E−09 |
| chr3 | 0.45354 | 0.008121 | 1.79 | 3.67 | 0.70741 | 0.01126 | 1.59 | 9.04E−13 |
| chr4 | 0.52543 | 0.005306 | 1.01 | 2.39 | 0.82144 | 0.01192 | 1.45 | 5.86E−16 |

TABLE 4-continued

| Qualified Chromosome Dose, Variance and Differentiability for chromosomes 13, X and Y | | | | | | | | |
|---|---|---|---|---|---|---|---|---|
| chr5 | 0.51228 | 0.008273 | 1.61 | 3.95 | 0.79921 | 0.01100 | 1.38 | 2.32E−13 |
| chr6 | 0.53756 | 0.008901 | 1.66 | 3.91 | 0.83880 | 0.01261 | 1.50 | 3.64E−13 |
| chr7 | 0.58908 | 0.018508 | 3.14 | 2.83 | 0.91927 | 0.02700 | 2.94 | 1.86E−08 |
| chr8 | 0.60695 | 0.015797 | 2.60 | 3.05 | 0.94675 | 0.02173 | 2.30 | 3.40E−10 |
| chr9 | 0.75816 | 0.033107 | 4.37 | 2.59 | 1.18180 | 0.04827 | 4.08 | 9.63E−06 |
| chr10 | 0.62018 | 0.029891 | 4.82 | 2.56 | 0.96642 | 0.04257 | 4.40 | 4.55E−05 |
| chr11 | 0.63248 | 0.029204 | 4.62 | 2.55 | 0.98643 | 0.04222 | 4.28 | 1.82E−05 |
| chr12 | 0.66574 | 0.023047 | 3.46 | 2.76 | 1.03840 | 0.03301 | 3.18 | 1.26E−07 |
| chr13 | | | | | 1.56355 | 0.01370 | 0.88 | 6.33E−17 |
| chr14 | 0.98358 | 0.035331 | 3.59 | 2.67 | 1.58114 | 0.08076 | 5.11 | 2.29E−04 |
| chr15 | 1.01432 | 0.055806 | 5.50 | 2.39 | 1.53464 | 0.12719 | 8.29 | 2.01E−02 |
| chr16 | 0.98577 | 0.085933 | 8.72 | 2.17 | 1.61094 | 0.14829 | 9.21 | 2.68E−02 |
| chr17 | 1.03217 | 0.100389 | 9.73 | 2.13 | 1.74904 | 0.07290 | 4.17 | 1.62E−04 |
| chr18 | 1.13489 | 0.040058 | 3.53 | 2.62 | 2.38397 | 0.30515 | 12.80 | 1.07E−01 |
| chr19 | 1.52678 | 0.203732 | 13.34 | 1.98 | 1.88186 | 0.14674 | 7.80 | 1.56E−02 |
| chr20 | 1.20919 | 0.100371 | 8.30 | 2.27 | 3.71853 | 0.22406 | 6.03 | 4.21E−04 |
| chr21 | 2.38087 | 0.132418 | 5.56 | 2.29 | 3.35158 | 0.40246 | 12.01 | 8.66E−02 |
| chr22 | 2.14557 | 0.271281 | 12.64 | 2.13 | 0.58035 | 0.02706 | 4.66 | 5.68E−05 |
| chrX | 0.66883 | 0.029157 | 4.36 | 1.04 | | | | |
| chr2-6 | 0.46965 | 0.006987 | 1.49 | 4.17 | | | | |
| chr3-6 | 0.50496 | 0.005373 | 1.06 | 5.16 | | | | |

| | Y (n = 25) | | | |
|---|---|---|---|---|
| | Avg | Stdev | CV | T Test |
| Chr 1-22, X | 0.00728 | 0.00227 | 31.19 | 1.30E−13 |

Examples of diagnoses of T21, T13, T18 and Turner syndrome obtained using the normalizing chromosomes, chromosome doses and differentiability for each of the chromosomes of interest are described in Example 6.

Example 5

Selection of Autosomal SNPs for the Determination of Fetal Fraction

A set of 28 autosomal SNPs were selected from a list of 92 SNPs (Pakstis et al., Hum Genet 127:315-324 [2010]), and SNP sequences available from Applied Biosystems on the world wide web at appliedbiosystems.com, and validated for use in multiplexed PCR amplification and for massively parallel sequencing. Primers were designed to hybridize to a sequence close to the SNPs site on the cfDNA to ensure that it be included in the 36 bp read generated from the massively parallel sequencing on the Illumina Analyzer GII, and to generate amplicons of sufficient length to undergo bridge-amplification during cluster formation. Thus, primers were designed to generate amplicons that were at least 110 bp, which when combined with the universal adaptors (Illumina Inc., San Diego, Calif.) used for cluster amplification, resulted in DNA molecules of at least 200 bp. Primer sequences were identified, and primer sets i.e. forward and reverse primers, were synthesized by Integrated DNA Technologies (San Diego, Calif.), and stored as a 1 μM solution to be used for amplifying polymorphic target sequences as described in Examples 5-8. Table 5 provides the RefSNP (rs) accession ID numbers, the primers used for amplifying the target cfDNA sequence, and the sequences of the amplicons comprising the possible SNP alleles that would be generated using the primers. The SNPs given in Table 5 were used for the simultaneous amplification of 13 target sequences in a multiplexed assay. The panel provided in Table 5 is an exemplary SNP panel. Fewer or more SNPs can be employed to enrich the fetal and maternal DNA for polymorphic target nucleic acids. Additional SNPs that can be used include the SNPs given in Table 6. The SNP alleles are shown in bold and are underlined. Other SNPs that can be used to determine fetal fraction according to the present method include rs315791, rs3780962, rs1410059, rs279844, rs38882, rs9951171, rs214955, rs6444724, rs2503107, rs1019029, rs1413212, rs1031825, rs891700, rs1005533, rs2831700, rs354439, rs1979255, rs1454361, rs8037429, and rs1490413, which have been analyzed for determining fetal fraction by TaqMan PCR, and are disclosed in U.S. Provisional applications 61/296,358 and 61/360,837, which are herein incorporated by reference in their entirety.

TABLE 5

| SNP Panel for the Determination of Fetal Fraction | | | | | |
|---|---|---|---|---|---|
| SNP ID | Chr | Amplicon: Allele 1 | Amplicon: Allele 2 | Forward Primer Sequence, name and SEQ ID NO: | Reverse Primer Sequence, name and SEQ ID NO: |
| rs560681 | 1 | CACATGCACAGCCA GCAACCCTGTCAGC AGGAGTTCCCACCA GTTTCTTTCTGAGAA CATCTGTTCAGGTTT CTCTCCATCTCTATT | CACATGCACAGCCA GCAACCCTGTCAGC AGGAGTTCCCACCA GTTTCTTTCTGAGAA CATCTGTTCAGGTTT CTCTCCATCTCTGTT | CACATGCA CAGCCAGC AACCC (rs560681_ C1_1_F; SEQ ID NO: 57) | CCCCAAGGTC CTGTGACCTGA GT (rs560681_C1_1_ R; SEQ ID NO: 58) |

TABLE 5-continued

SNP Panel for the Determination of Fetal Fraction

| SNP ID | Chr | Amplicon: Allele 1 | Amplicon: Allele 2 | Forward Primer Sequence, name and SEQ ID NO: | Reverse Primer Sequence, name and SEQ ID NO: |
|---|---|---|---|---|---|
| | | TACTCAGGTCACAGGACCTTGGGG (SEQ ID NO: 1) | TACTCAGGTCACAGGACCTTGGGG (SEQ ID NO: 2) | | |
| rs1109037 | 2 | TGAGGAAGTGAGGCTCAGAGGGTAAGAAACTTTGTCACAGAGCTGGTGGTGAGGGTGGAGATTTTACACTCCCTGCCTCCCACACCAGTTTCTCC**A**GAGTGGAAAGACTTTCATCTCGCACTGGCA (SEQ ID NO: 3) | TGAGGAAGTGAGGCTCAGAGGGTAAGAAACTTTGTCACAGAGCTGGTGGTGAGGGTGGAGATTTTACACTCCCTGCCTCCCACACCAGTTTCTCC**G**GAGTGGAAAGACTTTCATCTCGCACTGGCA (SEQ ID NO: 4) | TGAGGAAGTGAGGCTCAGAGGGT (rs110937_C2_1_F; SEQ ID NO: 59) | TGCCAGTGCGAGATGAAAGTCTTT (rs110937_C2_1_R; SEQ ID NO: 60) |
| rs9866013 | 3 | GTGCCTTCAGAACCTTTGAGATCTGATTCTATTTTTAAAGCTTCTTAGAAGAGAGATTGCAAAGTGGGTTGTTTCTCTAGCCAGACAGGGCAGG**C**AAATAGGGGTGGCTGGTGGGATGGGA (SEQ ID NO: 5) | GTGCCTTCAGAACCTTTGAGATCTGATTCTATTTTTAAAGCTTCTTAGAAGAGAGATTGCAAAGTGGGTTGTTTCTCTAGCCAGACAGGGCAGG**T**AAATAGGGGTGGCTGGTGGGATGGGA (SEQ ID NO: 6) | GTGCCTTCAGAACCITTGAGATCTGAT (rs9866013_C3_1_F; SEQ ID NO: 61) | TCCCATCCCACCAGCCACCC (rs9866013_C3_1_R; SEQ ID NO: 62) |
| rs13182883 | 5 | AGGTGTGTCTCTCTTTTGTGAGGGGAGGGGTCCCTTCTGGCCTAGTAGAGGGCCTGGCCTGCAGTGAGCATTCAAATCCTC**A**AGGAACAGGGTGGGGAGGTGGGACAAAGG (SEQ ID NO: 7) | AGGTGTGTCTCTCTTTTGTGAGGGGAGGGGTCCCTTCTGGCCTAGTAGAGGGCCTGGCCTGCAGTGAGCATTCAAATCCTC**G**AGGAACAGGGTGGGGAGGTGGGACAAAGG (SEQ ID NO: 8) | AGGTGTGTCTCTCTTTTGTGAGGGG (rs13182883_C5_1_F; SEQ ID NO: 63) | CCTTTGTCCCACCTCCCCACC (rs13182883_C5_1_R; SEQ ID NO: 64) |
| rs13218440 | 6 | CCTCGCCTACTGTGCTGTTTCTAACCATCATGCTTTTCCCTGAATCTCTTGAGTCTTTTTCTGCTGTGGACTGAAACTTGATCCTGAGATTCACCTCTAGTCCCTCTG**A**GCAGCCTCCTGGAATACTCAGCTGGGATGG (SEQ ID NO: 9) | CCTCGCCTACTGTGCTGTTTCTAACCATCATGCTTTTCCCTGAATCTCTTGAGTCTTTTTCTGCTGTGGACTGAAACTTGATCCTGAGATTCACCTCTAGTCCCTCTG**G**GCAGCCTCCTGGAATACTCAGCTGGGATGG (SEQ ID NO: 10) | CCTCGCCTACTGTGCTGTTTCTAACC (rs13218440_C6_1_F; SEQ ID NO: 65) | CCATCCCAGCTGAGTATTCCAGGAG (rs13218440_C6_1_R; SEQ ID NO: 66) |
| rs7041158 | 9 | AATTGCAATGGTGAGAGGTTGATGGTAAAATCAAACGGAACTTGTTATTTTGTCATTCTGATGGACTGGAACTGAGGATTTTCAATTTCCT**C**TCCAACCCAAGACACTTCTCACTGG (SEQ ID NO: 11) | AATTGCAATGGTGAGAGGTTGATGGTAAAATCAAACGGAACTTGTTATTTTGTCATTCTGATGGACTGGAACTGAGGATTTTCAATTTCCT**T**TCCAACCCAAGACACTTCTCACTGG (SEQ ID NO: 12) | AATTGCAATGGTGAGAGGTTGATGGT (SEQ ID NO: 67) | CCAGTGAGAAGTGTCTTGGGTTGG (SEQ ID NO: 68) |
| rs740598 | 10 | GAAATGCCTTCTCAGGTAATGGAAGGTTATCCAAATATTTTTCGTAAGTATTTCAAATAGCAATGGCTCGTCTATGGTTAGTCTC**A**CAGCCACATTCTCAGAACTGCTCAAACC (SEQ ID NO: 13) | GAAATGCCTTCTCAGGTAATGGAAGGTTATCCAAATATTTTTCGTAAGTATTTCAAATAGCAATGGCTCGTCTATGGTTAGTCTC**G**CAGCCACATTCTCAGAACTGCTCAAACC (SEQ ID NO: 14) | GAAATGCCTTCTCAGGTAATGGAAGGT (SEQ ID NO: 69) | GGTTTGAGCAGTTCTGAGAATGTGGCT (SEQ ID NO: 70) |
| rs10773760 | 12 | ACCCAAAACACTGGAGGGGCCTCTTCTCATTTTCGGTAGACTGCAAGTGTTAGCCGTCGGGACCAGCTTCTGT | ACCCAAAACACTGGAGGGGCCTCTTCTCATTTTCGGTAGACTGCAAGTGTTAGCCGTCGGGACCAGCTTCTGT | ACCCAAAACACTGGAGGGGCCT (SEQ ID NO: 71) | CCCTTATCTGCTATGTGGCATACTTGG (SEQ ID NO: 72) |

TABLE 5-continued

SNP Panel for the Determination of Fetal Fraction

| SNP ID | Chr | Amplicon: Allele 1 | Amplicon: Allele 2 | Forward Primer Sequence, name and SEQ ID NO: | Reverse Primer Sequence, name and SEQ ID NO: |
|---|---|---|---|---|---|
| | | CTGGAAGTTCGTCA<br>AATTGCAGTTA**A**GTC<br>CAAGTATGCCACAT<br>AGCAGATAAGGG<br>(SEQ ID NO: 15) | CTGGAAGTTCGTCA<br>AATTGCAGTTA**G**GT<br>CCAAGTATGCCACA<br>TAGCAGATAAGGG<br>(SEQ ID NO: 16) | | |
| rs4530059 | 14 | GCACCAGAATTTAA<br>ACAACGCTGACAAT<br>AAATATGCAGTCGA<br>TGATGACTTCCCAGA<br>GCTCCAGAAGCAAC<br>TCCAGCACAC**A**GAG<br>AGGCGCTGATGTGC<br>CTGTCAGGTGC (SEQ<br>ID NO: 17) | GCACCAGAATTTAA<br>ACAACGCTGACAAT<br>AAATATGCAGTCGA<br>TGATGACTTCCCAGA<br>GCTCCAGAAGCAAC<br>TCCAGCACAC**G**GAG<br>AGGCGCTGATGTGC<br>CTGTCAGGTGC (SEQ<br>ID NO: 18) | GCACCAGA<br>ATTTAAAC<br>AACGCTGA<br>CAA (SEQ<br>ID NO: 73) | GCACCTGACA<br>GGCACATCAG<br>CG (SEQ ID<br>NO: 74) |
| rs7205345 | 16 | TGACTGTATACCCCA<br>GGTGCACCCTTGGGT<br>CATCTCTATCATAGA<br>ACTTATCTCACAGAG<br>TATAAGAGCTGATTT<br>CTGTGTCTGCCT**C**TC<br>ACACTAGACTTCCAC<br>ATCCTTAGTGC (SEQ<br>ID NO: 19) | TGACTGTATACCCCA<br>GGTGCACCCTTGGGT<br>CATCTCTATCATAGA<br>ACTTATCTCACAGAG<br>TATAAGAGCTGATTT<br>CTGTGTCTGCCT**G**TC<br>ACACTAGACTTCCAC<br>ATCCTTAGTGC (SEQ<br>ID NO: 20) | TGACTGTA<br>TACCCCAG<br>GTGCACCC<br>(SEQ ID<br>NO: 75) | GCACTAAGGA<br>TGTGGAAGTCT<br>AGTGTG (SEQ<br>ID NO: 76) |
| rs8078417 | 17 | TGTACGTGGTCACCA<br>GGGGACGCCTGGCG<br>CTGCGAGGGAGGCC<br>CCGAGCCTCGTGCCC<br>CCGTGAAGCTTCAG<br>CTCCCCTCCC**C**GGCT<br>GTCCTTGAGGCTCTT<br>CTCACACT (SEQ ID<br>NO: 21) | TGTACGTGGTCACCA<br>GGGGACGCCTGGCG<br>CTGCGAGGGAGGCC<br>CCGAGCCTCGTGCCC<br>CCGTGAAGCTTCAG<br>CTCCCCTCCC**T**GGCT<br>GTCCTTGAGGCTCTT<br>CTCACACT (SEQ ID<br>NO: 22) | TGTACGTG<br>GTCACCAG<br>GGGACG<br>(SEQ ID<br>NO: 77) | AGTGTGAGAA<br>GAGCCTCAAG<br>GACAGC (SEQ<br>ID NO: 78) |
| rs576261 | 19 | CAGTGGACCCTGCT<br>GCACCTTTCCTCCCC<br>TCCCATCAACCTCTT<br>TTGTGCCTCCCCCTC<br>CGTGTACCACCTTCT<br>CTGTCACCA**A**CCCTG<br>GCCTCACAACTCTCT<br>CCTTTGCCAC (SEQ<br>ID NO: 23) | CAGTGGACCCTGCT<br>GCACCTTTCCTCCCC<br>TCCCATCAACCTCTT<br>TTGTGCCTCCCCCTC<br>CGTGTACCACCTTCT<br>CTGTCACCA**C**CCCTG<br>GCCTCACAACTCTCT<br>CCTTTGCCAC (SEQ<br>ID NO: 24) | CAGTGGAC<br>CCTGCTGC<br>ACCTT<br>(SEQ ID<br>NO: 79) | GTGGCAAAGG<br>AGAGAGTTGT<br>GAGG (SEQ ID<br>NO: 80) |
| rs2567608 | 20 | CAGTGGCATAGTAG<br>TCCAGGGGCTCCTCC<br>TCAGCACCTCCAGC<br>ACCTTCCAGGAGGC<br>AGCAGCGCAGGCAG<br>AGAACCCGCTGGAA<br>G**A**ATCGGCGGAAGT<br>TGTCGGAGAGG (SEQ<br>ID NO: 25) | CAGTGGCATAGTAG<br>TCCAGGGGCTCCTCC<br>TCAGCACCTCCAGC<br>ACCTTCCAGGAGGC<br>AGCAGCGCAGGCAG<br>AGAACCCGCTGGAA<br>G**G**ATCGGCGGAAGT<br>TGTCGGAGAGG (SEQ<br>ID NO: 26) | CAGTGGCA<br>TAGTAGTC<br>CAGGGGCT<br>(SEQ ID<br>NO: 81) | CCTCTCCGACA<br>ACTTCCGCCG<br>(SEQ ID NO: 82) |

TABLE 6

SNP Panel for the Determination of Fetal Fraction

| SNP ID | Chr | Amplicon: Allele 1 | Amplicon: Allele 2 | Forward Primer Sequence, name and SEQ ID NO: | Reverse Primer Sequence, name and SEQ ID NO: |
|---|---|---|---|---|---|
| rs430046 | 16 | AGGTCTGGGGGCC<br>GCTGAATGCCAAGC<br>TGGGAATCTTAAAT | AGGTCTGGGGGCCGC<br>TGAATGCCAAGCTGG<br>GAATCTTAAATGTTA | AGGTCTGG<br>GGGCCGCT<br>GAAT | TCCTCCCATTA<br>AACCCAGCAC<br>CT |

TABLE 6-continued

SNP Panel for the Determination of Fetal Fraction

| SNP ID | Chr | Amplicon: Allele 1 | Amplicon: Allele 2 | Forward Primer Sequence, name and SEQ ID NO: | Reverse Primer Sequence, name and SEQ ID NO: |
|---|---|---|---|---|---|
| | | GTTAAGGAACAAG<br>GTCATACAATGAAT<br>GGTGTGATGTAAAA<br>GCTTGGGAGGTGAT<br>TT**C**TGAGGGTAGGT<br>GCTGGGTTTAATGG<br>GAGGA (SEQ ID<br>NO: 27) | AGGAACAAGGTCATA<br>CAATGAATGGTGTGA<br>TGTAAAAGCTTGGGA<br>GGTGATTT**T**TGAGGG<br>TAGGTGCTGGGTTTA<br>ATGGGAGGA (SEQ ID<br>NO: 28) | (rs430046_C1_<br>1_F; SEQ<br>ID NO: 83) | (rs430046_C1_1_<br>R; SEQ ID<br>NO: 84) |
| rs9951171 | 18 | ACGGTTCTGTCCTG<br>TAGGGGAGAAAAG<br>TCCTCGTTGTTCCT<br>CTGGGATGCAACAT<br>GAGAGAGCAGCAC<br>ACTGAGGCTTTATG<br>G**A**TTGCCCTGCCAC<br>AAGTGAACAGG<br>(SEQ ID NO: 29) | ACGGTTCTGTCCTGT<br>AGGGGAGAAAAGTCC<br>TCGTTGTTCCTCTGGG<br>ATGCAACATGAGAGA<br>GCAGCACACTGAGGC<br>TTTATGG**G**TTGCCCT<br>GCCACAAGTGAACAG<br>G (SEQ ID NO: 30) | ACGGTTCT<br>GTCCTGTA<br>GGGGAGA<br>(rs9951171_<br>C1_1_F; SEQ<br>ID NO: 85) | CCTGTTCACTT<br>GTGGCAGGGC<br>A<br>(rs9951171_C1_1_<br>R; SEQ ID<br>NO: 86) |
| rs338882 | 5 | GCGCAGTCAGATG<br>GGCGTGCTGGCGTC<br>TGTCTTCTCTCTCTC<br>CTGCTCTCTGGCTT<br>CATTTTTCTCTCCTT<br>CTGTCTCACCTTCT<br>TTCGTGTGCCTGTG<br>CA**C**ACACACGTTTG<br>GGACAAGGG<br>CTGGA (SEQ ID<br>NO: 31) | GCGCAGTCAGATGGG<br>CGTGCTGGCGTCTGT<br>CTTCTCTCTCTCCTGC<br>TCTCTGGCTTCATTTT<br>TCTCTCCTTCTGTCTC<br>ACCTTCTTTCGTGTGC<br>CTGTGCA**T**ACACACG<br>TTTGGGACAAGGG<br>CTGGA (SEQ ID NO: 32) | GCGCAGTC<br>AGATGGGC<br>GTGC<br>(rs338882_C1_<br>1_F; SEQ<br>ID NO: 87) | TCCAGCCCTTG<br>TCCCAAACGT<br>GT<br>(rs338882_C1_1_<br>R; SEQ ID<br>NO: 88) |
| rs10776839 | 9 | GCCGGACCTGCGA<br>AATCCCAAAATGCC<br>AAACATTCCCGCCT<br>CACATGATCCCAGA<br>GGAGAGGGACCCA<br>GTGTTCCCAGCTTG<br>CAGCTGAGGAGCC<br>CGAG**G**TTGCCGTCA<br>GATCAGAGCCCCA<br>GTTGCCCG (SEQ ID<br>NO: 33) | GCCGGACCTGCGAAA<br>TCCCAAAATGCCAAA<br>CATTCCCGCCTCACA<br>TGATCCCAGAGAGAG<br>GGGACCCAGTGTTCC<br>CAGCTTGCAGCTGAG<br>GAGCCCGAG**T**TTGCC<br>GTCAGATCAGAGCCC<br>CAGTTGCCCG (SEQ ID<br>NO: 34) | GCCGGACC<br>TGCGAAAT<br>CCCAA<br>(rs10776839<br>C1_1_F; SEQ<br>ID NO: 89) | CGGGCAACTG<br>GGGCTCTGATC<br>(rs10776839_C1_<br>1_R; SEQ ID<br>NO: 90) |
| rs9905977 | 17 | AGCAGCCTCCCTCG<br>ACTAGCTCACACTA<br>CGATAAGGAAAAT<br>TCATGAGCTGGTGT<br>CCAAGGAGGGCTG<br>GGTGACTCGTGGCT<br>CAGTCAGC**A**TCAAG<br>ATTCCTTTCGTCTTT<br>CCCCTCTGCC (SEQ<br>ID NO: 35) | AGCAGCCTCCCTCGA<br>CTAGCTCACACTACG<br>ATAAGGAAAATTCAT<br>GAGCTGGTGTCCAAG<br>GAGGGCTGGGTGACT<br>CGTGGCTCAGTCAGC<br>**G**TCAAGATTCCTTTC<br>GTCTTTCCCCTCTGCC<br>(SEQ ID NO: 36) | AGCAGCCT<br>CCCTCGAC<br>TAGCT<br>(rs9905977_<br>C1_1_F; SEQ<br>ID NO: 91) | GGCAGAGGGG<br>AAAGACGAAA<br>GGA<br>(rs9905977_C1_1_<br>R; SEQ ID<br>NO: 92) |
| rs1277284 | 4 | TGGCATTGCCTGTA<br>ATATACATAGCCAT<br>GGTTTTTTATAGGC<br>AATTTAAGATGAAT<br>AGCTTCTAAACTAT<br>AGATAAGTTTCATT<br>ACCCCAGGAAGCT<br>GAACTATAGCTACT<br>TT**A**CCCAAAATCAT<br>TAGAATGGTGCTT<br>(SEQ ID NO: 37) | TGGCATTGCCTGTAA<br>TATACATAGCCATGG<br>TTTTTTATAGGCAATT<br>TAAGATGAATAGCTT<br>CTAAACTATAGATAA<br>GTTTCATTACCCCAG<br>GAAGCTGAACTATAG<br>CTACTTT**C**CCCAAAA<br>TCATTAGAATGGTGC<br>TT (SEQ ID NO: 38) | TGGCATTG<br>CCTGTAAT<br>ATACATAG<br>(rs1277284_<br>C4_1_F; SEQ<br>ID NO: 93) | AAGCACCATT<br>CTAATGATTTT<br>GG<br>(rs1277284_C4_1_<br>R; SEQ ID<br>NO: 94) |
| rs258684 | 7 | ATGAAGCCTTCCAC<br>CAACTGCCTGTATG<br>ACTCATCTGGGGAC<br>TTCTGCTCTATACT<br>CAAAGTGGCTTAGT<br>CACTGCCAATGTAT | ATGAAGCCTTCCACC<br>AACTGCCTGTATGAC<br>TCATCTGGGGACTTC<br>TGCTCTATACTCAAA<br>GTGGCTTAGTCACTG<br>CCAATGTATTTCCAT | ATGAAGCC<br>TTCCACCA<br>ACTG<br>(rs258684_<br>C7_1_F; SEQ<br>ID NO: 95) | GATCAGTTGTT<br>GTTTCTATATT<br>TCCTT<br>(rs258684_C7_1_<br>R; SEQ ID<br>NO: 96) |

TABLE 6-continued

SNP Panel for the Determination of Fetal Fraction

| SNP ID | Chr | Amplicon: Allele 1 | Amplicon: Allele 2 | Forward Primer Sequence, name and SEQ ID NO: | Reverse Primer Sequence, name and SEQ ID NO: |
|---|---|---|---|---|---|
| | | TTCCATATGAGGGA CG**A**TGATTACTAAG GAAATATAGAAAC AACAACTGATC (SEQ ID NO: 39) | ATGAGGGACG**G**TGAT TACTAAGGAAATATA GAAACAACAACTGAT C (SEQ ID NO: 40) | | |
| rs1347696 | 8 | ACAACAGAATCAG GTGATTGGAGAAA AGATCACAGGCCTA GGCACCCAAGGCTI GAAGGATGAAAGA ATGAAAGATGGAC GGAA**C**AAAATTAG GACCTTAATTCTTT GTTCAGTTCAG (SEQ ID NO: 41) | ACAACAGAATCAGGT GATTGGAGAAAAGAT CACAGGCCTAGGCAC CCAAGGCTTGAAGGA TGAAAGAATGAAAGA TGGACGGAA**G**AAAAT TAGGACCTTAATTCTT TGTTCAGTTCAG (SEQ ID NO: 42) | ACAACAGA ATCAGGTG ATTGGA (rs1347696_ C8_4_F; SEQ ID NO: 97) | CTGAACTGAA CAAAGAATTA AGGTC (rs1347696_C8_4_ F; SEQ ID NO: 98) |
| rs508485 | 11 | TTGGGGTAAATTTT CATTGTCATATGTG GAATTTAAATATAC CATCATCTACAAAG AATTCCACAGAGTT AAATATCTTAAGTT AAACACTTAAAATA AGTGTTTGCGTGAT ATTTTGATGA**C**AGA TAAACAGAGTCTAA TTCCCACCCC (SEQ ID NO: 43) | TTGGGGTAAATTTTC ATTGTCATATGTGGA ATTTAAATATACCAT CATCTACAAAGAATT CCACAGAGTTAAATA TCTTAAGTTAAACAC TTAAAATAAGTGTTT GCGTGATATTTTGAT GA**T**AGATAAACAGAG TCTAATTCCCACCCC (SEQ ID NO: 44) | TTGGGGTA AATTTTCA TTGTCA (rs508485_ C11_1_F; SEQ ID NO: 99) | GGGGTGGGAA TTAGACTCTG (rs508485_C11_1_ R; SEQ ID NO100) |
| rs9788670 | 15 | TGCAATTCAAATCA GGAAGTATGACCA AAAGACAGAGATC TTTTTTGGATGATC CCTAGCCTAGCAAT GCCTGGCAGCCATG CAGGTGCAATGTCA ACCTTAAATAATGT ATTGCAAA**C**TCAGA GCTGACAAACCTCG ATGTTGC (SEQ ID NO: 45) | TGCAATTCAAATCAG GAAGTATGACCAAA GACAGAGATCTTTTT TGGATGATCCCTAGC CTAGCAATGCCTGGC AGCCATGCAGGTGCA ATGTCAACCTTAAAT AATGTATTGCAAA**T**T CAGAGCTGACAAACC TCGATGTTGC (SEQ ID NO: 46) | TGCAATTC AAAATCAGG AAGTATG (rs9788670_ c15_2_F; SEQ ID NO: 101) | GCAACATCGA GGTTTGTCAG (rs9788670_c15_ 2_R; SEQ ID NO: 102) |
| rs8137254 | 22 | CTGTGCTCTGCGAA TAGCTGCAGAAGTA ACTTGGGGACCCAA AATAAAGCAGAAT GCTAATGTCAAGTC CTGAGAACCAAGC CCTGGGACTCTGGT GCCATTT**C**GGATTC TCCATGAGCATGGT (SEQ ID NO: 47) | CTGTGCTCTGCGAAT AGCTGCAGAAGTAAC TTGGGGACCCAAAAT AAAGCAGAATGCTAA TGTCAAGTCCTGAGA ACCAAGCCCTGGGAC TCTGGTGCCATTT**T**G GATTCTCCATGAGCA TGGT (SEQ ID NO: 48) | CTGTGCTC TGCGAATA GCTG (rs8137254_ c22_2_F: SEQ ID NO: 103) | ACCATGCTCAT GGAGAATCC (rs8137254_c22_ 2_R; SEQ ID NO: 104) |
| rs3143 | 19 | TTTTTCCAGCCAAC TCAAGGCCAAAAA AAATTTCTTAATAT AGTTATTATGCGAG GGGAGGGGAAGCA AAGGAGCACAGGT AGTCCACAGAATA **A**GACACAAGAAAC CTCAAGCTGTG (SEQ ID NO: 49) | TTTTTCCAGCCAACTC AAGGCCAAAAAAAAT TTCTTAATATAGTTAT TATGCGAGGGGAGGG GAAGCAAAGGAGCA CAGGTAGTCCACAGA ATA**G**GACACAAGAA ACCTCAAGCTGTG (SEQ ID NO: 50) | TTTTTCCA GCCAACTC AAGG (rs3143_c19_ 2_F: SEQ ID NO: 105) | CACAGCTTGA GGTTTCTTGTG (rs3143_c19_2_R; SEQ ID NO: 106) |

TABLE 6-continued

SNP Panel for the Determination of Fetal Fraction

| SNP ID | Chr | Amplicon: Allele 1 | Amplicon: Allele 2 | Forward Primer Sequence, name and SEQ ID NO: | Reverse Primer Sequence, name and SEQ ID NO: |
|---|---|---|---|---|---|
| rs2182957 | 13 | TCTTCTCGTCCCCTAAGCAAACAACATCCGCTTGCTTCTGTCTGTGTAACCACAGTGAATGGGTGTGCACGCTTG**A**TGGGCCTCTGAGCCCCTGTTGCACAAACCAGAAA (SEQ ID NO: 51) | TCTTCTCGTCCCCTAAGCAAACAACATCCGCTTGCTTCTGTCTGTGTAACCACAGTGAATGGGTGTGCACGCTTG**G**TGGGCCTCTGAGCCCCTGTTGCACAAACCAGAAA (SEQ ID NO: 52) | TCTTCTCGTCCCCTAAGC AA (rs2182957_c13_1_F: SEQ ID NO: 107) | TTTCTGGTTTGTGCAACAGG (rs2182957_c13_1_R; SEQ ID NO: 108) |
| rs3739005 | 2 | CACATGGGGGCATTAAGAATCGCCCAGGGAGGAGGAGGGAGAACGCGTGCTTTTCACATTTGCATTTGAATTTT**C**GAGTTCCCAGGATGTGTTTTTGTGCTCATCGATGT (SEQ ID NO: 53) | CACATGGGGCATTAAGAATCGCCCAGGGAGGAGGGAGAACGCGTGCTTTTCACATTTGCATTTGAATTTT**T**GAGTTCCCAGGATGTGTTTTTGTGCTCATCGATGT (SEQ ID NO: 54) | CACATGGGGGCATTAAGANT (rs3739005_c2_2_F; SEQ ID NO: 109) | ACATCGATGAGCACAAAAACAC (rs3739005_c2_2_R; SEQ ID NO: 110) |
| rs530022 | 1 | GGGCTCTGAGGTGTGTGAAATAAAAACAAATGTCCATGTCTGTCCTTTTATGGCATTTTGGGACTTTACATTTCAAACATTTCAGACATGTATCACAACACGA**A**GGAATAACAGTTCCAGGGATATCT (SEQ ID NO: 55) | GGGCTCTGAGGTGTGTGAAATAAAAACAAATGTCCATGTCTGTCCTTTTATGGCATTTTGGGACTTTACATTTCAAACATTTCAGACATGTATCACAACACGA**G**GGAATAACAGTTCCAGGGATATCT (SEQ ID NO: 56) | GGGCTCTGAGGTGTGTGAAA (rs530022_c1_2_F; SEQ ID NO: 111) | AGATATCCCTGGAACTGTTATTCC (rs530022_c1_2_R; SEQ ID NO: 112) |

Example 6

Simultaneous Determination of Aneuploidy and Fetal Fraction

Enrichment of Fetal and Maternal Nucleic Acids in a cfDNA Sequencing Library Sample To enrich the fetal and maternal cfDNA contained in a primary sequencing library constructed using purified fetal and maternal cfDNA, a portion of a purified cfDNA sample was used for amplifying polymorphic target nucleic acid sequences, and for preparing a sequencing library of amplified polymorphic target nucleic acids, which was used to enrich the fetal and maternal nucleic acid sequences comprised in the primary library.

A primary sequencing library was prepared using purified cfDNA as described in Example 1.

A target sequencing library was prepared as follows, cfDNA contained in 51 μl of purified cfDNA was amplified in a reaction volume of 50 μl containing 7.5 μl of a 1 μM primer mix (Table 5), 10 μl of NEB 5× Mastermix and 27 μl water. Thermal cycling was performed with the Gene Amp9700 (Applied Biosystems). Using the following cycling conditions: incubating at 95° C. for 1 minute, followed by 30 cycles at 95° C. for 20 seconds, 68° C. for 1 minute, and 68° C. for 30 s, which was followed by a final incubation at 68° C. for 5 minutes. A final hold at 4° C. was added until the samples were removed for combining with the unamplified portion of the purified cfDNA sample. The amplified product was purified using the Agencourt AMPure XP PCR purification system (Part No. A63881; Beckman Coulter Genomics, Danvers, Mass.). A final hold at 4° C. was added until the samples were removed for preparing the target library. The amplified product was analyzed with a 2100 Bioanalyzer (Agilent Technologies, Sunnyvale, Calif.), and the concentration of amplified product determined. One fifth of the purified amplified product was used to prepare a target sequencing library of amplified polymorphic nucleic acids as described in Example 2. The primary and the target sequencing libraries were each diluted to 10 nM, and the target library was combined at a ratio of 1:9 with the sequencing library to provide an enriched sequencing library. Sequencing of the enriched library and analysis of the sequencing data was performed as described in Example 3.

a. Determination of Fetal Fraction

Determination of fetal fraction was performed as described in Example 5, and fetal fraction was calculated as described above i.e.

$$\%\ \text{fetal fraction allele}_x = ((\Sigma\text{Fetal sequence tags for allele}_x)/(\Sigma\text{Maternal sequence tags for allele}_x)) \times 100$$

TABLE 7

Simultaneous Determination of Aneuploidy and Fetal Fraction: Determination of Fetal Fraction

| Sample ID (karyotype) | SNP | SNP TAG COUNTS | FETAL FRACTION (%) |
|---|---|---|---|
| 11409 | rs13182883.1\|Chr.5\|length = 111\|allele = A | 261 | 4.41 |
| (47, XY + 21) | rs13182883.2\|Chr.5\|length = 111\|allele = G | 5918 | |
| | rs740598.1\|Chr.10\|length = 114\|allele = A | 5545 | 7.30 |
| | rs740598.2\|Chr.10\|length = 114\|allele = G | 405 | |
| | rs8078417.1\|Chr.17\|length = 110\|allele = C | 8189 | 6.74 |
| | rs8078417.2\|Chr.17\|length = 110\|allele = T | 121470 | |
| | rs576261.1\|Chr.19\|length = 114\|allele = A | 58342 | 7.62 |
| | rs576261.2\|Chr.19\|length = 114\|allele = C | 4443 | |
| Fetal Fraction (Mean ± S.D.) = 6.5 ± 1.5 | | | |
| 95133 | rs1109037.1\|Chr.2\|length = 126\|allele = A | 12229 | 2.15 |
| (47, XX + 18) | rs1109037.2\|Chr.2\|length = 126\|allele = G | 263 | |
| | rs13218440.1\|Chr.6\|length = 139\|allele = A | 55949 | 3.09 |
| | rs13218440.2\|Chr.6\|length = 139\|allele = G | 1729 | |
| | rs7041158.1\|Chr.9\|length = 117\|allele = C | 7281 | 4.12 |
| | rs7041158.2\|Chr.9\|length = 117\|allele = T | 300 | |
| | rs7205345.1\|Chr.16\|length = 116\|allele = C | 53999 | 2.14 |
| | rs7205345.2\|Chr.16\|length = 116\|allele = G | 1154 | |
| Fetal Fraction (Mean ± S.D.) = 2.9 ± 0.9 | | | |
| 51236 | rs13218440.1\|Chr.6\|length = 139\|allele = A | 1119 | 1.65 |
| (46, XY + 13) | rs13218440.2\|Chr.6\|length = 139\|allele = G | 67756 | |
| | rs560681.1\|Chr.1\|length = 111\|allele = A | 14123 | 5.18 |
| | rs560681.2\|Chr.1\|length = 111\|allele = G | 732 | |
| | rs7205345.1\|Chr.16\|length = 116\|allele = C | 18176 | 1.63 |
| | rs7205345.2\|Chr.16\|length = 116\|allele = G | 296 | |
| | rs9866013.1\|Chr.3\|length = 121\|allele = C | 117 | 2.33 |
| | rs9866013.2\|Chr.3\|length = 121\|allele = T | 5024 | |
| Fetal Fraction (Mean ± S.D.) = 2.7 ± 1.7 | | | |
| 54430 | rs1109037.1\|Chr.2\|length = 126\|allele = A | 19841 | 1.80 |
| (45, XO) | rs1109037.2\|Chr.2\|length = 126\|allele = G | 357 | |
| | rs9866013.1\|Chr.3\|length = 121\|allele = C | 12931 | 3.81 |
| | rs9866013.2\|Chr.3\|length = 121\|allele = T | 493 | |
| | rs7041158.1\|Chr.9\|length = 117\|allele = C | 2800 | 4.25 |
| | rs7041158.2\|Chr.9\|length = 117\|allele = T | 119 | |
| | rs740598.1\|Chr.10\|length = 114\|allele = A | 12903 | 4.87 |
| | rs740598.2\|Chr.10\|length = 114\|allele = G | 628 | |
| | rs10773760.1\|Chr.12\|length = 128\|allele = A | 46324 | 4.65 |
| | rs10773760.2\|Chr.12\|length = 128\|allele = G | 2154 | |

Fetal Fraction (Mean ± S.D.) = 3.9 ± 1.2 b. Determination of Aneuploidy

Determination of aneuploidy of chromosomes 21, 13, 18 and X was performed using chromosome doses as described in Example 4. Chromosome 21 dose was determined using chromosome 14 as the normalizing chromosome; chromosome 13 dose was determined using the group of chromosomes 3, 4, 5, and 6 as the normalizing chromosome; chromosome 18 dose was determined using chromosome 8 as the normalizing chromosome; and chromosome X dose was determined using chromosome 4 as the normalizing chromosome. Thresholds were calculated to be 2 standard deviations above and below the mean determined in the qualified samples.

Table 7 shows the data for the determination of fetal fraction in exemplary samples. Calculated chromosome dose values for chromosomes 21, 18, 13, X and Y in corresponding exemplary test samples are given in Tables 8, 9, 10, 11, and 12, respectively.

Trisomy 21

Table 8 provides the calculated dose for chromosome 21 in the test sample (11409). Chromosome 14 was used as the normalizing chromosomes. The calculated threshold for the positive diagnosis of T21 aneuploidy was set at 2 standard deviations from the mean of the qualified (normal) samples. A diagnosis for T21 was given based on the chromosome dose in the test sample being greater than the set threshold. All twelve of the T21 samples that were confirmed to be T21 by karyotype were identified in a population of 48 blood samples.

TABLE 8

Chromosome Dose for a T21 aneuploidy

| Chromosome | Sequence Tag Density | Chromosome Dose for Chr 21 | Threshold |
|---|---|---|---|
| Chr21 | 264,404 | 0.439498 | 0.410634 |
| Chr14 | 601,605 | | |

Trisomy 18

Table 9 provides the calculated dose for chromosome 18 in a test sample (95133). Chromosome 8 was used as the normalizing chromosome. In this instance, chromosome 8 had the lowest variability and greatest differentiability. The calculated threshold for the positive diagnosis of T18 aneuploidy was set at greater than 2 standard deviations from the mean of the qualified (non-T18) samples. A diagnosis for T18 was given based on the chromosome dose in the test sample being greater than the set threshold. Eight T18 samples were identified using chromosome doses, and were confirmed to be T18 by karotyping.

TABLE 9

| Chromosome Dose for a T18 aneuploidy | | | |
|---|---|---|---|
| Chromosome | Sequence Tag Density | Chromosome Dose for Chr 18 | Threshold |
| Chr18 | 604,291 | 0.550731 | 0.533297 |
| Chr8 | 1,097,253 | | |

Trisomy 13

Tables 10 and 11 provide the calculated dose for chromosome 13 in a test sample (51236). The calculated threshold for the positive diagnosis of T13 aneuploidy was set at 2 standard deviations from the mean of the qualified (non-T13) samples. The chromosome dose for chromosome 13 provided in Table 10 was calculated using sequence tag density for chromosome 4 as the normalizing chromosome, while the dose given on Table 11 was determined using the average of the sequence tag densities ratios for the group of chromosomes 3, 4, 5, and 6 as the normalizing chromosome. A diagnosis for T13 was given based on the chromosome dose in the test sample being greater than the set threshold. One T13 sample was identified using chromosome doses, and were confirmed to be T13 by karyotyping.

The data show that the combination of chromosomes 3, 4, 5, and 6 provide a variability (1.06) that is similar than that of chromosome 4 (1.01), demonstrating that a group of chromosomes can be used as the normalizing chromosome to determine chromosome doses and identify aneuploidies.

TABLE 10

| Chromosome Dose for a T13 aneuploidy | | | |
|---|---|---|---|
| Chromosome | Sequence Tag Density | Chromosome Dose for Chr 13 | Threshold |
| Chr13 | 669,872 | 0.538140 | 0.536044 |
| Chr4 | 1,244,791 | | |

TABLE 11

| Chromosome Dose for a T13 aneuploidy | | | |
|---|---|---|---|
| Chromosome | Sequence Tag Density | Chromosome Dose for Chr 13 | Threshold |
| Chr13 | 669,872 | 0.532674 | 0.515706 |
| Chr3 | 1,385,881 | | |
| Chr4 | 1,244,791 | | |
| Chr5 | 1,229,257 | | |
| Chr6 | 1,170,331 | | |

Turner Syndrome (Monosomy X)

Three samples having a chromosome dose less than that of the set threshold were identified as having less than one X chromosome. The same samples were determined to have a Y chromosome dose that was less than the set threshold, indicating that the samples did not have a Y chromosome.

The calculated doses for chromosomes X and Y in the exemplary monosomy X test sample (54430) are given in Table 12. Chromosome 4 was selected as the normalizing chromosome to calculate the dose for chromosome X; and all chromosomes i.e. 1-22, and Y, were used as the normalizing chromosomes. The calculated threshold for the positive diagnosis of Turner Syndrome (monosomy X) was set for the X chromosome at <–2 standard deviations from the mean, and for the absence of the Y chromosome at <–2 standard deviations from the mean for qualified (non-monosomy X) samples.

TABLE 12

| Chromosome Dose for a Turner Syndrome (monosomy X) | | | |
|---|---|---|---|
| Chromosome | Sequence Tag Density | Chromosome Dose for Chr X | Threshold |
| ChrX | 904,049 | 0.777990 | 0.797603 |
| Chr4 | 1,162,031 | | |
| ChrY | 390 | 0.0004462 | 0.002737754 |
| Chr (1-22, X) [average] | 874,108.1 | | |

Thus, the method enables the simultaneous determination of chromosomal aneuploidies and fetal fraction by massively parallel sequencing of a maternal sample comprising a mixture of fetal and maternal cfDNA that has been enriched for a plurality of polymorphic sequences each comprising a SNP. In this example, the mixture of fetal and maternal nucleic acids was enriched by combining a portion of a sequencing library that was constructed from amplified fetal and maternal polymorphic sequences with a sequencing library that was constructed from the remaining unamplified original fetal and maternal cfDNA mixture.

Example 7

Simultaneous Determination of Aneuploidy and Fetal Fraction

Enrichment of Fetal and Maternal Nucleic Acids in a Purified cfDNA Sample

To enrich the fetal and maternal cfDNA contained in a purified sample of cfDNA extracted from a maternal plasma sample, a portion of the purified cfDNA was used for amplifying polymorphic target nucleic acid sequences each comprising one SNP chosen from the panel of SNPs given in Table 6.

Cell-free plasma was obtained from a maternal blood sample, and cfDNA was purified from the plasma sample as described in Example 1. The final concentration was determined to be 92.8 pg/μl.

cfDNA contained in 5 μl of purified cfDNA was amplified in a reaction volume of 50 μl containing 7.5 μl of a 1 uM primer mix (Table 5), 10 μl of NEB 5× Mastermix and 27 μl water. Thermal cycling was performed with the Gene Amp9700 (Applied Biosystems). Using the following cycling conditions: incubating at 95° C. for 1 minute, followed by 30 cycles at 95° C. for 20 seconds, 68° C. for 1 minute, and 68° C. for 30 s, which was followed by a final incubation at 68° C. for 5 minutes. A final hold at 4° C. was added until the samples were removed for combining with the unamplified portion of the purified cfDNA sample. The amplified product was purified using the Agencourt AMPure XP PCR purification system (Part No. A63881; Beckman Coulter Genomics, Danvers, Mass.), and the concentration quantified using the Nanodrop 2000 (Thermo Scientific, Wilmington, Del.). The purified amplification product was diluted 1:10 in water and 0.9 μl (371 pg) added to 40 μl of purified cfDNA sample to obtain a 10% spike. The enriched fetal and maternal cfDNA present in the purified cfDNA sample was used for preparing a sequencing library, and was sequenced as described in Example 2.

Table 13 provides the tag counts obtained for each of chromosomes 21, 18, 13, X and Y i.e. sequence tag density, and the tag counts obtained for the informative polymorphic sequences contained in the SNP reference genome i.e. SNP tag density. The data show that sequencing information can be obtained from sequencing a single library constructed from a purified maternal cfDNA sample that has been enriched for sequences comprising SNPs to simultaneously determine the presence or absence of aneuploidy and the fetal fraction. In the example given, the data show that the fraction of fetal DNA in plasma sample AFR105 was quantifiable from the sequencing results of five informative SNPs and determined to be 3.84%. Sequence tag densities are provided for chromosomes 21, 13, 18, X and Y. Sample AFR105 was the only sample that was subjected to the protocol of enriching purified cfDNA for amplified polymorphic sequences. Thus, coefficients of variation and tests for differentiability were not provided. However, the example shows that the enrichment protocol provides the requisite tag counts for determining aneuploidy and fetal fraction from a single sequencing process.

dCTP, dGTP and dTTP). Thermal cycling was performed with the Gene Amp9700 (Applied Biosystems) using the following cycling conditions: incubating at 95° C. for 3 minutes, followed by 35 cycles at 95° C. for 20 seconds, 55° C. for 30 s, and 70° C. for 1 minute, which was followed by a final incubation at 68° C. for 5 minutes. A final hold at 4° C. was added until the samples were removed for combining with the unamplified portion of the cell-free plasma. The amplified product was diluted 1:2 with water and analyzed using the Bioanalyzer. An additional 3 μl of amplified product was diluted with 11.85 μl of water to obtain a final concentration of 2 ng/μl. 2.2 μl of the diluted amplified product was combined with the remaining plasma sample. The enriched fetal and maternal cfDNA present in the plasma sample was purified as described in Example 1, and

TABLE 13

Simultaneous Determination of Aneuploidy and Fetal Fraction:
Enrichment of fetal and maternal nucleic acids in a purified cfDNA sample Aneuploidy

| | Chromosome 21 | Chromosome 18 | Chromosome 13 | Chromosome X | Chromosome Y |
|---|---|---|---|---|---|
| Sequence Tag Density | 178763 | 359529 | 388204 | 572330 | 2219 |
| Karyotype | Unaffected | Unaffected | Unaffected | Unaffected | Unaffected |

Fetal Fraction

| SNP | SNP TAG DENSITY | FETAL FRACTION (%) |
|---|---|---|
| rs10773760.1\|Chr.12\|length = 128\|allele = A | 18903 | 2.81 |
| rs10773760.2\|Chr.12\|length = 128\|allele = G | 532 | |
| rs1109037.1\|Chr.2\|length = 126\|allele = A | 347 | 5.43 |
| rs1109037.2\|Chr.2\|length = 126\|allele = G | 6394 | |
| rs2567608.1\|Chr.20\|length = 110\|allele = A | 94503 | 1.74 |
| rs2567608.2\|Chr.20\|length = 110\|allele = G | 1649 | |
| rs7041158.1\|Chr.9\|length = 117\|allele = C | 107 | 5.61 |
| rs7041158.2\|Chr.9\|length = 117\|allele = T | 6 | |
| rs8078417.1\|Chr.17\|length = 110\|allele = C | 162668 | 3.61 |
| rs8078417.2\|Chr.17\|length = 110\|allele = T | 5877 | |

Fetal Fraction (Mean ± S.D.) = 3.8 ± 1.7

Example 8

Simultaneous Determination of Aneuploidy and Fetal Fraction

Enrichment of Fetal and Maternal Nucleic Acids in a Plasma Sample

To enrich the fetal and maternal cfDNA contained in an original plasma sample derived from a pregnant woman, a portion the original plasma sample was used for amplifying polymorphic target nucleic acid sequences each comprising one SNP chosen from the panel of SNPs given in Table 14, and a portion of the amplified product was combined with the remaining original plasma sample.

cfDNA contained in 15 μl of cell-free plasma was amplified in a reaction volume of 50 μl containing 9 ul of a 1 μM mixture of primers (15 plexTable 5), 1 μl of Phusion blood DNA polymerase, 25 ul of the 2× Phusion blood PCR buffer containing deoxynucleotide triphosphates (dNTPs: dATP, used for preparing a sequencing library. Sequencing and analysis of the sequencing data was performed as described in Examples 2 and 3.

The results are given in Table 14. In the example given, the data show that the fraction of fetal DNA in plasma sample SAC2517 was quantifiable from the sequencing results of one informative SNP and determined to be 9.5%. In the example given, sample SAC2517 was shown by karyotyping to be unaffected for aneuploidies of chromosomes 21, 13, 18, X and Y. Sequence tag densities are provided for chromosomes 21, 13, 18, X and Y. Sample SAC2517 was the only sample that was subjected to the protocol of enriching plasma cfDNA for amplified polymorphic sequences. Thus, coefficients of variation and tests for differentiability could not determined. The example demonstrates that enriching the mixture of fetal and maternal cfDNA present in a plasma sample for nucleic acid sequences that comprise at least one informative SNP can be used to provide the requisite sequence and SNP tag counts for determining aneuploidy and fetal fraction from a single sequencing process.

TABLE 14

| Simultaneous Determination of Aneuploidy and fetal fraction: Enrichment of fetal and maternal nucleic acids in a plasma sample | | | | | |
|---|---|---|---|---|---|
| Aneuploidy | | | | | |
| | Chromosome 21 | Chromosome 18 | Chromosome 13 | Chromosome X | Chromosome Y |
| Sequence Tag Density | 183851 | 400582 | 470526 | 714055 | 2449 |
| Karyotype | Unaffected | Unaffected | Unaffected | Unaffected | Unaffected |

| Fetal Fraction | | |
|---|---|---|
| SNP | TAG COUNTS | FETAL FRACTION (%) |
| rs10773760.1\|Chr.12\|length = 128\|allele = A | 8536 | 9.49 |
| rs10773760.2\|Chr.12\|length = 128\|allele = G | 89924 | |

Example 9

Simultaneous Determination of Aneuploidy and Fetal Fraction in Maternal Samples Enriched for Polymorphic Sequences Comprising STRs To simultaneously determine the presence or absence of an aneuploidy and the fetal fraction in a mixture of fetal and maternal cfDNA obtained from a maternal sample, the mixture is enriched for polymorphic sequences comprising STRs, sequenced and analyzed. Enrichment can be of a sequencing library as described in Example 6, of a purified cfDNA sample as described in Example 7, or of a plasma sample as described in Example 8. In each case, sequencing information is obtained from sequencing a single library, which enables for simultaneously determining the presence or absence of an aneuploidy and the fetal fraction. STRs that are amplified are chosen from the codis and non-codis STRs disclosed in Table 9, and amplification of the polymorphic STR sequences is obtained using the corresponding sets of primers provided. The STRs of Table 9 have been disclosed previously, and STRs CSF1PO, FGA, D7S820, D13S317, D16S539, D18S51, D21S11, D2S1338 (see Table 5), have been used to determine fetal fraction in plasma cfDNA samples obtained from women pregnant with either male or female fetuses (see U.S. Provisional applications 61/296,358 and 61/360,837). Quantification of the STRs was performed using capillary electrophoresis (see Example 11). Example 11 shows that STRs can be used to determine fetal fraction.

TABLE 15

| CODIS and NON-CODIS miniSTRs | | | | |
|---|---|---|---|---|
| STR Locus (Marker Name) | Chromosome Location | Site Range (bp) | GenBank Accession | Primer Sequences Forward/Reverse |
| Codis miniSTR loci* | | | | |
| CSF1PO | 5q33.1 | 89-129 | X14720 | ACAGTAACTGCCTTCATAGATAG (CSF1PO_F; SEQ ID NO: 113) GTGTCAGACCCTGTTCTAAGTA (CSF1PO_R; SEQ ID NO: 114) |
| FGA | 4q31.3 | 125-281 | M64982 | AAATAAAATTAGGCATATTTACAAGC (FGA_F; SEQ ID NO: 115) GCTGAGTGATTTGTCTGTAATTG(FGA_R; SEQ ID NO: 116) |
| TH01 | 11p5.5 | 51-98 | D00269 | CCTGTTCCTCCCTTATTTCCC(TH01_F; SEQ ID NO: 117) GGGAACACAGACTCCATGGTG(TH01_R; SEQ ID NO: 118) |
| TPOX | 2p25.3 | 65-101 | M68651 | CTTAGGGAACCCTCACTGAATG(TPOX_F; SEQ ID NO: 119) GTCCTTGTCAGCGTTTATTTGC(TPOX_R; SEQ ID NO: 120) |
| vWA | 12p13.31 | 88-148 | M25858 | AATAATCAGTATGTGACTTGGATTGA (vWA_F; SEQ ID NO: 121) ATAGGATGGATGGATAGATGGA(vWA_R; SEQ ID NO: 122) |
| D3S1358 | 3p21.31 | 72-120 | NT_005997 | CAGAGCAAGACCCTGTCTCAT(D3S1358_F; SEQ ID NO: 123) TCAACAGAGGCTTGCATGTAT(D3S1358_R; SEQ ID NO: 124) |

TABLE 15-continued

| STR Locus (Marker Name) | Chromosome Location | Site Range (bp) | GenBank Accession | Primer Sequences Forward/Reverse |
|---|---|---|---|---|
| CODIS and NON-CODIS miniSTRs | | | | |
| D5S818 | 5q23.2 | 81-117 | AC008512 | GGGTGATTTTCCTCTTTGGT(D5S818_F; SEQ ID NO: 125)<br>AACATTTGTATCTTTATCTGTATCCTTAT ITAT(D5S818_R; SEQ ID NO: 126) |
| D7S820 | 7q21.11 | 136-176 | AC004848 | GAACACTTGTCATAGTTTAGAACGAAC (D7S820_F; SEQ ID NO: 127)<br>TCATTGACAGAATTGCACCA(D7S820_R; SEQ ID NO: 128) |
| D8S1179 | 8q24.13 | 86-134 | AF216671 | TTTGTATTTCATGTGTACATTCGTATC (D7S820_F; SEQ ID NO: 129)<br>ACCTATCCTGTAGATTATTTTCACTGTG (D7S820_R; SEQ ID NO: 130) |
| D13S317 | 13q31.1 | 88-132 | AL353628 | TCTGACCCATCTAACGCCTA(D13S317_F; SEQ ID NO: 131)<br>CAGACAGAAAGATAGATAGATGATTGA (D13S317_R; SEQ ID NO: 132) |
| D16S539 | 16q24.1 | 81-121 | AC024591 | ATACAGACAGACAGACAGGTG(D16S539_ F; SEQ ID NO: 133)<br>GCATGTATCTATCATCCATCTCT(D16S539_ R; SEQ ID NO: 134) |
| D18S51 | 18q21.33 | 113-193 | AP001534 | TGAGTGACAAATTGAGACCTT(D18S51_F; SEQ ID NO: 135)<br>GTCTTACAATAACAGTTGCTACTATT (D18S51_R; SEQ ID NO: 136) |
| D21S11 | 21q21.1 | 153-221 | AP000433 | ATTCCCCAAGTGAATTGC(D21S1I_F; SEQ ID NO: 137)<br>GGTAGATAGACTGGATAGATAGACGA (D21S11_R; SEQ ID NO: 138) |
| D2S1338 | 2q35 | 90-142 | AC01036 | TGGAAACAGAAATGGCTTGG(D2S1338_F; SEQ ID NO: 139)<br>GATTGCAGGAGGGAAGGAAG(D2S1338_ R; SEQ ID NO: 140) |
| Penta D | 21q22.3 | 94-167 | AP001752 | GAGCAAGACACCATCTCAAGAA(Penta D_F; SEQ ID NO: 141)<br>GAAATTTTACATTTATGTTTATGATTCTC T(Penta D_R; SEQ ID NO: 142) |
| Penta E | 15q26.2 | 80-175 | AC027004 | GGCGACTGAGCAAGACTC(Penta E_F; SEQ ID NO: 143)<br>GGTTATTAATTGAGAAAACTCCTTACA (Penta E_R; SEQ ID NO: 144) |
| Non-Codis miniSTR loci* | | | | |
| D22S1045 | 22q12.3 | 82-115 | AL022314 (17) | ATTTTCCCCGATGATAGTAGTCT (D22S1045_F; SEQ ID NO: 145)<br>GCGAATGTATGATTGGCAATATTTTT (D22S1045_R; SEQ ID NO: 146) |
| D20S1082 | 20q13.2 | 73-101 | AL158015 | ACATGTATCCCAGAACTTAAAGTAAAC (D20S1082_F; SEQ ID NO: 147)<br>GCAGAAGGGAAAATTGAAGCTG(D20S1082_ R; SEQ ID NO: 148) |
| D20S482 | 20p13 | 85-126 | AL121781 (14) | CAGAGACACCGAACCAATAAGA(D20S482_ F; SEQ ID NO: 149)<br>GCCACATGAATCAATTCCTATAATAAA (D20S482_R; SEQ ID NO: 150) |
| D18W853 | 18p11.31 | 82-104 | AP005130 (11) | GCACATGTACCCTAAAACTTAAAAT (D18S853F; SEQ ID NO: 151)<br>GTCAACCAAAACTCAACAAGTAGTAA (D18S853_R; SEQ ID NO: 152) |
| D17W1301 | 17q25.1 | 114-139 | AC016888 (12) | AAGATGAAATTGCCATGTAAAAATA (D17S1301_F; SEQ ID NO: 153)<br>GTGTGTATAACAAAATTCCTATGATGG (D17S1301R; SEQ ID NO: 154) |
| D17S974 | 17p13.1 | 114-139 | AC034303 (10) | GCACCCAAAACTGAATGTCATA(D17S974_ F; SEQ ID NO: 155)<br>GGTGAGAGTGAGACCCIGTC(D17S974_R; SEQ ID NO: 156) |
| D14S1434 | 14q32.13 | 70-98 | AL121612 (13) | TGTAATAACTCTACGACTGTCTGTCTG (D14S1434_F; SEQ ID NO: 157)<br>GAATAGGAGGTGGATGGATGG(D14S1434_ R; SEQ ID NO: 158) |

TABLE 15-continued

CODIS and NON-CODIS miniSTRs

| STR Locus (Marker Name) | Chromosome Location | Site Range (bp) | GenBank Accession | Primer Sequences Forward/Reverse |
|---|---|---|---|---|
| D12ATA63 | 12q23.3 | 76-106 | AC009771 (13) | GAGCGAGACCCTGTCTCAAG(D12ATA63_F; SEQ ID NO: 159) GGAAAAGACATAGGATAGCAATTT (D12ATA63_R; SEQ ID NO: 160) |
| D11S4463 | 11q25 | 88-116 | AP002806 (14) | TCTGGATTGATCTGTCTGTCC(D11S4463_F; SEQ ID NO: 161) GAATTAAATACCATCTGAGCACTGAA (D11S4463_R; SEQ ID NO: 162) |
| D10S1435 | 10p15.3 | 82-139 | AL354747 (11) | TGTTATAATGCATTGAGTTTTATTCTG (D10S1435_F; SEQ ID NO: 163) GCCTGTCTCAAAAATAAAGAGATAGAC A(D10S1435_R; SEQ ID NO: 164) |
| D10S1248 | 10q26.3 | 79-123 | AL391869 (13) | TTAATGAATTGAACAAATGAGTGAG (D10S1248_F; SEQ ID NO: 165) GCAACTCTGGTTGTATTGTCTTCAT (D10S1248_R; SEQ ID NO: 166) |
| D9S2157 | 9q34.2 | 71-107 | AL162417 (10) | CAAAGCGAGACTCTGTCTCAA(D9S2157_F; SEQ ID NO: 167) GAAAATGCTATCCTCTTTGGTATAAAT (D9S2157_R; SEQ ID NO: 168) |
| D9S1122 | 9q21.2 | 93-125 | AL161789 (12) | GGGTATTTCAAGATAACTGTAGATAGG (D9S1122_F; SEQ ID NO: 168) GCTTCTGAAAGCTTCTAGTTTACC(D9S1122_R; SEQ ID NO: 170) |
| D8S1115 | 8p11.21 | 63-96 | AC090739 (9) | TCCACATCCTCACCAACAC(D8S1115_F; SEQ ID NO: 171) GCCTAGGAAGGCTACTGTCAA(D8S1115_R; SEQ ID NO: 172) |
| D6S1017 | 6p21.1 | 81-110 | AL035588 10) | CCACCCGTCCATTTAGGC(D6S1017_F; SEQ ID NO: 173) GTGAAAAAGTAGATATAATGGTTGGTG (D6S1017_R; SEQ ID NO: 174) |
| D6S474 | 6q21 | 107-136 | AL357514 (17) | GGTTTTCCAAGAGATAGACCAATTA (D6S474_F; SEQ ID NO: 175) GTCCTCTCATAAATCCCTACTCATATC (D6S474_R; SEQ ID NO: 176) |
| D5S2500 | 5q11.2 | 85-126 | AC008791 (17) | CTGTTGGTACATAATAGGTAGGTAGGT (D5S2500_F; SEQ ID NO: 177) GTCGTGGGCCCCATAAATC(D5S2500_R; SEQ ID NO: 178) |
| D4S2408 | 4p15.1 | 85-109 | AC110763 (9) | AAGGTACATAACAGTTCAATAGAAAGC (D4S2408_F; SEQ ID NO: 179) GTGAAATGACTGAAAAATAGTAACCA (D4S2408_R; SEQ ID NO: 180) |
| D4S2364 | 4q22.3 | 67-83 | AC022317 (9) | CTAGGAGATCATGTGGGTATGATT (D4S2364U_F; SEQ ID NO: 181) GCAGTGAATAAATGAACGAATCTGGA (D4S2364_R; SEQ ID NO: 182) |
| D3S4529 | 3p12.1 | 111-139 | AC117452 (13) | CCCAAAATTACTTGAGCCAAT(D3S452_F; SEQ ID NO: 18:3) GAGACAAAATGAAGAAACAGACAG(D3S452_R; SEQ ID NO: 184) |
| D3S3053 | 3q26.31 | 84-108 | AC069259 (9) | TCTTTGCTCTCATGAATAGATCAGT (D3S3053_F; SEQ ID NO: 185) GTTTGTGATAATGAACCCACTCAG (D3S3053)R; SEQ ID NO: 186) |
| D2S1776 | 2q24.3 | 127-161 | AC009475 (11) | TGAACACAGATGTTAAGTGTGTATATG (D2S1776_F; SEQ ID NO: 187) GTCTGAGGTGGACAGTTATGAAA(D2S1776_R; SEQ ID NO: 188) |
| D2S441 | 2p14 | 78-110 | AC079112 (12) | CTGTGGCTCATCTATGAAAACTT(D2S441_F; SEQ ID NO: 189) GAAGTGGCTGTGGTGTTATGAT(D2S441_R; SEQ ID NO: 190) |
| D1S1677 | 1q23.3 | 81-117 | AL513307 (15) | TTCTGTTGGTATAGAGCAGTGTTT(D1S1677_F; SEQ ID NO: 191) GTGACAGGAAGGACGGAATG(D1S1677_R; SEQ ID NO: 192) |
| D1S1627 | 1p21.1 | 81-100 | AC093119 (13) | CATGAGGTTTGCAAATACTATCTTAAC (D1S1627_F; SEQ ID NO: 193) GTTTTAATTTTCTCCAAATCTCCA(D1S1627_R; SEQ ID NO: 194) |

TABLE 15-continued

CODIS and NON-CODIS miniSTRs

| STR Locus (Marker Name) | Chromosome Location | Site Range (bp) | GenBank Accession | Primer Sequences Forward/Reverse |
|---|---|---|---|---|
| D1GATA113 | 1p36.23 | 81-105 | Z97987 (11) | TCTTAGCCTAGATAGATACTTGCTTCC (D1GATA113_F; SEQ ID NO: 195) GTCAACCTTTGAGGCTATAGGAA (D1GATA113_R; SEQ ID NO: 196) |

*(Butler et al., J Forensic Set 5: 1054-1064; Hill et al., Poster #44- 17th International Symposium on Human Identification - 2006)

Sequencing of the library enriched for polymorphic STR sequences is performed using a NGS technology e.g. sequencing by synthesis. Sequence reads of lengths of at least 100 bp are aligned to a reference genome e.g. the human reference genome NCBI36/hg18 sequence, and to an STR genome, and the number of sequence tags and STR tags obtained is used to determine the presence or absence of aneuploidy and the fetal fraction, respectively. The STR reference genome includes the sequences of amplicons amplified from the given primers.

Example 10

Simultaneous Determination of Aneuploidy and Fetal Fraction in Maternal Samples Enriched for Polymorphic Sequences Comprising Tandem SNPs To determine simultaneously aneuploidy and fetal fraction in maternal samples comprising fetal and maternal nucleic acids, plasma samples, purified cfDNA samples, and sequencing library samples are enriched for polymorphic target nucleic acid sequences each comprising a pair of tandem SNPs selected from rs7277033-rs2110153; rs2822654-rs1882882; rs368657-rs376635; rs2822731-rs2822732; rs1475881-rs7275487; rs1735976-rs2827016; rs447340-rs2824097; rs418989-rs13047336; rs987980-rs987981; rs4143392-rs4143391; rs1691324-rs13050434; rs11909758-rs9980111; rs2826842-rs232414; rs1980969-rs1980970; rs9978999-rs9979175; rs1034346-rs12481852; rs7509629-rs2828358; rs4817013-rs7277036; rs9981121-rs2829696; rs455921-rs2898102; rs2898102-rs458848; rs961301-rs2830208; rs2174536-rs458076; rs11088023-rs11088024; rs1011734-rs1011733; rs2831244-rs9789838; rs8132769-rs2831440; rs8134080-rs2831524; rs4817219-rs4817220; rs2250911-rs2250997; rs2831899-rs2831900; rs2831902-rs2831903; rs11088086-rs2251447; rs2832040-rs11088088; rs2832141-rs2246777; rs2832959-rs9980934; rs2833734-rs2833735; rs933121-rs933122; rs2834140-rs12626953; rs2834485-rs3453; rs9974986-rs2834703; rs2776266-rs2835001; rs1984014-rs1984015; rs7281674-rs2835316; rs13047304-rs13047322; rs2835545-rs4816551; rs2835735-rs2835736; rs13047608-rs2835826; rs2836550-rs2212596; rs2836660-rs2836661; rs465612-rs8131220; rs9980072-rs8130031; rs418359-rs2836926; rs7278447-rs7278858; rs385787-rs367001; rs367001-rs386095; rs2837296-rs2837297; and rs2837381-rs4816672. The primers used for amplifying the target sequences comprising the tandem SNPs are designed to encompass both SNP sites. For example, the forward primer is designed to encompass the first SNP, and the reverse primer is designed to encompass the second of the tandem SNP pair i.e. each of the SNP sites in the tandem pair is encompassed within the 36 bp generated by the sequencing method. Paired-end sequencing can be used to identify all sequences encompassing the tandem SNP sites. Exemplary sets of primers that are used to amplify the tandem SNPs disclosed herein are set rs7277033-rs2110153_F: TCCTGGAAACAAAAGTATT (SEQ ID NO: 197) and rs7277033-rs2110153_R: AACCTTACAACAAAGCTAGAA (SEQ ID NO:198), set rs2822654-rs1882882_F: ACTAAGCCTTGGGGATCCAG (SEQ ID NO:199) and rs2822654-rs1882882_R: TGCTGTGGAAATACTAAAAGG (SEQ ID NO:200), set rs368657-rs376635_F:CTCCAGAGGTAATCCTGTGA (SEQ ID NO:201) and rs368657-rs376635_R:TGGTGTGAGATGGTATCTAGG (SEQ ID NO:202), rs2822731-rs2822732_F:GTATAATCCATGAATCTTGTTF (SEQ ID NO:203) and rs2822731-rs2822732_R:TTCAAATTGTATATAAGAGAGT (SEQ ID NO:204), rs1475881-rs7275487_F:GCAGGAAAGTTATITITAAT (SEQ ID NO:205) and rs1475881-rs7275487_R:TGCTTGAGAAAGCTAACACTT (SEQ ID NO:206), rs1735976-rs2827016_F:CAGTGTITTGGAAATTGTCTG (SEQ ID NO:207) and rs1735976-rs2827016_R:GGCACTGGGAGATTATTGTA (SEQ ID NO:208), rs447349-rs2824097_F:TCCTGTTGTTAAGTACACAT (SEQ ID NO:209) and rs447349-rs2824097_R:GGGCCGTAATTACTTTTG (SEQ ID NO:210), rs418989-rs13047336_F: ACTCAGTAGGCACTTTGTGTC (SEQ ID NO:211) and rs418989-rs13047336_R:TCTTCCACCACACCAATC (SEQ ID NO:212), rs987980-rs987981_F:TGGCTTTTCAAAGGTAAAA (SEQ ID NO:213) and rs987980-rs987981_R: GCAACGTTAACATCTGAATTT (SEQ ID NO:214), rs4143392-rs4143391_F: rs4143392-rs4143391 (SEQ ID NO:215) and rs4143392-rs4143391_R:ATTTTATATGTCATGATCTAAG (SEQ ID NO:216), rs1691324-rs13050434_F: AGAGATTACAGGTGTGAGC (SEQ ID NO:217) and rs1691324-rs13050434_R: ATGATCCTCAACTGCCTCT (SEQ ID NO:218), rs11909758-rs9980111_F: TGAAACTCAAAAGAGAAAAG (SEQ ID NO:219) and rs11909758-rs9980111_R: ACAGATTTCTACTTAAAAAT (SEQ ID NO:220), rs2826842-rs232414_F: TGAAACTCAAAAGAGAAAAG (SEQ ID NO:221) and rs2826842-rs232414_R: ACAGATTTCTACTTAAAATT (SEQ ID NO:22), rs2826842-rs232414_F: GCAAAGGGGTACTCTATGTA (SEQ ID NO:223) and rs2826842-rs232414_R: TATCGGGTCATCTTGTTAAA (SEQ ID NO:224), rs1980969-rs1980970_F: TCTAACAAAGCTCTGTCCAAAA (SEQ ID NO:225) and rs1980969-rs1980970_R: CCACACTGAATAACTGGAACA (SEQ ID NO:226), rs9978999-rs9979175_F: GCAAGCAAGCTCTCTACCTC (SEQ ID NO:227) and rs9978999-rs9979175_R: TGTTCTTCCAAAATTCACATGC (SEQ ID NO:228), rs1034346-rs12481852_F: ATTTCACTATTCCTTCATTTT (SEQ ID NO:229) and rs1034346-rs12481852_R: TAATTGTTGCACACTAAAT- TAC (SEQ ID NO:230), rs4817013-rs7277036_F: AAAAAGCCACAGAAATCAGTC (SEQ ID NO:231) and rs4817013-rs7277036_R: TTCTTATATCTCACTGGGCATT (SEQ ID NO:232), rs9981121-rs2829696_F: GGATGGTAGAAGAGAAGAAAGG (SEQ ID NO:233) and rs9981121-rs2829696_R: GGATGGTAGAAGAGAAGAAAGG (SEQ ID NO:234), rs455921-rs2898102_F: TGCAAAGATGCAGAACCAAC (SEQ ID NO:235) and rs455921-rs2898102_R: TTTGTTCCTTGTCCTGGCTGA (SEQ ID NO:236), rs2898102-rs458848_F: TGCAAAGATGCAGAACCAAC (SEQ ID NO:237) and rs2898102-rs458848_R: GCCTCCAGCTCTATCCAAGTT (SEQ ID NO:238), rs961301-rs2830208_F: CCTTAATATCTTCCCATGTCCA (SEQ ID NO:239) and rs961301-rs2830208_R: ATTGTTAGTGCCTCTTCTGCTT (SEQ ID NO:240), rs2174536-rs458076_F: GAGAAGTGAGGTCAGCAGCT (SEQ ID NO:241) and rs2174536-rs458076_R: TTTCTAAATTTCCATTGAACAG (SEQ ID NO:242), rs11088023-rs11088024_F: GAAATTGGCAATCTGATTCT (SEQ ID NO:243) and rs11088023-rs11088024_R: CAACTTGTCCTTTATTGATGT (SEQ ID NO:244), rs1011734-rs1011733_F: CTATGTTGATAAAACATTGAAA (SEQ ID NO:245) and rs1011734-rs1011733_R: GCCTGTCTGGAATATAGTTT (SEQ ID NO:246), rs2831244-rs9789838_F: CAGGGCATATAATCTAAGCTGT (SEQ ID NO:247) and rs2831244-rs9789838_R: CAATGACTCTGAGTTGAGCAC (SEQ ID NO:248), rs8132769-rs2831440_F: ACTCTCTCCCTCCCCTCT (SEQ ID NO:249) and rs8132769-rs2831440_R: TATGGCCCCAAAACTATTCT (SEQ ID NO:250), rs8134080-rs2831524_F: ACAAGTACTGGGCAGATTGA (SEQ ID NO:251) and rs8134080-rs2831524_R: GCCAGGTTTAGCTTTCAAGT (SEQ ID NO:252), rs4817219-rs4817220_F: TTTTATATCAGGAGAAACACTG (SEQ ID NO:253) and rs4817219-rs4817220_R: CCAGAATTTTGGAGGTTTAAT (SEQ ID NO:254), rs2250911-rs2250997_F: TGTCATTCCTCCTTTATCTCCA (SEQ ID NO:255) and rs2250911-rs2250997_R: TTCTTTGCCTCTCCCAAAG (SEQ ID NO:256), rs2831899-rs2831900_F: ACCCTGGCACAGTGTTGACT (SEQ ID NO:257) and rs2831899-rs2831900_R: TGGGCCTGAGTTGAGAAGAT (SEQ ID NO:258), rs2831902-rs2831903_F: AATTGTAAGTATGTGCAACG (SEQ ID NO:259) and rs2831902-rs2831903_R: TTTTTCCCATTTCCAACTCT (SEQ ID NO:260), rs11088086-rs2251447_F: AAAAGATGAGACAGGCAGGT (SEQ ID NO:261) and rs11088086-rs2251447_R: ACCCCTGTGAATCTCAAAAT (SEQ ID NO:262), rs2832040-rs11088088_F: GCACTTGCTTCTATTGTTGT (SEQ ID NO:263) and rs2832040-rs11088088_R: CCCTCCTCTCTTCCATTCT (SEQ ID NO:264), rs2832141-rs2246777_F: AGCACTGCAGGTA (SEQ ID NO:265) and rs2832141-rs2246777_R: ACAGATACCAAAGAACTGCAA (SEQ ID NO:266), rs2832959-rs9980934_F: TGGACACCTTTCAACTTAGA (SEQ ID NO:267) and rs2832959-rs9980934_R: GAACAGTAATGTGAACTTTTT (SEQ ID NO:268), rs2833734-rs2833735_F: TCTTGCAAAAAGCTTAGCACA (SEQ ID NO:269) and rs2833734-rs2833735_R: AAAAAGATCTCAAAGGGTCCA (SEQ ID NO:270), rs933121-rs933122_F: GCTTTTGCTGAACATCAAGT (SEQ ID NO:271) and rs933121-rs933122_R: CCTTCCAGCAGCATAGTCT (SEQ ID NO:272), rs2834140-rs12626953_F: AAATCCAGGATGTGCAGT (SEQ ID NO:273) and rs2834140-rs12626953_R: ATGATGAGGTCAGTGGTGT (SEQ ID NO:274), rs2834485-rs3453_F: CATCACAGATCATAGTAAATGG (SEQ ID NO:275) and rs2834485-rs3453_R: AATTATTATTTTGCAGGCAAT (SEQ ID NO:276), rs9974986-rs2834703_F: CATGAGGCAAACACCTTTCC (SEQ ID NO:277) and rs9974986-rs2834703_R: GCTGGACTCAGGATAAAGAACA (SEQ ID NO:278), rs2776266-rs2835001_F: TGGAAGCCTGAGCTGACTAA (SEQ ID NO:279) and rs2776266-rs2835001_R: CCTTCTTCCCCCAGAATC (SEQ ID NO:280), rs1984014-rs1984015_F:TAGGAGAACAGAAGATCAGAG (SEQ ID NO:281) and rs984014-rs1984015_R:AAAGACTATTGCTAAATGCTTG (SEQ ID NO:282), rs7281674-rs2835316_F: TAAGCGTAGGGCTGTGTGTG (SEQ ID NO:283) and rs7281674-rs2835316_R: GGACGGATAGACTCCAGAAGG (SEQ ID NO:284), rs13047304-rs13047322_F: GAATGACCTTGGCACTTTTATCA (SEQ ID NO:285) and rs13047304-rs13047322_R: AAGGATAGAGATATACAGATGAATGGA (SEQ ID NO:286), rs2835735-rs2835736_F: CATGCACCGCGCAAATAC (SEQ ID NO:287) and rs2835735-rs2835736_R: ATGCCTCACCCACAAACAC (SEQ ID NO:288), rs13047608-rs2835826_F: TCCAAGCCCTTCTCACTCAC (SEQ ID NO:289) and rs13047608-rs2835826_R: CTGGGACGGTGACATTTTCT (SEQ ID NO:290), rs2836550-rs2212596_F: CCCAGGAAGAGTGGAAAGATT (SEQ ID NO:291) and rs2836550-rs2212596_R: TTAGCTGCATGTACCTGTGT (SEQ ID NO:292), rs2836660-rs2836661_F: AGCTAGATGGGGTGAATTTT (SEQ ID NO:293) and _R: TGGGCTGAGGGGAGATTC (SEQ ID NO:294), rs465612-rs8131220_F: ATCAAGCTAATTAATGTTATCT (SEQ ID NO:295) and rs465612-rs8131220_R: AATGAATAAGGTCCTCAGAG (SEQ ID NO:296), rs9980072-rs8130031_F:TTTAATCTGATCATTGCCCTA (SEQ ID NO:297) and rs9980072-rs8130031_R: AGCTGTGGGTGACCTTGA (SEQ ID NO:298), rs418359-rs2836926_F: TGTCCCACCATTGTGTATTA (SEQ ID NO:299) and rs418359-rs2836926_R: TCAGACTGAAGTCCAGGAT (SEQ ID NO:300), rs7278447-rs7278858_F: GCTTCAGGGGTGTTAGTTTT (SEQ ID NO:301) and rs7278447-rs7278858_R: CTTTGTGAAAAGTCGTCCAG (SEQ ID NO:302), rs385787-rs367001_F:CCATCATGGAAAGCATGG (SEQ ID NO:303) and rs385787-rs367001_R: TCATCTCCATGACTGCACTA (SEQ ID NO:304), rs367001-rs386095_F: GAGATGACGGAGTAGCTCAT (SEQ ID NO:305) and rs367001-rs386095_R: CCCAGCTGCACTGTCTAC (SEQ ID NO:306), rs2837296-rs2837297_F: TCTTGTTCCAATCACAGGAC (SEQ ID NO:307) and rs2837296-rs2837297_R: ATGCTGTTAGCTGAAGCTCT (SEQ ID NO:308), and rs2837381-rs4816672_F: TGAAAGCTCCTAAAGCAGAG (SEQ ID NO:309) and rs2837381-rs4816672_R:TTGAAGAGATGTGCTATCAT (SEQ ID NO:310). Polynucleotide sequences e.g. GC clamp sequences, can be included to ensure specific hybridization of AT-rich primers (Ghanta et al., PLOS ONE 5(10): doi10.1371/journal.pone.0013184 [2010], available on the world wide web at plosone.org). An example of a GC clamp sequence that can be included either 5' of the forward primer or 3' of the reverse primer is GCCGCCTGCAGCCCGCGCCCCCCGTGCCCCCGCCCCGCCGCCGCGCCCGGGCGCC (SEQ ID NO:311). Sample preparation and enrichment of cfDNA sequencing library, a purified cfDNA sample, and a plasma sample is performed according to the method described in Examples 6, 7, and 8, respectively. All sequencing libraries are prepared as described in Example 2a., and sequencing is performed as described in Example 2b and including paired-end sequencing. Analysis of the sequencing data for the determination of fetal aneuploidy is performed as described in Examples 3 and 4. Concomitant to the analysis for determining aneuploidy, the sequencing data is analyzed to determine the fetal fraction as follows. Following the transfer of the image and base call files to the Unix server running the Illumina "Genome Analyzer Pipeline" software version 1.51 as described in Example 3a., the 36 bp reads are aligned to a 'tandem SNP genome' using the BOWTIE program. The tandem SNP genome is identified as the grouping of the DNA sequences that encompass the alleles of the 58 tandem SNP pairs disclosed above. Only reads that mapped uniquely to the tandem SNP genome are used for the analysis of fetal fraction. Reads that match perfectly to the tandem SNP genome are counted as tags and filtered. Of the remaining reads, only reads having one or two mismatches are counted as tags and included in the analysis. Tags mapped to each of the tandem SNP alleles are counted, and the fetal fraction is determined essentially as described in Example 6 above but accounting for tags mapped to the two tandem SNP alleles x and y present on each of the amplified polymorphic target nucleic acid sequences that are amplified to enrich the samples i.e.

$$\% \text{ fetal fraction allele}_{x+y}=((\Sigma\text{Fetal sequence tags for allele}_{x+y})/(\Sigma\text{Maternal sequence tags for allele}_{x+y}))\times 100$$

Only informative tandem SNPs are used to determine the fetal fraction.

Optionally, the fraction of fetal nucleic acids in the mixture of fetal and maternal nucleic acids is calculated for each of the informative allele (allele$_{x+y}$) as follows:

$$\% \text{ fetal fraction allele}_{x+y}=((2\times\Sigma\text{Fetal sequence tags for allele}_{x+y})/(\Sigma\text{Maternal sequence tags for allele}_{x+y}))\times 100,$$

to compensate for the presence of 2 sets of tandem fetal alleles, one being masked by the maternal background.

The percent fetal fraction is calculated for at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40 or more informative sets of tandem alleles. In one embodiment, the fetal fraction is the average fetal fraction determined for at least 3 informative sets of tandem alleles.

Example 11

Determination of Fetal Fraction by Capillary Electrophoresis of Polymorphic Sequences Comprising STRs To determine fetal fraction in maternal samples comprising fetal and maternal cfDNA, peripheral blood samples were collected from volunteer pregnant women carrying either male or female fetuses. Peripheral blood samples were obtained and processed to provide purified cfDNA as described in Example 1.

Ten microliters of cfDNA samples were analyzed using the AmpFISTR® MiniFiler™ PCR amplification kit (Applied Biosystems, Foster City, Calif.) according to the manufacturer's instructions. Briefly, cDNA contained in 10 μl was amplified in a reaction volume of 25 μl containing 5 μL fluorescently labeled primers (AmpFISTR® MiniFiler™ Primer Set), and the AmpFISTR® MiniFiler™ Master Mix, which includes AmpliTaq Gold® DNA polymerase and associated buffer, salt (1.5 mM MgCl2), and 200 μM deoxynucleotide triphosphates (dNTPs: dATP, dCTP, dGTP and dTTP). The fluorescently labeled primers are forward primers that are labeled with 6FAM™, VIC™, NED™, and PET™ dyes. Thermal cycling was performed with the Gene Amp9700 (Applied Biosystems) using the following cycling conditions: incubating at 95° C. for 10 minutes, followed by 30 cycles at 94° C. for 20 seconds, 59° C. for 2 minute, and 72° C. for 1 minute, which was followed by a final incubation at 60° C. for 45 minutes. A final hold at 4° C. was added until the samples were removed for analysis. The amplified product was prepared by diluting 1 ul of amplified product in 8.7 ul Hi-Di™ formamide (Applied Biosystems) and 0.3 μl GeneScan™-500 LIZ_internal size standard (Applied Biosystems), and analyzed with an ABI PRISM3130xl Genetic Analyzer (Applied Biosystems) using Data Collection HID_G5_POP4 (Applied Biosystems), and a 36-cm capillary array. All genotyping was performed with GeneMapper_ID v3.2 software (Applied Biosystems) using manufacturer provided allelic ladders and bins and panels.

All genotyping measurement were performed on the Applied Biosystems 3130xl Genetic Analyzer, using a ±0.5-nt "window" around the size obtained for each allele to allow for detection and correct assignment of alleles. Any sample allele whose size was outside the ±0.5-nt window was determined to be OL i.e. "Off Ladder". OL alleles are alleles of a size that is not represented in the AmpFISTR® MiniFiler™ Allelic Ladder or an allele that does not correspond to an allelic ladder, but whose size is just outside a window because of measurement error. The minimum peak height threshold of >50 RFU was set based on validation experiments performed to avoid typing when stochastic effects are likely to interfere with accurate interpretation of mixtures. The calculation of fetal fraction is based on averaging all informative markers. Informative markers are identified by the presence of peaks on the electropherogram that fall within the parameters of preset bins for the STRs that are analyzed.

Calculations of fetal fraction were performed using the average peak height for major and minor alleles at every STR locus determined from triplicate injections. The rules applied to the calculation are:

1. off-ladder allele (OL) data for alleles are not included in the calculation; and
2. only peak heights derived from >50 RFU (relative fluorescence units) are included in the calculation
3. if only one bin is present the marker is deemed non-informative; and
4. if a second bin is called but the peaks of the first and second bins are within 50-70% of their relative fluorescence units (RFU) in peak height, the minority fraction is not measured and the marker is deemed not informative.

The fraction of the minor allele for any given informative marker is calculated by dividing the peak height of the minor component by the sum of the peak height for the major component, and expressed as a percent was first calculated for each informative locus as $$\text{fetal fraction}=(\text{peak height of minor allele}/\Sigma\text{peak height of major allele(s)})\times 100,$$

The fetal fraction for a sample comprising two or more informative STRs, would be calculated as the average of the fetal fractions calculated for the two or more informative markers.

Table 16 provides the data obtained from analyzing cfDNA of a subject pregnant with a male fetus.

TABLE 16

Fetal Fraction Determined in cfDNA of a Pregnant Subject by Analysis of STRs

| STR | Allele 1 | Allele 2 | Allele 3 | Allele1 Height | Allele 2 Height | Allele 3 Height | Fetal Fraction | Fetal Fraction (Mean/STR) |
|---|---|---|---|---|---|---|---|---|
| AMEL | X | Y | | 3599 | 106 | | 2.9 | |
| AMEL | X | Y | | 3602 | 110 | | 3.1 | |
| AMEL | X | Y | | 3652 | 109 | | 3.0 | 3.0 |
| CSF1PO | 11 | 12 | | 2870 | 2730 | | | |
| CSF1PO | 11 | 12 | | 2924 | 2762 | | | |
| CSF1PO | 11 | 12 | | 2953 | 2786 | | | |
| D13S317 | 11 | 12 | | 2621 | 2588 | | | |
| D13S317 | 11 | 12 | | 2680 | 2619 | | | |
| D13S317 | 11 | 12 | | 2717 | 2659 | | | |
| D16S539 | 9 | 11 | | 1056 | 1416 | | | |
| D16S539 | 9 | 11 | | 1038 | 1394 | | | |
| D16S539 | 9 | 11 | | 1072 | 1437 | | | |
| D18S51 | 13 | 15 | | 2026 | 1555 | | | |
| D18S51 | 13 | 15 | | 2006 | 1557 | | | |
| D18S51 | 13 | 15 | | 2050 | 1578 | | | |
| D21S11 | 28 | 31.2 | | 2450 | 61 | | 2.5 | |
| D21S11 | 28 | 31.2 | | 2472 | 62 | | 2.5 | |
| D21S11 | 28 | 31.2 | | 2508 | 67 | | 2.7 | 2.6 |
| D2S1338 | 20 | 23 | | 3417 | 3017 | | | |
| D2S1338 | 20 | 23 | | 3407 | 3020 | | | |
| D2S1338 | 20 | 23 | | 3493 | 3055 | | | |
| D7S820 | 9 | 12 | 13 | 2373 | 178 | 1123 | 5.1 | |
| D7S820 | 9 | 12 | 13 | 2411 | 181 | 1140 | 5.1 | |
| D7S820 | 9 | 12 | 13 | 2441 | 182 | 1156 | 5.1 | 5.1 |
| FGA | 17.2 | 22 | 25 | 68 | 1140 | 896 | 3.3 | |
| FGA | 17.2 | 22 | 25 | 68 | 1144 | 909 | 3.1 | |
| FGA | 17.2 | 22 | 25 | 68 | 1151 | 925 | 3.3 | 3.2 |

Fetal Fraction = 3.5

The results show that minSTRs can be used to discern fetal and maternal alleles in cfDNA from a maternal plasma sample. It is expected that the miniSTRs can be used in massively parallel sequencing for the simultaneous determination of aneuploidy and fetal fraction.

What is claimed is:

1. A method for simultaneously determining fetal aneuploidy and fetal fraction in a maternal plasma sample comprising an unamplified mixture of fetal and maternal cell-free DNA (cfDNA) molecules, wherein said fetal fraction is the fraction of said DNA molecules contributed by a fetus to said unamplified mixture of fetal and maternal DNA molecules, said method comprising:

(a) enriching a portion of said unamplified mixture for a plurality of polymorphic target nucleic acids, wherein each of said target nucleic acids is known to compromise at least one polymorphic site, and wherein said enriching comprises:

(i) dividing said unamplified mixture into a first portion and a second portion, and specifically amplifying said plurality of target nucleic acids in the first portion using primer pairs each capable of amplifying a target nucleic acid sequence comprising a polymorphic site in a multiplex PCR reaction to generate an amplified product comprising a panel of amplified polymorphic sites that contains a sufficient number of polymorphic sites such that at least two are informative polymorphic sites; and (ii) combining at least a portion or all of the amplified product with at least a portion of the second portion of said unamplified mixture to obtain an enriched mixture;

(b) performing massively parallel sequencing of at least a portion of the enriched mixture obtained in step (a), wherein said sequencing comprises providing a plurality of sequence reads and aligning each sequence read to a chromosome in a reference genome to identify a plurality of mapped sequence tags; and (c) based on said sequencing, simultaneously determining said fetal fraction and said aneuploidy, wherein:

(i) determining said fetal fraction is performed by a processor using computer readable software code and comprises:

(1) using the mapped sequence tags to identify at least two informative polymorphic sites in said panel of amplified polymorphic sites, wherein said informative polymorphic sites are identified by the difference in the allelic sequences and the number of mapped sequence tags mapped to each of the possible alleles at each polymorphic site; and (2) calculating the fetal fraction based on the total number of mapped sequence tags that map to a first allele and the total number of mapped sequence tags that map to a second allele at each of said informative polymorphic sites; and (ii) determining said fetal aneuploidy is performed by a processor using computer readable software code and comprises quantification of the number of mapped sequence tags aligning to a chromosome of interest, and comparing the results obtained for the chromosome of interest to a threshold value, wherein the threshold value is a number that serves as a limit of diagnosis of an aneuploidy and wherein the presence of an aneuploidy for the chromosome of interest is identified if the threshold value is exceeded by the results obtained for the chromosome of interest.

2. The method of claim 1, wherein said enriching comprises amplifying a plurality of polymorphic target nucleic acids in a portion of a purified mixture of fetal and maternal nucleic acids.

3. The method of claim 1, wherein said polymorphic target nucleic acids are located on the same or on different chromosomes.

4. The method of claim 1, wherein each of said plurality of polymorphic target nucleic acids comprises at least one single nucleotide polymorphism (SNP).

5. The method of claim 4, wherein said at least one SNP is rs560681.

6. The method of claim 4, wherein said at least one SNP is a tandem SNP.

7. The method of claim 4, wherein said tandem SNP is selected from sets of tandem SNPs rs7277033-rs2110153; rs2822654-rs1882882; rs368657-rs376635; rs2822731-rs2822732; rs1475881-rs7275487; rs1735976-rs2827016; rs447340-rs2824097; rs418989-rs13047336; rs987980-rs987981; rs4143392-rs4143391; rs1691324-rs13050434; rs11909758-rs9980111; rs2826842-rs232414; rs1980969-rs1980970; rs9978999-rs9979175; rs1034346-rs12481852; rs7509629-rs2828358; rs4817013-rs7277036; rs9981121-rs2829696; rs455921-rs2898102; rs2898102-rs458848; rs961301-rs2830208; rs2174536-rs458076; rs11088023-rs11088024; rs1011734-rs1011733; rs2831244-rs9789838; rs8132769-rs2831440; rs8134080-rs2831524; rs4817219-rs4817220; rs2250911-rs2250997; rs2831899-rs2831900; rs2831902-rs2831903; rs11088086-rs2251447; rs2832040-rs11088088; rs2832141-rs2246777; rs2832959-rs9980934; rs2833734-rs2833735; rs933121-rs933122; rs2834140-rs12626953; rs2834485-rs3453; rs9974986-rs2834703; rs2776266-rs2835001; rs1984014-rs1984015; rs7281674-rs2835316; rs13047304-rs13047322; rs2835545-rs4816551; rs2835735-rs2835736; rs13047608-rs2835826; rs2836550-rs2212596; rs2836660-rs2836661; rs465612-rs8131220; rs9980072-rs8130031; rs418359-rs2836926; rs7278447-rs7278858; rs385787-rs367001; rs367001-rs386095; rs2837296-rs2837297; and rs2837381-rs4816672.

8. The method of claim 1, wherein each of said plurality of polymorphic target nucleic acids comprises at least one short tandem repeat (STR).

9. The method of claim 1, wherein each of said plurality of polymorphic target nucleic acids is an STR selected from CSF1PO, FGA, TH01, TPDX, vWA, D3S1358, D5S818, D7S820, D8S1179, D13S317, D16S539, D18S51, D21S11, D2S1338, Penta D, Penta E, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627 and D1GATA113.

10. The method of claim 8, wherein said at least one STR is less than about 300 base pairs.

11. The method of claim 1, wherein said sequencing is next generation sequencing (NGS).

12. The method of claim 1, wherein said sequencing is massively parallel sequencing using sequencing-by-synthesis with reversible dye terminators.

13. The method of claim 1, wherein said sequencing is sequencing-by-ligation.

14. The method of claim 1, wherein said sequencing comprises an amplification.

15. The method of claim 1, wherein said sequencing is single molecule sequencing.

16. The method of claim 1, wherein said aneuploidy is a chromosomal aneuploidy.

17. The method of claim 1, wherein the plurality of mapped sequence tags comprises at least $3\times10^6$ sequence tags.

* * * * *

UNITED STATES PATENT AND TRADEMARK OFFICE
CERTIFICATE OF CORRECTION

| | | |
|---|---|---|
| PATENT NO. | : 11,130,995 B2 | |
| APPLICATION NO. | : 15/664008 | |
| DATED | : September 28, 2021 | |
| INVENTOR(S) | : Stephen Quake et al. | |

It is certified that error appears in the above-identified patent and that said Letters Patent is hereby corrected as shown below:

In the Claims

Column 309, Claim 7, Line 1, "claim 4" should read -claim 6-.

Signed and Sealed this
Third Day of May, 2022

Katherine Kelly Vidal
*Director of the United States Patent and Trademark Office*